US008067428B2

(12) United States Patent
Scarborough et al.

(10) Patent No.: US 8,067,428 B2
(45) Date of Patent: Nov. 29, 2011

(54) PLATELET ADP RECEPTOR INHIBITORS

(75) Inventors: Robert M. Scarborough, Half Moon Bay, CA (US); Hans-Michael Jantzen, San Francisco, CA (US); Wolin Huang, Foster City, CA (US); David M. Sedlock, Burlingame, CA (US); Charles K. Marlowe, Redwood City, CA (US); Kim A. Kane-McGuire, Belmont, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/559,389

(22) Filed: Sep. 14, 2009

(65) Prior Publication Data

US 2010/0234350 A1 Sep. 16, 2010

Related U.S. Application Data

(63) Continuation of application No. 11/841,711, filed on Aug. 20, 2007, now Pat. No. 7,622,474, which is a continuation of application No. 11/293,026, filed on Dec. 1, 2005, now Pat. No. 7,358,257, which is a continuation of application No. 10/941,053, filed on Sep. 13, 2004, now Pat. No. 7,056,926, which is a continuation of application No. 09/920,325, filed on Aug. 2, 2001, now Pat. No. 6,906,063, which is a continuation-in-part of application No. 09/775,812, filed on Feb. 5, 2001, now abandoned.

(60) Provisional application No. 60/230,447, filed on Sep. 6, 2000, provisional application No. 60/202,072, filed on May 5, 2000, provisional application No. 60/180,208, filed on Feb. 4, 2000.

(51) Int. Cl.

| | |
|---|---|
| ***C07D 521/00*** | (2006.01) |
| ***C07D 409/12*** | (2006.01) |
| ***C07D 209/48*** | (2006.01) |
| ***A61K 31/4035*** | (2006.01) |
| ***A61P 7/02*** | (2006.01) |

(52) U.S. Cl. .................... 514/266.24; 544/288; 544/290

(58) Field of Classification Search .................. 544/288, 544/290; 514/266.24

See application file for complete search history.

(56) References Cited

U.S. PATENT DOCUMENTS

| | | | |
|---|---|---|---|
| 3,847,925 | A | 11/1974 | Beregi et al. |
| 5,475,025 | A | 12/1995 | Tjoeng et al. |
| 6,413,724 | B1 | 7/2002 | Gordeev et al. |

FOREIGN PATENT DOCUMENTS

| | | | |
|---|---|---|---|
| DE | 845 042 | | 7/1952 |
| JP | 08-081442 | A | 3/1996 |
| JP | 10-502630 | A | 3/1998 |
| JP | 10-195323 | A | 7/1998 |
| JP | 2000-204081 | A | 7/2000 |
| JP | 2003-522177 | A | 7/2003 |
| WO | WO 94/19341 | A1 | 9/1994 |
| WO | WO 94/21602 | A1 | 9/1994 |
| WO | WO 96/02508 | A1 | 2/1996 |
| WO | WO 99/36425 | A1 | 7/1999 |
| WO | WO 01/57037 | A1 | 8/2001 |

OTHER PUBLICATIONS

Hatzelmann, A., “Mode of action of the new selective leukotriene synthesis inhibitor BAY X 1005{(R)-2-[4-(quinolin-2-yl-methoxy)phenyl]-2-cyclopentyl acetic acid} and structurally related compounds,” *Biochemical Pharmacology*, 1993, vol. 45, No. 1, pp. 101-111.

Holland, *Journal of Organic Chemistry*, 1961, vol. 26, pp. 1662-1665.

Lacan, F., “Synthesis, structural characterization and thromboxane A2 receptor antagonistic activity of 3-substiuted 2-[(aryslulfonyl) imino]-2, 3-dihydrothiaozyl derivatives,” *European Journal of Medicinal Chemistry*, 1999, vol. 34, No. 4, pp. 311-328.

Plotnikova, et al., “Arenesulfonamides, LXXX. Aroylarenesulfonamides”, Database CA Online Chemical Abstracts Service, Columbus, OH, US, retrieved from STN Database Accession No. 82 139564 XP002215531, abstract & *Vopr. Khim. Khim. Tekhnol.* (1974), 33, 20-5.

Stack, D. “Electron Withdrawing and Electron Donating Groups”, 2010, (http://myweb.unomaha.edu/-dstack/2250/Problems/EWG_EDG.doc) 4 pp.

Vippagunta, S.R. et al., “Crystalline solids,” *Advanced Drug Delivery Reviews*, 2001, vol. 48, pp. 3-26.

*Primary Examiner* — Bruck Kifle

(74) *Attorney, Agent, or Firm* — Kilpatrick Townsend and Stockton LLP

(57) ABSTRACT

Novel compounds of formulae (I) to (VIII), which more particularly include sulfonylurea derivatives, sulfonylthiourea derivatives, sulfonylguanidine derivatives, sulfonylcyanoguanidine derivatives, thioacylsulfonamide derivatives, and acylsulfonamide derivatives which are effective platelet ADP receptor inhibitors. These derivatives may be used in various pharmaceutical compositions, and are particularly effective for the prevention and/or treatment of cardiovascular diseases, particularly those diseases related to thrombosis. The invention also relates to a method for preventing or treating thrombosis in a mammal comprising the step of administering a therapeutically effective amount of a compound of formulae (I) to (VIII), or a pharmaceutically acceptable salt thereof.

8 Claims, No Drawings

PLATELET ADP RECEPTOR INHIBITORS

This application is a Continuation of U.S. patent application Ser. No. 11/841,711, filed Aug. 20, 2007, now U.S. Pat. No. 7,622,474, which is a Continuation of U.S. patent application Ser. No. 11/293,026, filed Dec. 1, 2005, now U.S. Pat. No. 7,358,257, which is a Continuation of U.S. patent application Ser. No. 10/941,053, filed Sep. 13, 2004, now U.S. Pat. No. 7,059,926, which is a Continuation of U.S. patent application Ser. No. 09/920,325, filed Aug. 2, 2001, now U.S. Pat. No. 6,906,063 which is a Continuation in Part of U.S. patent application Ser. No. 09/775,812, filed Feb. 5, 2001, now Abandoned, which further claims the benefit under 35 U.S.C. §119(e) of U.S. Provisional Patent Application No. 60/230,447 filed Sep. 6, 2000, 60/202,072 filed May 5, 2000 and U.S. Provisional Patent Application No. 60/180,208, filed Feb. 4, 2000. The disclosures of each of the foregoing applications are hereby incorporated herein by reference.

FIELD OF THE INVENTION

The invention relates to novel compounds of formula (I), formula (II), formula (III), formula (IV), formula (V), formula (VI), formula (VII) and formula (VIII) (hereinafter referred to as "formulae (I)-(VIII)"), which more particularly include sulfonylurea derivatives, sulfonylthiourea derivatives, sulfonylguanidine derivatives, sulfonylcyanoguanidine derivatives, thioacylsulfonamide derivatives, and acylsulfonamide derivatives which are effective platelet ADP receptor inhibitors. These derivatives may be used in various pharmaceutical compositions, and are particularly effective for the prevention and/or treatment of cardiovascular diseases, particularly those diseases related to thrombosis.

DESCRIPTION OF THE RELATED ART

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and protheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation by ADP results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives (Mills, D. C. B. (1996) *Thromb. Hemost.* 76:835-856). Therefore, platelet ADP receptors are members of the family of P2 receptors activated by purine and/or pyrimidine nucleotides (King, B. F., Townsend-Nicholson, A. & Burnstock, G. (1998) *Trends Pharmacol. Sci.* 19:506-514).

Recent pharmacological data using selective antagonists suggests that ADP-dependent platelet aggregation requires activation of at least two ADP receptors (Kunapuli, S. P. (1998), *Trends Pharmacol. Sci.* 19:391-394; Kunapuli, S. P. & Daniel, J. L. (1998) *Biochem. J.* 336:513-523; Jantzen, H. M. et al. (1999) *Thromb. Hemost.* 81:111-117). One receptor appears to be identical to the cloned $P2Y_1$ receptor, mediates phospholipase C activation and intracellular calcium mobilization and is required for platelet shape change. The second platelet ADP receptor important for aggregation mediates inhibition of adenylyl cyclase. Molecular cloning of the gene or cDNA for this receptor ($P2Y_{12}$) has recently been reported (Hollopeter, G. et. al. (2001) *Nature* 409:202-207). Based on its pharmacological and signaling properties this receptor has been previously termed $P2Y_{ADP}$ (Fredholm, B. B. et al. (1997) *TIPS* 18:79-82), $P2T_{AC}$ (Kunapuli, S. P. (1998), *Trends Pharmacol. Sci.* 19:391-394) or P2Ycyc (Hechler, B. et al. (1998) Blood 92, 152-159).

Various directly or indirectly acting synthetic inhibitors of ADP-dependent platelet aggregation with antithrombotic activity have been reported. The orally active antithrombotic thienopyridines ticlopidine and clopidogrel inhibit ADP-induced platelet aggregation, binding of radiolabeled ADP receptor agonist 2-methylthioadenosine 5'-diphosphate to platelets, and other ADP-dependent events indirectly, probably via formation of an unstable and irreversible acting metabolite (Quinn, M. J. & Fitzgerald, D. J. (1999) Circulation 100:1667-1667). Some purine derivatives of the endogenous antagonist ATP, e.g., AR-C (formerly FPL or ARL) 67085MX and AR-C69931MX, are selective platelet ADP receptor antagonists which inhibit ADP-dependent platelet aggregation and are effective in animal thrombosis models (Humphries et al. (1995), *Trends Pharmacol. Sci.* 16, 179; Ingall, A. H. et al. (1999) J. Med. Chem. 42, 213-230). Novel triazolo[4,5-d]pyrimidine compounds have been disclosed as $P_{2T}$-antagonists (WO 99/05144). Tricyclic compounds as platelet ADP receptor inhibitors have also been disclosed in WO 99/36425. The target of these antithrombotic compounds appears to be the platelet ADP receptor mediating inhibition of adenylyl cyclase.

Despite these compounds, there exists a need for more effective platelet ADP receptor inhibitors. In particular, there is a need for platelet ADP receptor inhibitors having antithrombotic activity that are useful in the prevention and/or treatment of cardiovascular diseases, particularly those related to thrombosis.

SUMMARY OF THE INVENTION

The invention provides compounds of formula (I), formula (II), formula (III), formula (IV), formula (V), formula (VI), formula (VII) and formula (VIII):

I

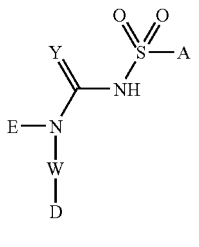

-continued

II

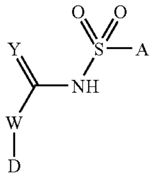

III

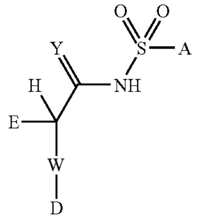

IV

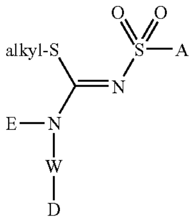

V

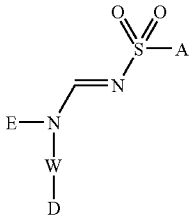

VI

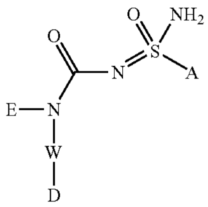

VII

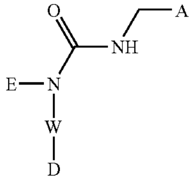

VIII

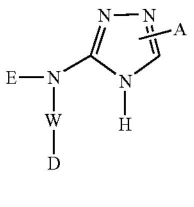

A is selected from the group consisting of aryl, substituted aryl, heteroaryl, substituted heteroaryl, alkylaryl, and alkylheteroaryl.

W is selected from the group consisting of aryl, substituted aryl, heteroaryl, and substituted heteroaryl.

E is selected from the group consisting of H, $-C_1$-$C_8$ alkyl, polyhaloalkyl, $-C_{3-8}$-cycloalkyl, aryl, alkylaryl, substituted aryl, heteroaryl, and substituted heteroaryl.

D is selected from the group consisting of $NR^1-(C{=}O)-R^2$, $-O-R^1$;

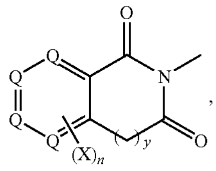, 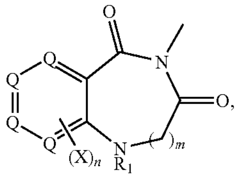

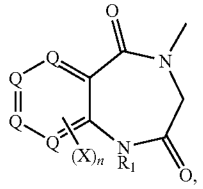 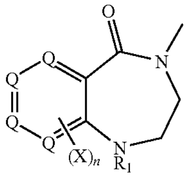,

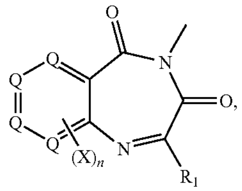 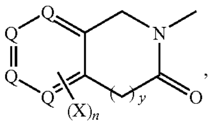,

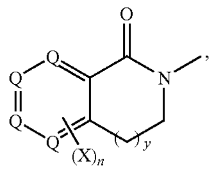 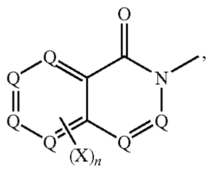

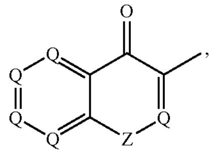 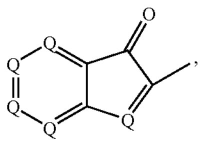

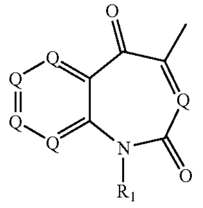 and 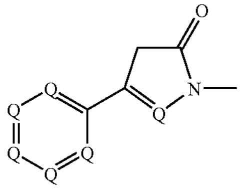

wherein:

$R^1$ is independently selected from the group consisting of:

H, $C_1$-$C_8$ alkyl, polyhaloalkyl, $-C_{3-8}$-cycloalkyl, aryl, alkylaryl, substituted aryl, heteroaryl, substituted heteroaryl, $-(C{=}O)-C_1$-$C_3$ alkyl, $-(C{=}O)$-aryl, $-(C{=}O)$-substituted aryl, $-(C{=}O)$-heteroaryl and $-(C{=}O)$-substituted heteroaryl;

$R^2$ is independently selected from the group consisting of aryl, substituted aryl, heteroaryl, substituted heteroaryl, or $R^1$ and $R^2$ can be direct linked or can be indirectly linked through a carbon chain that is from 1 to about 8 carbon atoms in length, n is 0-4, m is 0 or 1, y is 0-4 and Q is independently C or N, with the proviso that when Q is a ring carbon atom, each ring carbon atom is independently substituted by X.

X is in each case a member independently selected from the group consisting of:

H, halogen, polyhaloalkyl, —OR$^3$, —SR$^3$, —CN, —NO$_2$, —SO$_2$R$^3$, —C$_{1-10}$alkyl, —C$_{3-8}$-cycloalkyl, aryl, aryl-substituted by 1-4 R$^3$ groups, amino, amino-C$_{1-8}$-alkyl, C$_{1-3}$-acylamino, C$_{1-3}$-acylamino-C$_{1-8}$-alkyl, C$_{1-6}$-alkylamino, C$_{1-6}$-alkylamino C$_{1-8}$ alkyl, C$_{1-6}$ dialkylamino, C$_{1-6}$ dialkylamino C$_{1-8}$ alkyl, C$_{1-6}$ alkoxy, C$_{1-6}$ alkoxy-C$_{1-6}$-alkyl, carboxy-C$_{1-6}$-alkyl, C$_{1-3}$-alkoxycarbonyl, C$_{1-3}$-alkoxycarbonyl-C$_{1-4}$-alkyl, carboxy C$_{1-6}$ alkyloxy, hydroxy, hydroxy C$_{1-6}$ alkyl, and a 5 to 10 membered fused or non-fused aromatic or nonaromatic heterocyclic ring system, having 1 to 4 heteroatoms independently selected from N, O, and S, with the proviso that the carbon and nitrogen atoms, when present in the heterocyclic ring system, are unsubstituted, mono- or di-substituted independently with 0-2 R$^4$ groups.

R$^3$ and R$^4$ are each independently selected from the group consisting of:

H, halogen, —CN, —NO$_2$, —C$_{1-10}$ alkyl, C$_{3-4}$-cycloalkyl, aryl, amino, amino-C$_{1-8}$-alkyl, C$_{1-3}$-acylamino, C$_{1-3}$-acylamino-C$_{1-4}$-alkyl, C$_{1-6}$-alkylamino, C$_{1-6}$-alkylamino C$_{1-8}$ alkyl, C$_{1-6}$ dialkylamino, C$_{1-6}$ dialkylamino C$_{1-8}$ alkyl, C$_{1-6}$ alkoxy, C$_{1-6}$ alkoxy-C$_{1-6}$-alkyl, carboxy-C$_{1-6}$-alkyl, C$_{1-3}$-alkoxycarbonyl, C$_{1-3}$-alkoxycarbonyl-C$_{1-6}$-alkyl, carboxy-C$_{1-6}$-alkyloxy, hydroxy, hydroxy-C$_{1-6}$-alkyl, -thio and thio-C$_{1-6}$-alkyl.

Y is selected from the group consisting of O, S, N—OR$^5$, and NR$^S$, wherein R$^5$ is selected from the group consisting of:

H, C$_{1-10}$ alkyl, C$_{3-8}$-cycloalkyl, NR$^2$, and CN; and

Z is selected from the group consisting of NR$^1$ and O.

The invention also covers all pharmaceutically acceptable salts and prodrugs of the compounds of formulae (I)-(VIII).

In another aspect, the invention provides pharmaceutical compositions for preventing or treating thrombosis in a mammal containing a therapeutically effective amount of a compound of formulae (I)-(VIII) or a pharmaceutically acceptable salt thereof and a pharmaceutically acceptable carrier. The invention further provides a method for preventing or treating thrombosis in a mammal by administering a therapeutically effective amount of a compound of formulae (I)-(VIII) or a pharmaceutically acceptable salt thereof.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified, alkenyl and alkinyl each refer to radicals having from 2-12 carbon atoms.

The term "alkyl" refers to saturated aliphatic groups including straight-chain, branched-chain and cyclic groups having the number of carbon atoms specified, or if no number is specified, having up to about 12 carbon atoms. The term "cycloalkyl" as used herein refers to a mono-, bi-, or tricyclic aliphatic ring having 3 to about 14 carbon atoms and preferably 3 to about 7 carbon atoms.

The term "C$_1$-C$_6$ alkoxy" as used herein refers to an ether moiety whereby the oxygen is connected to a straight or branched chain of carbon atoms of the number indicated.

The term "mono-C$_1$-C$_6$ alkylamino" as used herein refers to an amino moiety whereby the nitrogen is substituted with one H and one C$_1$-C$_6$ alkyl substituent, the latter being defined as above.

The term "di-C$_1$-C$_6$ alkylamino" as used herein refers to an amino moiety whereby the nitrogen is substituted with two C$_1$-C$_6$ alkyl substituents as defined above.

The term "monoarylamino" as used herein refers to an amino moiety whereby the nitrogen is substituted with one H and one aryl substituent, such as a phenyl, the latter being defined as above.

The term "diarylamino" as used herein refers to an amino moiety whereby the nitrogen is substituted with two aryl substituents, such as phenyl, the latter being defined as above.

The term "C$_1$-C$_6$ alkylsulfonyl" as used herein refers to a dioxosulfur moiety with the sulfur atom also connected to one C$_1$-C$_6$ alkyl substituent, the latter being defined as above.

The term "C$_1$-C$_6$ alkoxycarbonyl" as used herein refers to a hydroxycarbonyl moiety whereby the hydrogen is replaced by a C$_1$-C$_6$ alkyl substituent, the latter being defined as above.

As used herein, the terms "carbocyclic ring structure" and "C$_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is an aromatic ring ("aryl") having six ring atoms ("phenyl"); a stable monocyclic non-aromatic ring having from 3 to about 7 ring atoms in the ring; a stable bicyclic ring structure having a total of from 7 to about 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from about 10 to about 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from lower alkoxy, lower alkyl, lower alkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

The term "phenyl" as used herein refers to a six carbon containing aromatic ring which can be variously mono- or poly-substituted with H, $C_1$-$C_6$ alkyl, hydroxyl, $C_1$-$C_6$ alkoxy, amino, mono-$C_1$-$C_6$ alkylamino, di-$C_1$-$C_6$ alkylamino, nitro, fluoro, chloro, bromo, iodo, hydroxycarbonyl, or $C_1$-$C_6$ alkoxycarbonyl.

As used herein, the term "heterocyclic ring" or "heterocyclic ring system" is intended to mean a substituted or unsubstituted member selected from the group consisting of a stable monocyclic ring having from 5-7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to $-CH_2-$.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Compound Embodiments of the Invention

Compounds of formula (I), formula (II), formula (III), formula (IV), formula (V), formula (VI), formula (VII) and formula (VIII) below represent one embodiment of the invention:

I

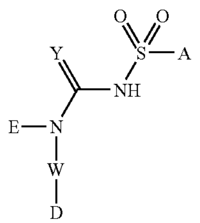

II

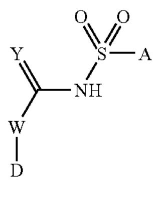

-continued

III

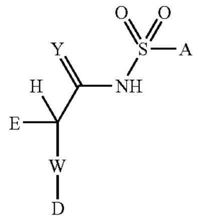

IV

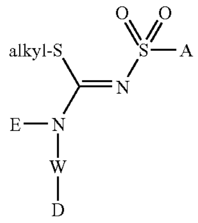

V

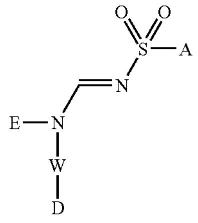

VI

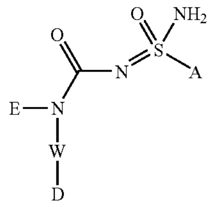

VII

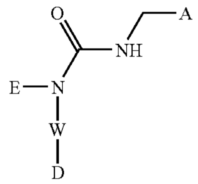

VIII

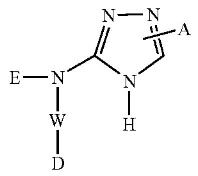

A is selected from the group consisting of aryl, substituted aryl, heteroaryl, substituted heteroaryl, alkylaryl, and alkylheteroaryl.

W is selected from the group consisting of aryl, substituted aryl, heteroaryl, and substituted heteroaryl.

E is selected from the group consisting of H, —$C_1$-$C_3$ alkyl, polyhaloalkyl, —$C_{3-8}$-cycloalkyl, aryl, alkylaryl, substituted aryl, heteroaryl, and substituted heteroaryl.

D is selected from the group consisting of $NR^1$—(C═O)—$R^2$, —O—$R^1$;

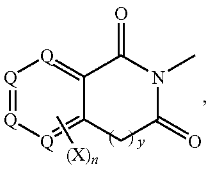
,
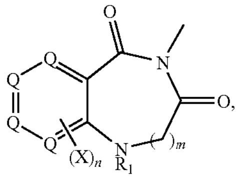

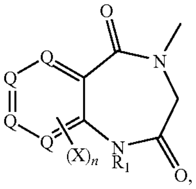

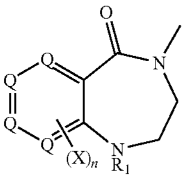
,
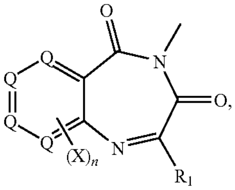

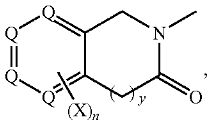
,
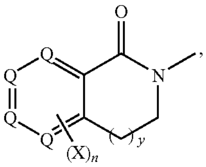
,
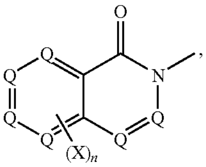
,
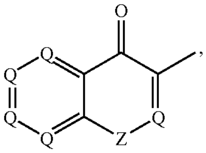
,
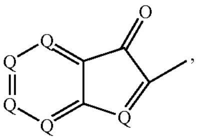
,
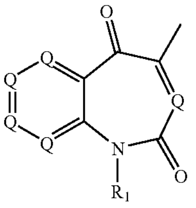
and
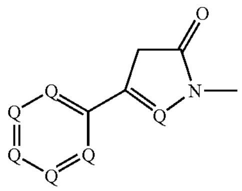

wherein:

$R^1$ is independently selected from the group consisting of:

H, $C_1$-$C_3$ alkyl, polyhaloalkyl, —$C_{3-8}$-cycloalkyl, aryl, alkylaryl, substituted aryl, heteroaryl, substituted heteroaryl, —(C═O)—$C_1$-$C_8$ alkyl, —(C═O)-aryl, —(C═O)-substituted aryl, —(C═O)-heteroaryl and —(C═O)-substituted heteroaryl;

$R^2$ is selected from the group consisting of: aryl, substituted aryl, heteroaryl, substituted heteroaryl, or $R^1$ and $R^2$ can be direct linked or can be indirectly linked through a carbon chain that is from 1 to about 8 carbon atoms in length, n is 0-4, m is 0 or 1, y is 0-4 and Q is independently C or N, with the proviso that when Q is a ring carbon atom, each ring carbon atom is independently substituted by X, wherein X is in each case a member independently selected from the group consisting of:

H, halogen, polyhaloalkyl, —$OR^3$, —$SR^3$, —CN, —$NO_2$, —$SO_2R^3$, —$C_{1-10}$-alkyl, —$C_{3-8}$-cycloalkyl, aryl, aryl-substituted by 1-4 $R^3$ groups, amino, amino-$C_{1-8}$-alkyl, $C_{1-3}$-acylamino, $C_{1-3}$-acylamino-$C_{1-8}$-alkyl, $C_{1-6}$-alkylamino, $C_{1-6}$-alkylamino $C_{1-8}$ alkyl, $C_{1-6}$ dialkylamino, $C_{1-6}$ dialkylamino $C_{1-8}$ alkyl, $C_{1-6}$ alkoxy, $C_{1-6}$ alkoxy-$C_{1-6}$-alkyl, carboxy-$C_{1-6}$-alkyl, $C_{1-3}$-alkoxycarbonyl, $C_{1-3}$-alkoxycarbonyl-$C_{1-6}$-alkyl, carboxy $C_{1-6}$ alkyloxy, hydroxy, hydroxy $C_{1-6}$ alkyl, and a 5 to 10 membered fused or non-fused aromatic or nonaromatic heterocyclic ring system, having 1 to 4 heteroatoms independently selected from N, O, and S, with the proviso that the carbon and nitrogen atoms, when present in the heterocyclic ring system, are unsubstituted, mono- or di-substituted independently with 0-2 $R^4$ groups, and wherein $R^3$ and $R^4$ are each independently selected from the group consisting of H, halogen, —CN, —$NO_2$, —$C_{1-10}$ alkyl, $C_{3-8}$-cycloalkyl, aryl, amino, amino-$C_{1-8}$-alkyl, $C_{1-3}$-acylamino, $C_{1-3}$-acylamino-$C_{1-8}$-alkyl, $C_{1-6}$-alkylamino, $C_{1-6}$-alkylamino $C_{1-8}$ alkyl, $C_{1-6}$ dialkylamino, $C_{1-6}$ dialkylamino $C_{1-8}$ alkyl, $C_{1-6}$ alkoxy, $C_{1-6}$ alkoxy-$C_{1-6}$-alkyl, carboxy-$C_{1-6}$-alkyl, $C_{1-3}$-alkoxycarbonyl, $C_{1-3}$-alkoxycarbonyl-$C_{1-6}$-alkyl, carboxy-$C_{1-6}$-alkyloxy, hydroxy, hydroxy-$C_{1-6}$-alkyl, -thio and thio-$C_{1-6}$-alkyl.

Y is selected from the group consisting of O, S, N—$OR^5$, and $NR^5$, wherein $R^5$ is selected from the group consisting of:

H, $C_{1-10}$ alkyl, $C_{3-8}$-cycloalkyl, and CN; and

Z is selected from the group consisting of $NR^1$ and O.

The invention also covers all pharmaceutically acceptable salts and prodrugs of the compounds of formula Ito formula VIII.

In a preferred embodiment of the invention, compounds of formulae (I)-(VIII)

I

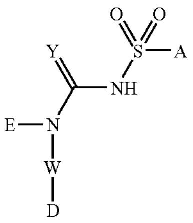

II

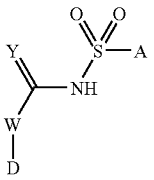

III

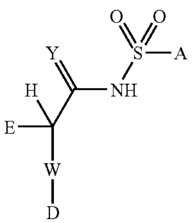

-continued
IV
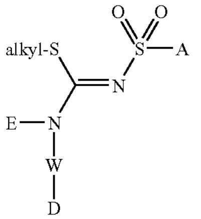
V
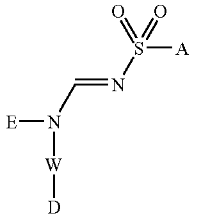
VI
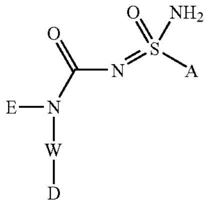
VII
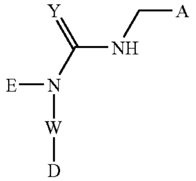
VIII
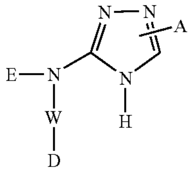
A is selected from the group consisting of:
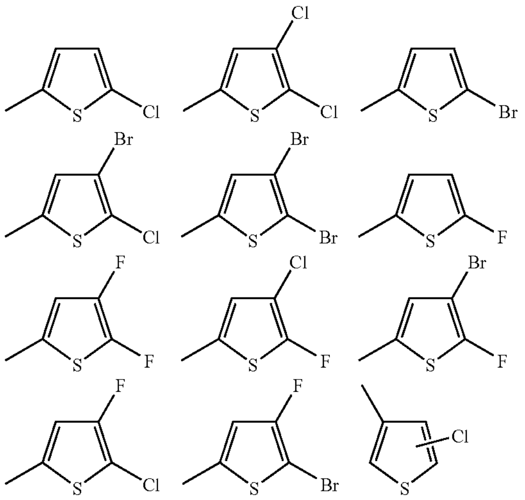
-continued
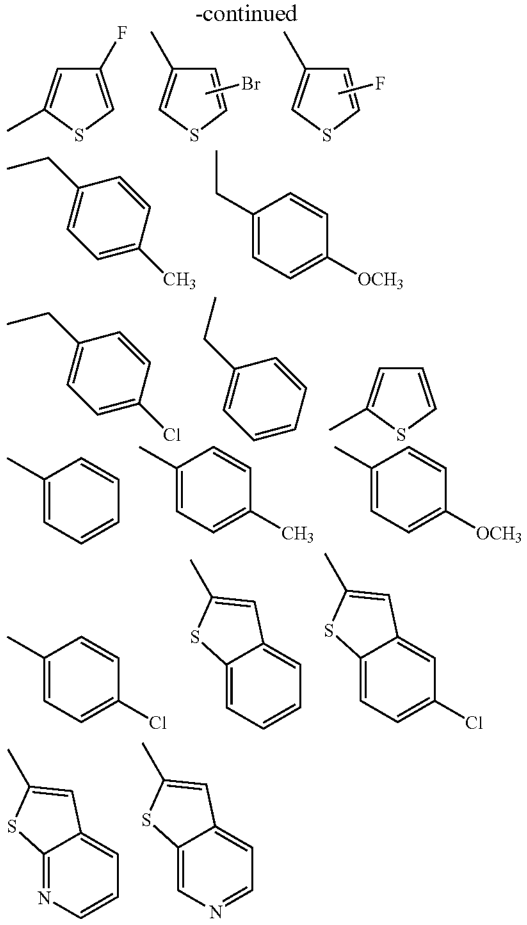
Y is selected from the group consisting of O, S, N—OR$^5$ and NR$^5$.
E is selected from the group consisting of H, or $C_{1-8}$ alkyl.
W is selected from the group consisting of:
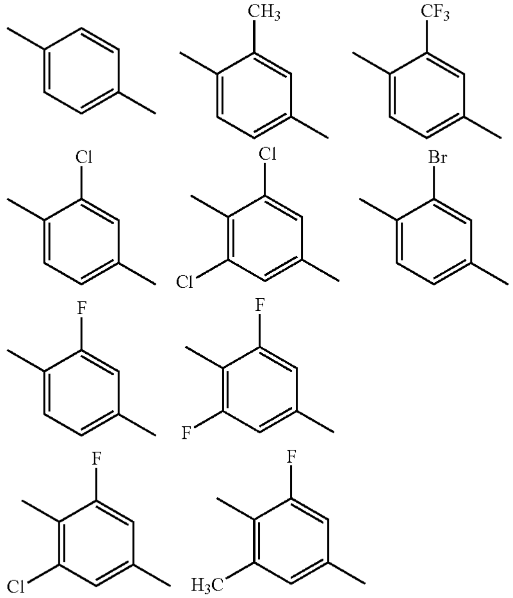

-continued
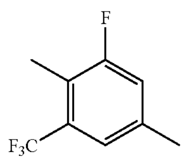 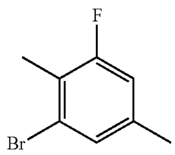 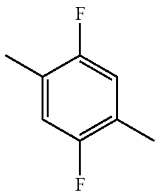
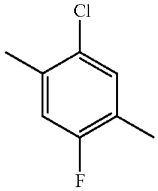 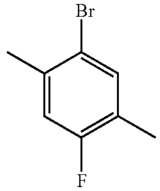 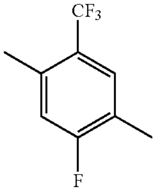
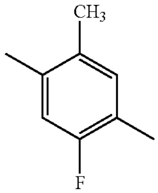 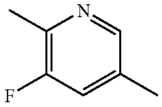 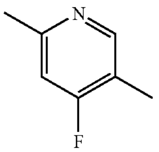
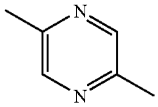 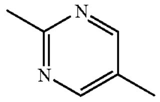 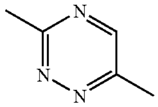
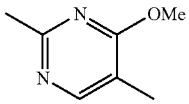 and 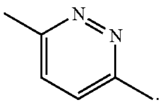
D is selected from the group consisting of:
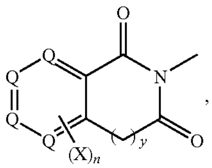, 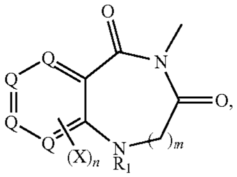
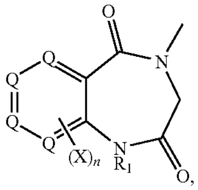 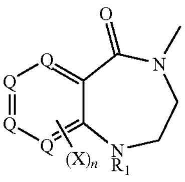,
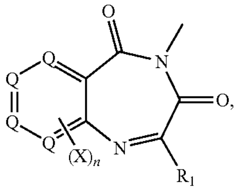 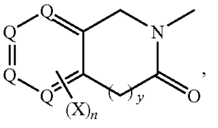,
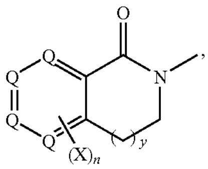 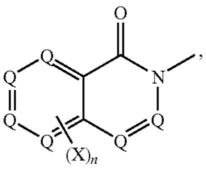
-continued
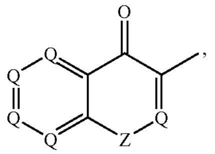 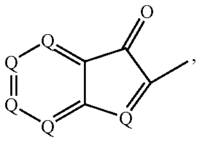
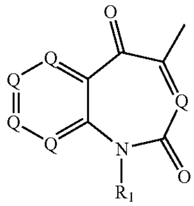 and 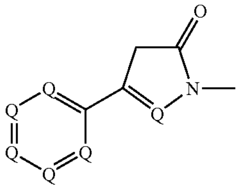
In a more preferred embodiment of the invention, compounds of formulae (I) to (VIII) include the compounds wherein:
D is selected from the group consisting of:
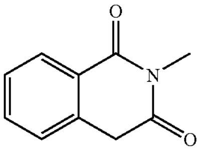 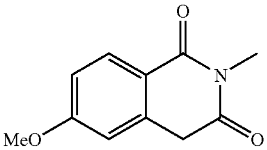
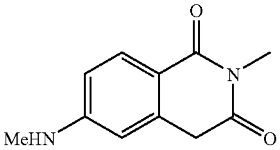
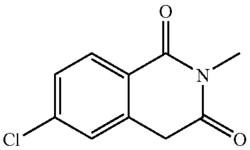
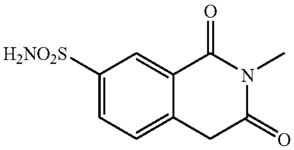
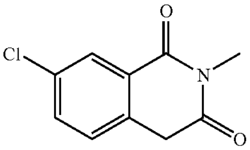 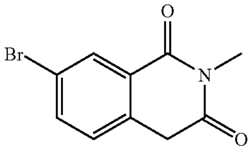
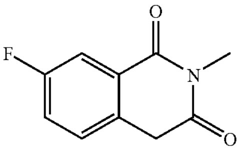 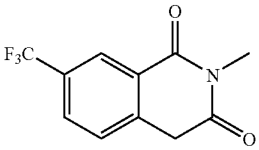
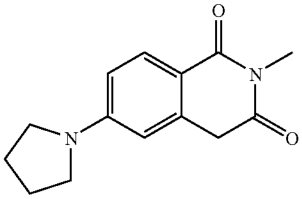

-continued
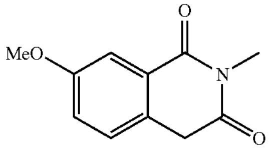
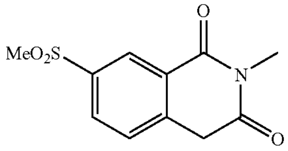
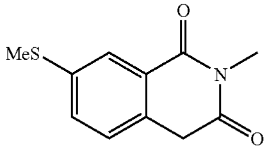
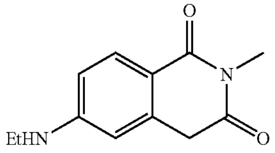
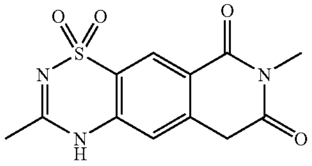
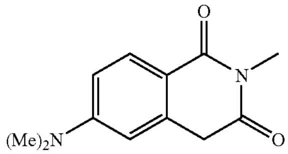
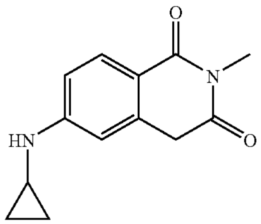
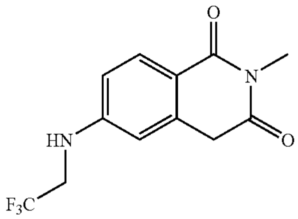
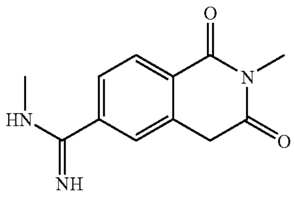
-continued
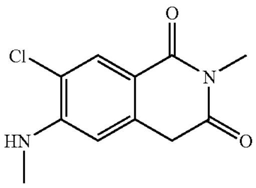
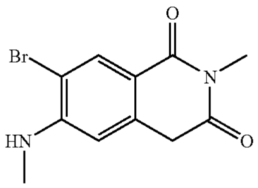
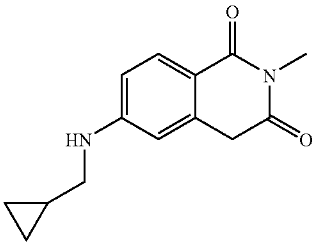
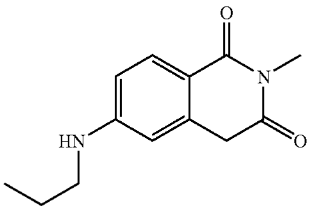
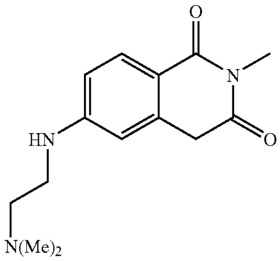
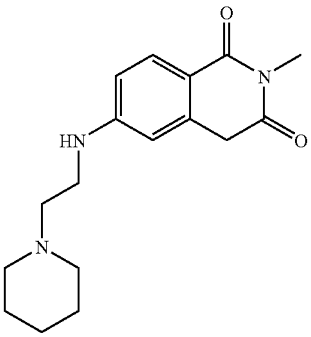
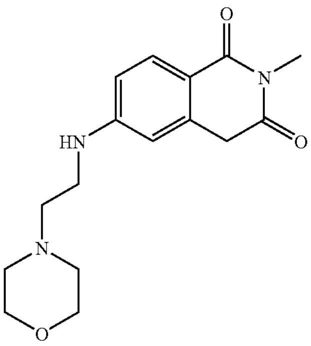

-continued
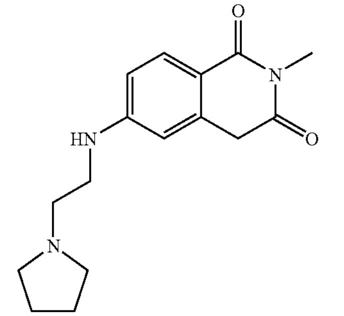
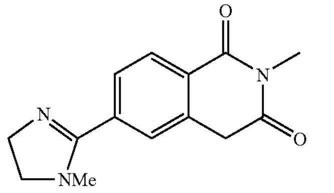
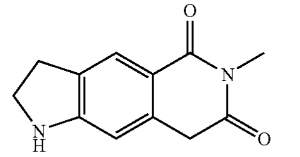
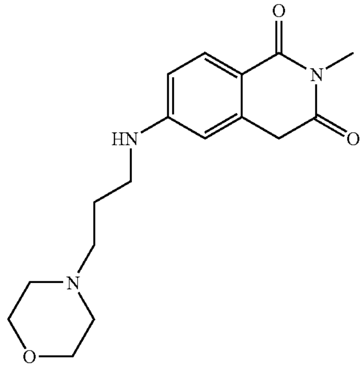
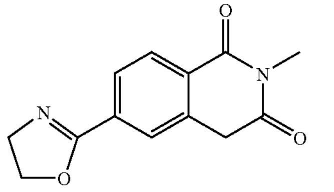
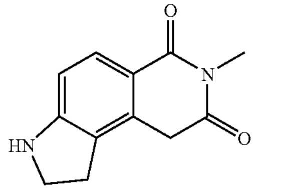
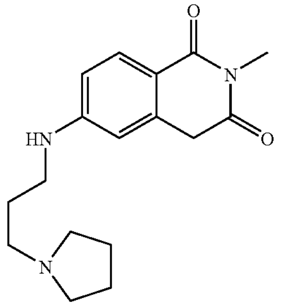
-continued
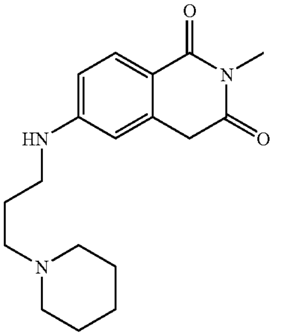
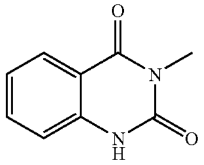
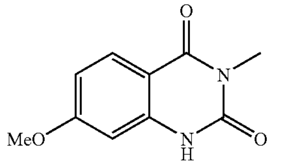
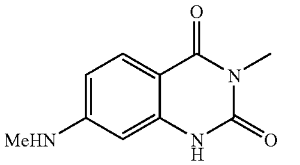
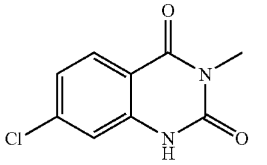
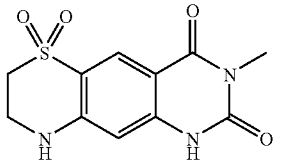
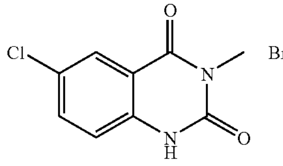
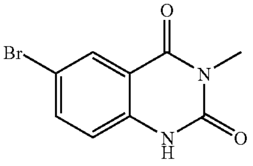
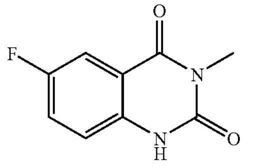
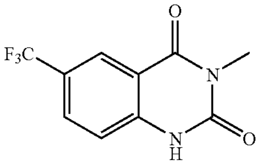
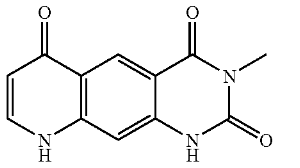
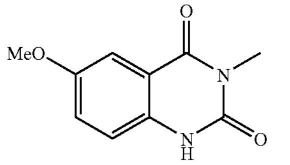

-continued
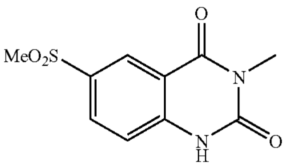
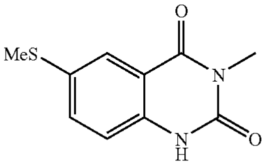
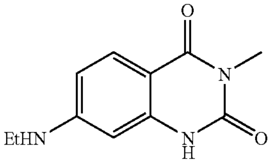
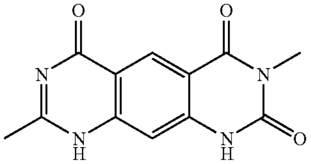
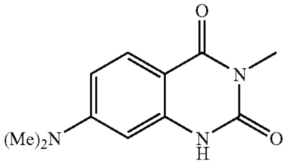
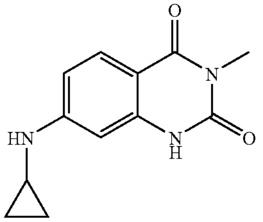
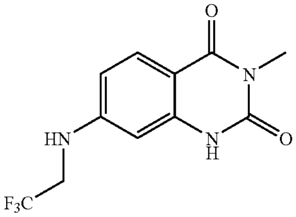
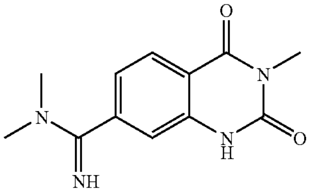
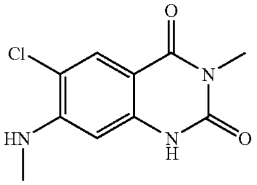
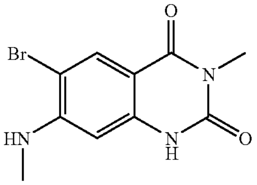
-continued
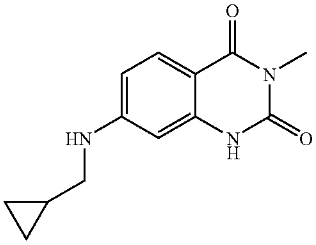
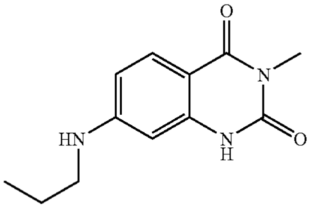
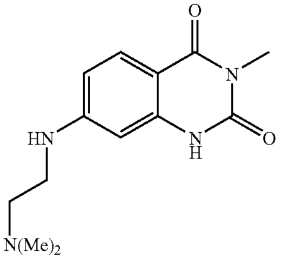
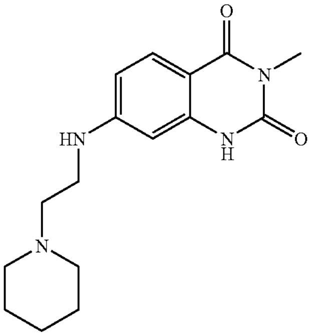
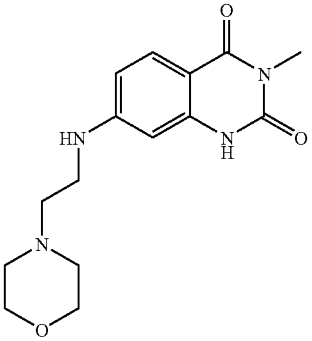
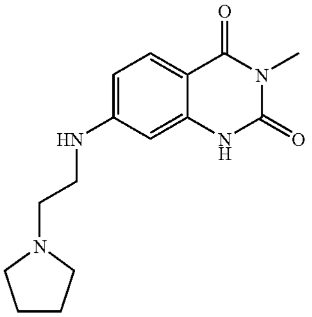

-continued
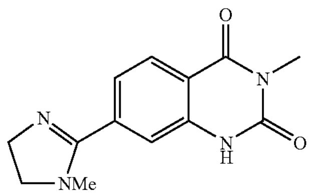
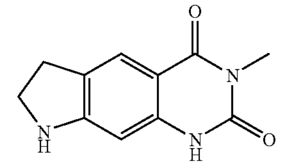
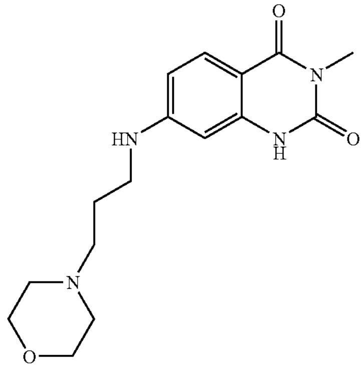
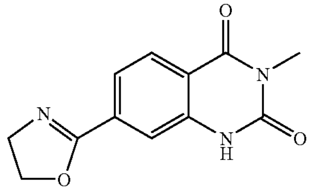
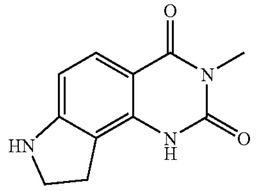
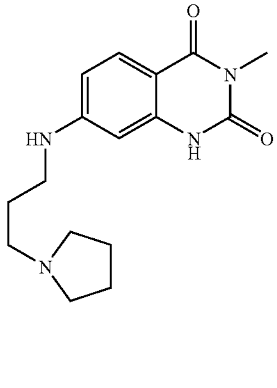
-continued
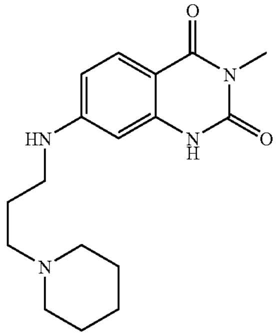
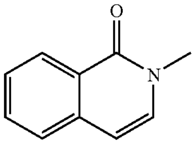
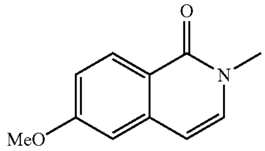
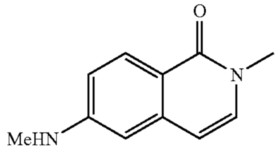
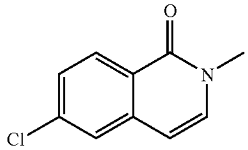
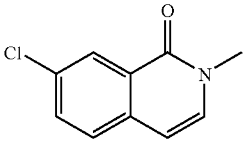
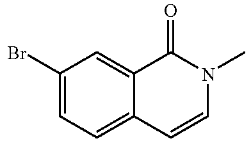
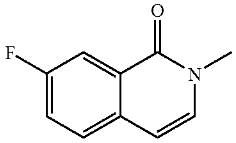
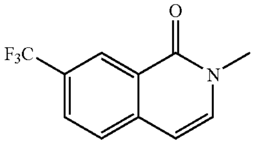
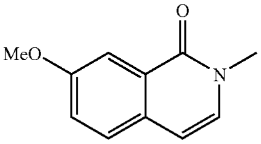
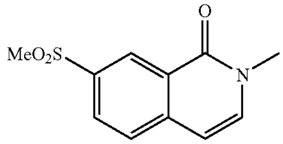
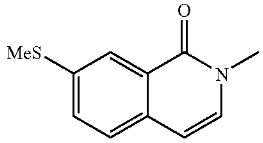
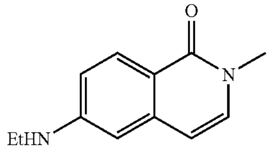
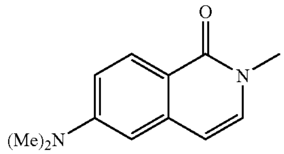

-continued
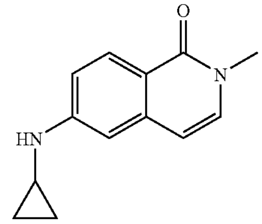
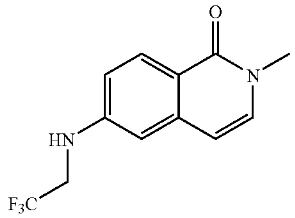
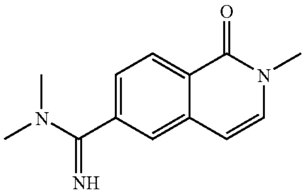
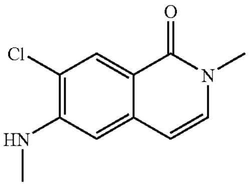
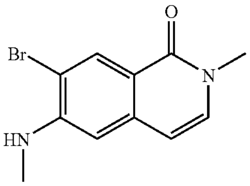
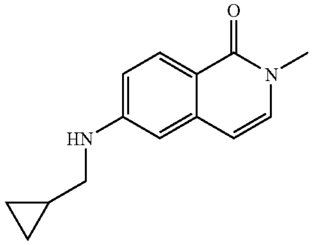
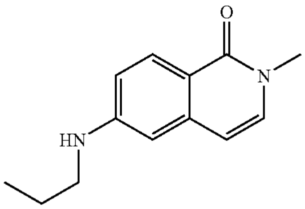
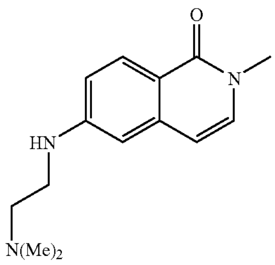
-continued
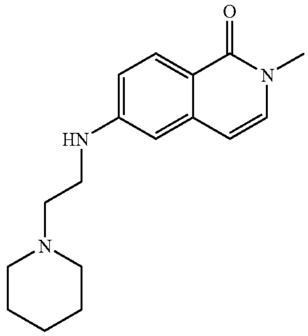
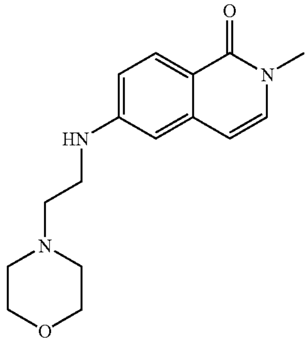
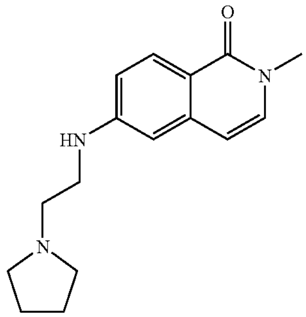
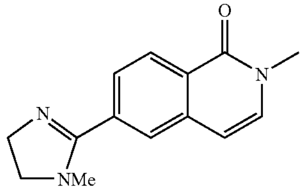
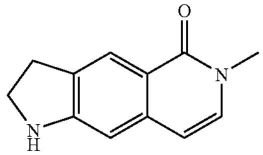
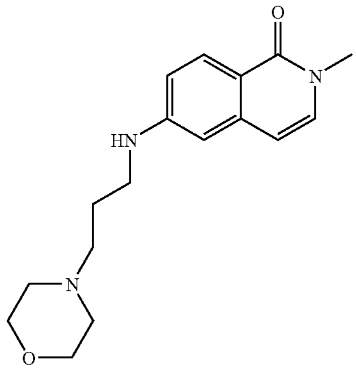

-continued
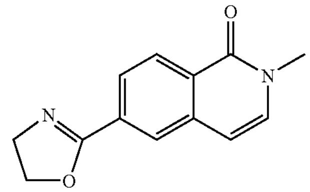
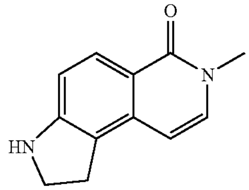
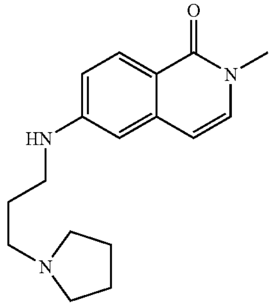
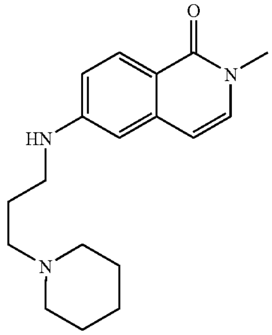
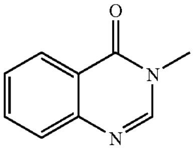
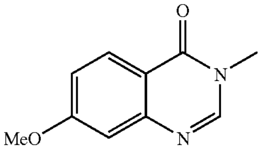
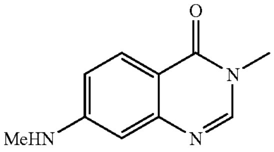
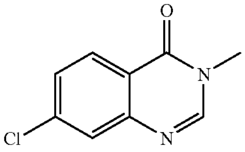
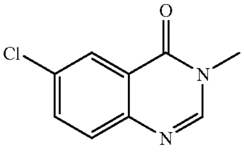
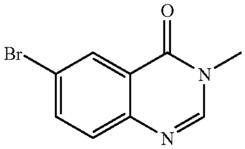
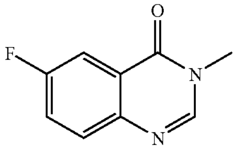
-continued
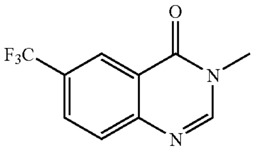
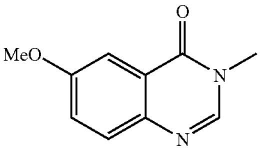
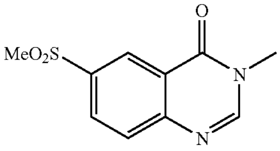
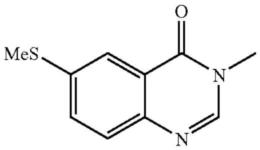
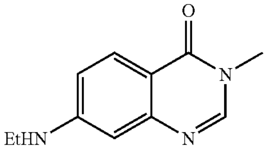
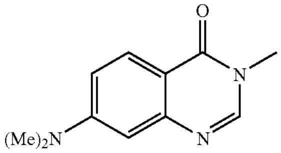
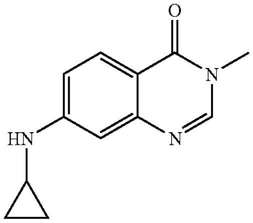
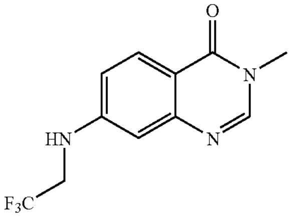
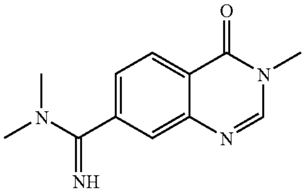
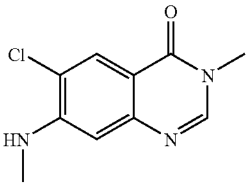
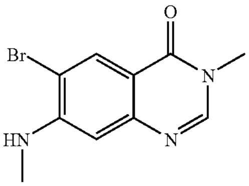

-continued
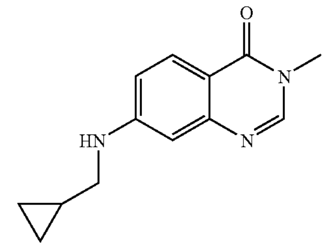
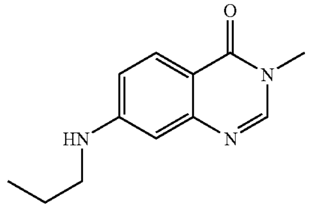
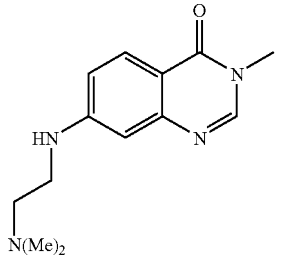
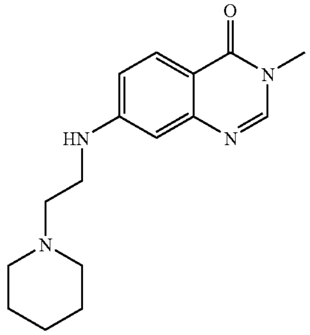
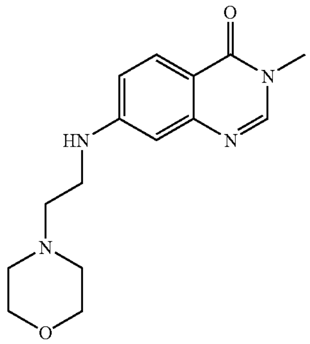
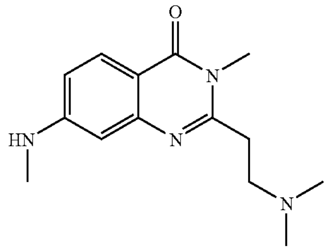
-continued
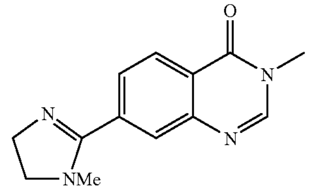
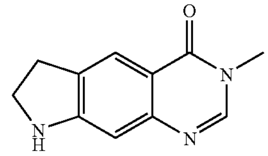
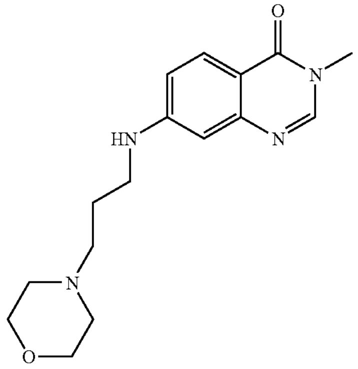
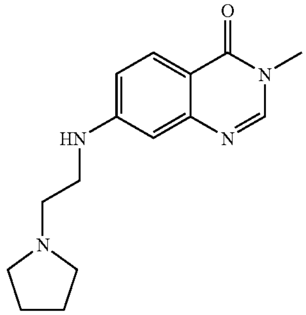
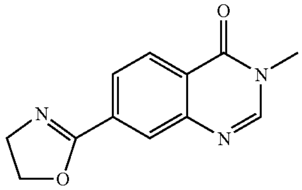
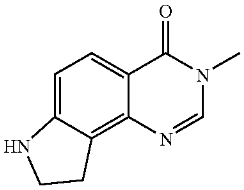
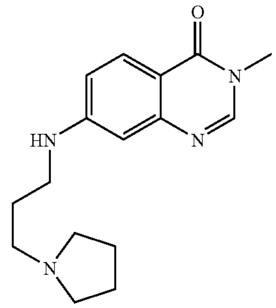

-continued
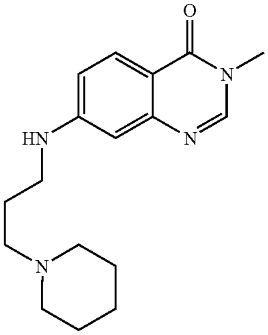
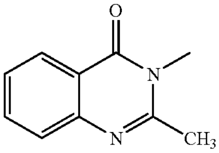
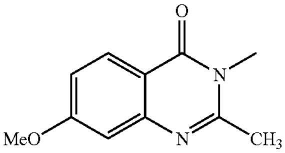
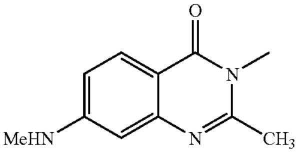
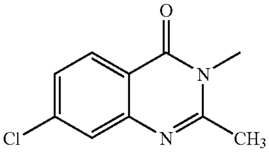
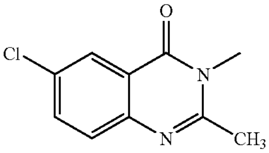
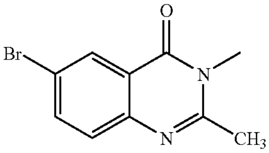
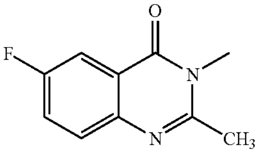
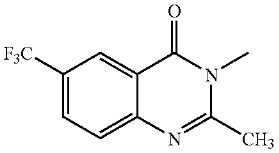
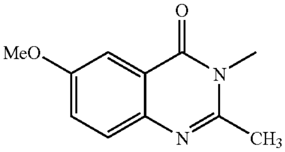
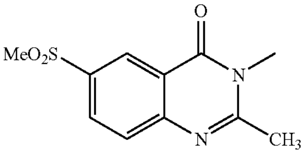
-continued
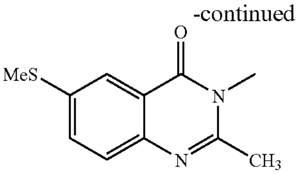
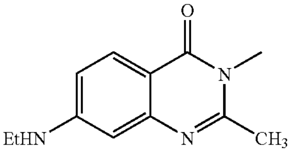
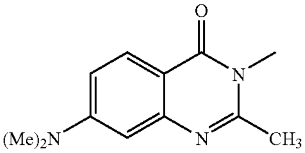
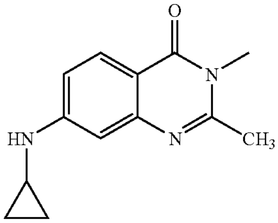
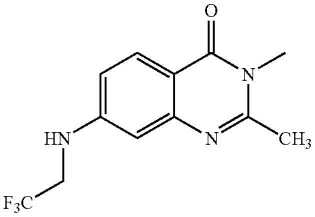
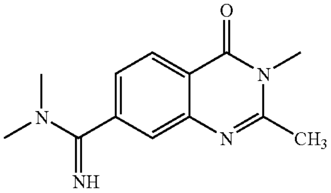
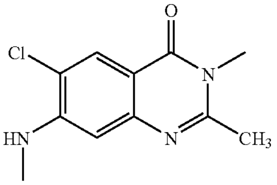
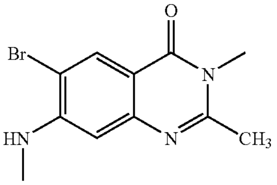
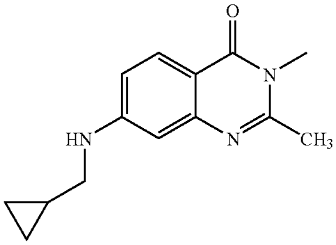

-continued
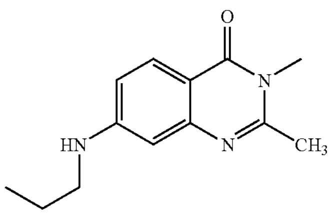
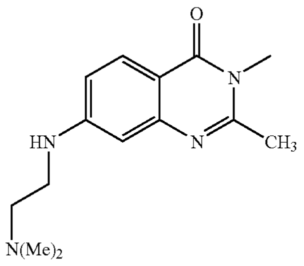
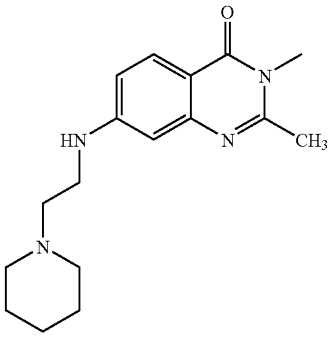
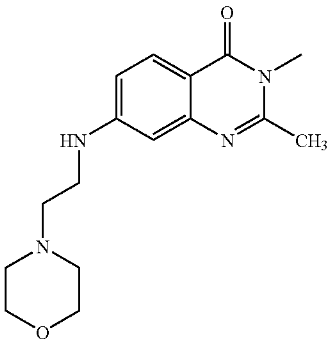
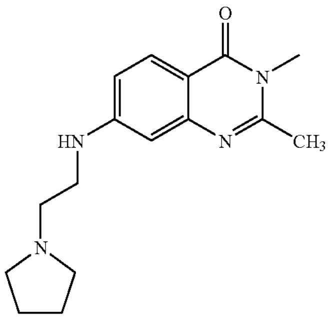
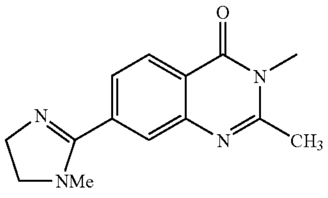
-continued
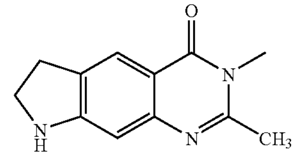
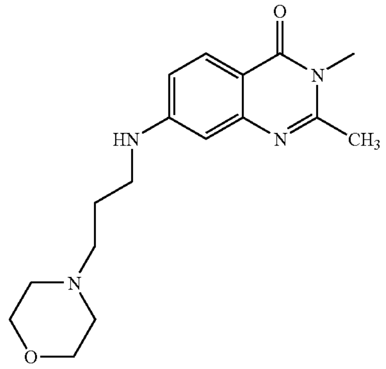
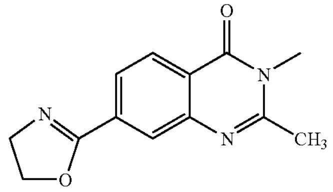
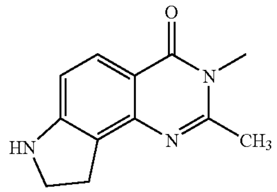
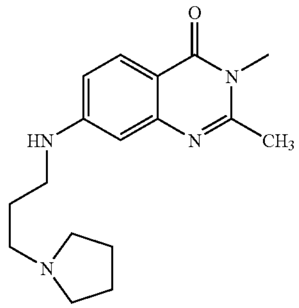
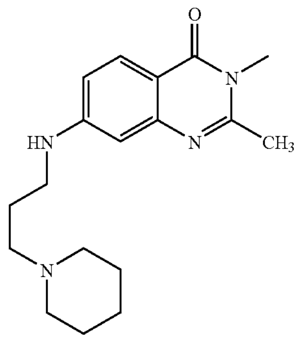

-continued
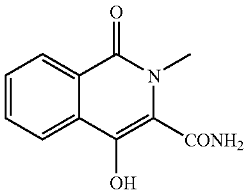
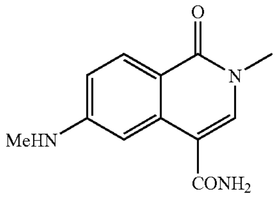
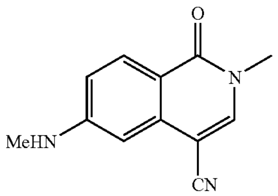
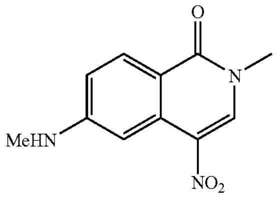
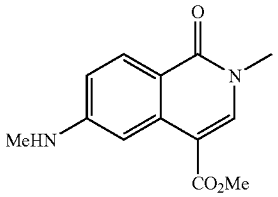
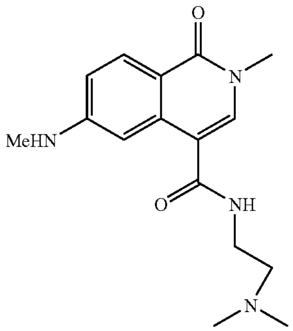
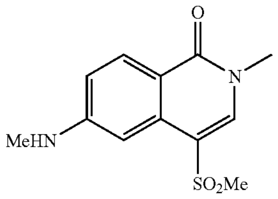
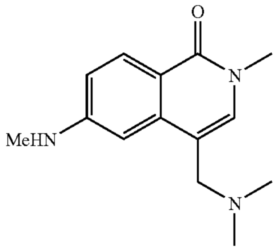
-continued
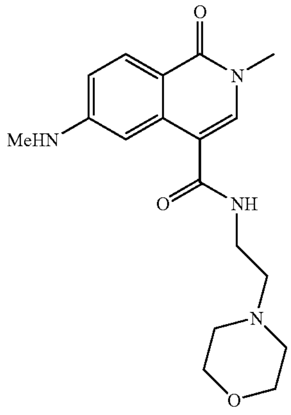
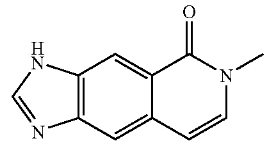
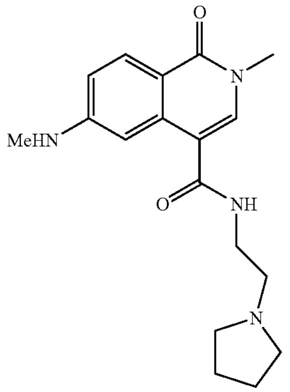
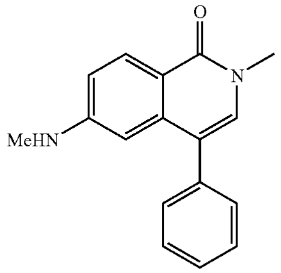
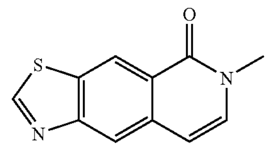
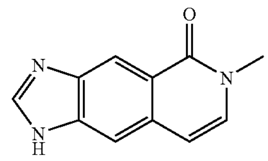

-continued
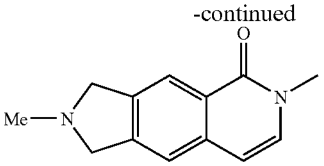
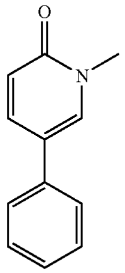
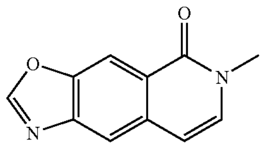
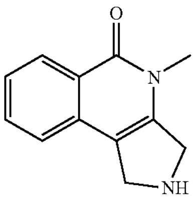
-continued
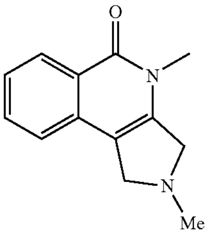
In another preferred embodiment of the invention, compounds of formulae (I)-(VI) include the compounds set forth below in Tables 1-4:
TABLE 1
Formula Ia
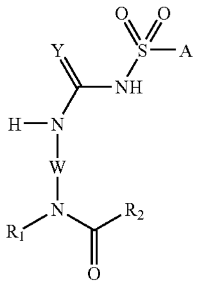
| $R_2$ | $R_1$ | W | Y | A |
|---|---|---|---|---|
| 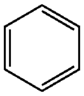 | H | 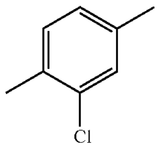 | O | 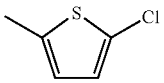 |
| 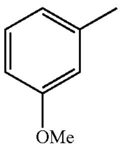 | H | 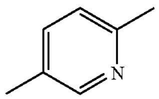 | O | 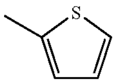 |
| 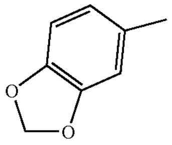 | H | 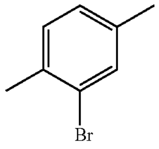 | S | 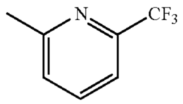 |
| 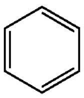 | H | 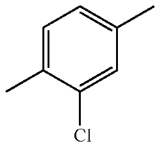 | N—C≡N | 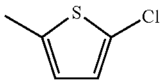 |

TABLE 1-continued
Formula Ia
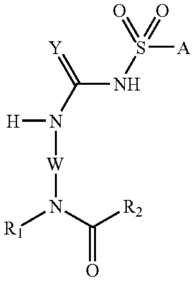
| $R_2$ | $R_1$ | W | Y | A |
| --- | --- | --- | --- | --- |
| 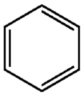 | H | 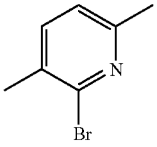 | O | 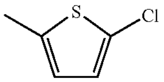 |
| 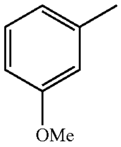 | H | 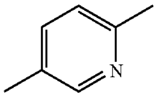 | NH | 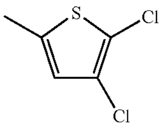 |
| 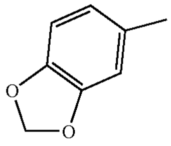 | Me | 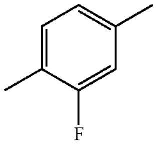 | NH | 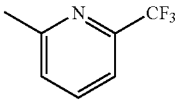 |
| 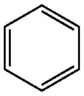 | 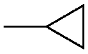 | 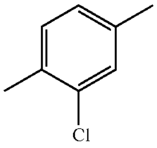 | $N{-}C{\equiv}N$ | 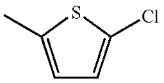 |
| 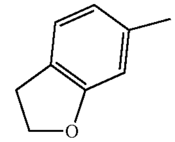 | Me | 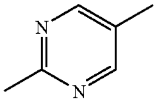 | O | 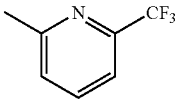 |
| 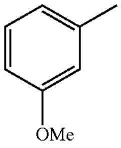 | H | 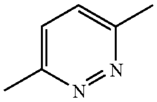 | O | 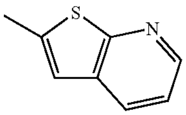 |
| 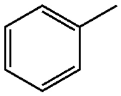 | H | 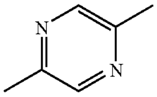 | 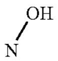 | 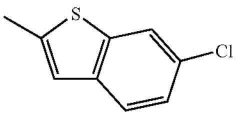 |

TABLE 2
Formula Ib
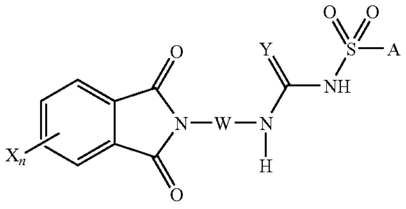
| X | W | Y | A |
|---|---|---|---|
| 3-Br | 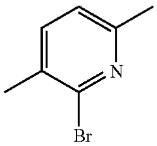 | O | 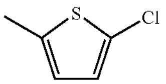 |
| 3-Cl | 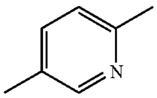 | NH | 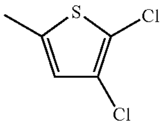 |
| 4-OMe | 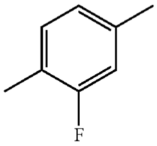 | O | 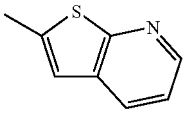 |
| H | 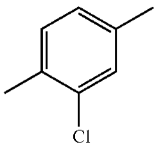 | N—C≡N | 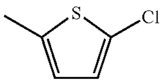 |
| 3,4-diMe | 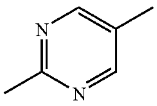 | NH | 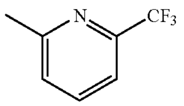 |
| 3-$SO_2$Me | 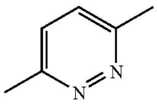 | O | 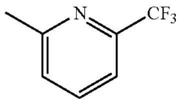 |
| 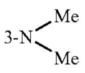 | 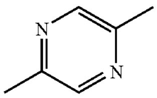 | 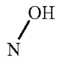 | 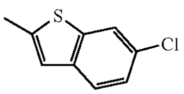 |
TABLE 3
A.
Formula Ic
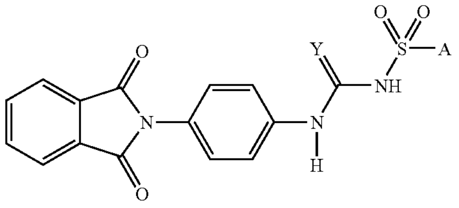
| Y | A |
|---|---|
| O | 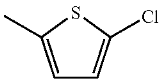 |
| NH | 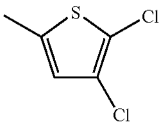 |
| O | 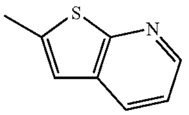 |
| N—C≡N | 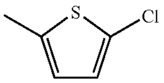 |
| NH | 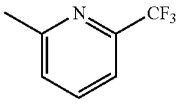 |
| O | 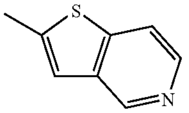 |
| 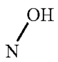 | 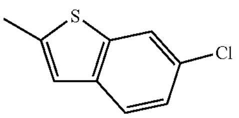 |

TABLE 4
B.
Formula Id
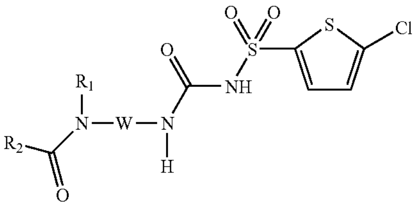
| $R_1$ | $R_2$ | W |
|---|---|---|
| H | 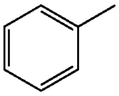 | 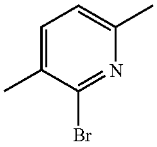 |
| Me | 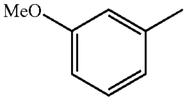 | 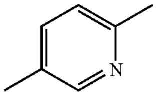 |
| 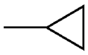 | 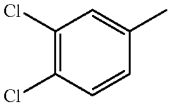 | 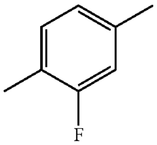 |
| H | 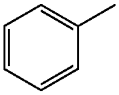 | 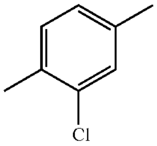 |
| H | 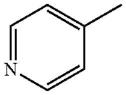 | 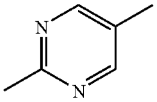 |
| Me | 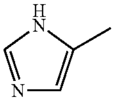 | 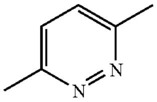 |
| H | 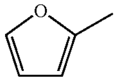 | 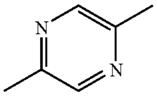 |
Examples of specific preferred compounds are listed below:
Example 1
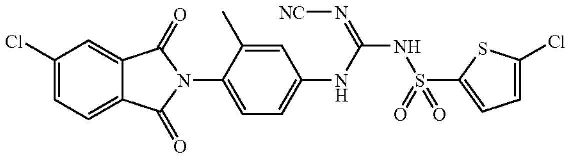
-continued
Example 2
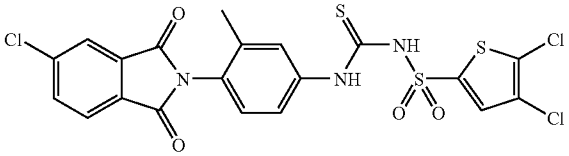
Example 3
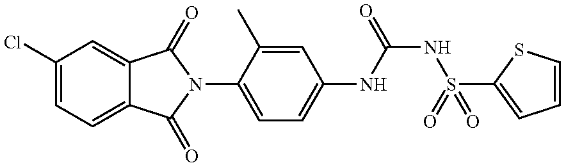
Example 4
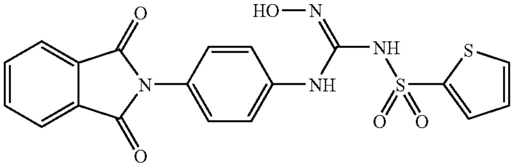
Example 5
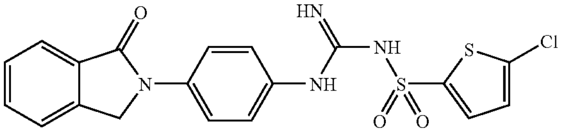
Example 6
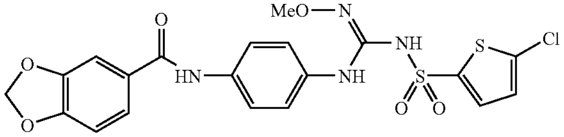
Example 7
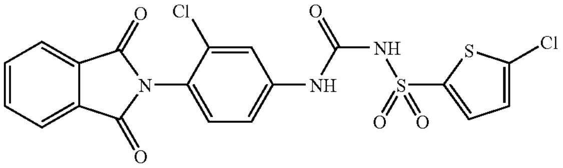
Example 8
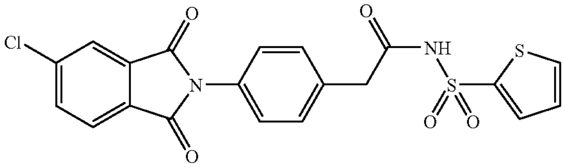
Example 9
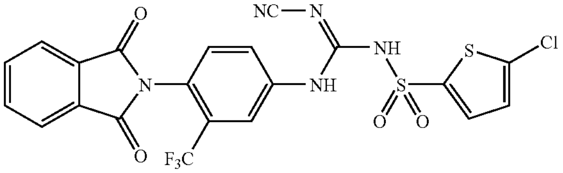

-continued
Example 10
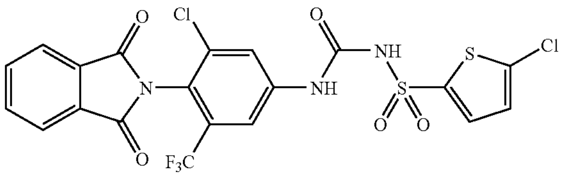
Example 11
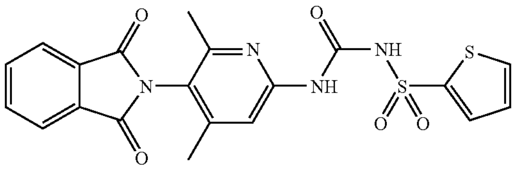
Example 12
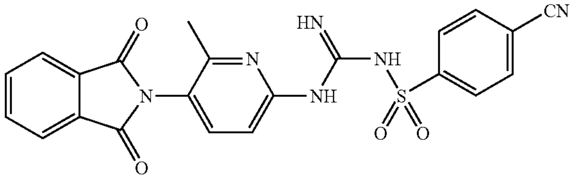
Example 13
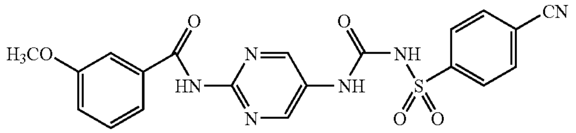
Example 14
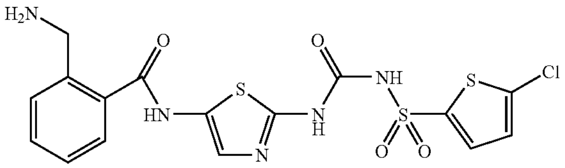
Example 15
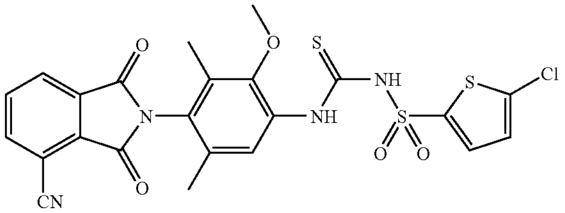
Example 16
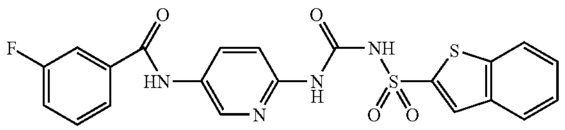
Example 17
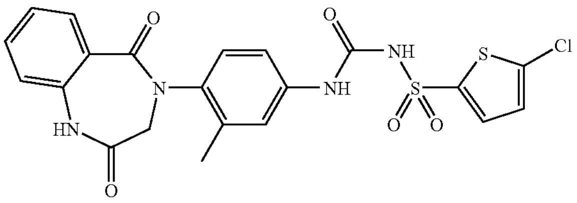
-continued
Example 18
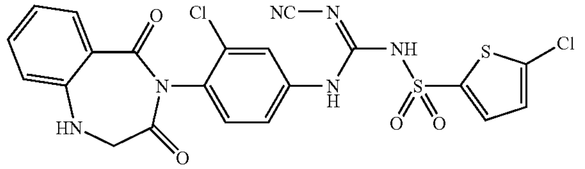
Example 19
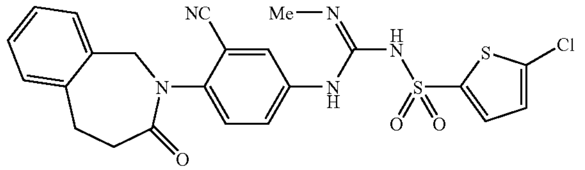
Example 20
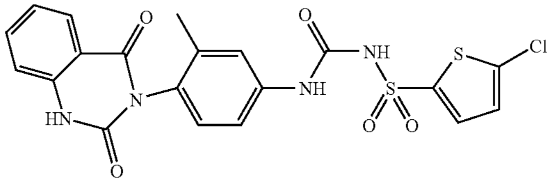
Example 21
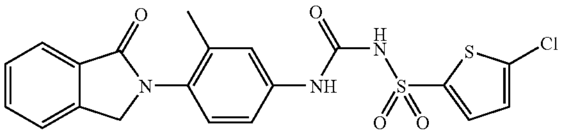
Example 22
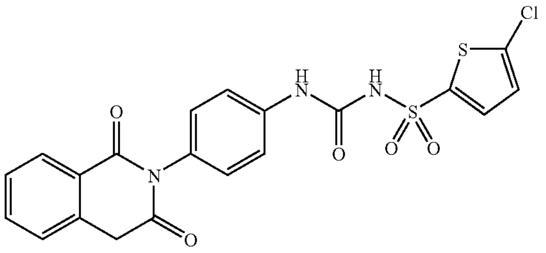
Example 23
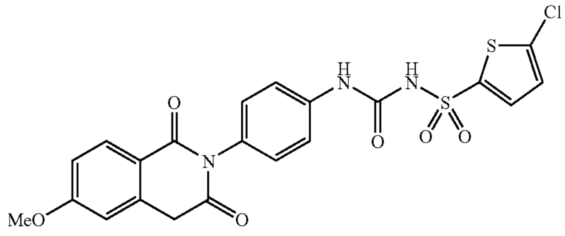
Example 24
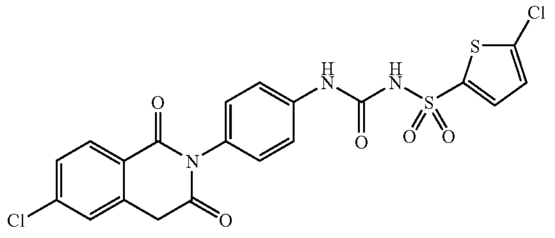

-continued
Example 25
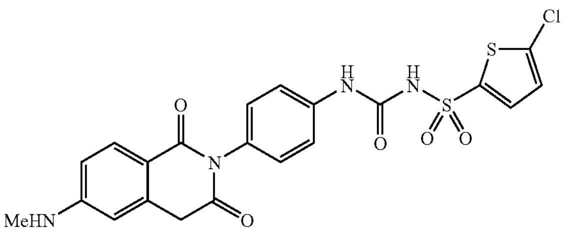
Example 26
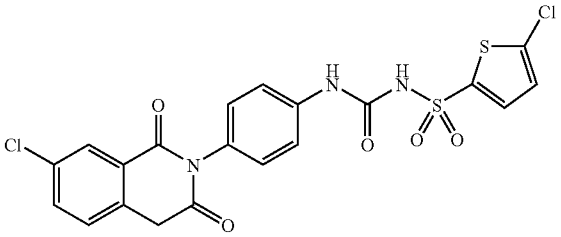
Example 27
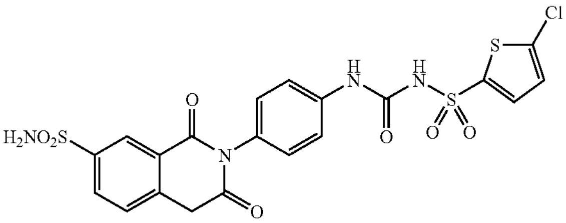
Example 28
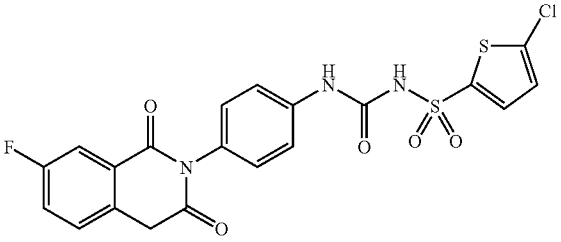
Example 29
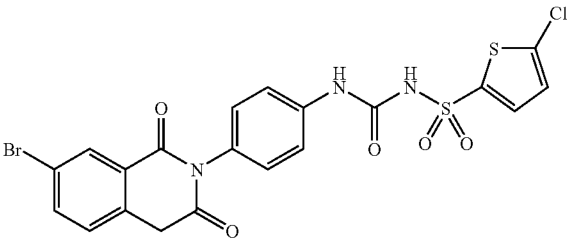
Example 30
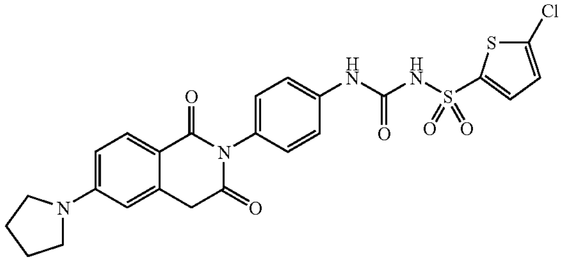
-continued
Example 31
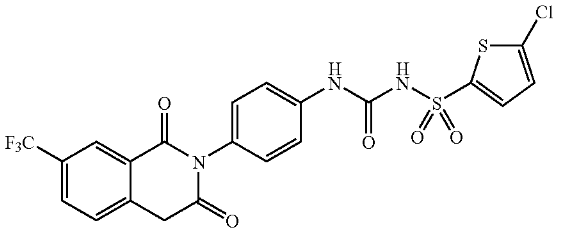
Example 32
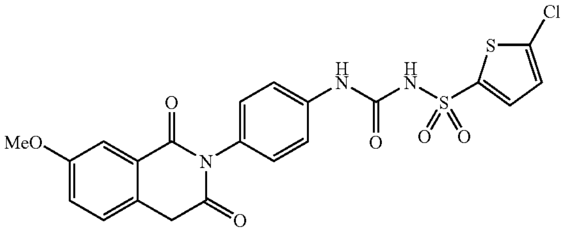
Example 33
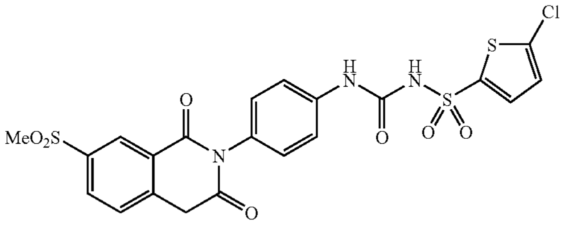
Example 34
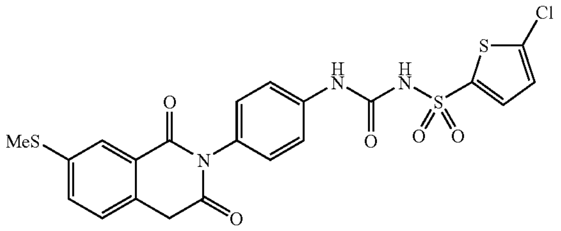
Example 35
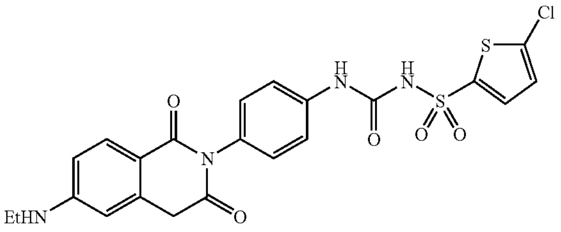
Example 36
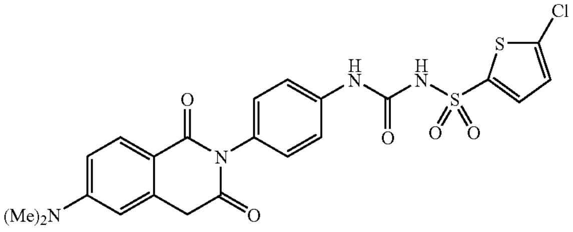

-continued
Example 37
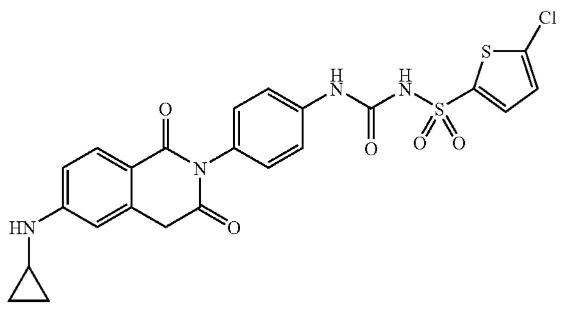
Example 38
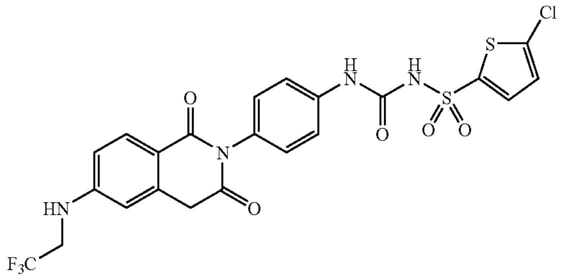
Example 39
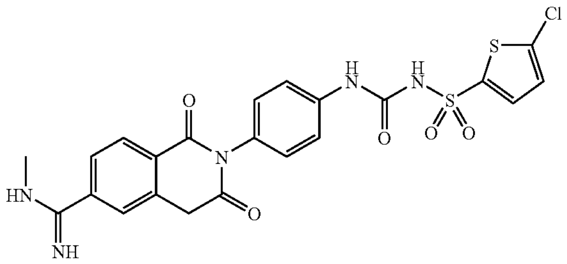
Example 40
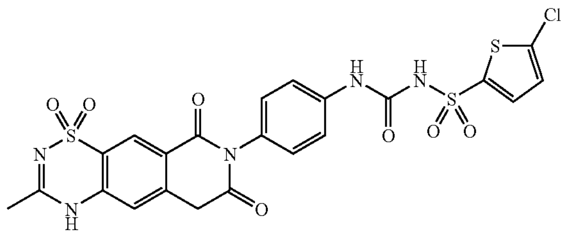
Example 41
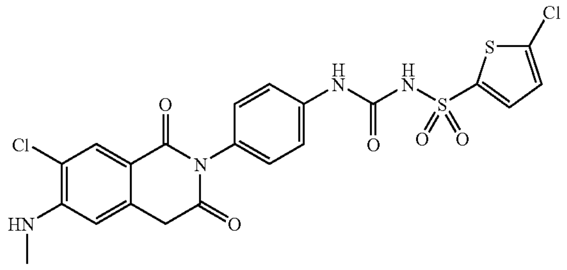
-continued
Example 42
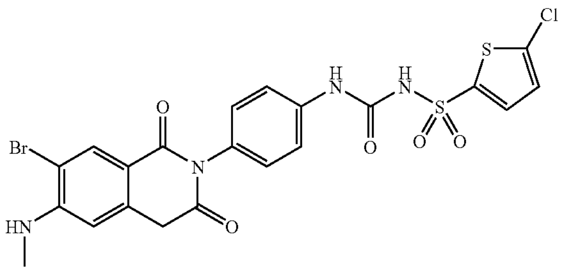
Example 43
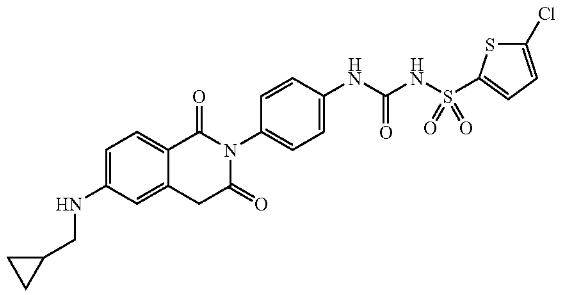
Example 44
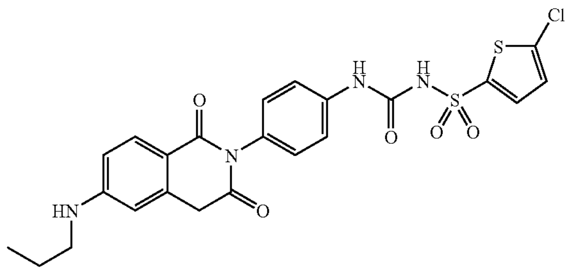
Example 45
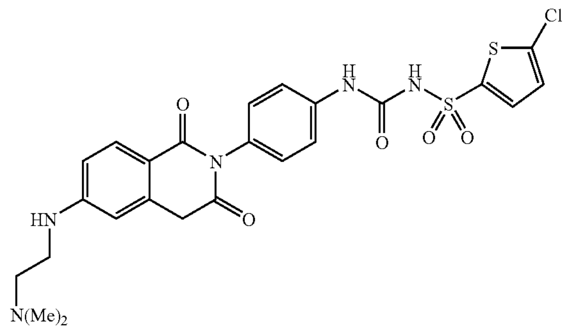
Example 46
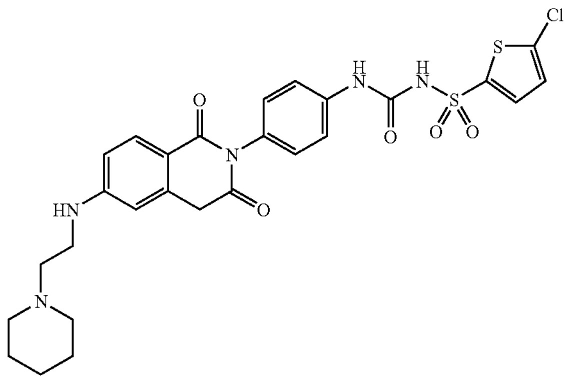

-continued
Example 47
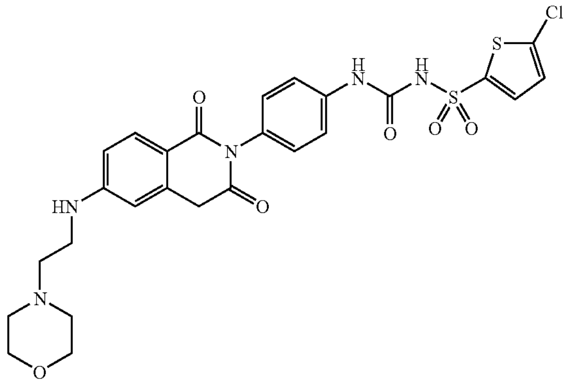
Example 48
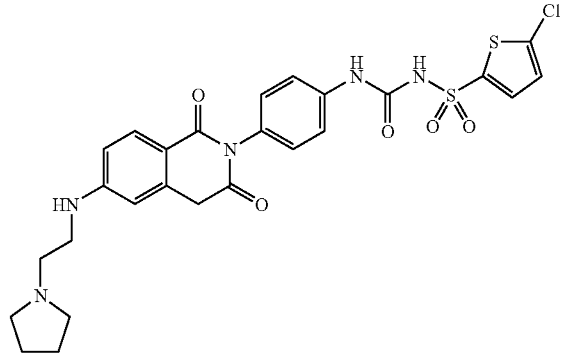
Example 49
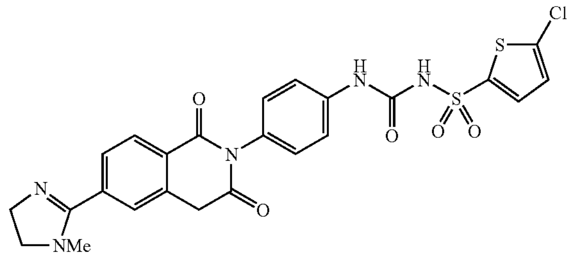
Example 50
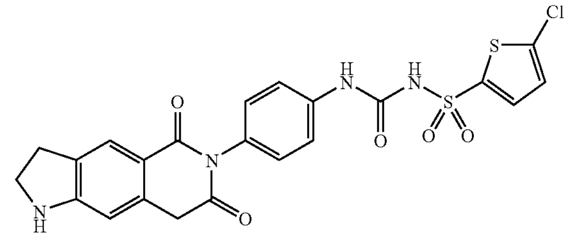
Example 51
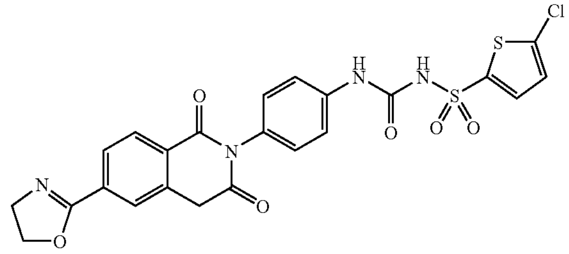
-continued
Example 52
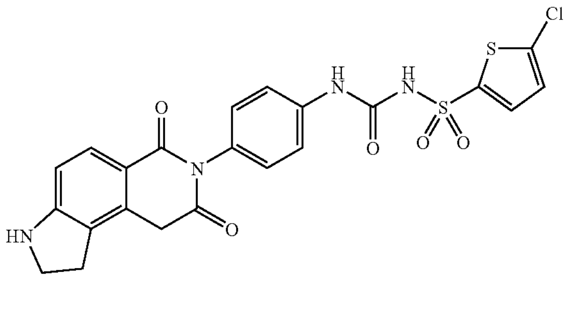
Example 53
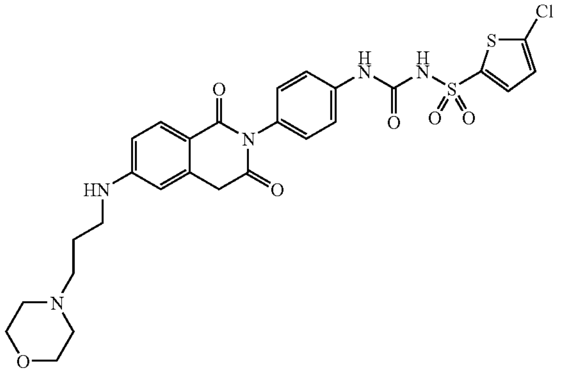
Example 54
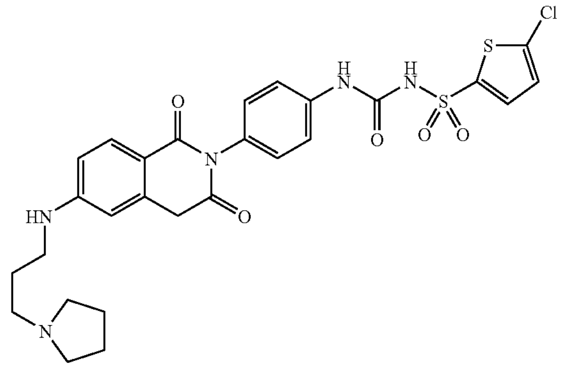
Example 55
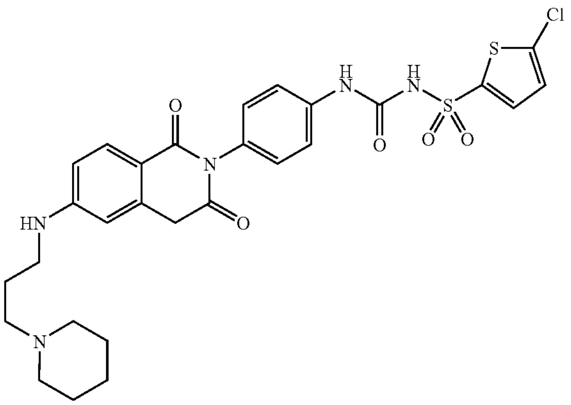

Example 56
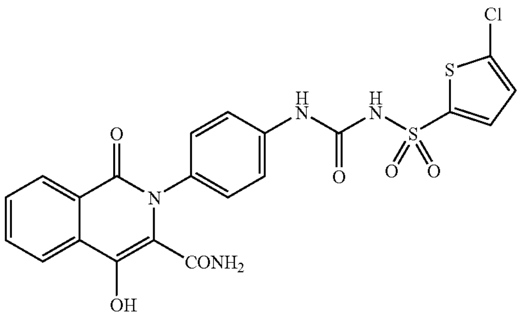
Example 57
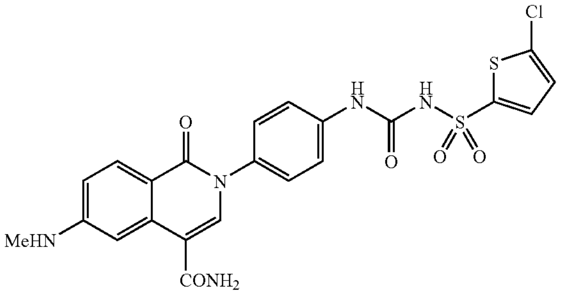
Example 58
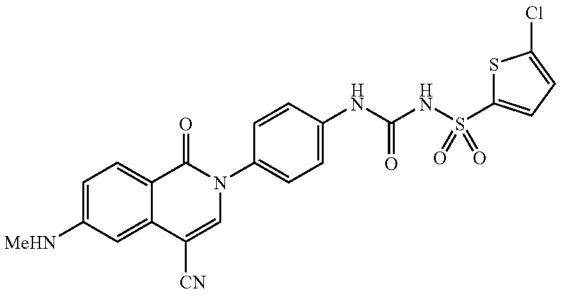
Example 59
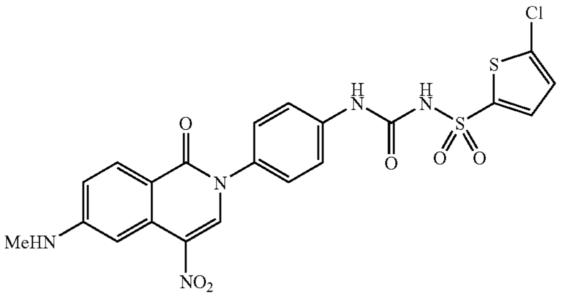
Example 60
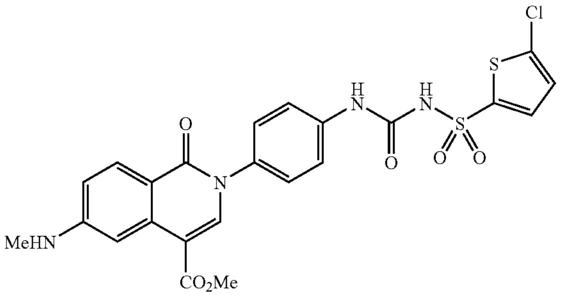
Example 61
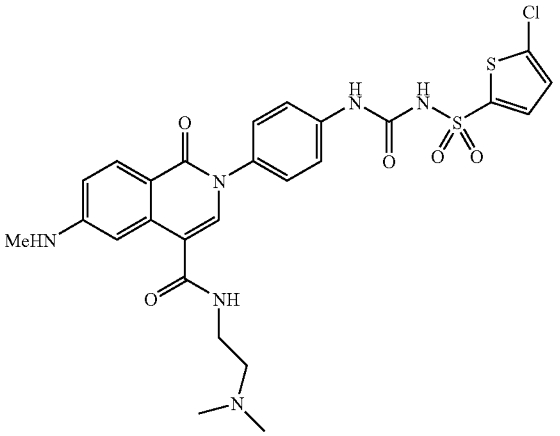
Example 62
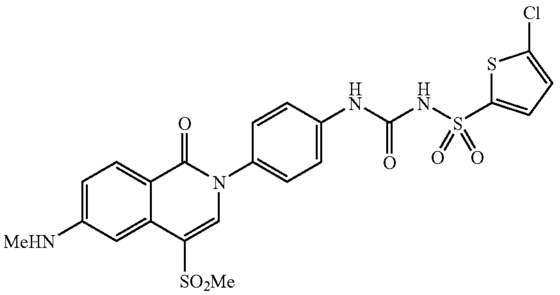
Example 63
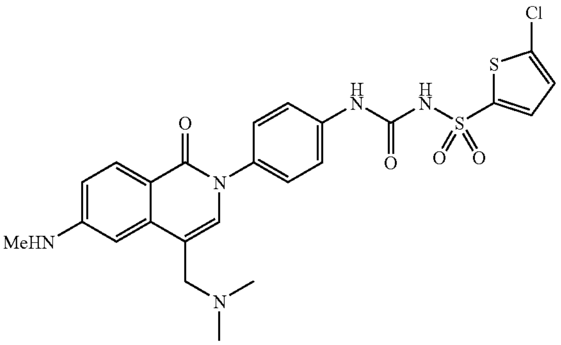
Example 64
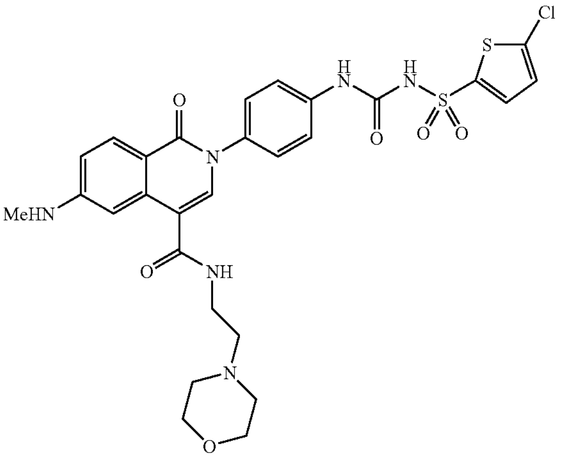

-continued
Example 65
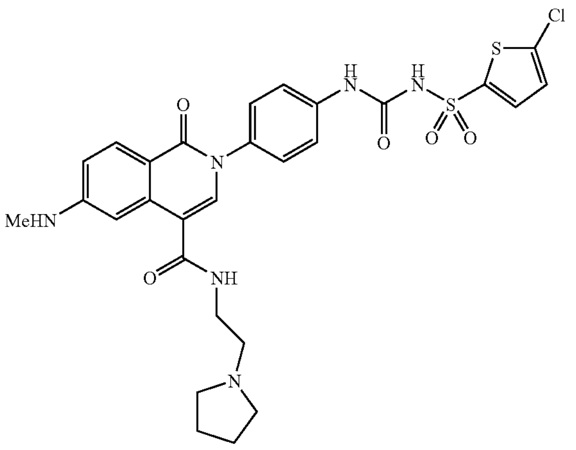
Example 66
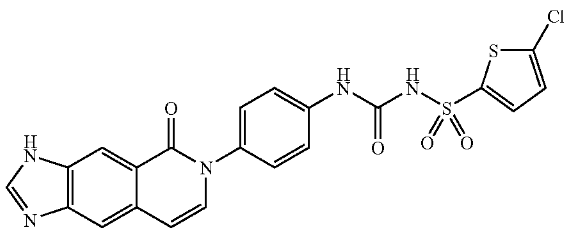
Example 67
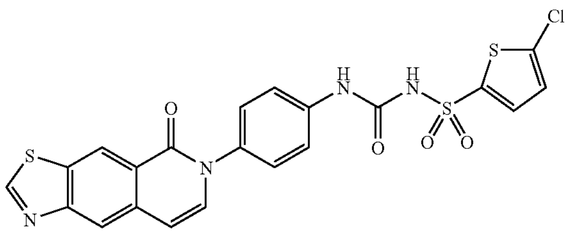
Example 68
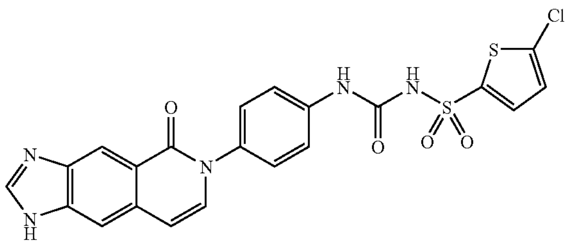
Example 69
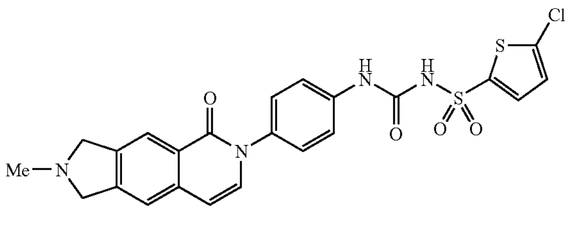
-continued
Example 70
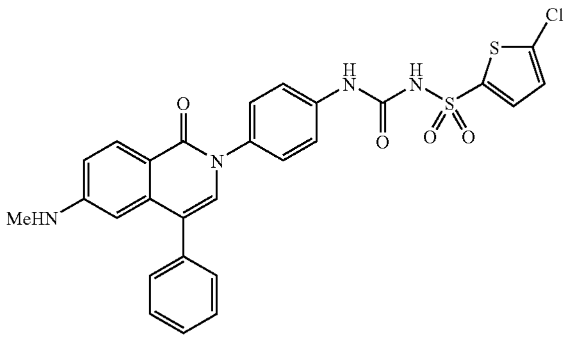
Example 71
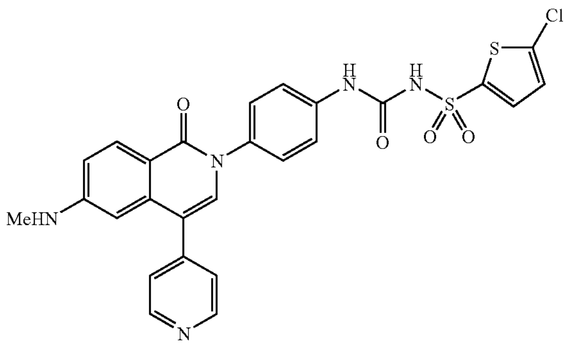
Example 72
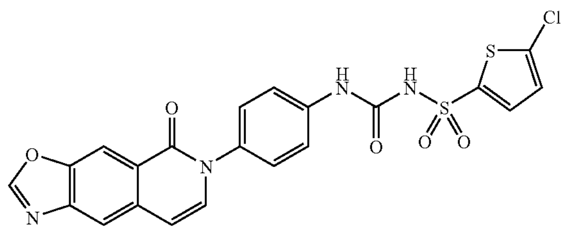
Example 73
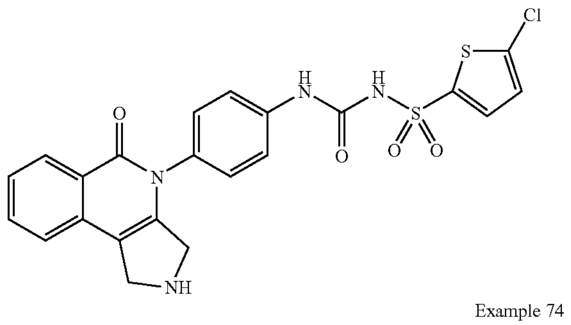
Example 74
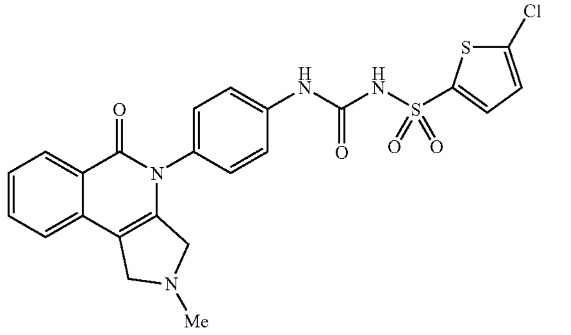

-continued
Example 75
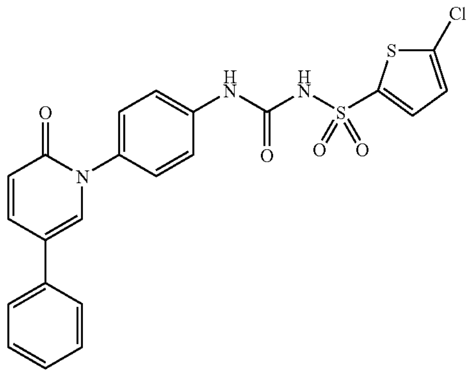
Example 76
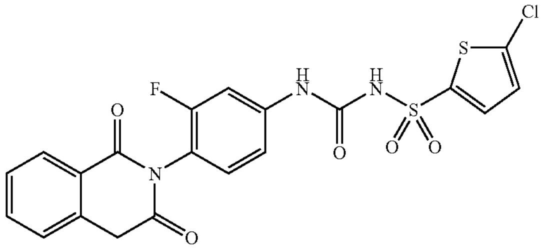
Example 77
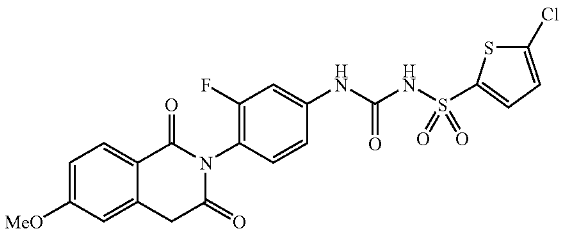
Example 78
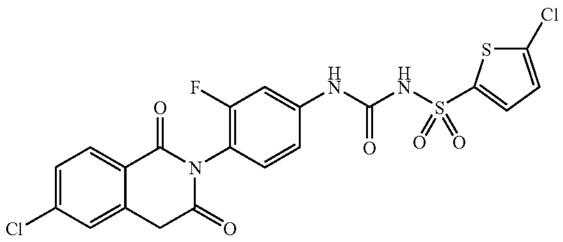
Example 79
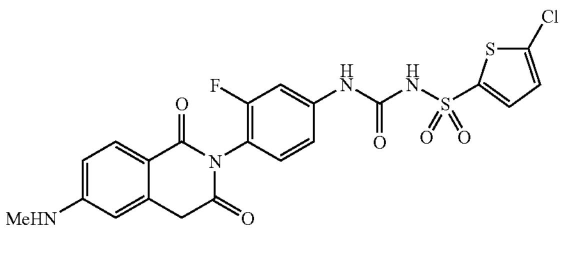
-continued
Example 80
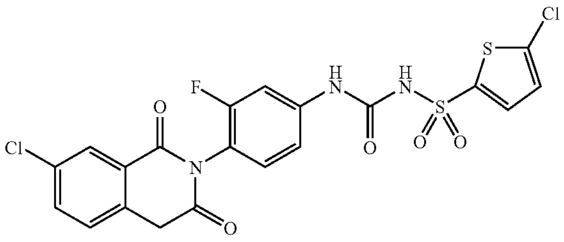
Example 81
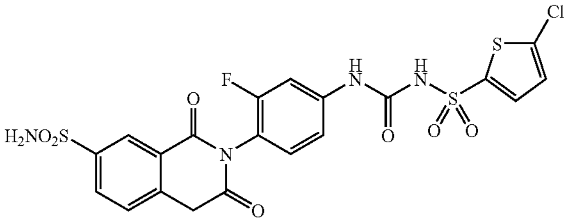
Example 82
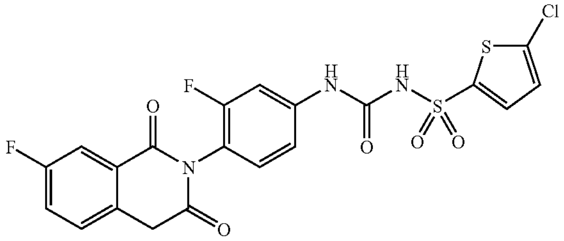
Example 83
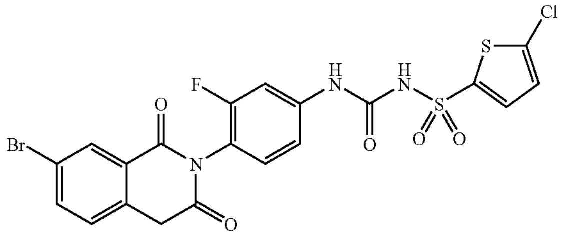
Example 84
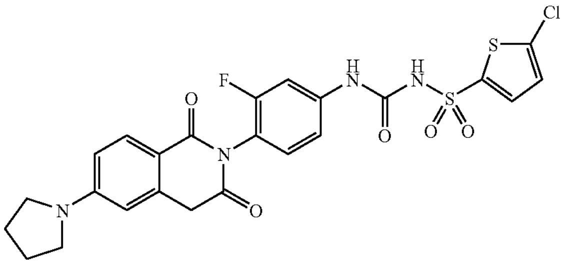
Example 85
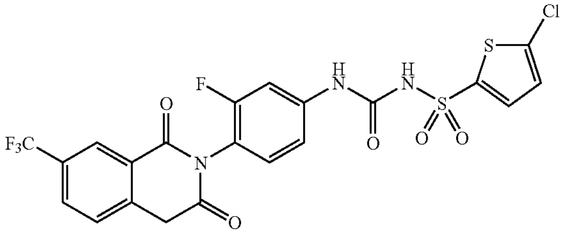

Example 86
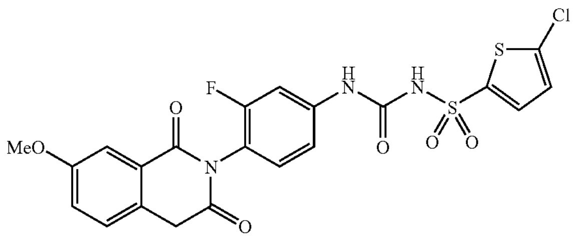
Example 87
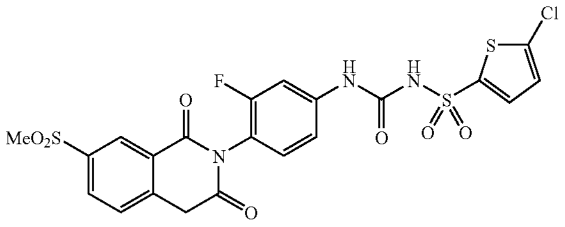
Example 88
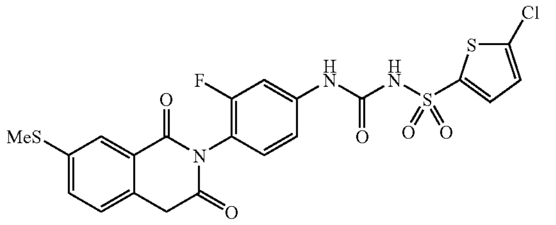
Example 89
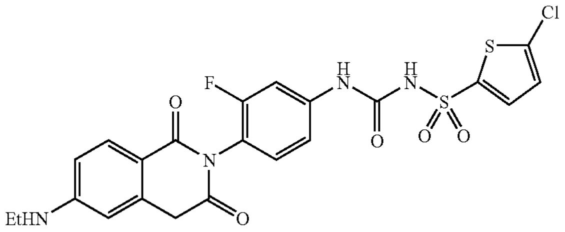
Example 90
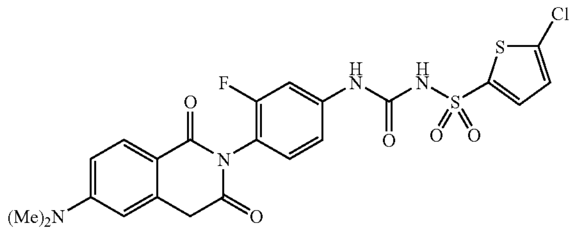
Example 91
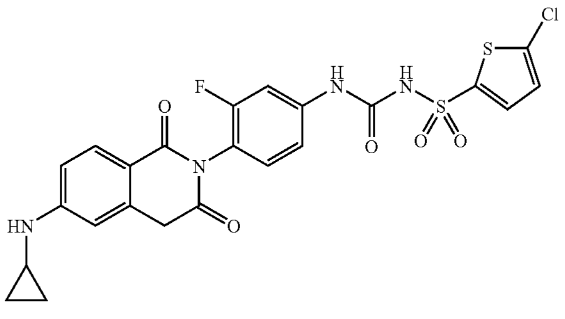
Example 92
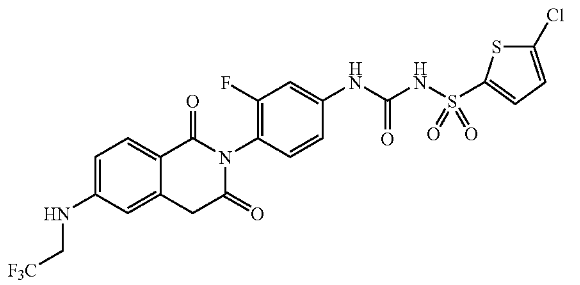
Example 93
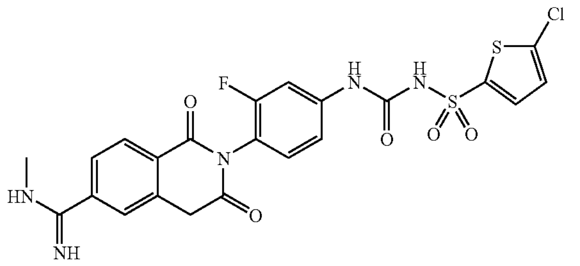
Example 94
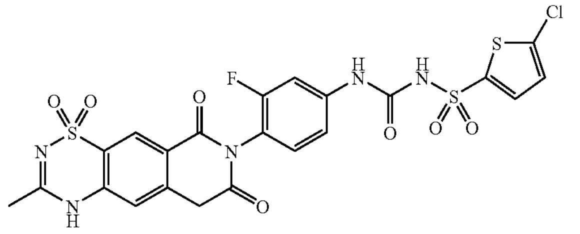
Example 95
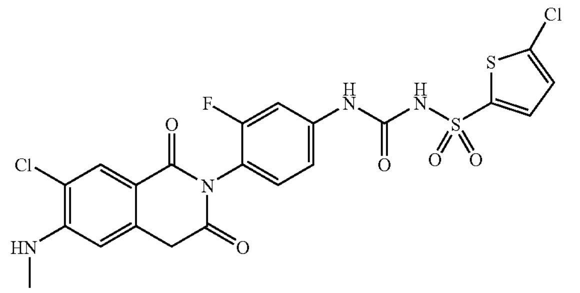
Example 96
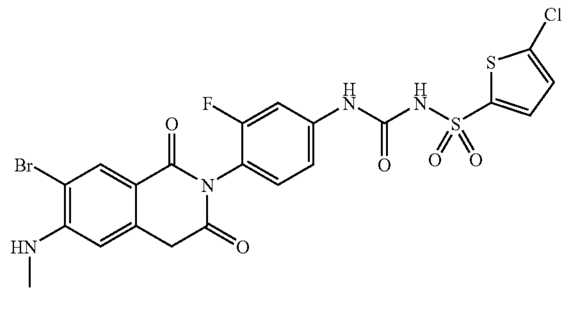

-continued
Example 97
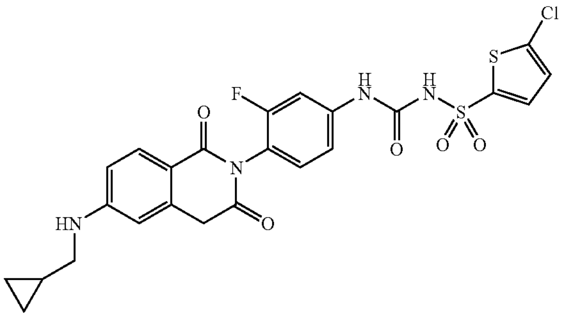
Example 98
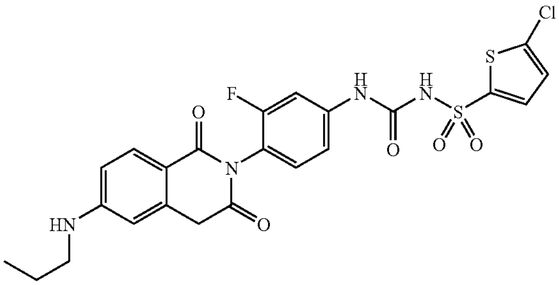
Example 99
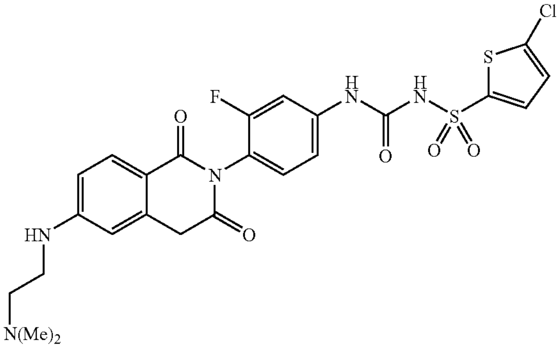
Example 100
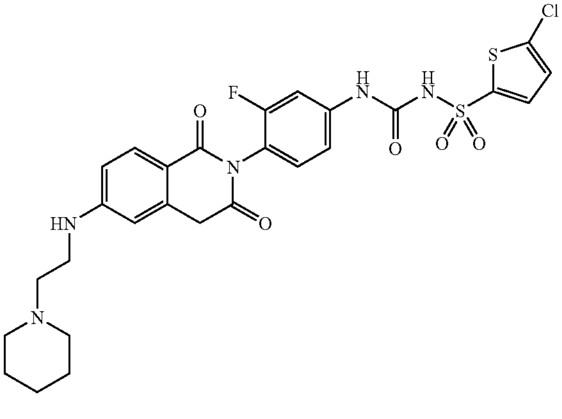
-continued
Example 101
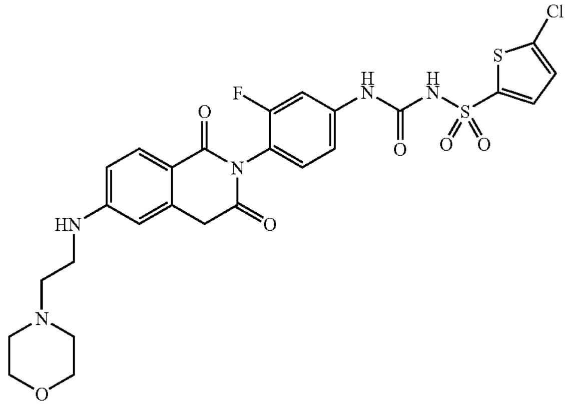
Example 102
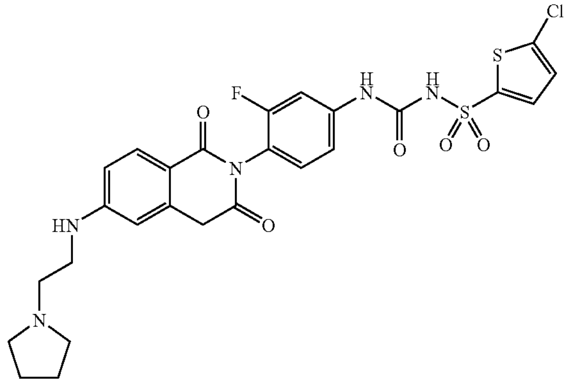
Example 103
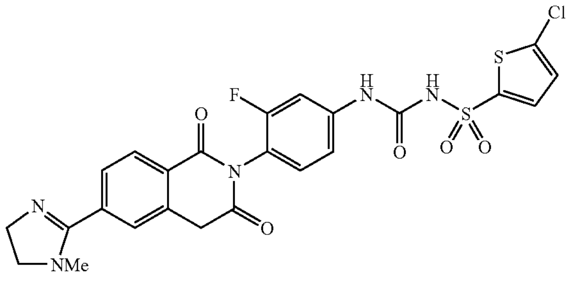
Example 104
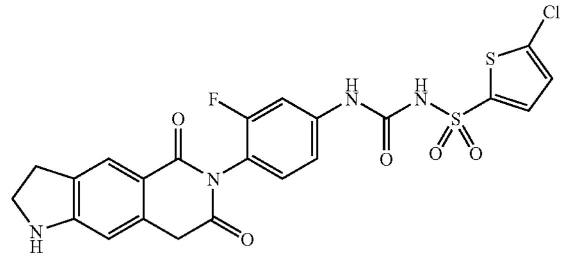

-continued
Example 105
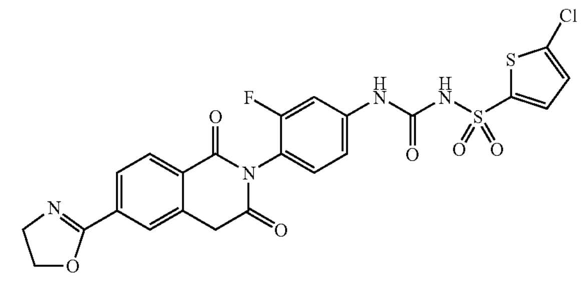
Example 106
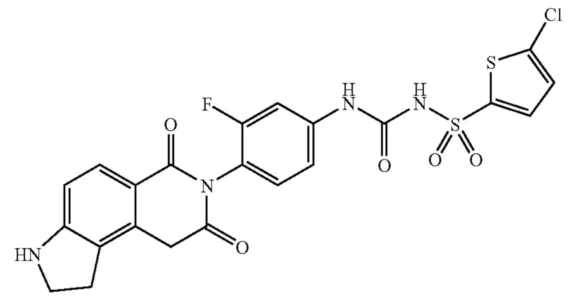
Example 107
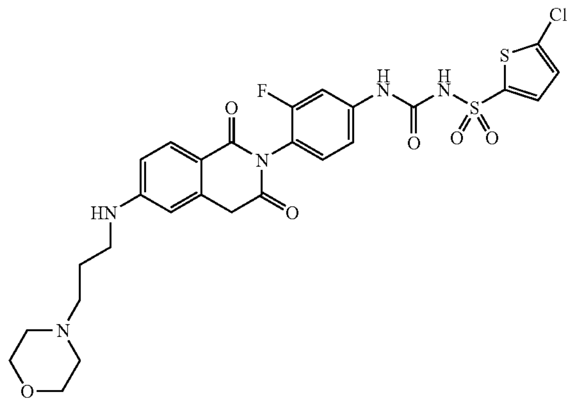
Example 108
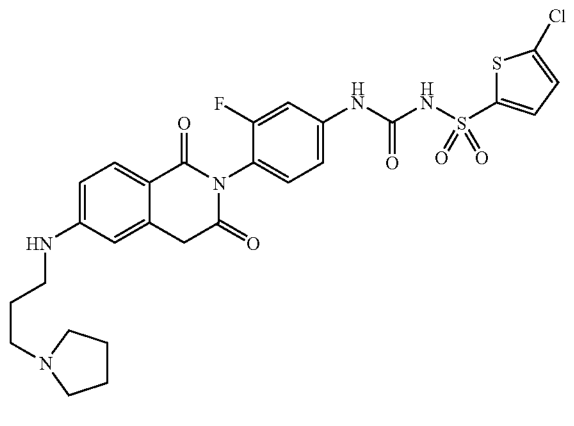
-continued
Example 109
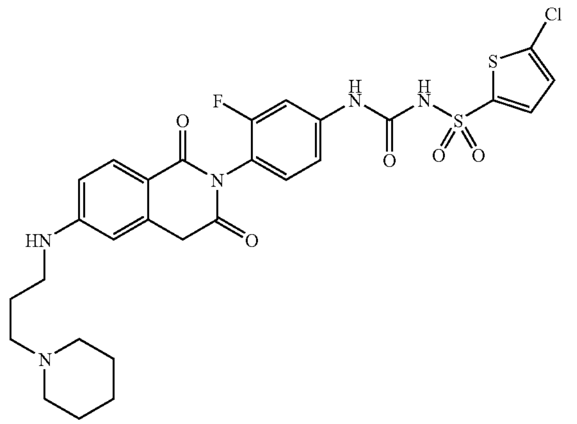
Example 110
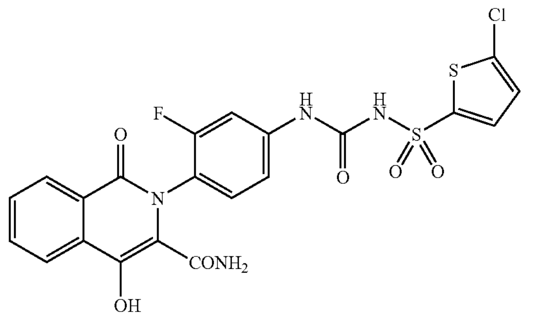
Example 111
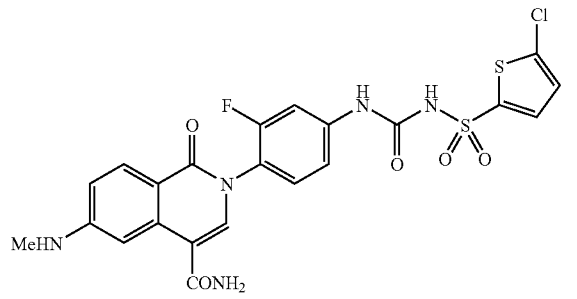
Example 112
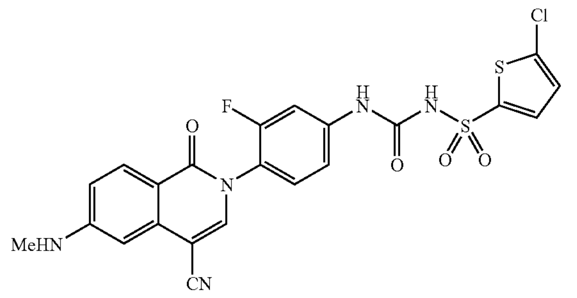

-continued
Example 113
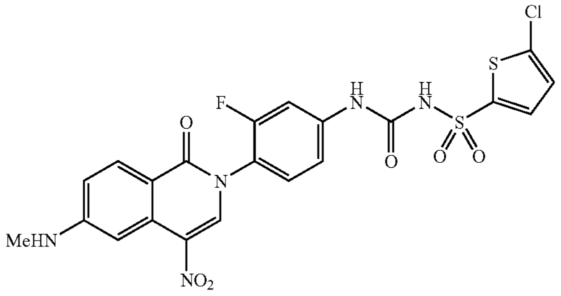
Example 114
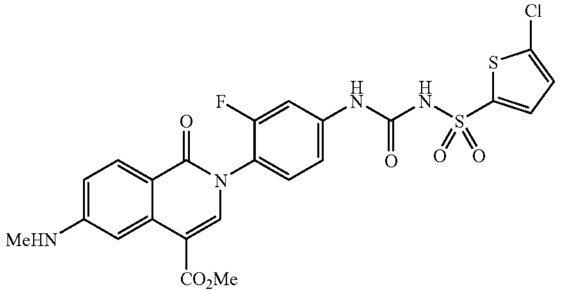
Example 115
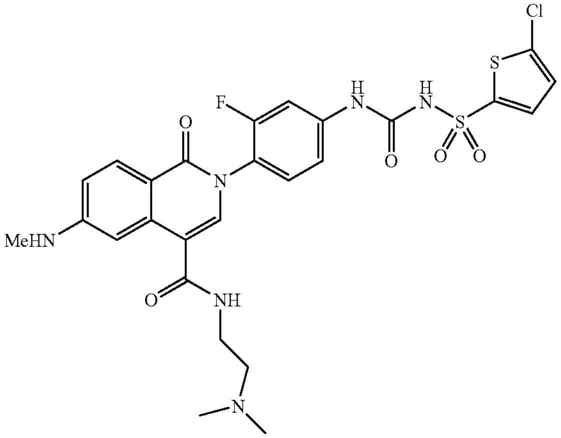
Example 116
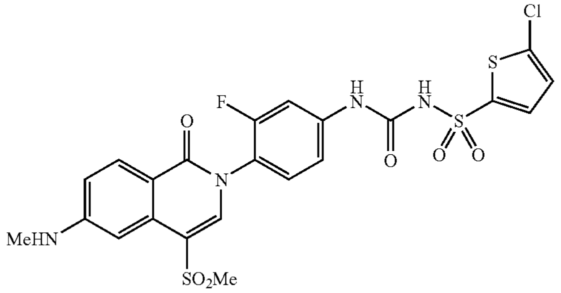
-continued
Example 117
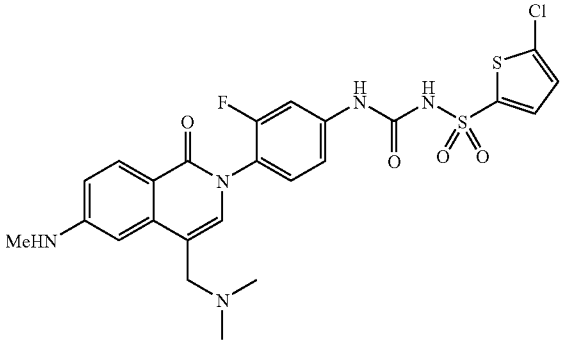
Example 118
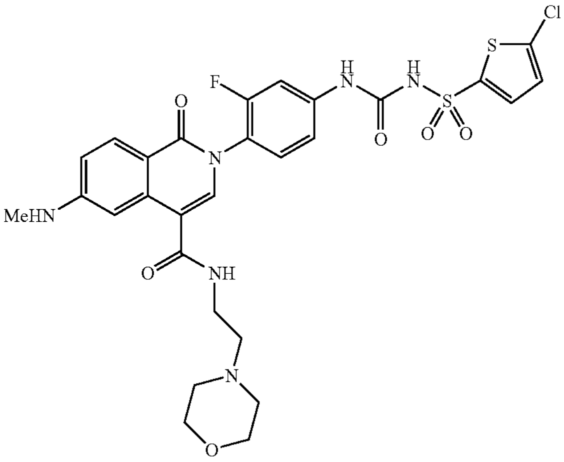
Example 119
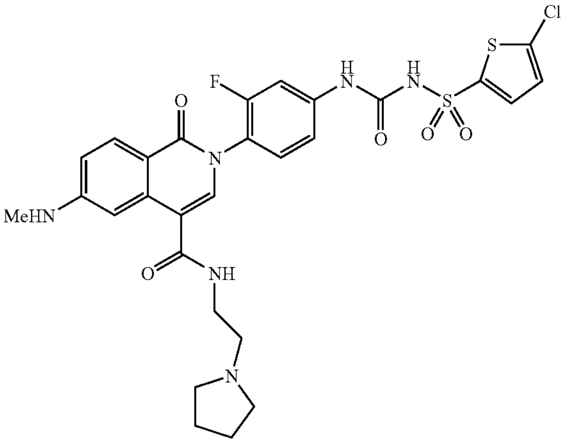
Example 120
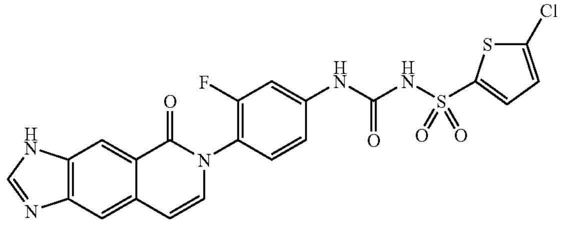

-continued
Example 121
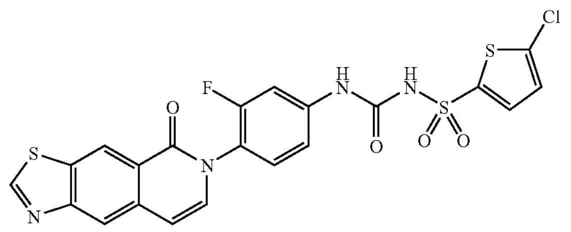
Example 122
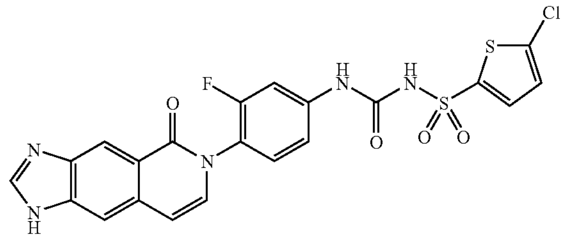
Example 123
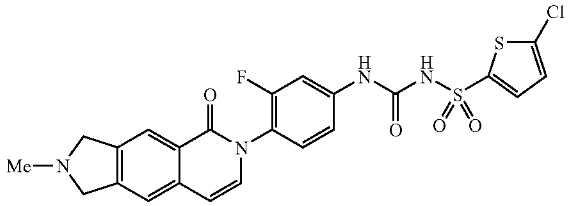
Example 124
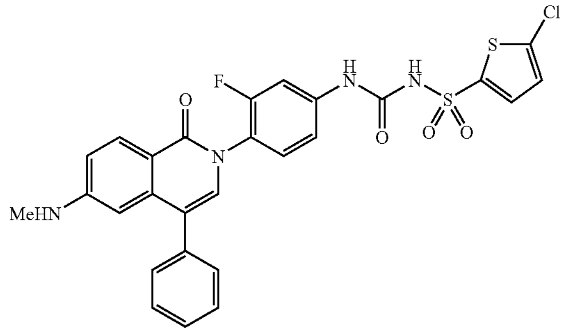
Example 125
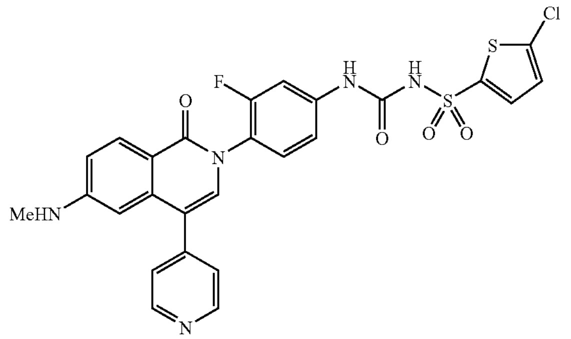
-continued
Example 126
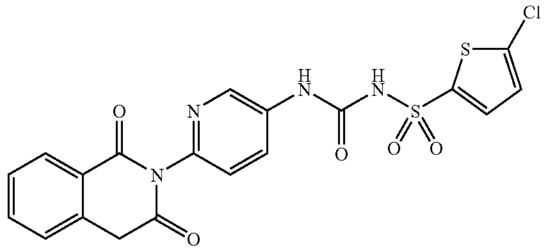
Example 127
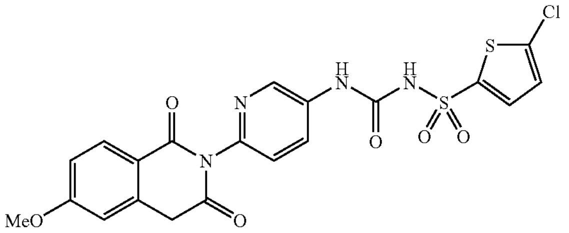
Example 128
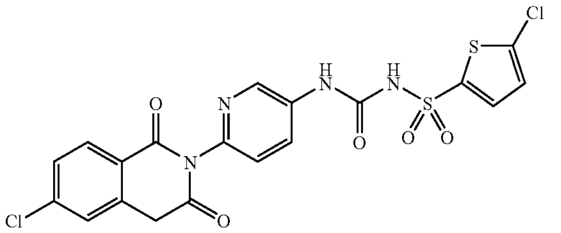
Example 129
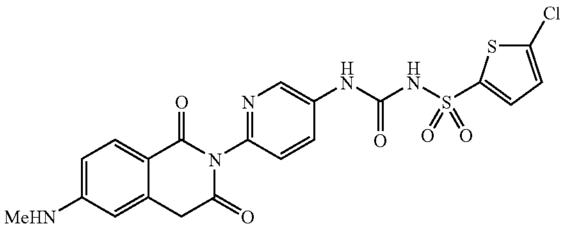
Example 130
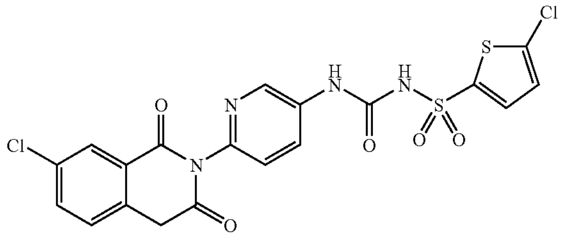
Example 131
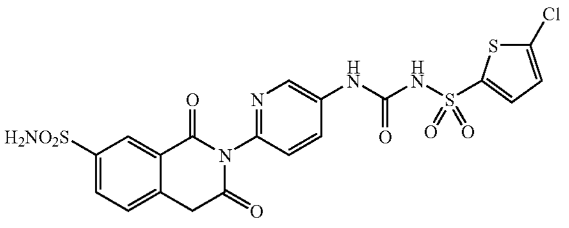

-continued
Example 132
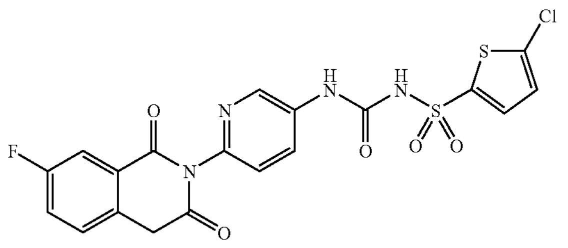
Example 133
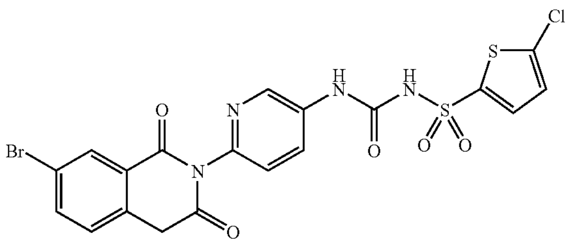
Example 134
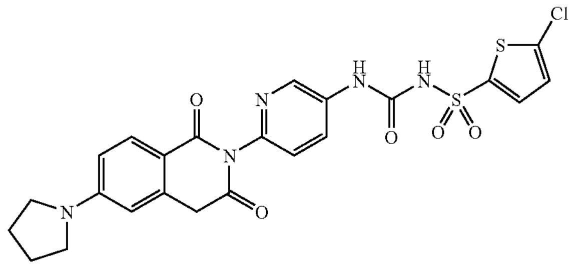
Example 135
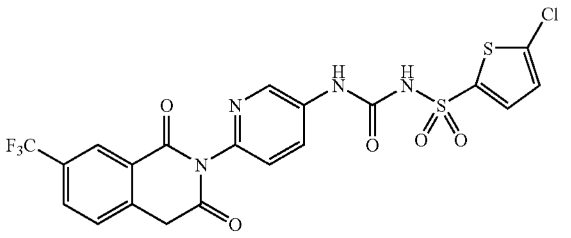
Example 136
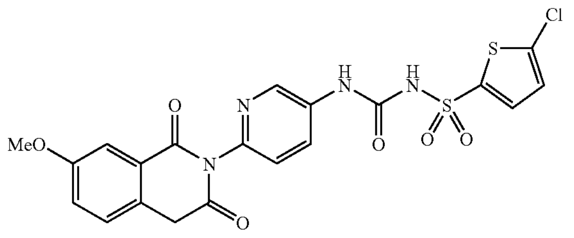
Example 137
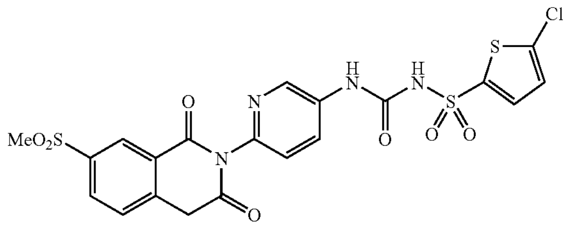
-continued
Example 138
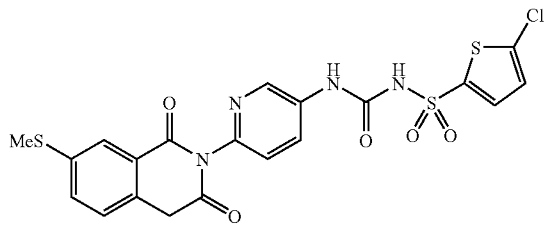
Example 139
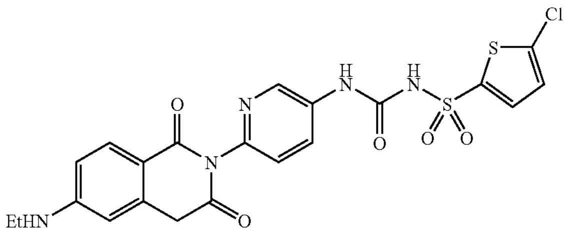
Example 140
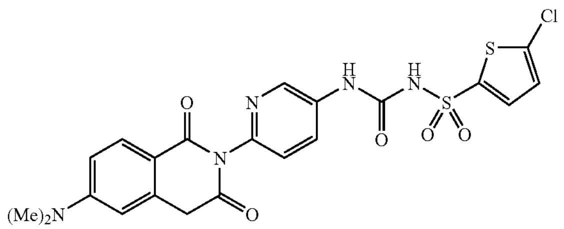
Example 141
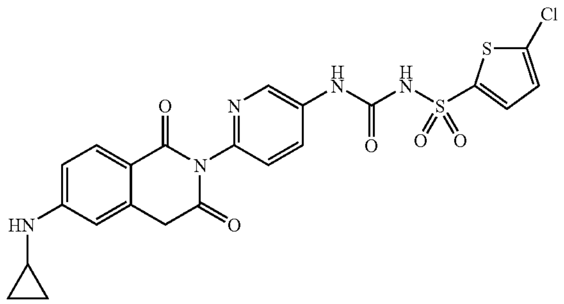
Example 142
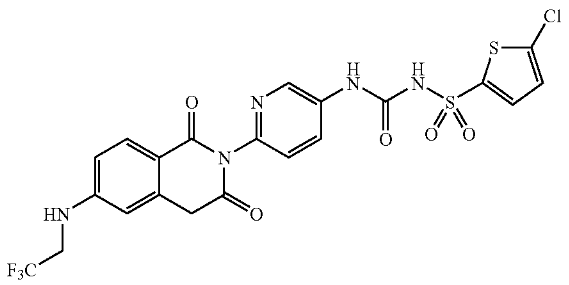

-continued
Example 143
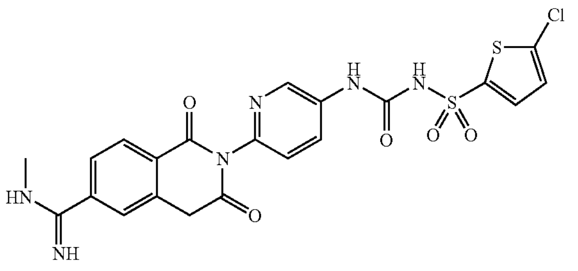
Example 144
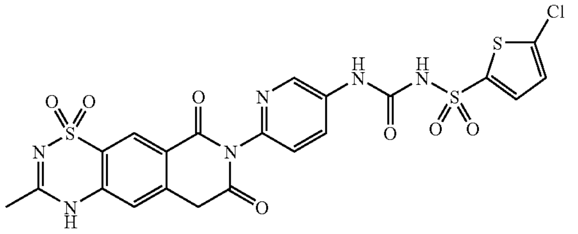
Example 145
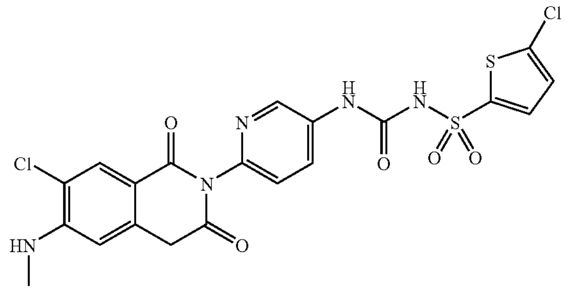
Example 146
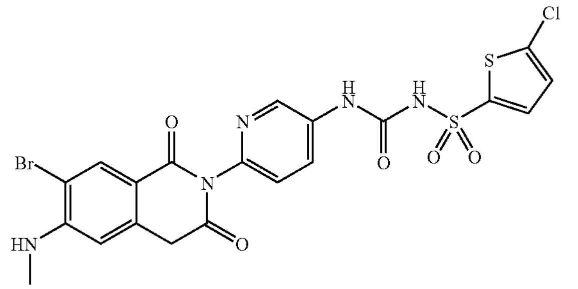
Example 147
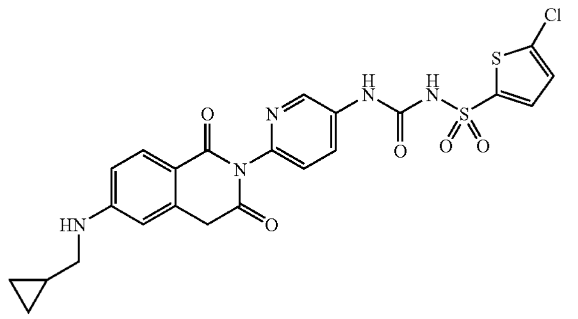
-continued
Example 148
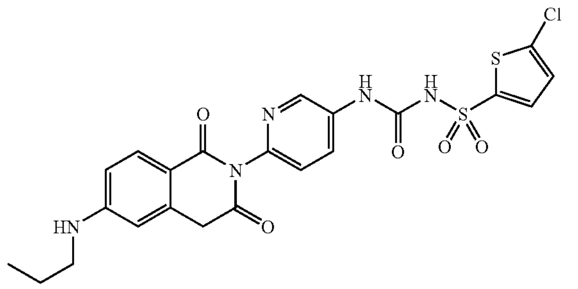
Example 149
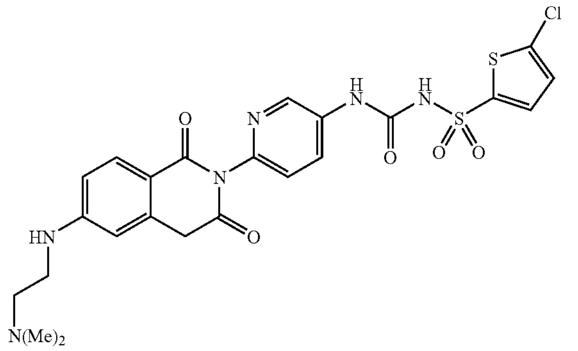
Example 150
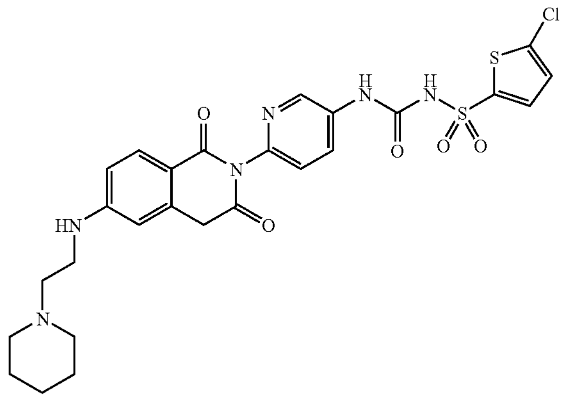
Example 151
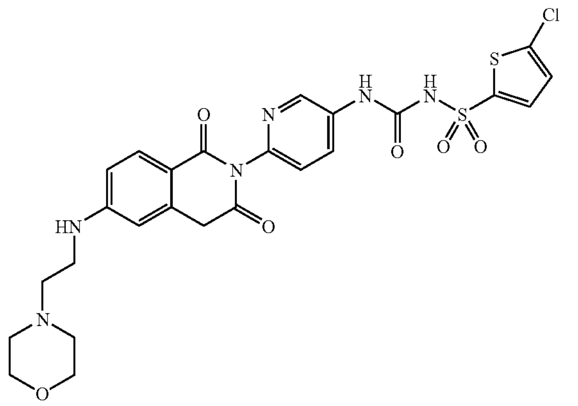

-continued
Example 152
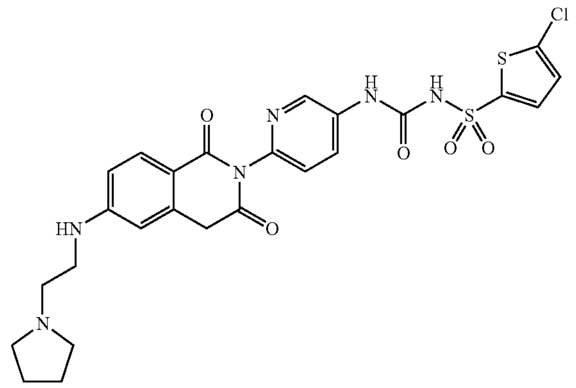
Example 153
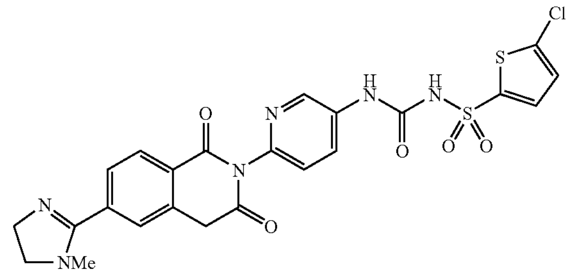
Example 154
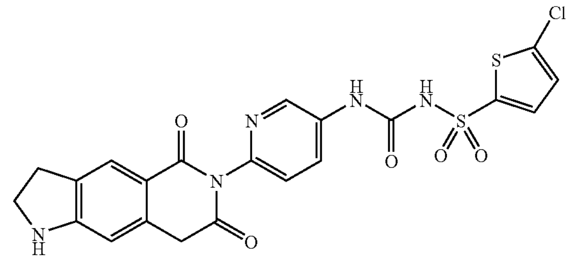
Example 155
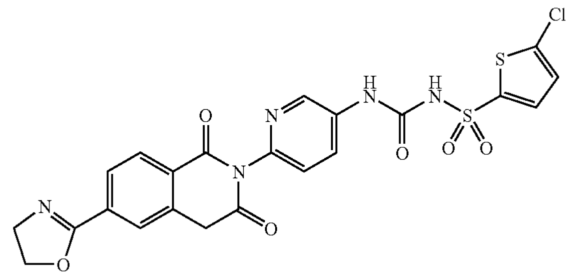
Example 156
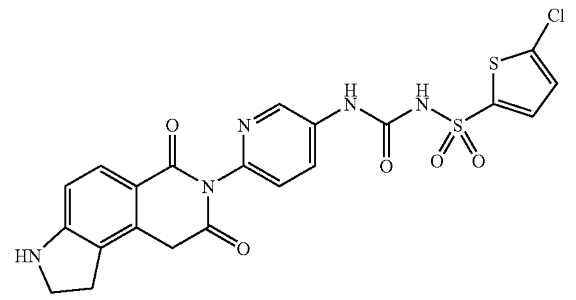
-continued
Example 157
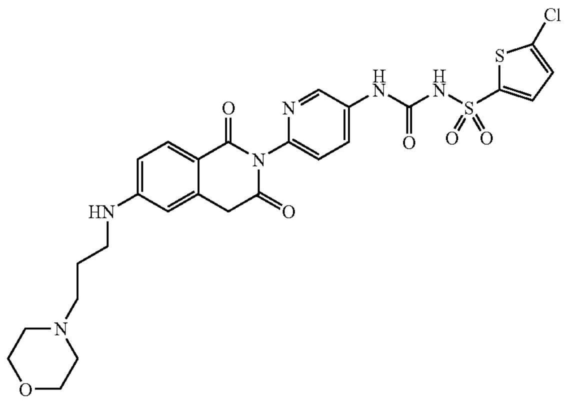
Example 158
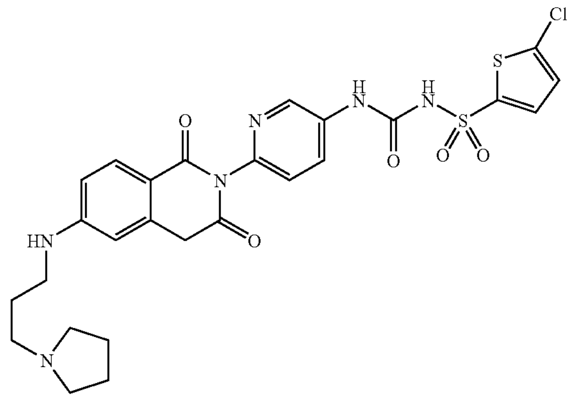
Example 159
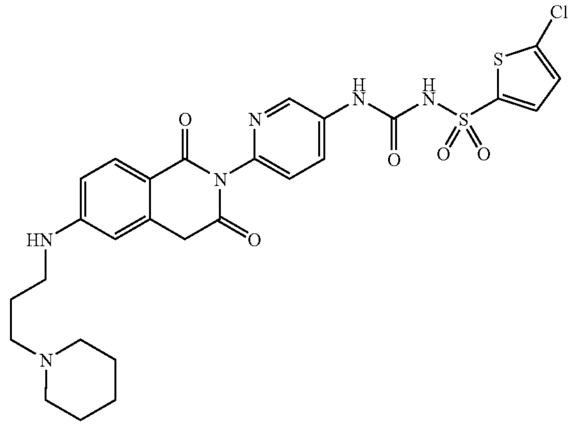
Example 160
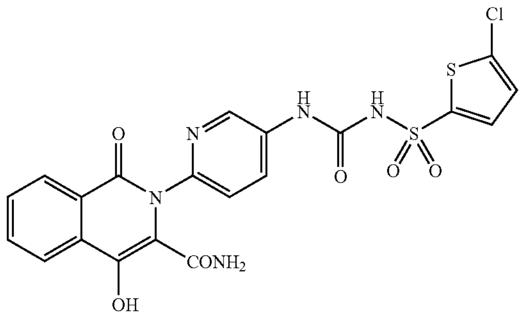

-continued
Example 161
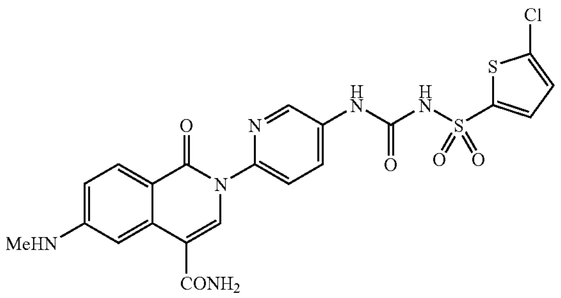
Example 162
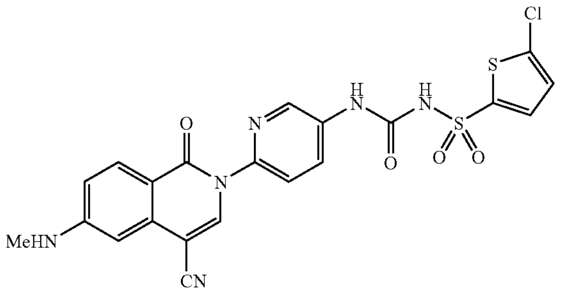
Example 163
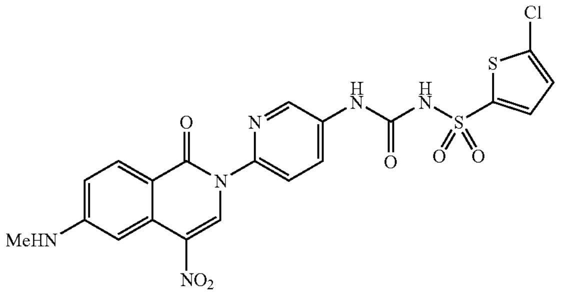
Example 164
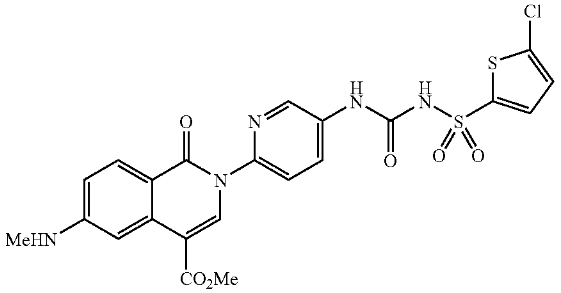
-continued
Example 165
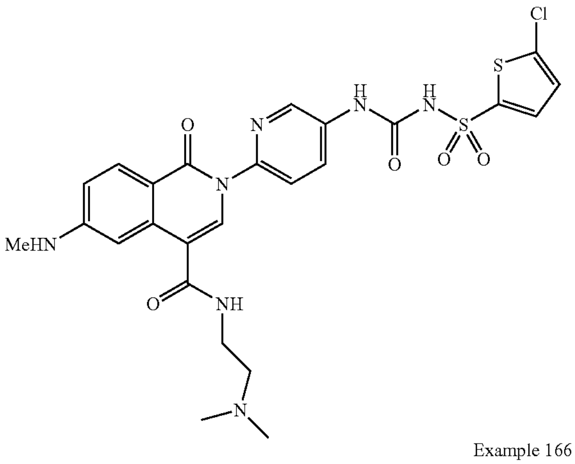
Example 166
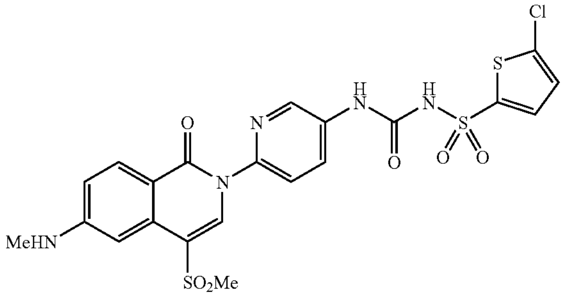
Example 167
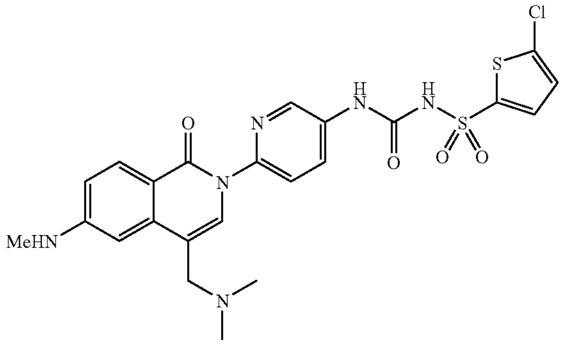
Example 168
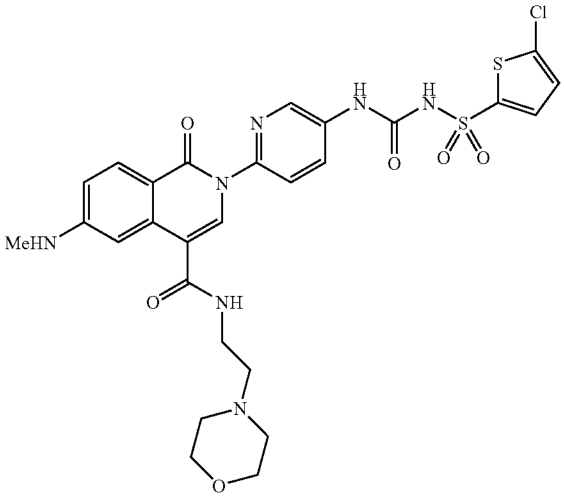

-continued
Example 169
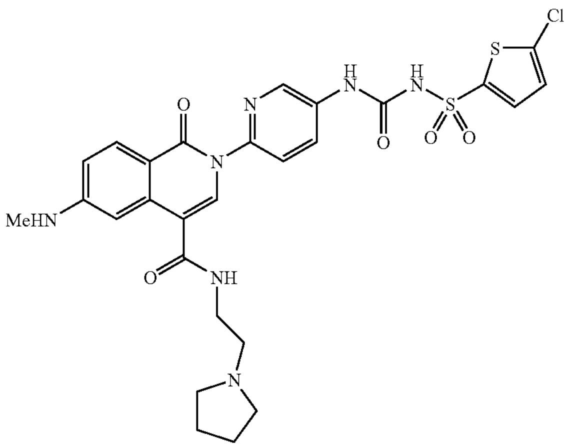
Example 170
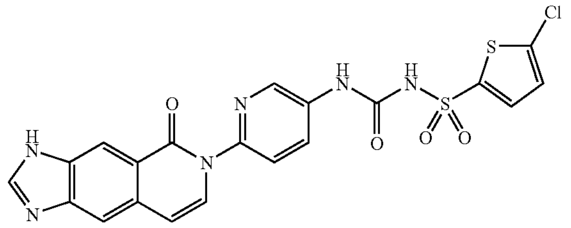
Example 171
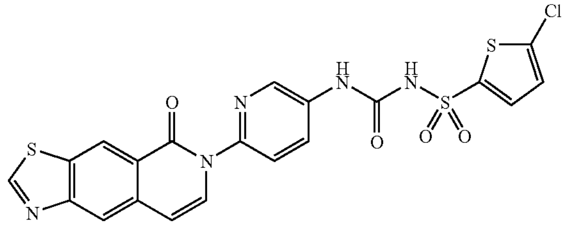
Example 172
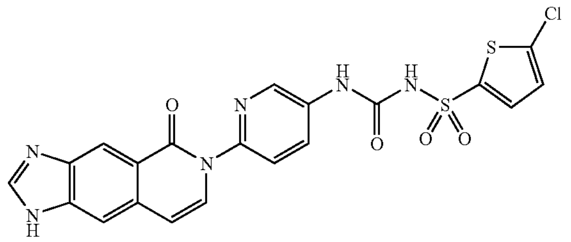
Example 173
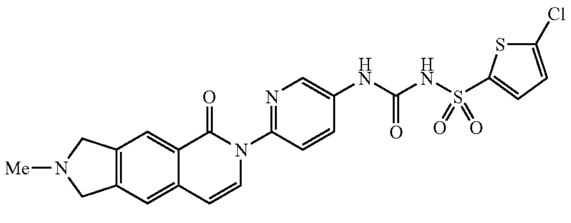
-continued
Example 174
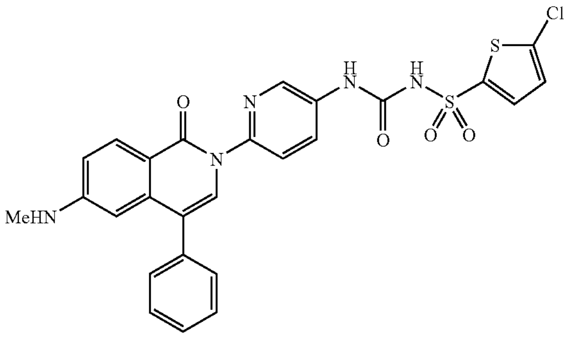
Example 175
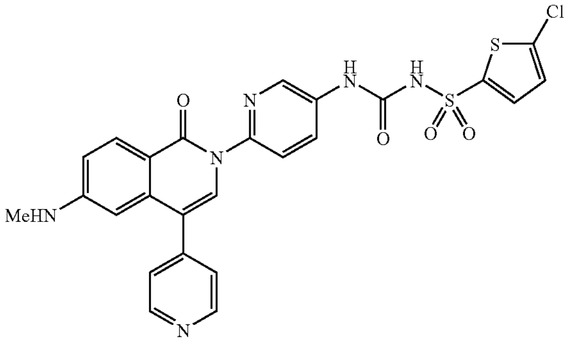
Example 176
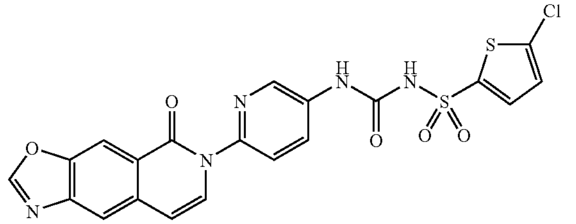
Example 177
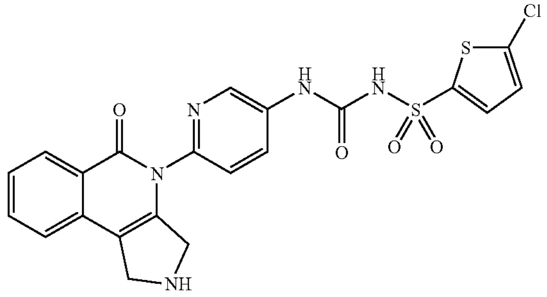
Example 178
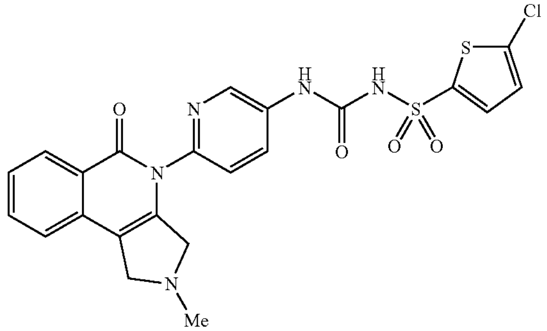

-continued
Example 179
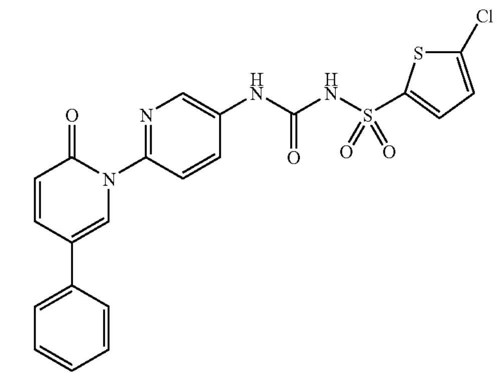
Example 180
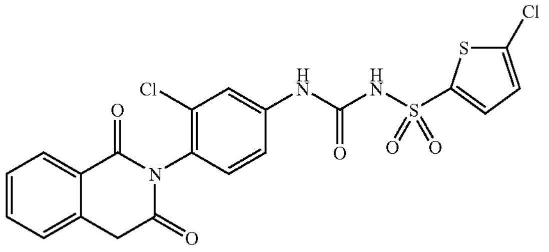
Example 181
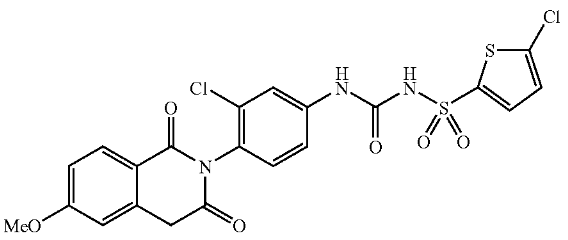
Example 182
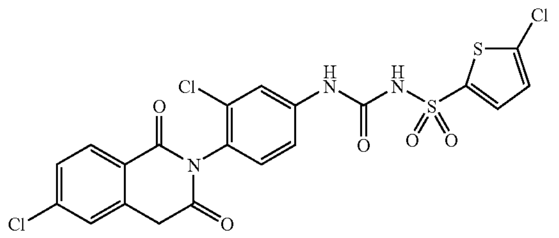
Example 183
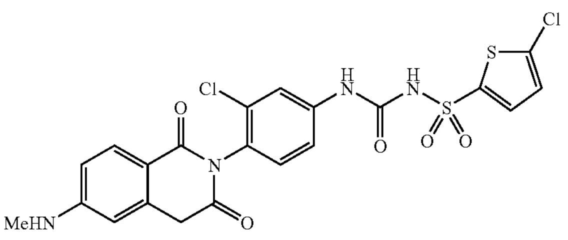
-continued
Example 184
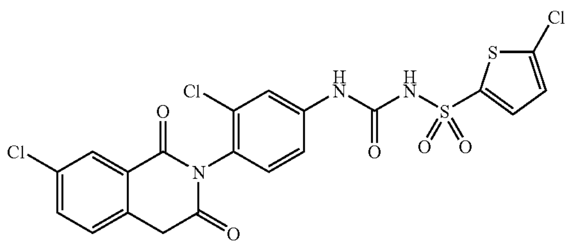
Example 185
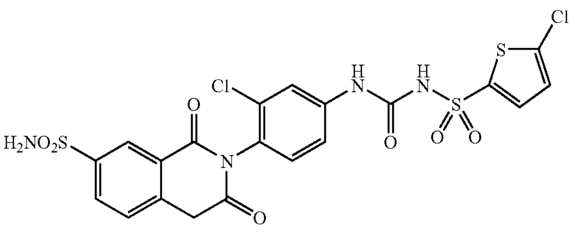
Example 186
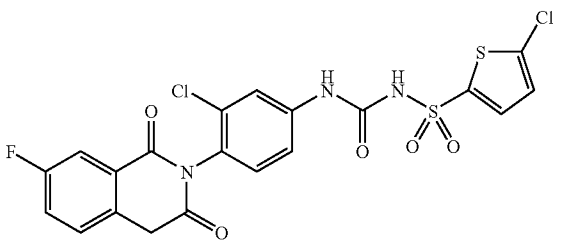
Example 187
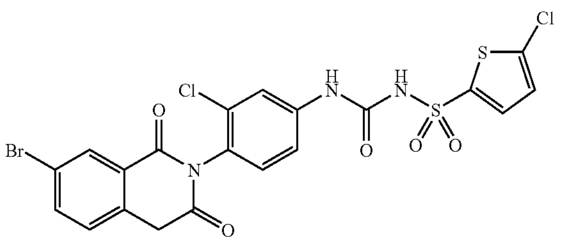
Example 188
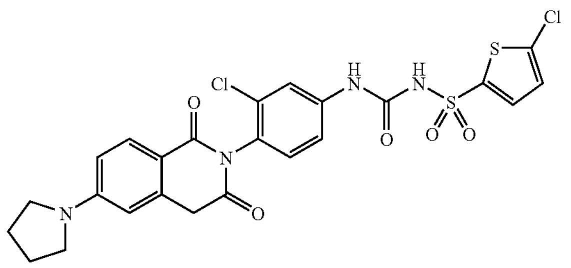
Example 189
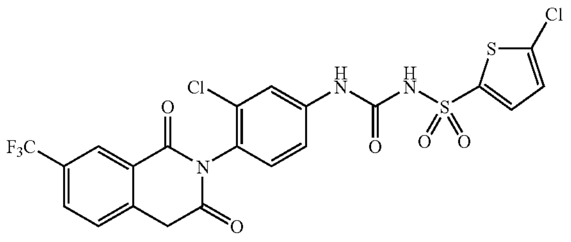

-continued
Example 190
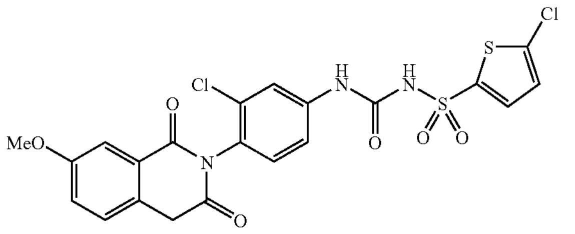
Example 191
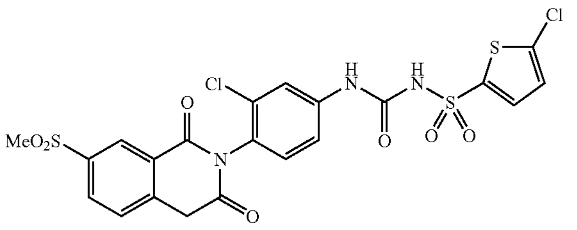
Example 192
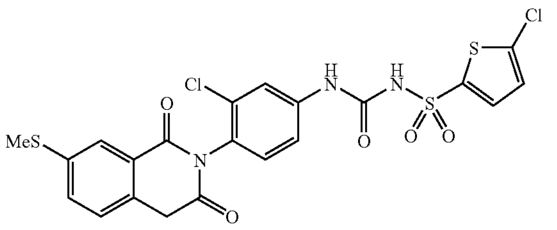
Example 193
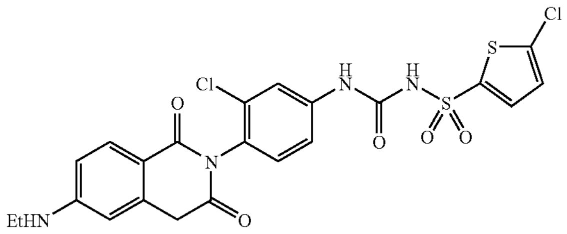
Example 194
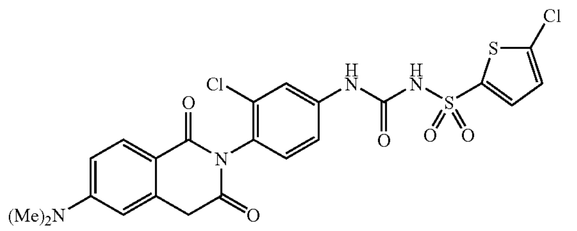
Example 195
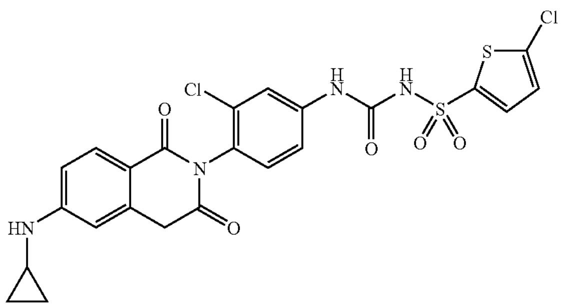
-continued
Example 196
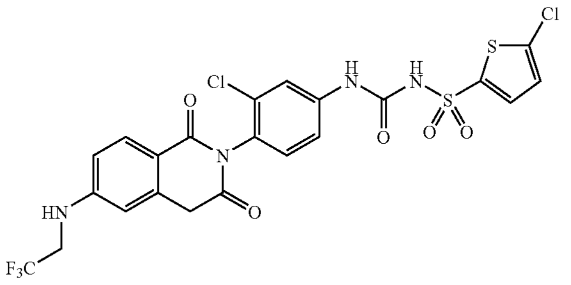
Example 197
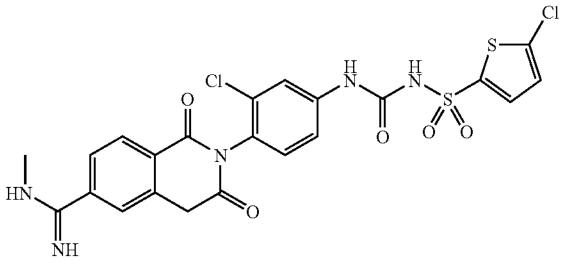
Example 198
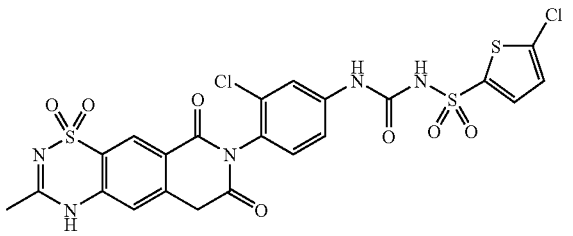
Example 199
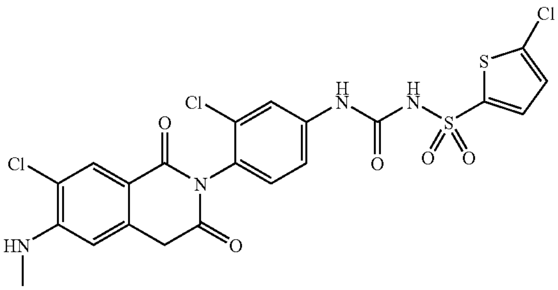
Example 200
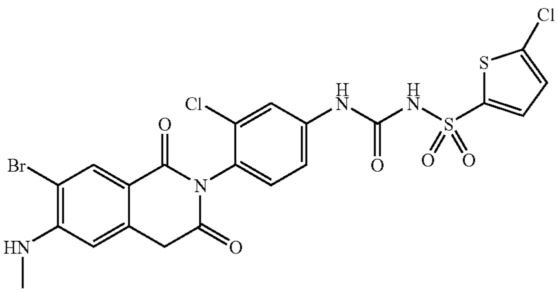

-continued
Example 201
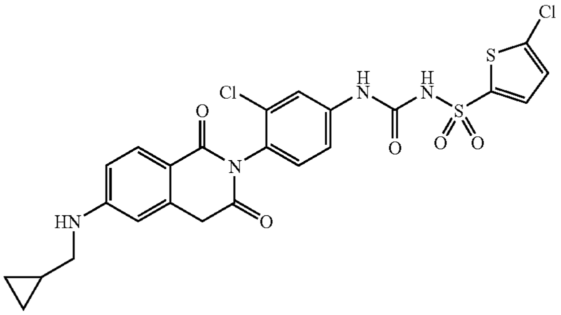
Example 202
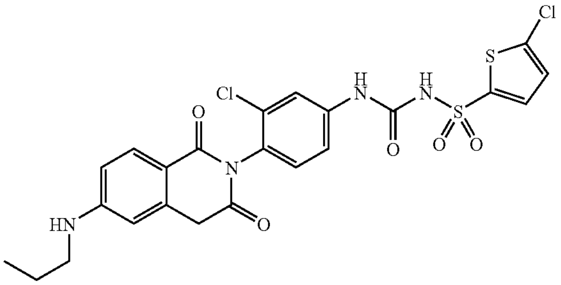
Example 203
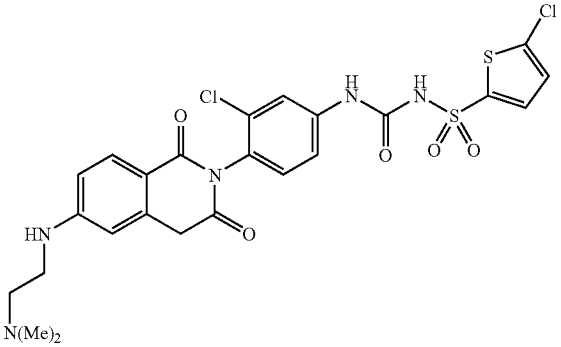
Example 204
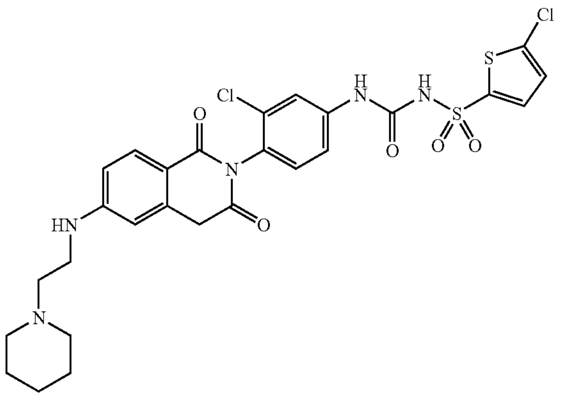
-continued
Example 205
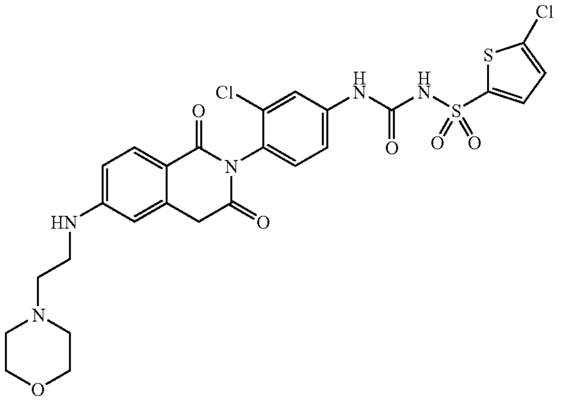
Example 206
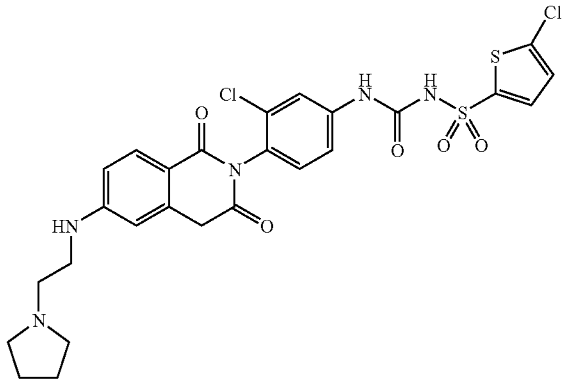
Example 207
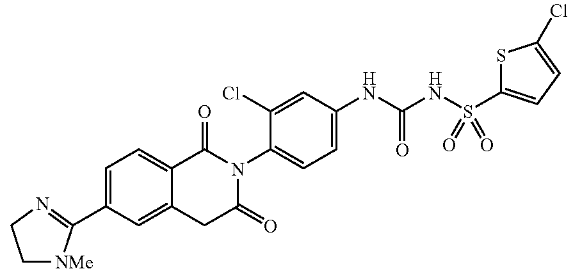
Example 208
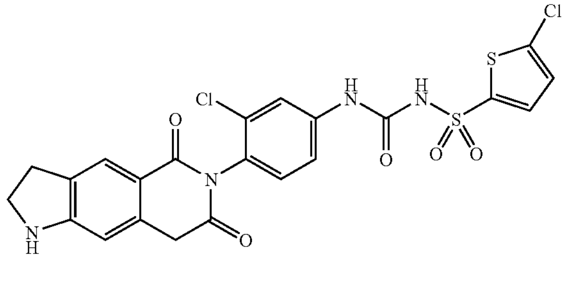

-continued
Example 209
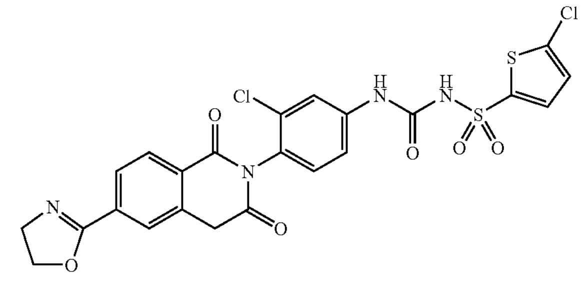
Example 210
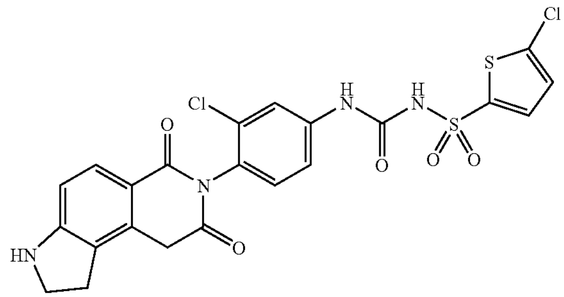
Example 211
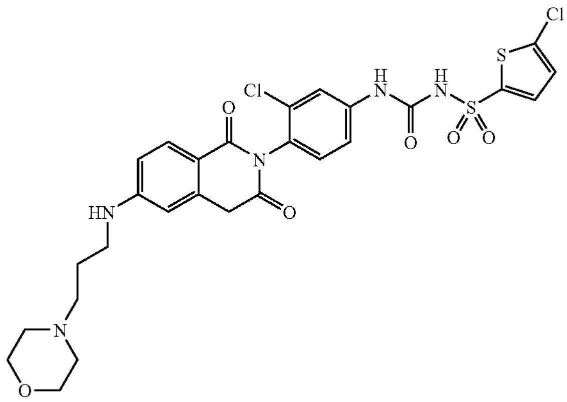
Example 212
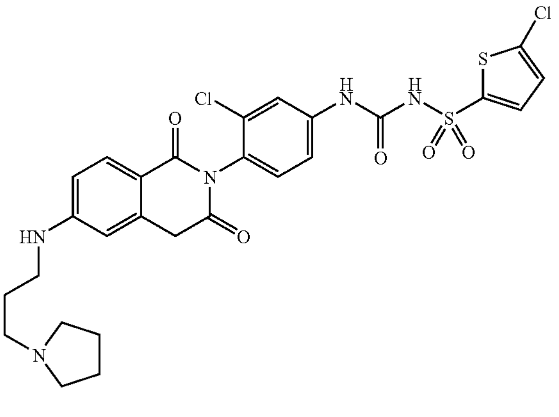
-continued
Example 213
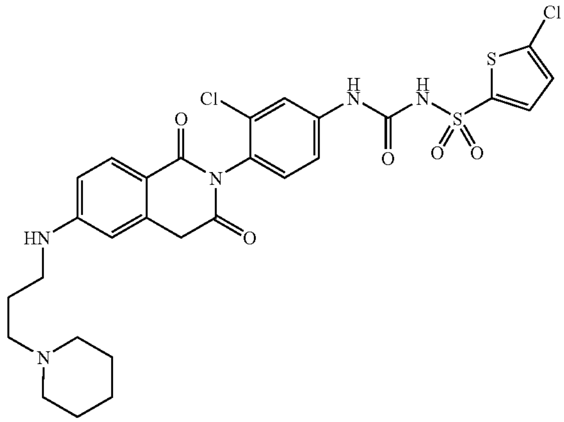
Example 214
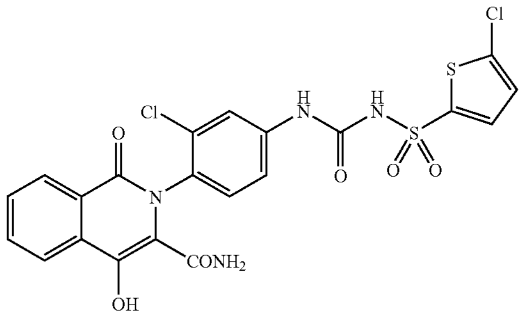
Example 215
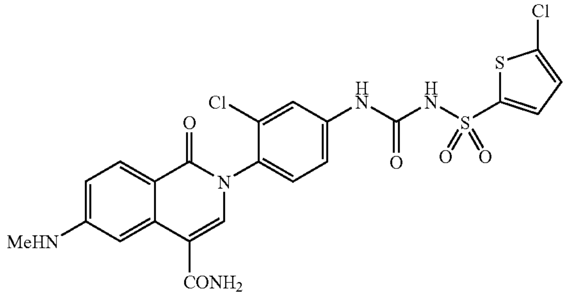
Example 216
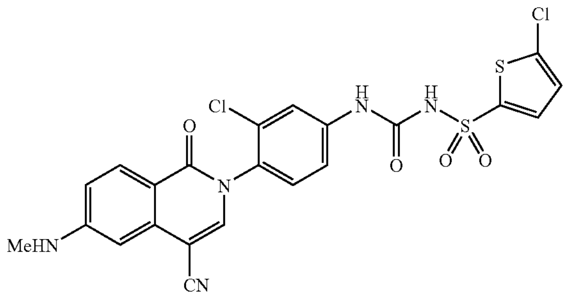

Example 217
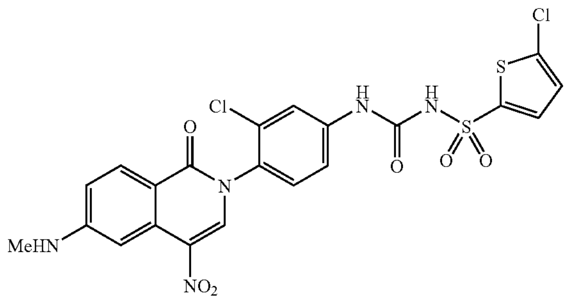
Example 218
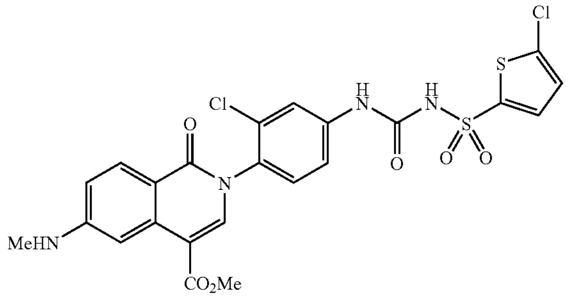
Example 219
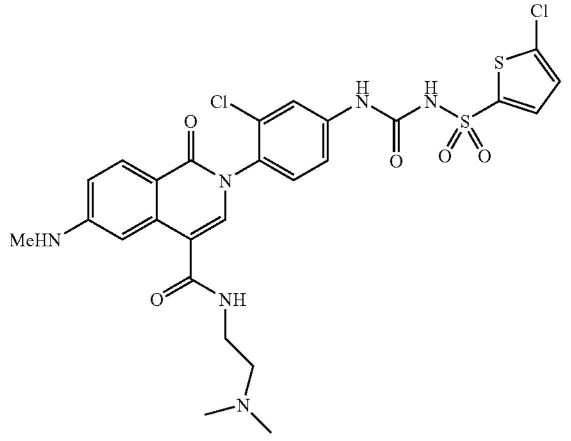
Example 220
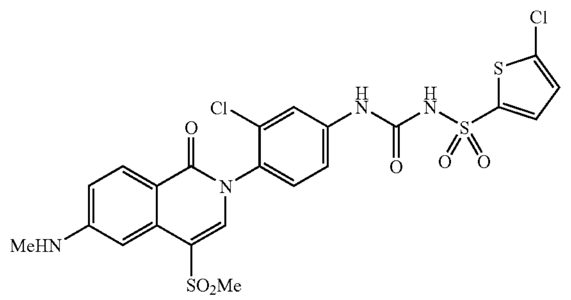
example 221
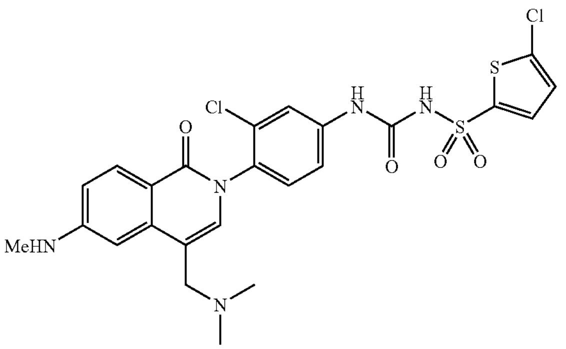
Example 222
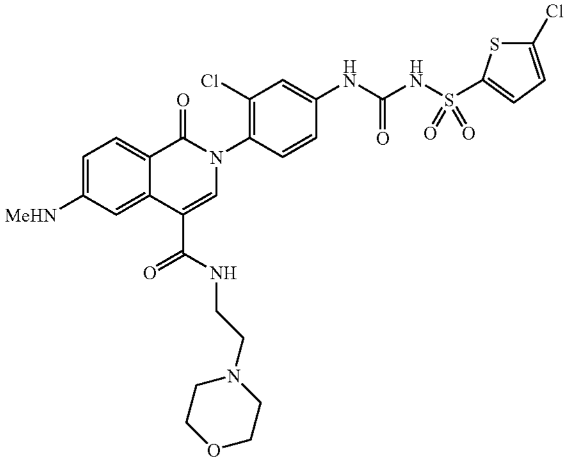
Example 223
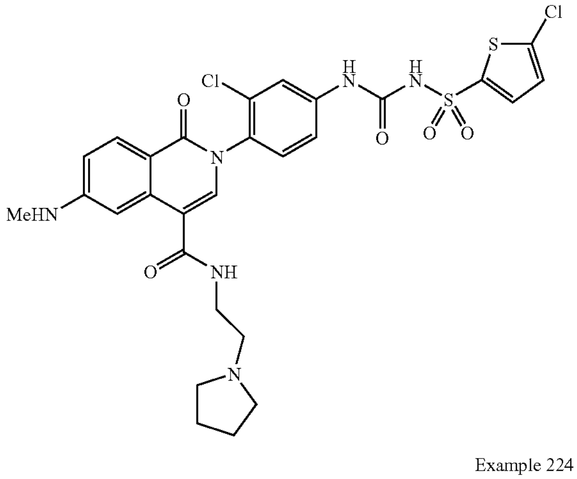
Example 224
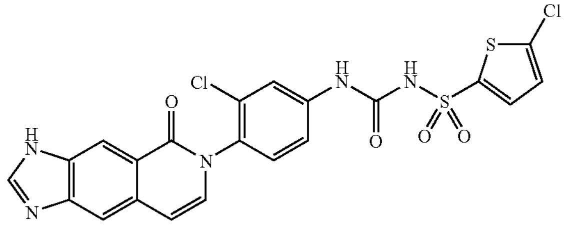

-continued
Example 225
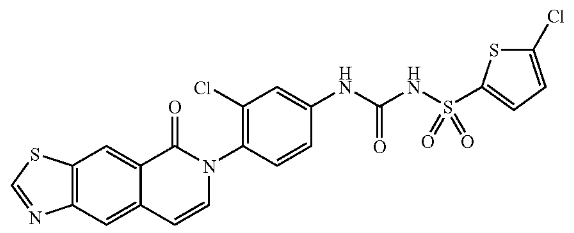
Example 226
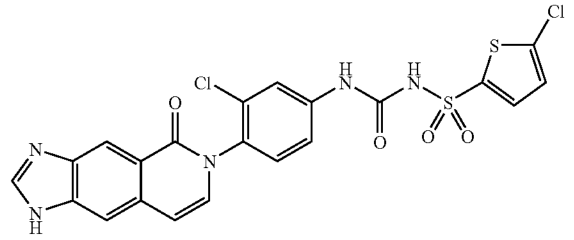
Example 227
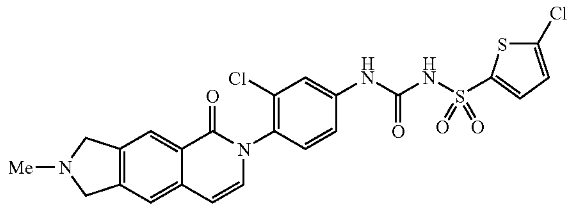
Example 228
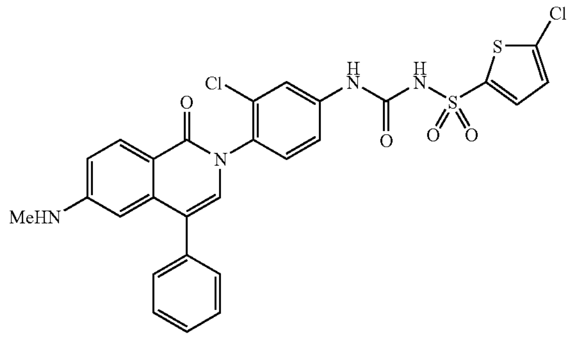
Example 229
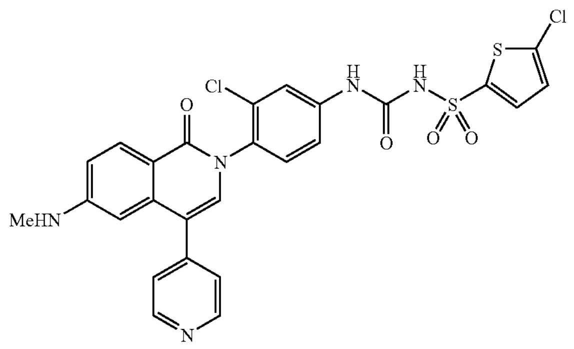
-continued
Example 230
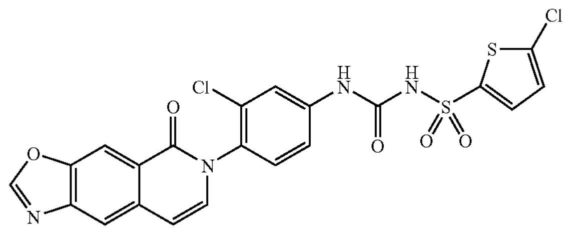
Example 231
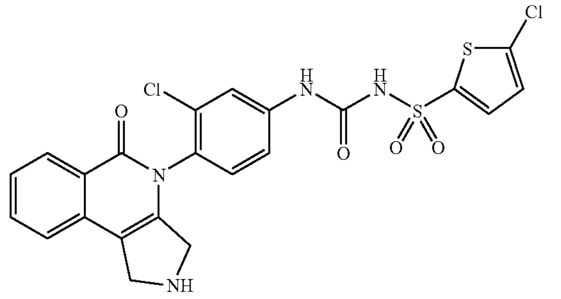
Example 232
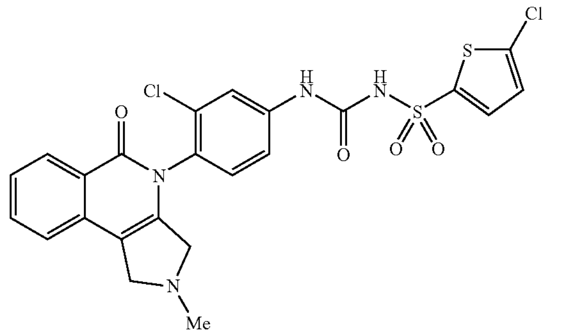
Example 233
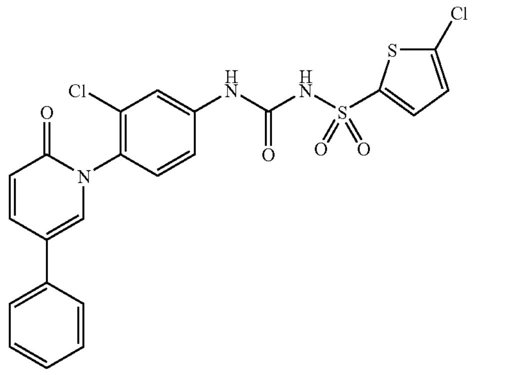
Example 234
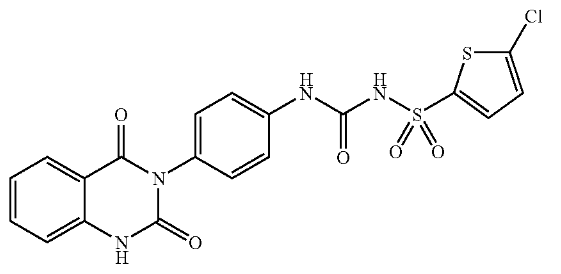

-continued
Example 235
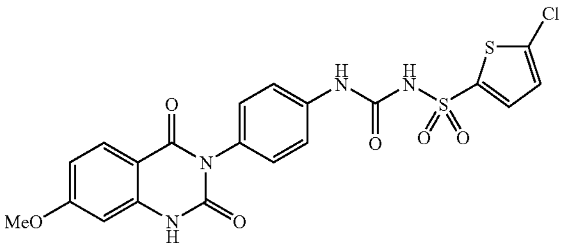
Example 236
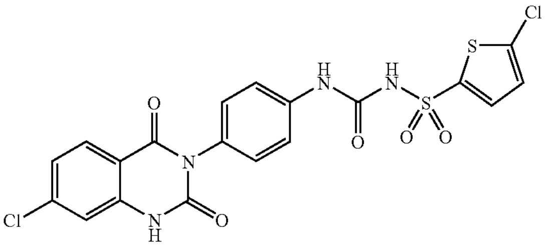
Example 237
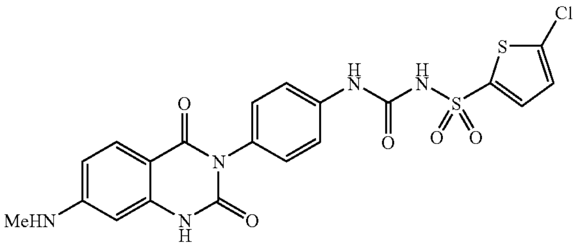
Example 238
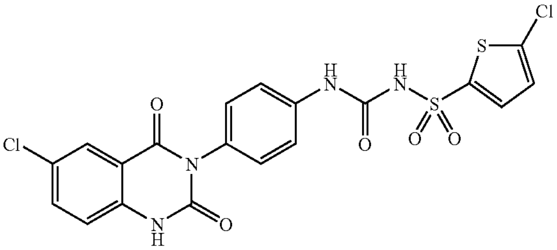
Example 239
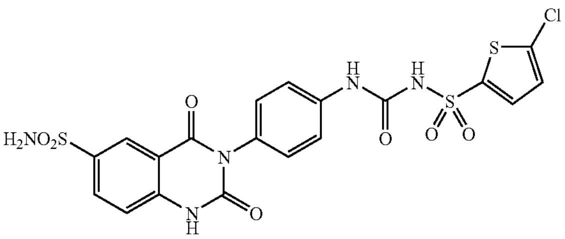
Example 240
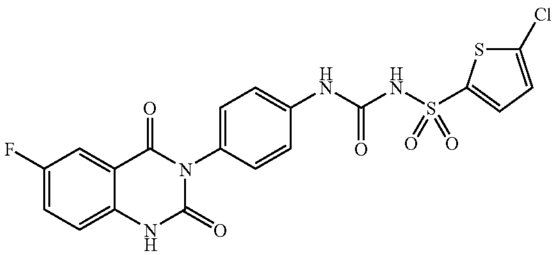
-continued
Example 241
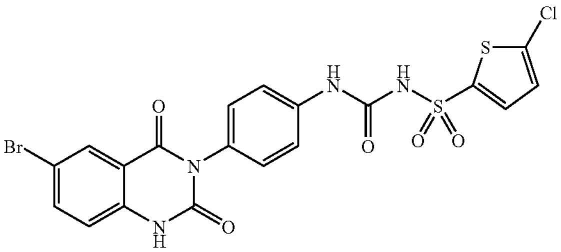
Example 242
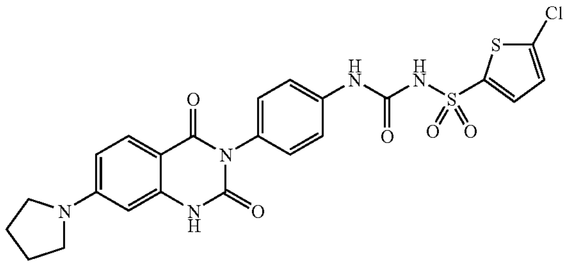
Example 243
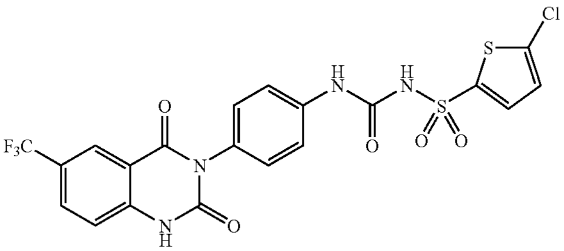
Example 244
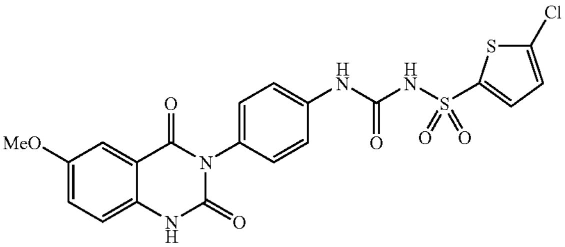
Example 245
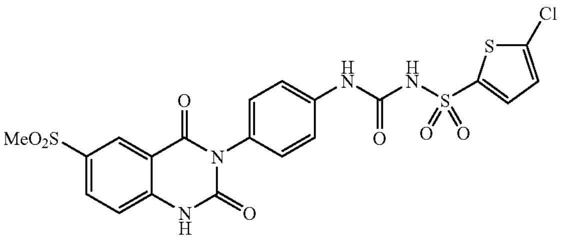
Example 246
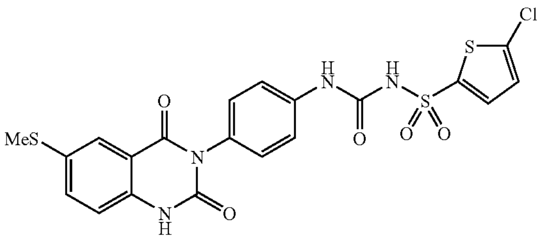

-continued
Example 247
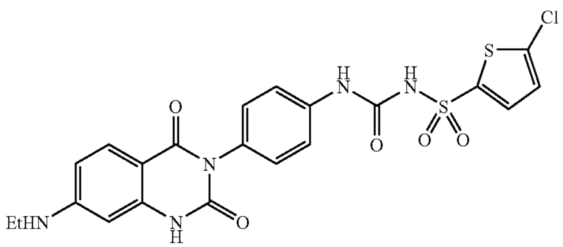
Example 248
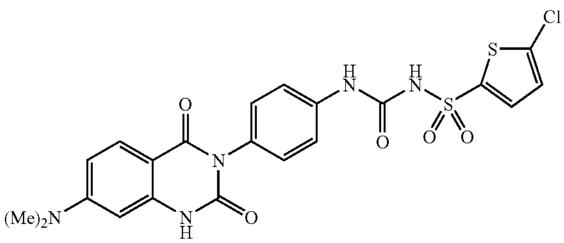
Example 249
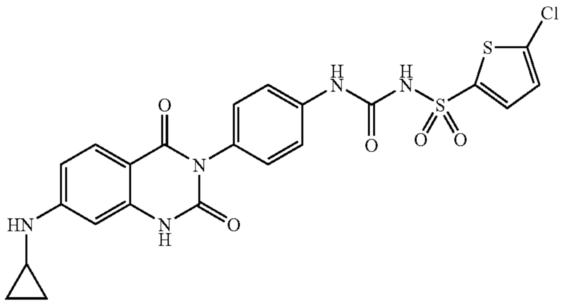
Example 250
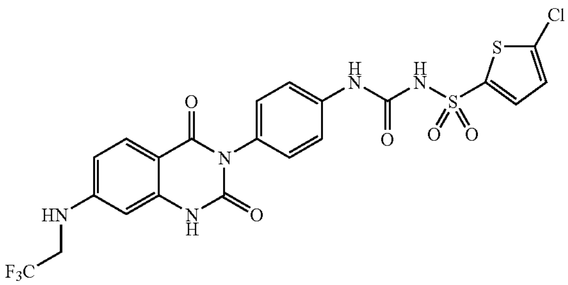
Example 251
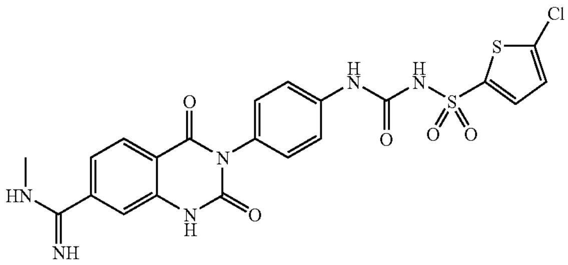
-continued
Example 252
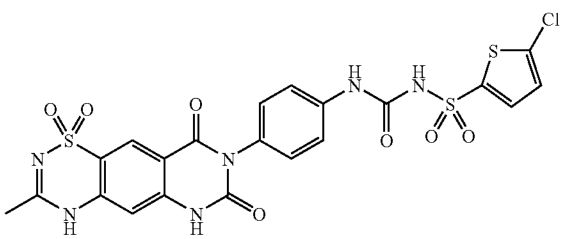
Example 253
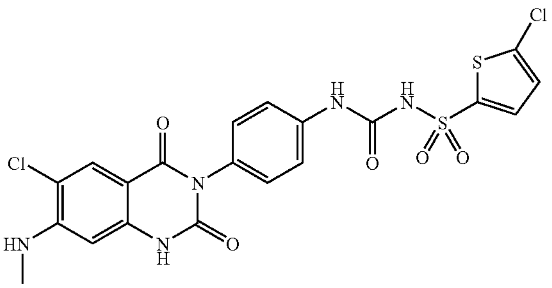
Example 254
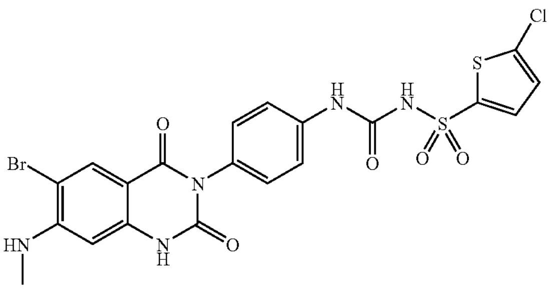
Example 255
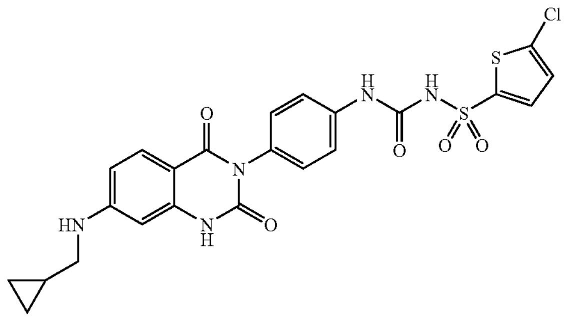
Example 256
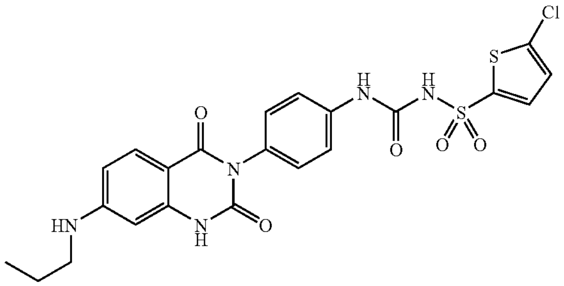

-continued
Example 257
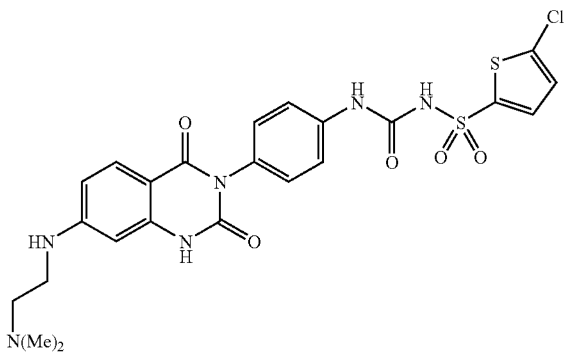
Example 258
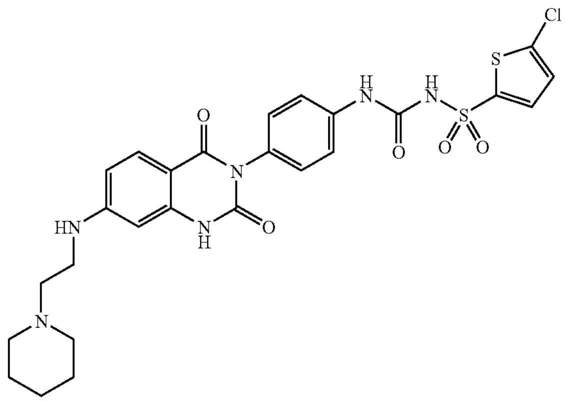
Example 259
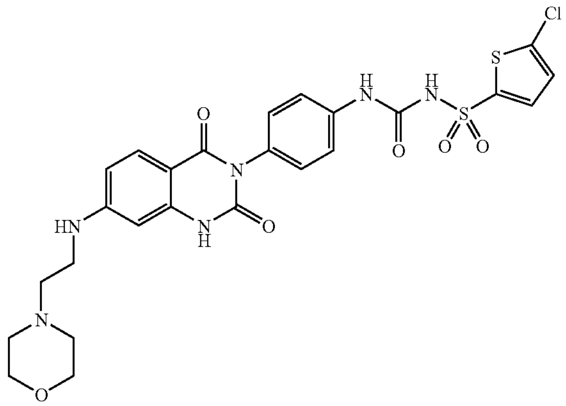
Example 260
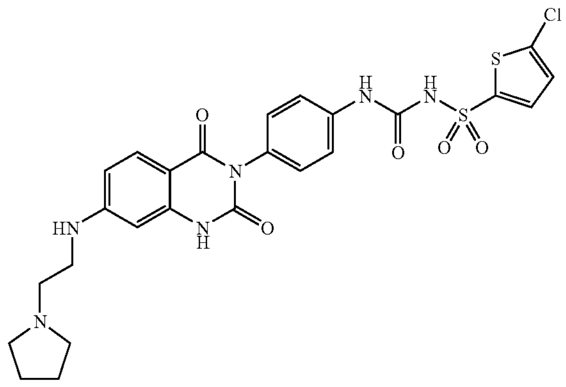
-continued
Example 261
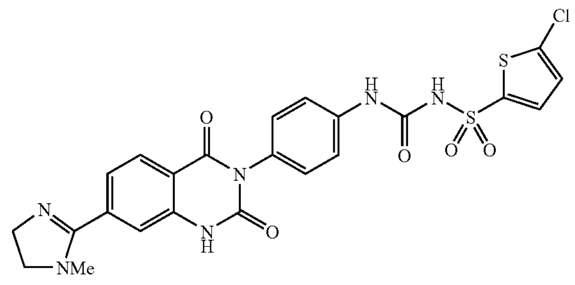
Example 262
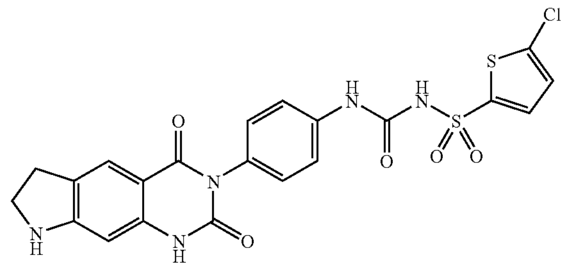
Example 263
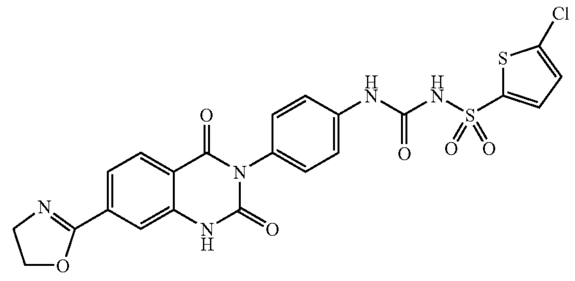
Example 264
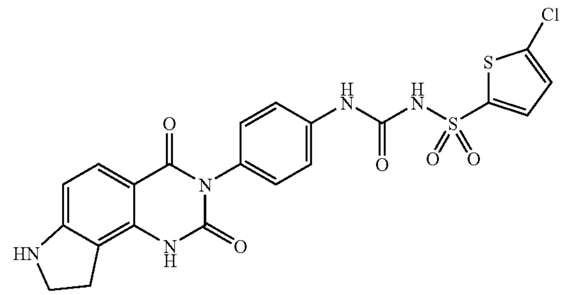
Example 265
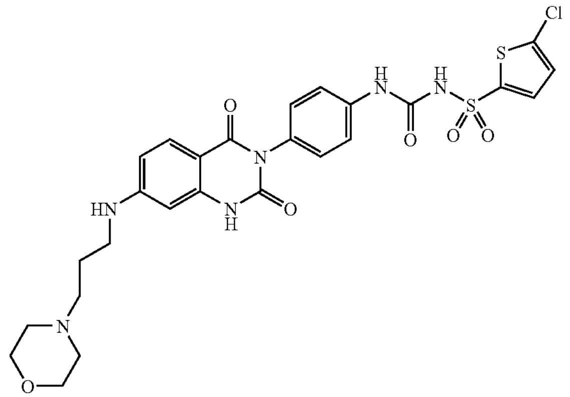

-continued
Example 266
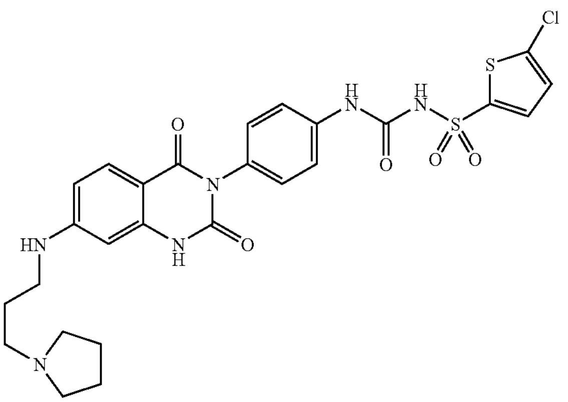
Example 267
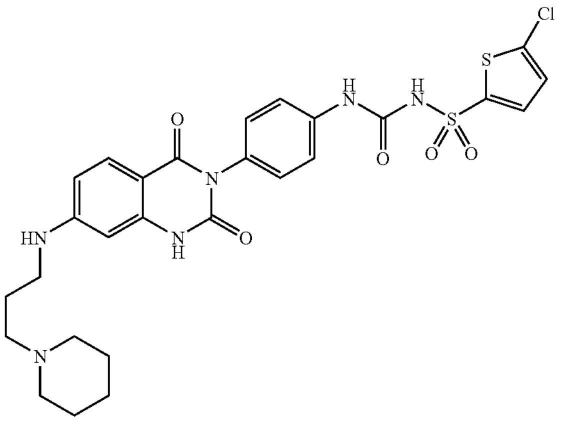
Example 268
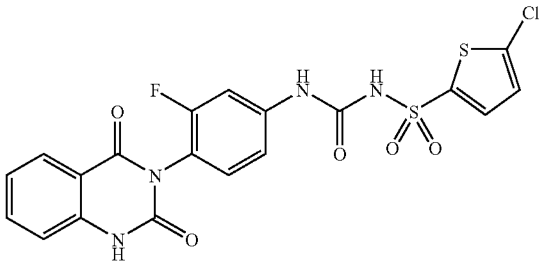
Example 269
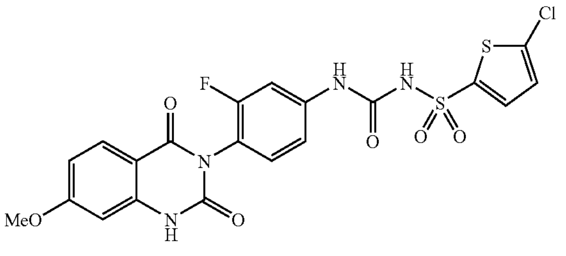
-continued
Example 270
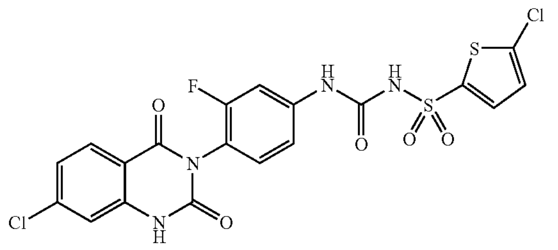
Example 271
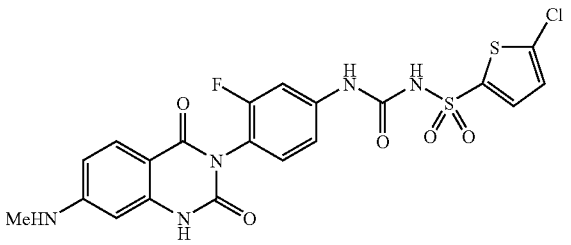
Example 272
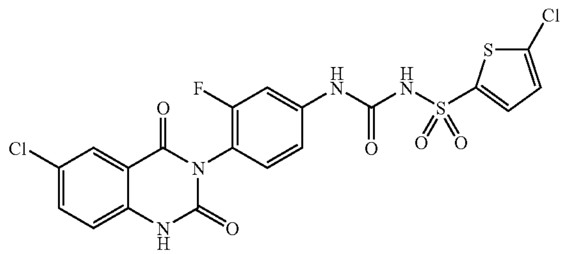
Example 273
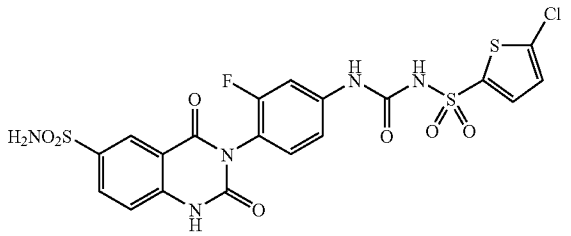
Example 274
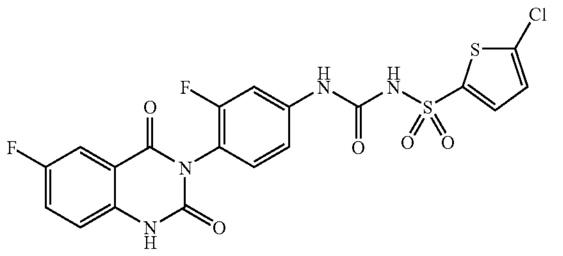
Example 275
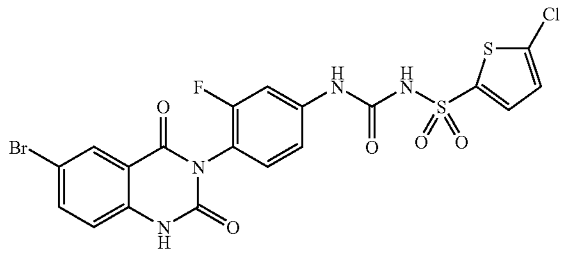

-continued
Example 276
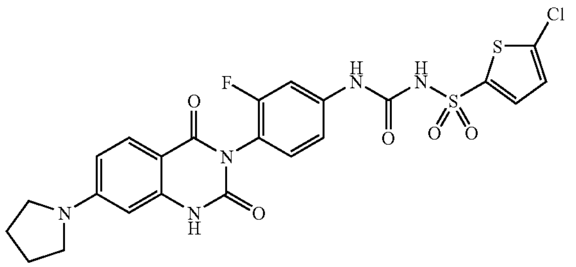
Example 277
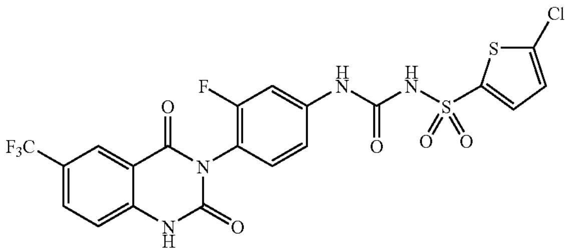
Example 278
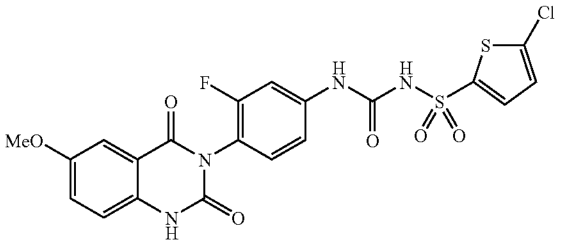
Example 279
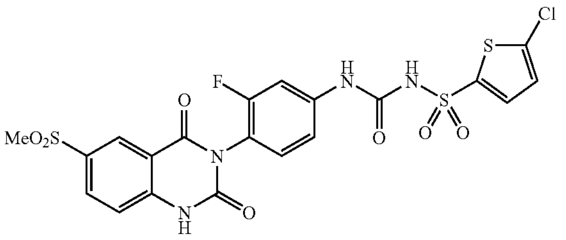
Example 280
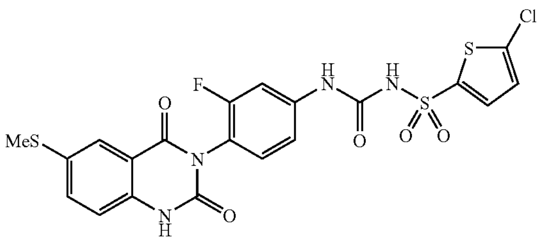
Example 281
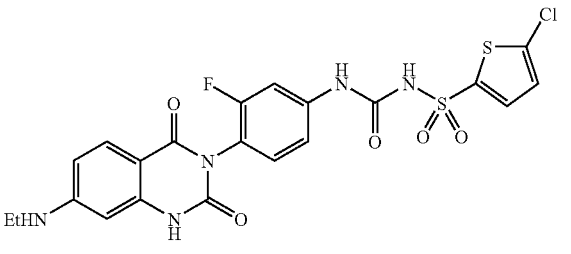
-continued
Example 282
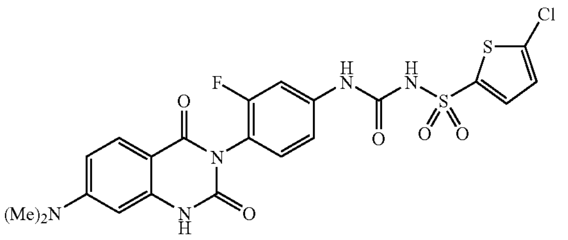
Example 283
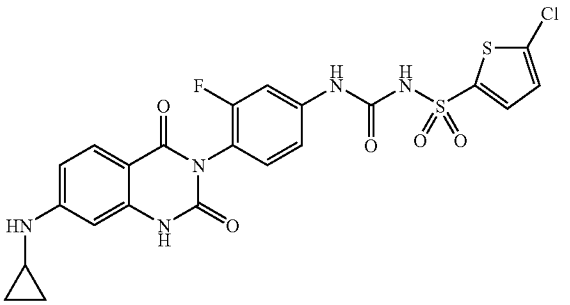
Example 284
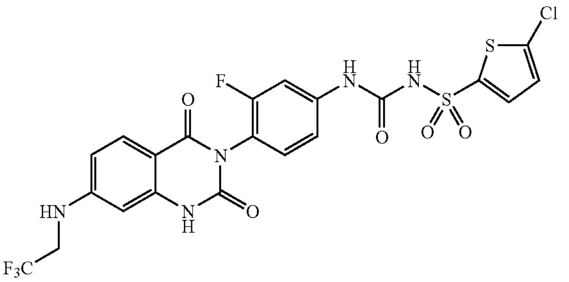
Example 285
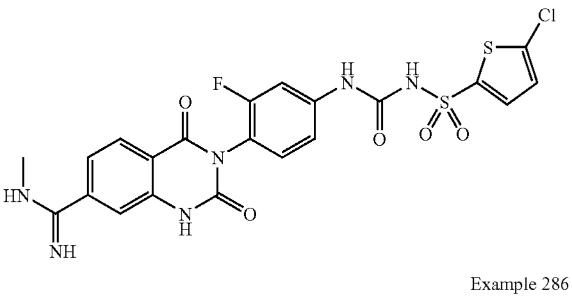
Example 286
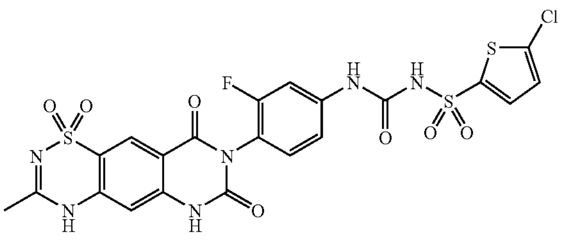

-continued
Example 287
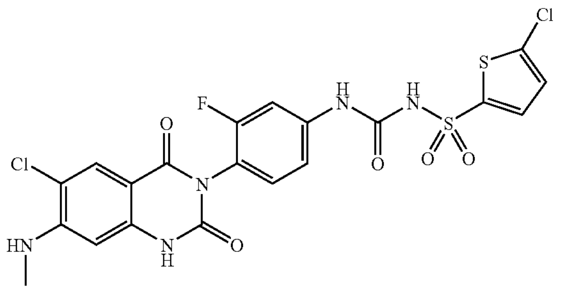
Example 288
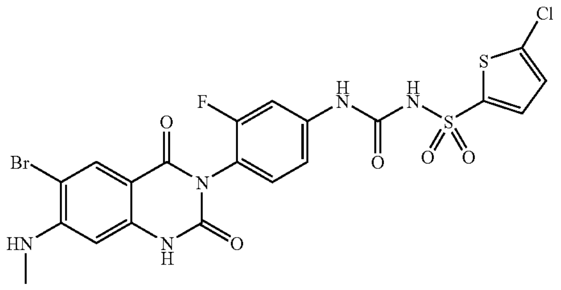
Example 289
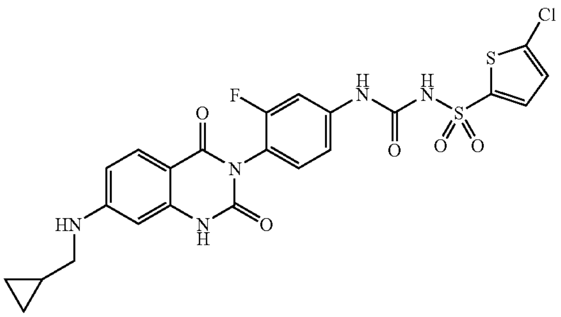
Example 290
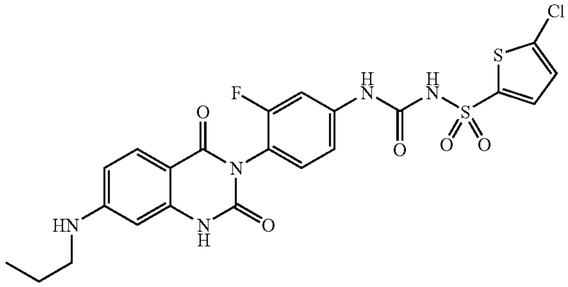
Example 291
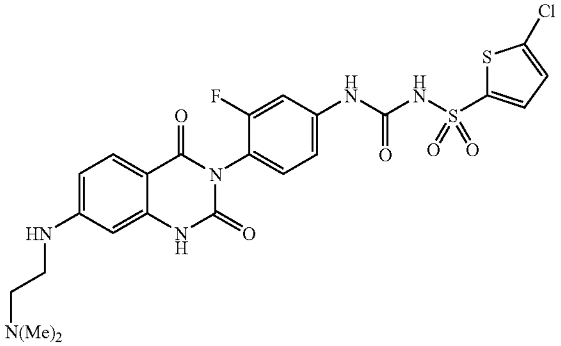
-continued
Example 292
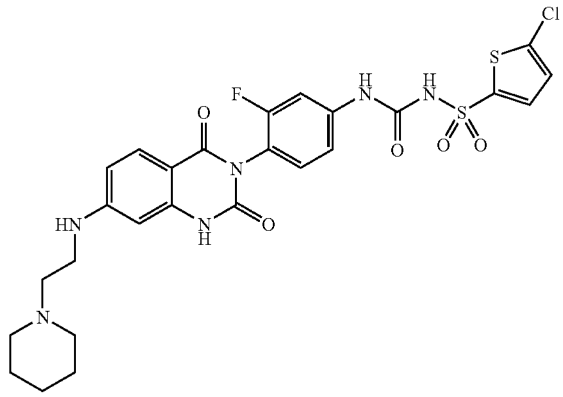
Example 293
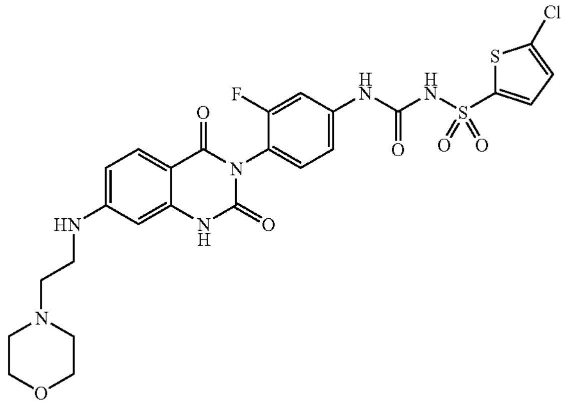
Example 294
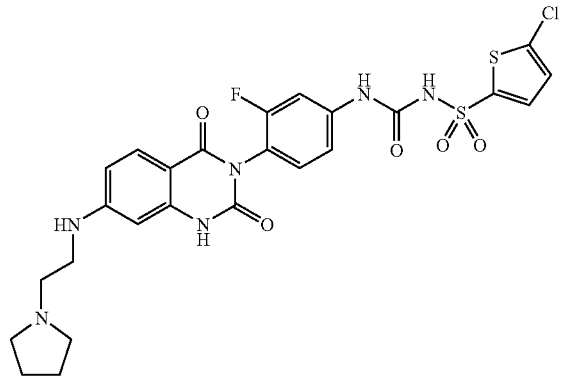
Example 295
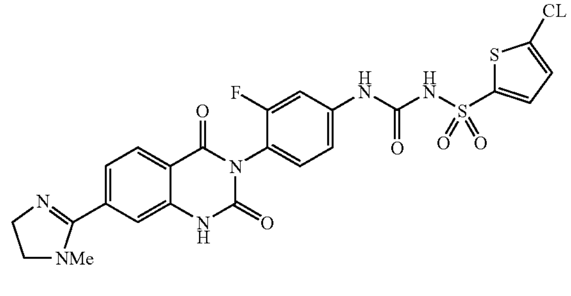

Example 296
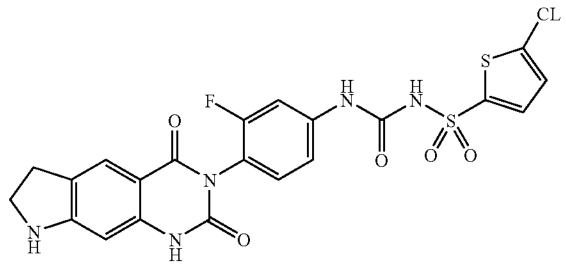
Example 297
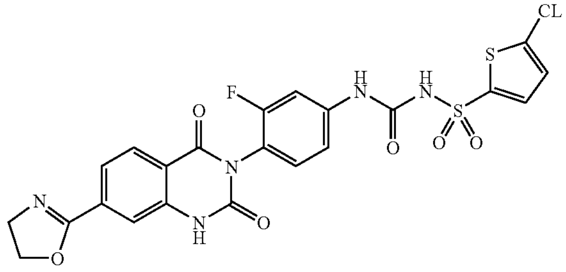
Example 298
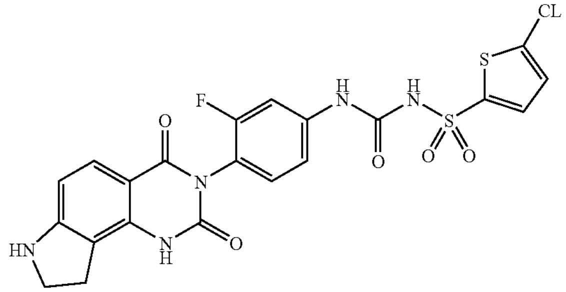
Example 299
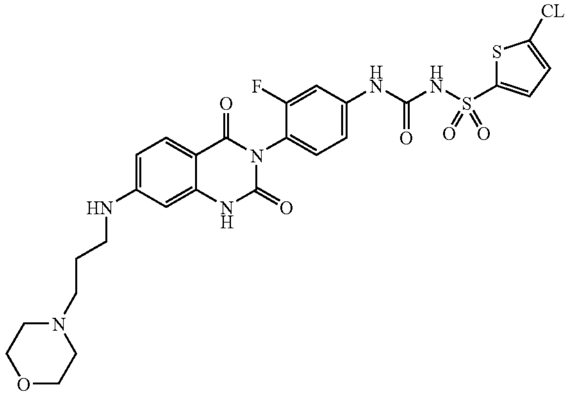
Example 300
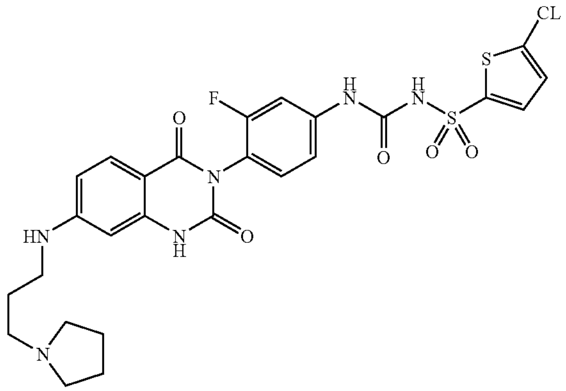
Example 301
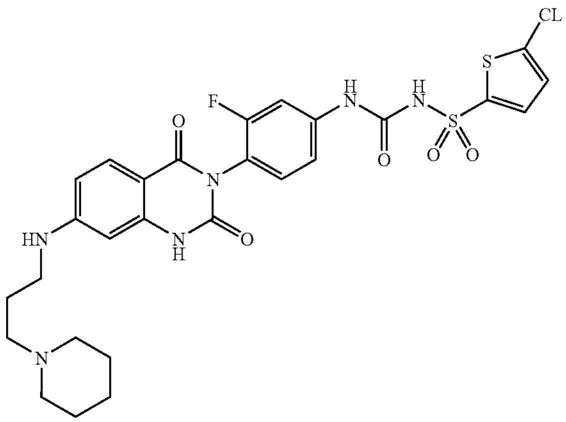
Example 302
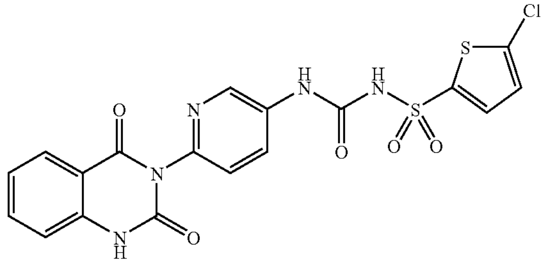
Example 303
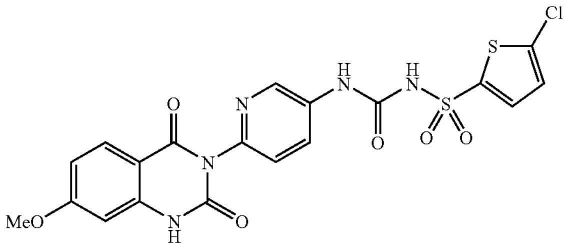

-continued
Example 304
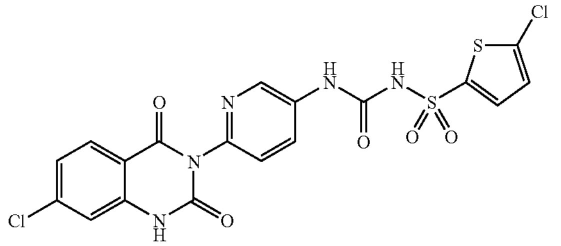
Example 305
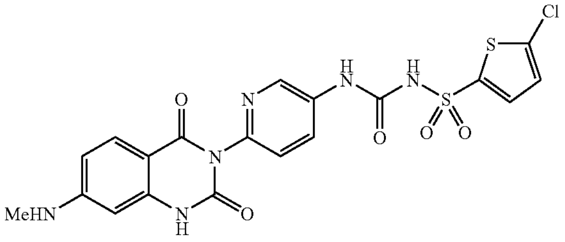
Example 306
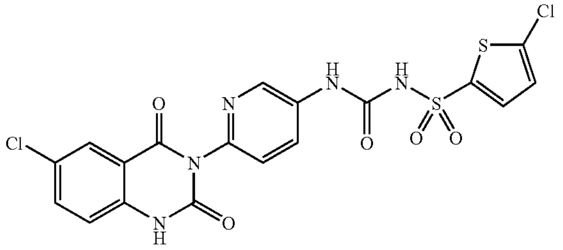
example 307
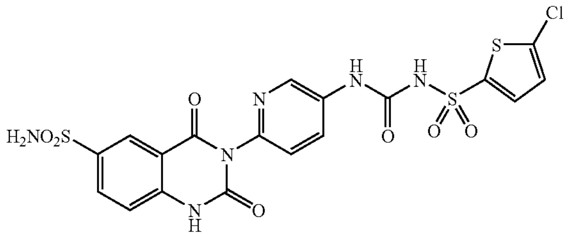
Example 308
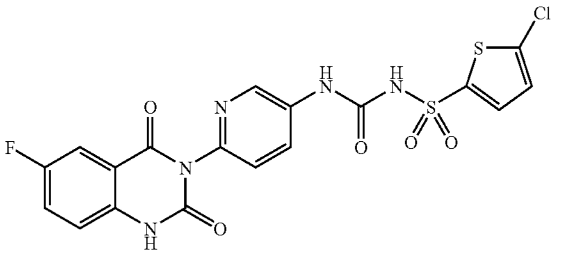
Example 309
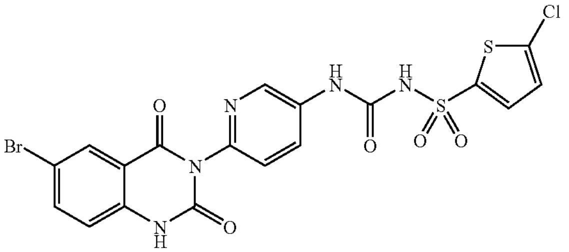
-continued
Example 310
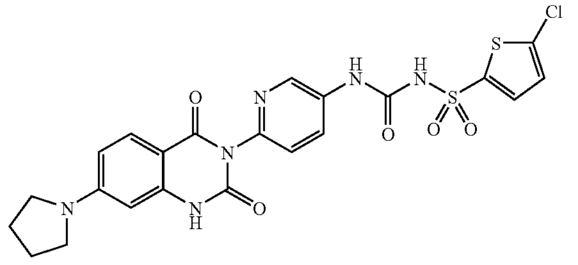
Example 311
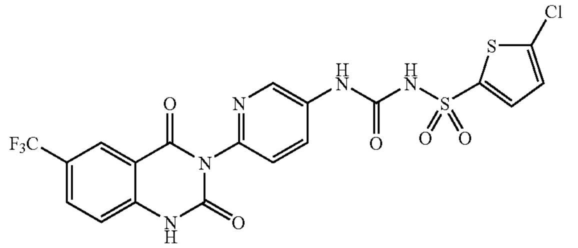
Example 312
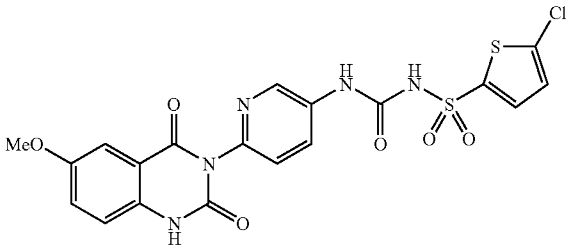
Example 313
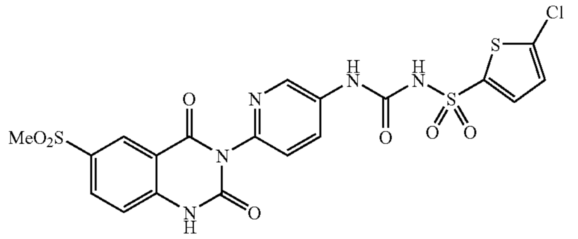
Example 314
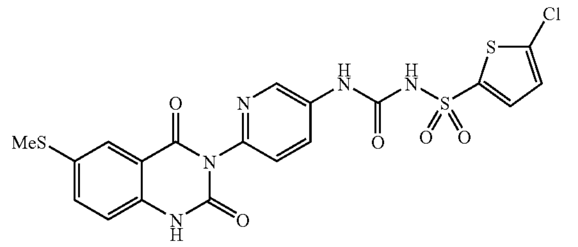
Example 315
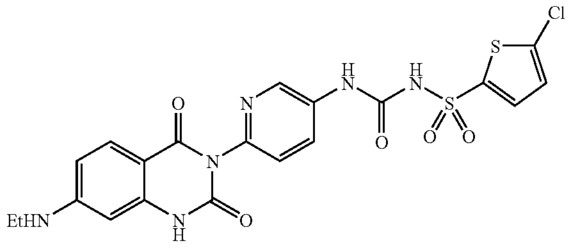

Example 316
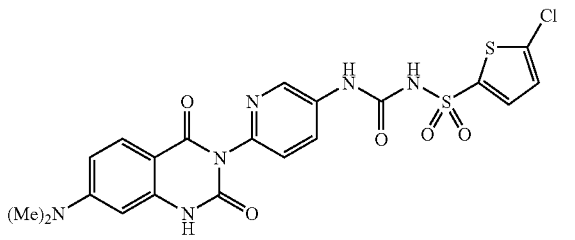
Example 317
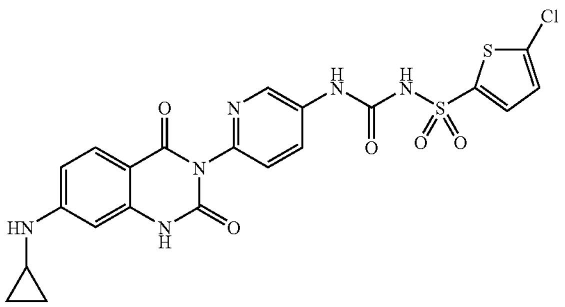
Example 318
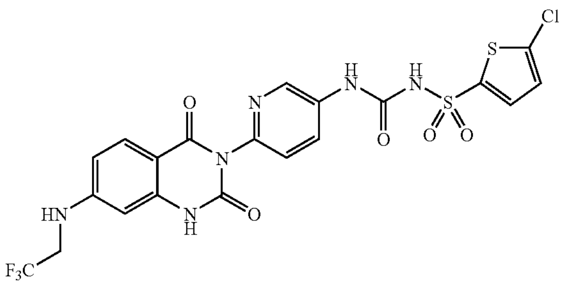
Example 319
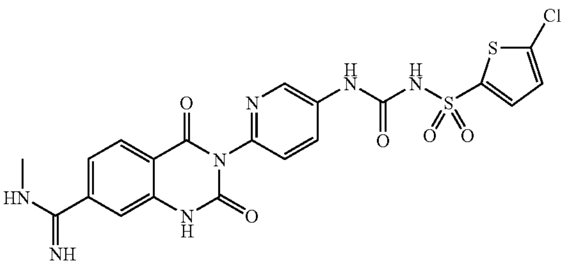
Example 320
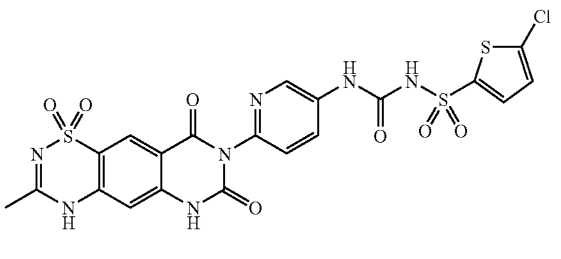
Example 321
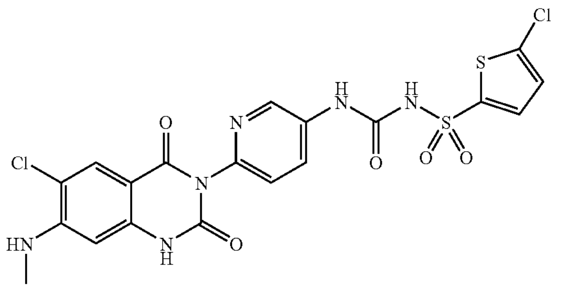
Example 322
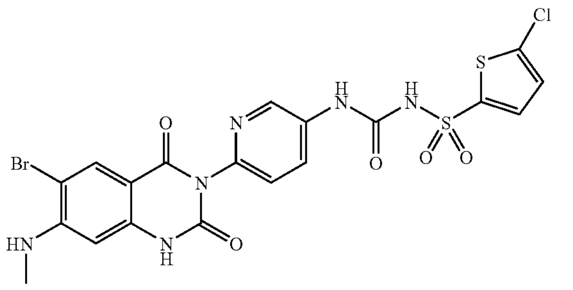
Example 323
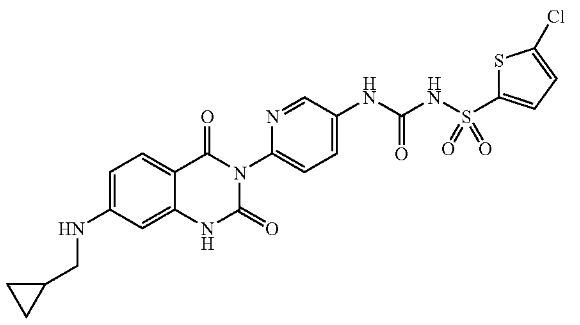
Example 324
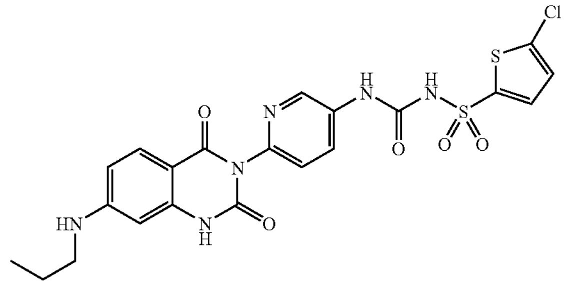
Example 325
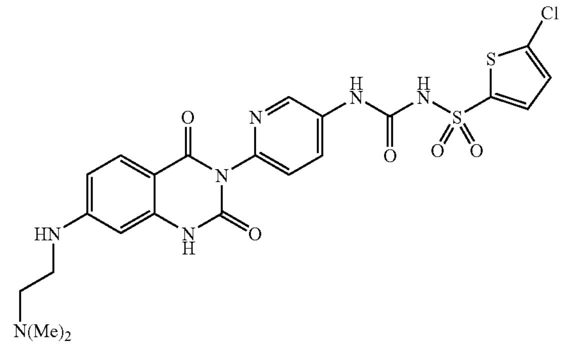

-continued
Example 326
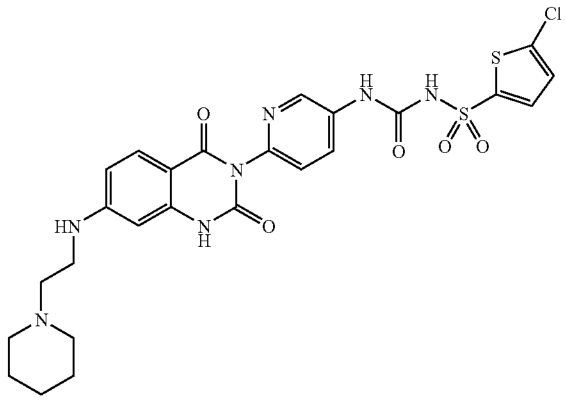
Example 327
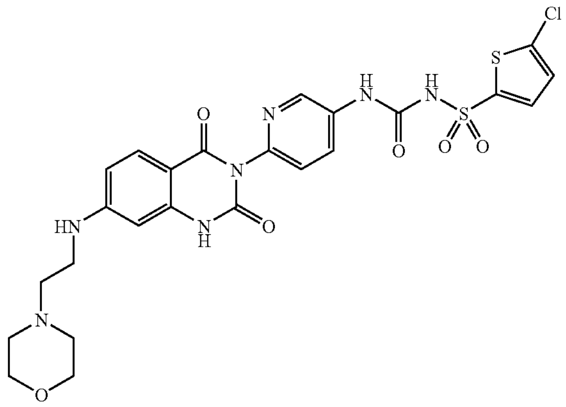
Example 328
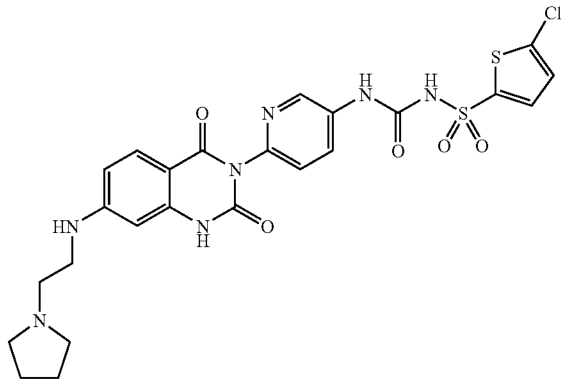
Example 329
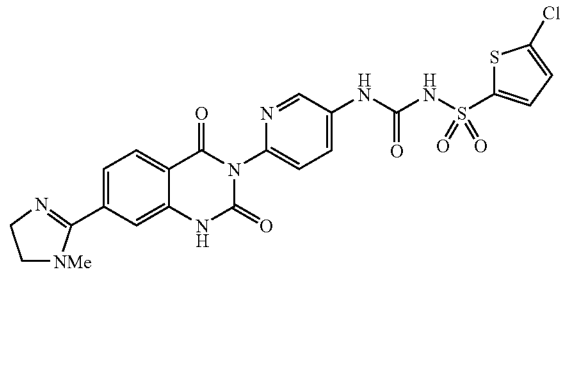
-continued
Example 330
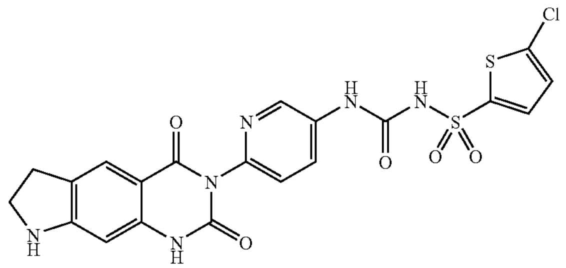
Example 331
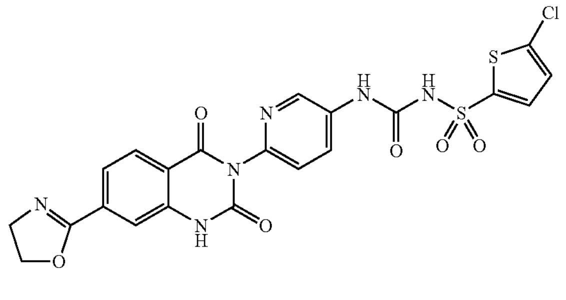
Example 332
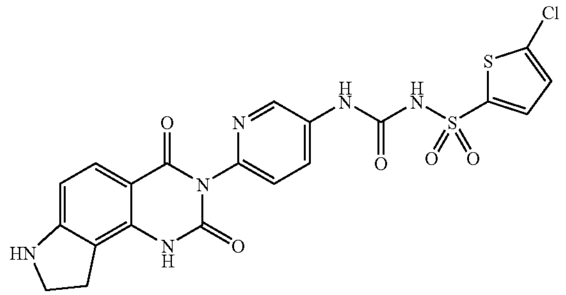
Example 333
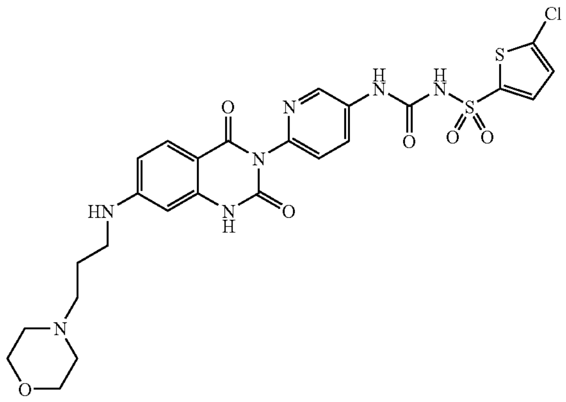

-continued
Example 334
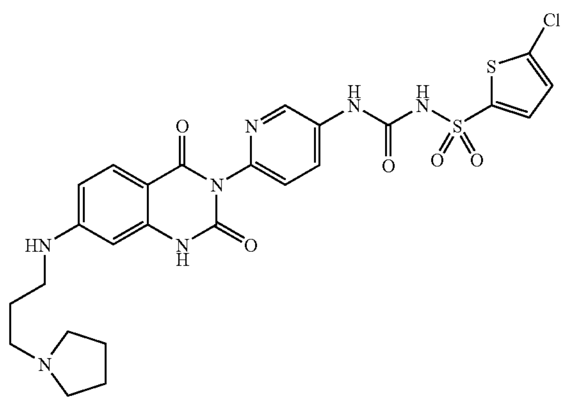
Example 335
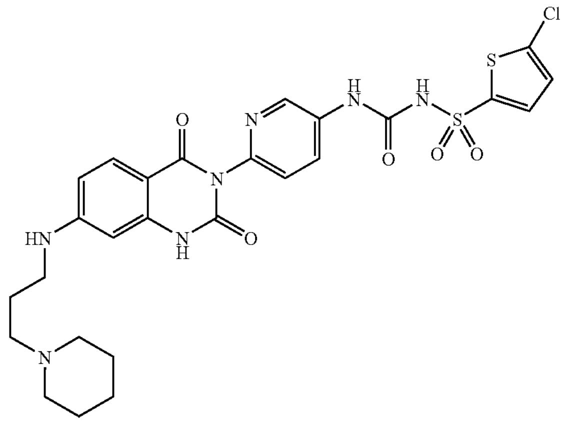
Example 336
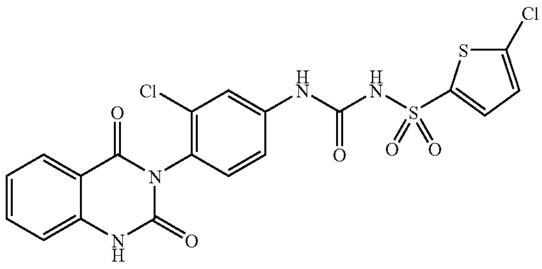
Example 337
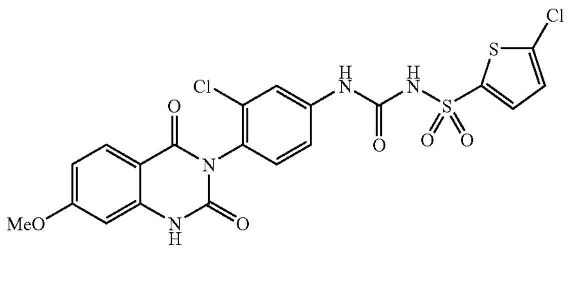
-continued
Example 338
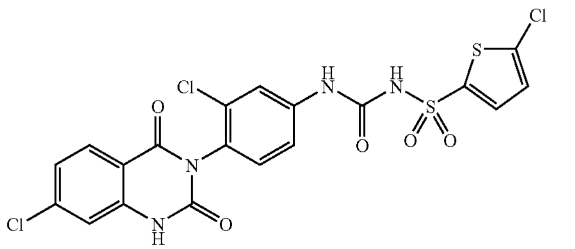
Example 339
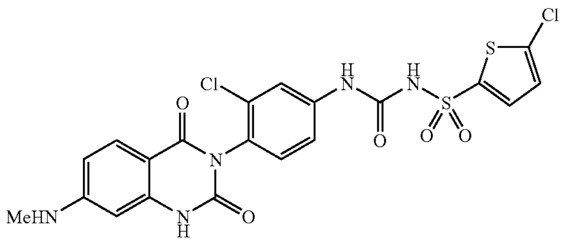
Example 340
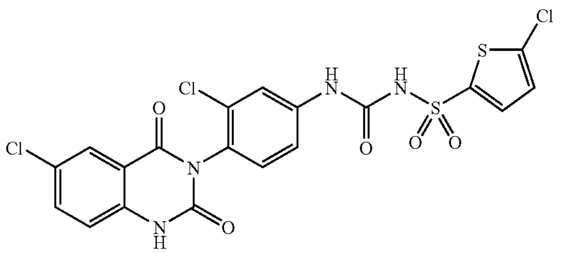
Example 341
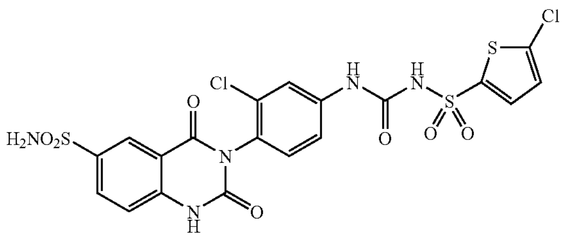
Example 342
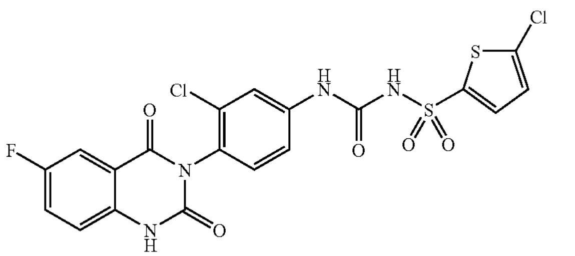
Example 343
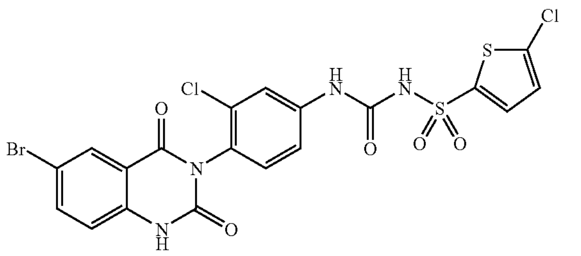

-continued
Example 344
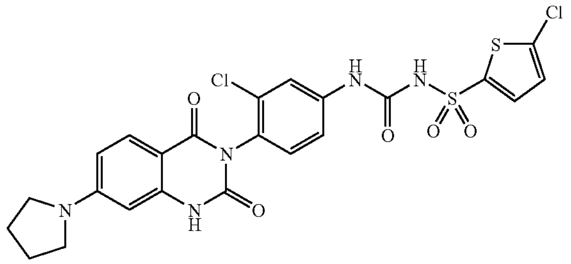
Example 345
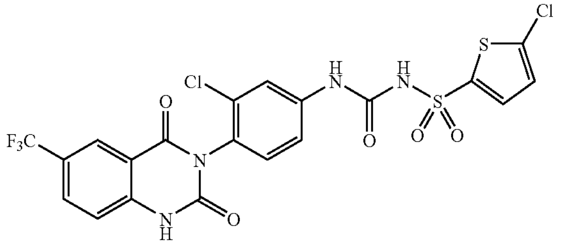
Example 346
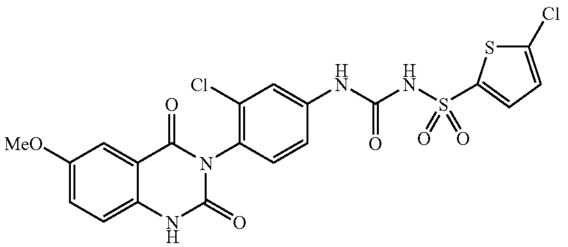
Example 347
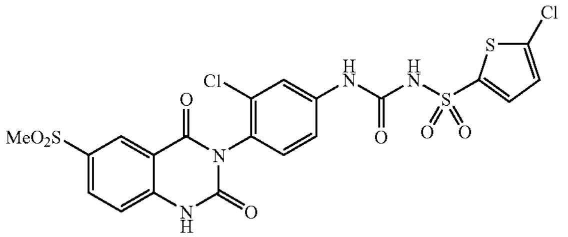
Example 348
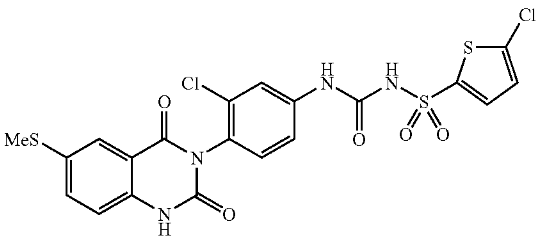
Example 349
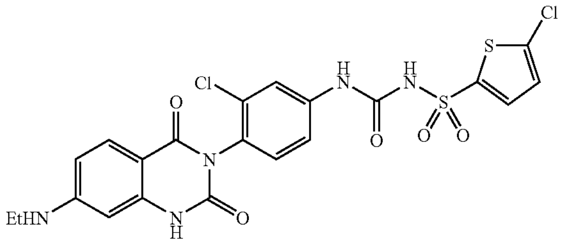
-continued
Example 350
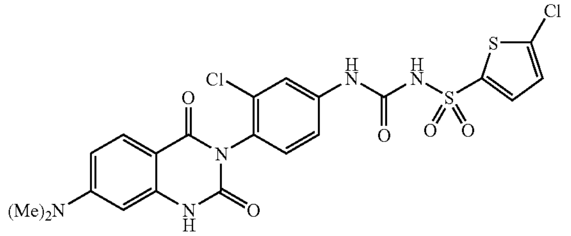
Example 351
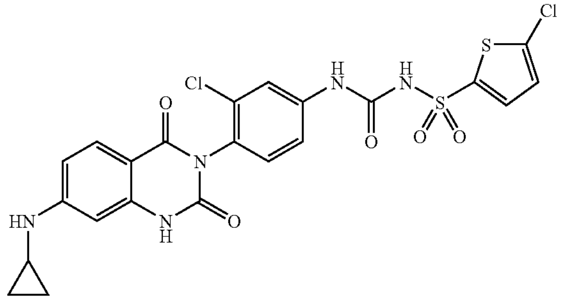
Example 352
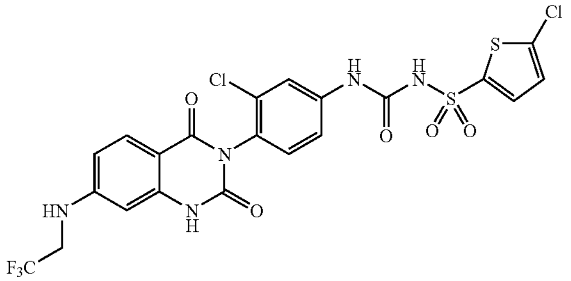
Example 353
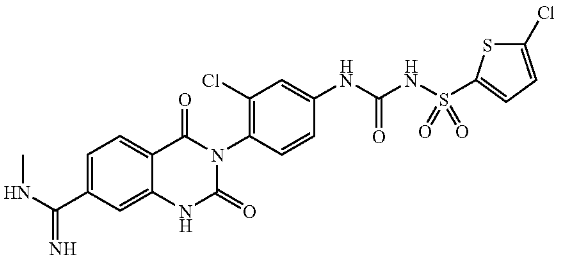
Example 354
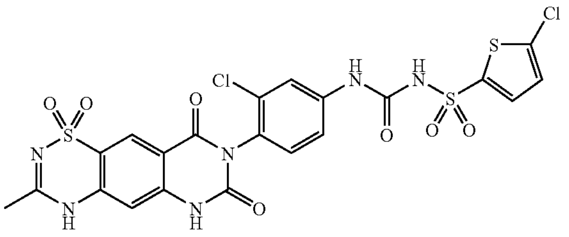

-continued
Example 355
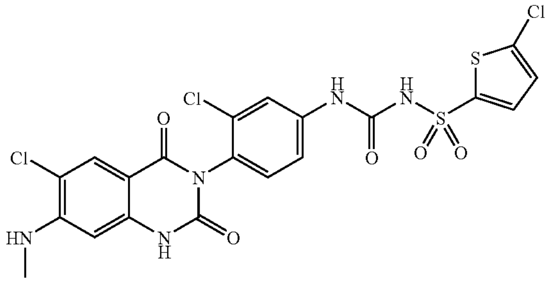
Example 356
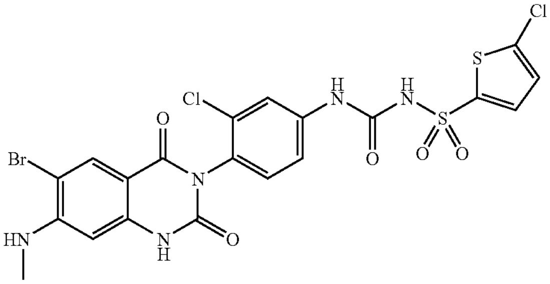
Example 357
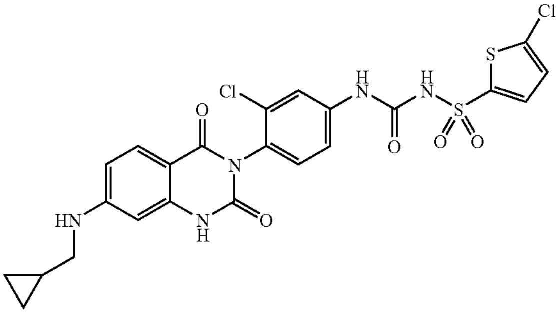
Example 358
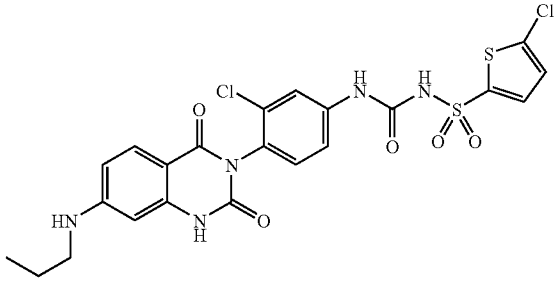
Example 359
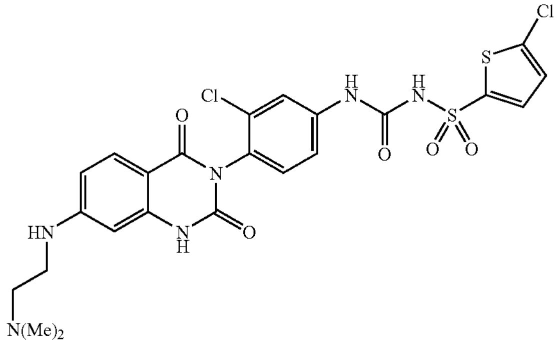
-continued
Example 360
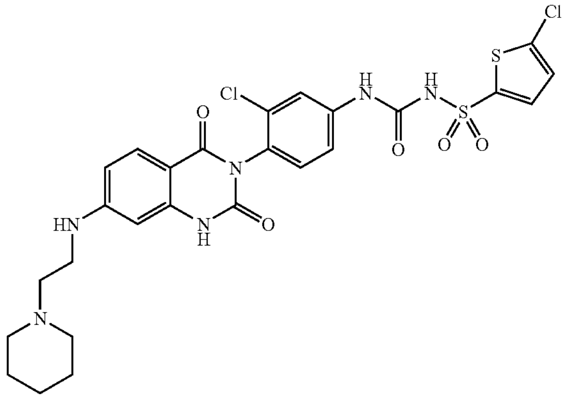
Example 361
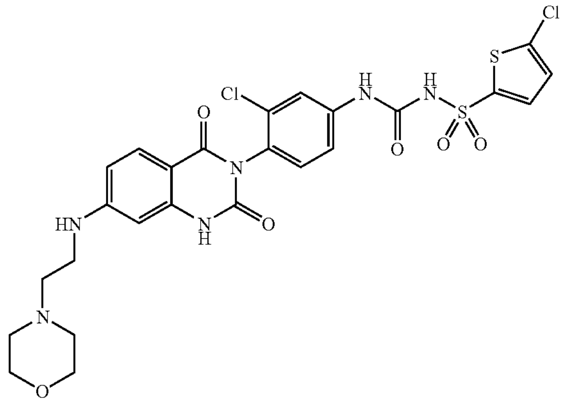
Example 362
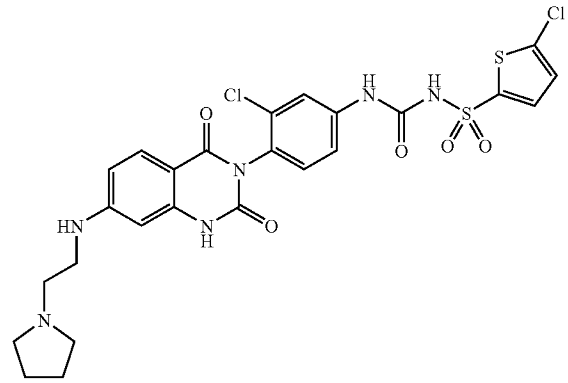
Example 363
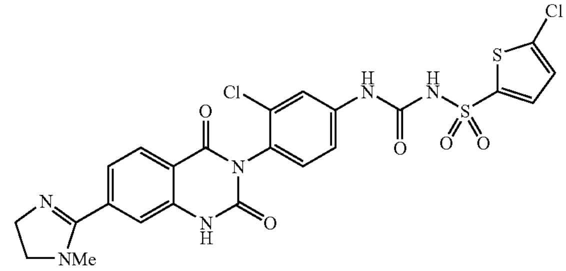

-continued
Example 364
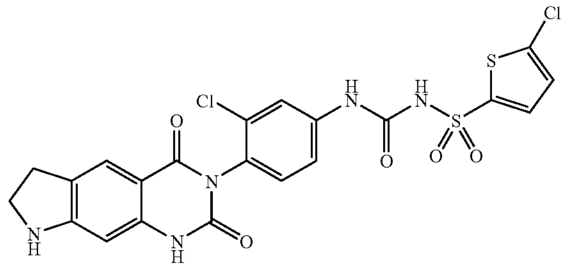
Example 365
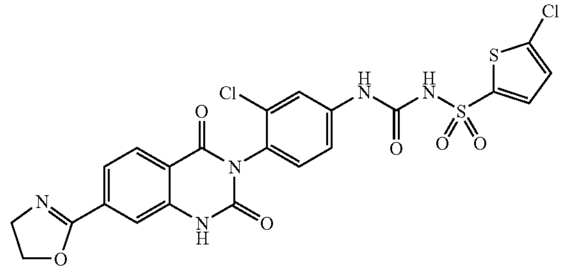
Example 366
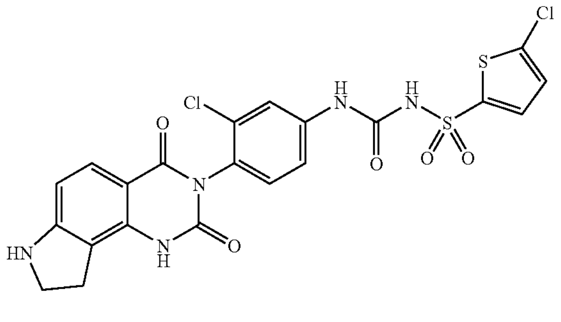
Example 367
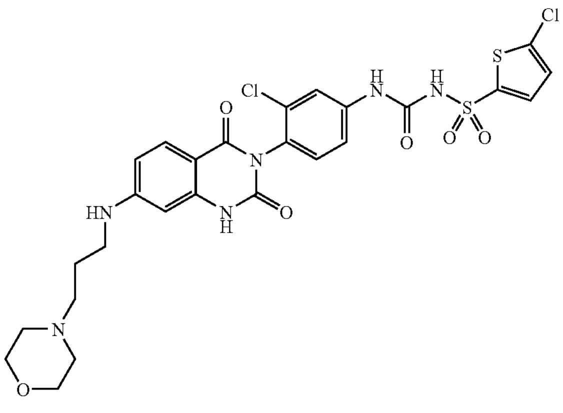
-continued
Example 368
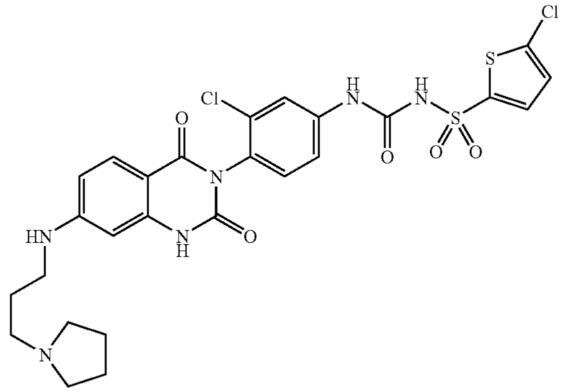
Example 369
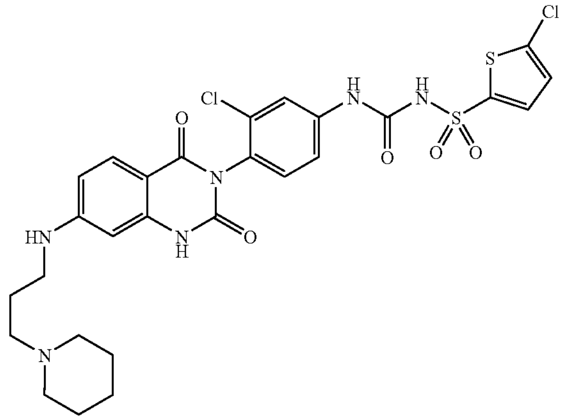
Example 370
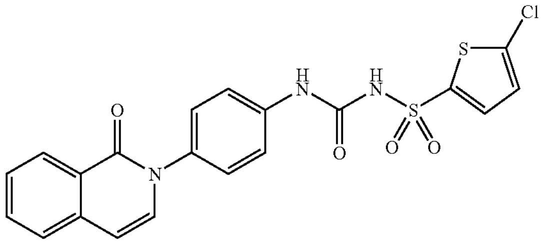
Example 371
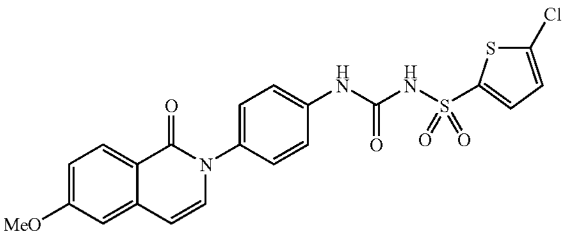
Example 372
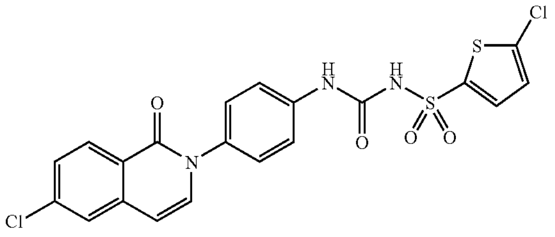

-continued
Example 373
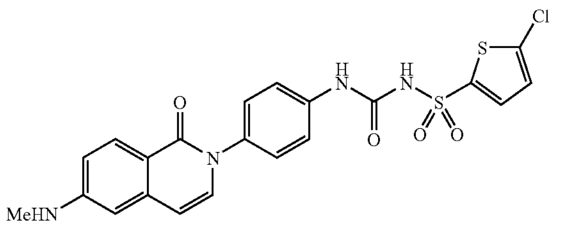
Example 374
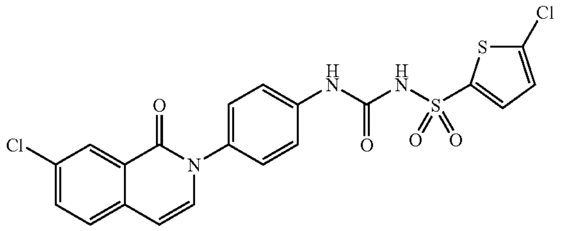
Example 375
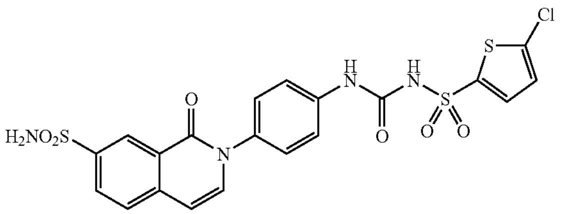
Example 376
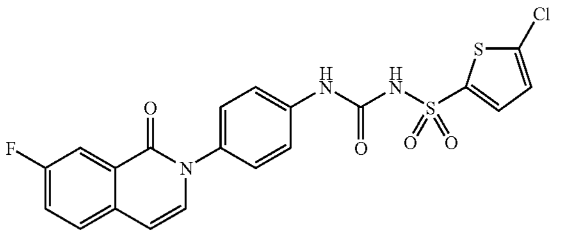
Example 377
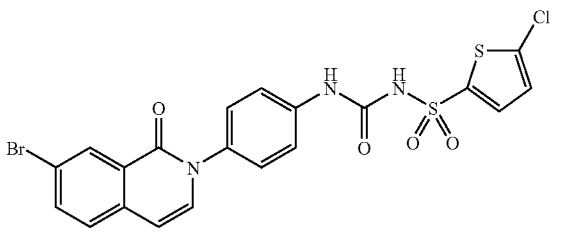
Example 378
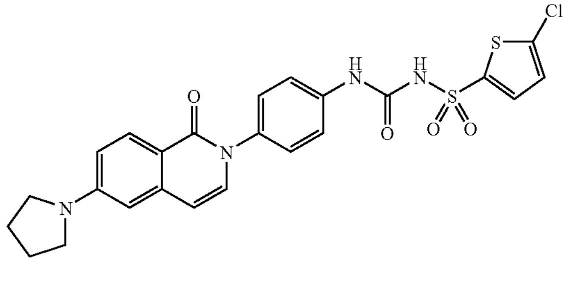
-continued
Example 379
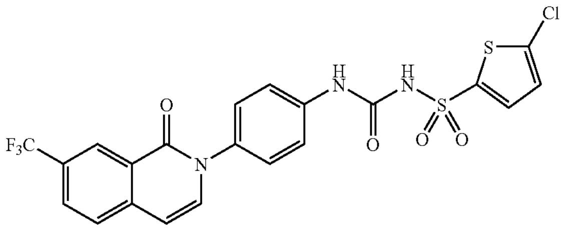
Example 380
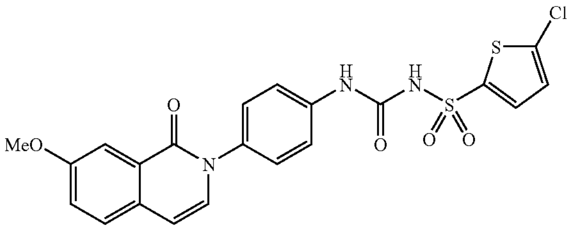
Example 381
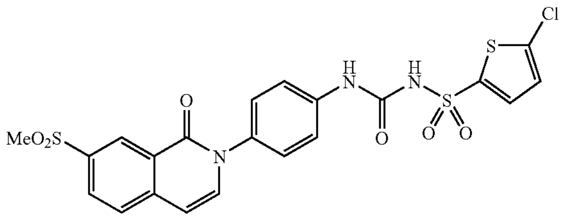
Example 382
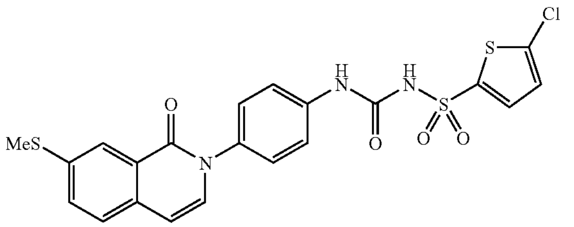
Example 383
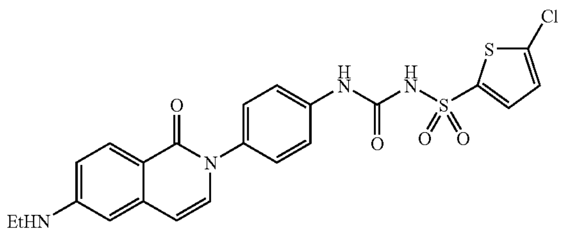
Example 384
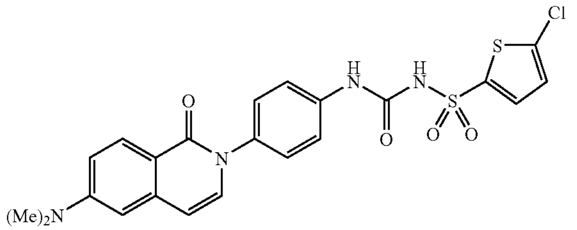

-continued
Example 385
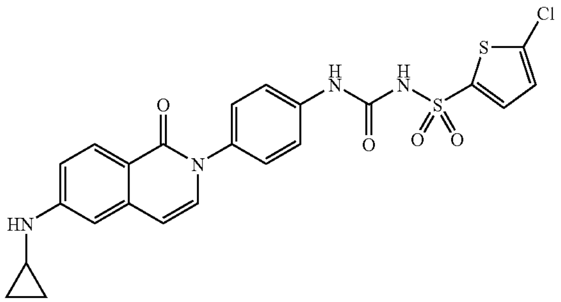
Example 386
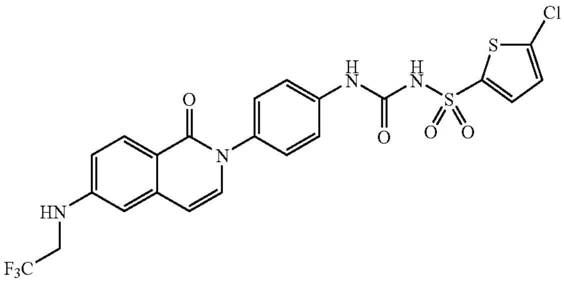
Example 387
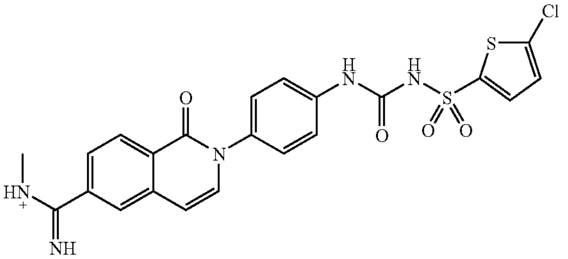
Example 388
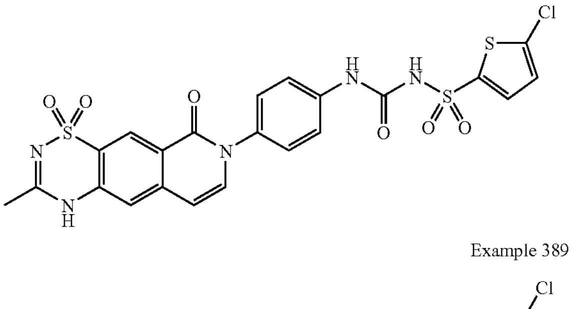
Example 389
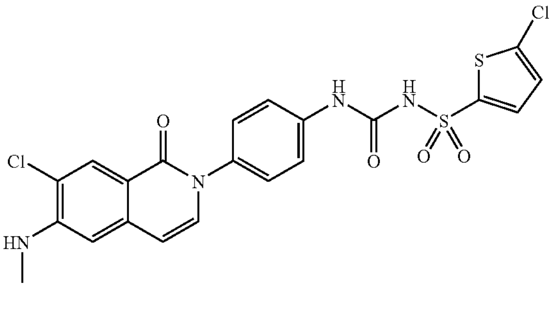
-continued
Example 390
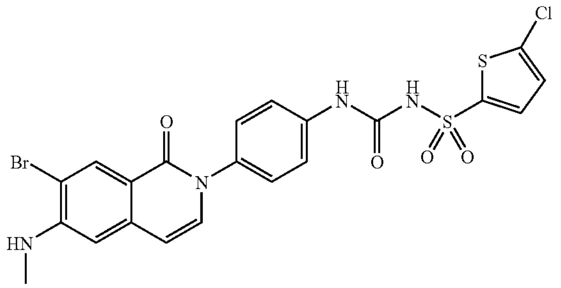
Example 391
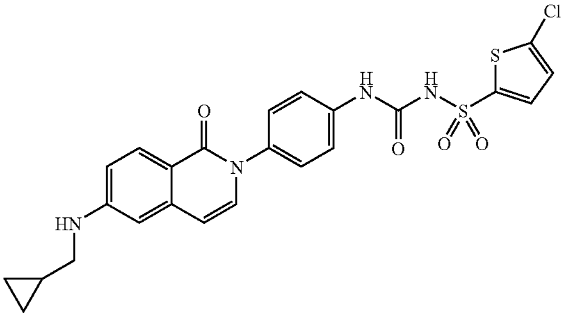
Example 392
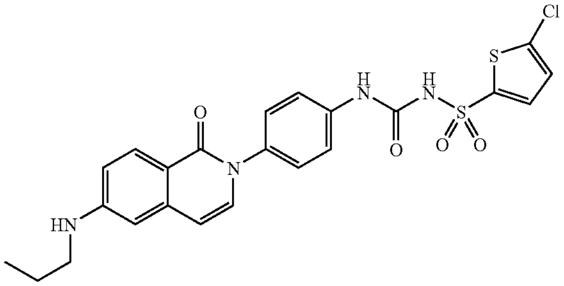
Example 393
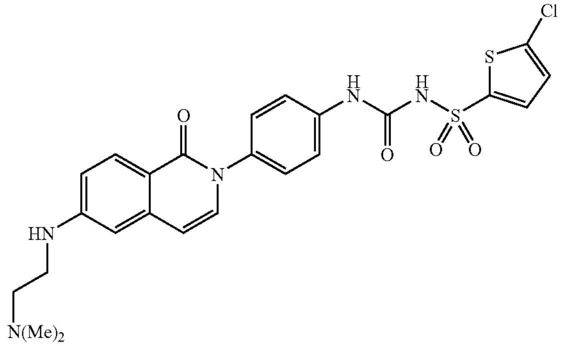

-continued
Example 394
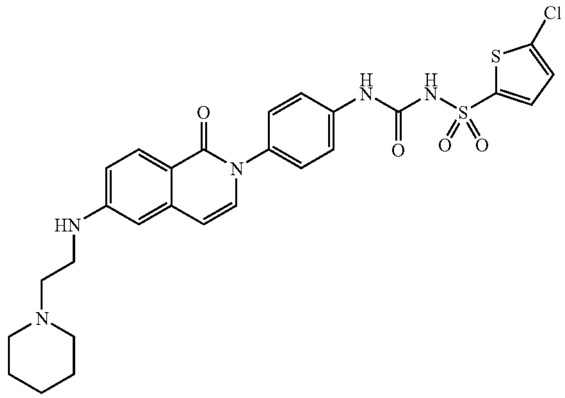
Example 395
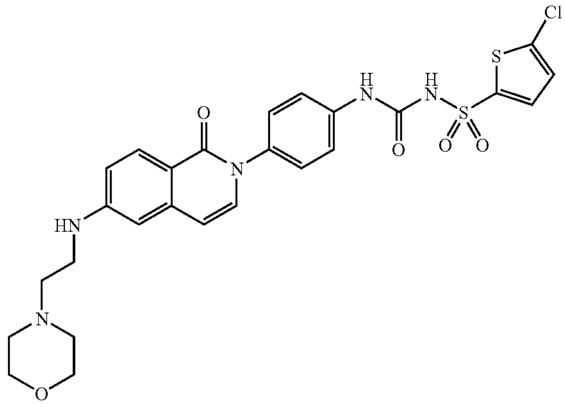
Example 396
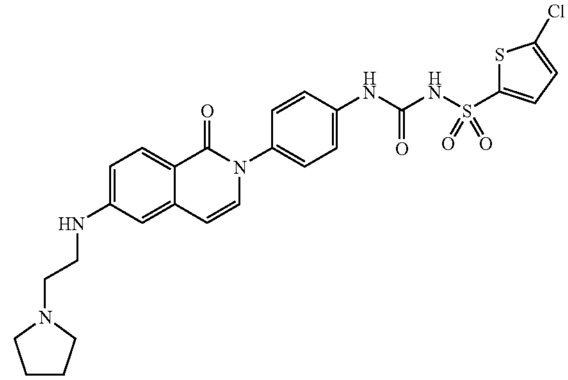
Example 397
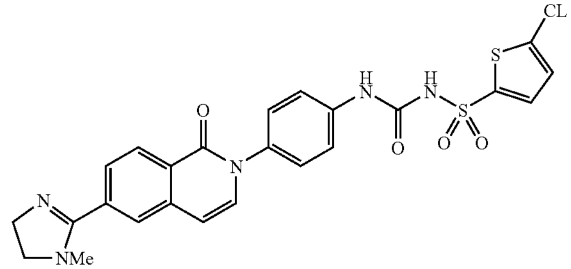
-continued
Example 398
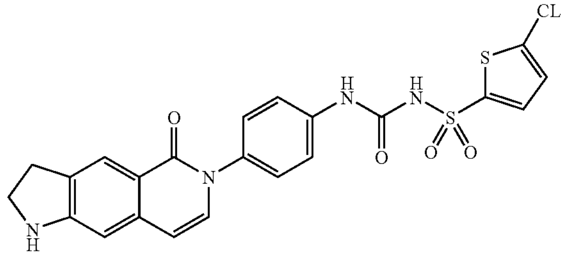
Example 399
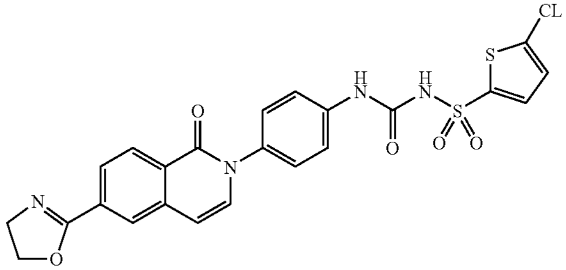
Example 400
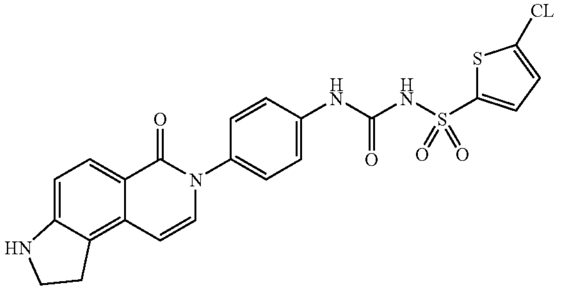
Example 401
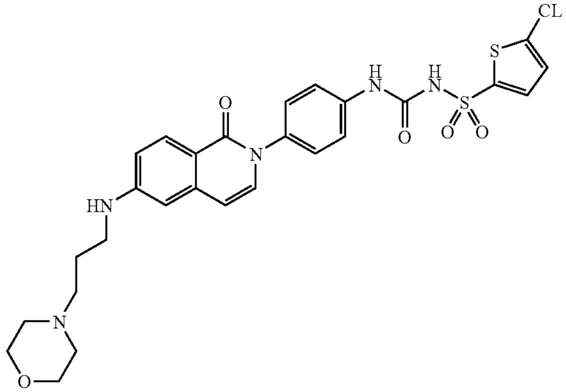

-continued
Example 402
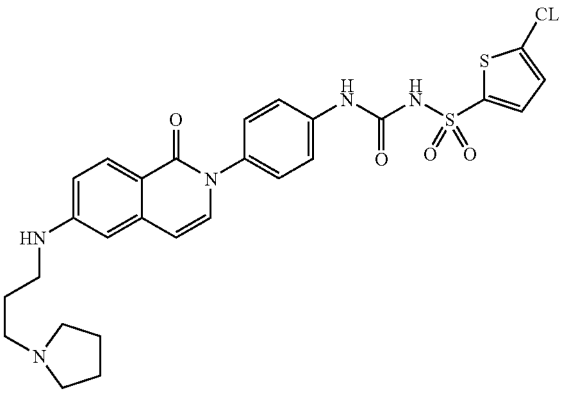
Example 403
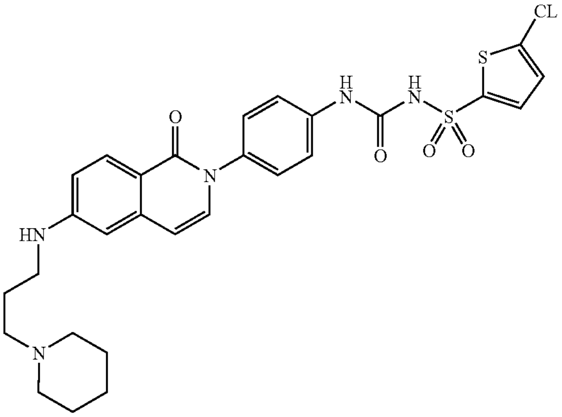
Example 404
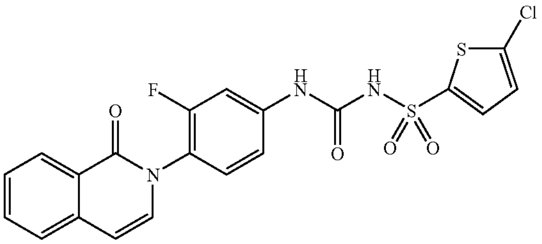
Example 405
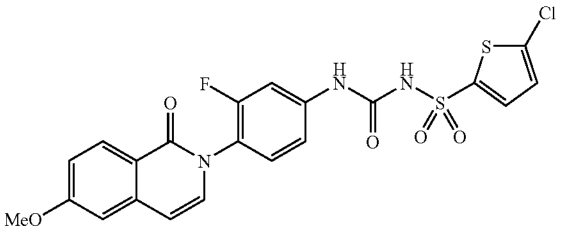
Example 406
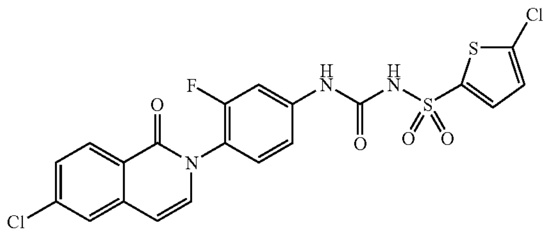
-continued
Example 407
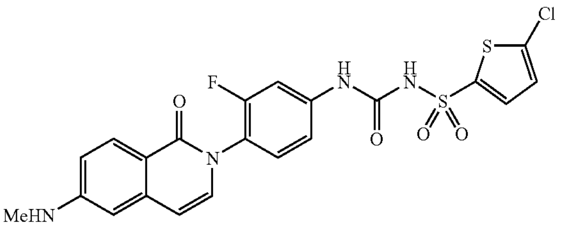
Example 408
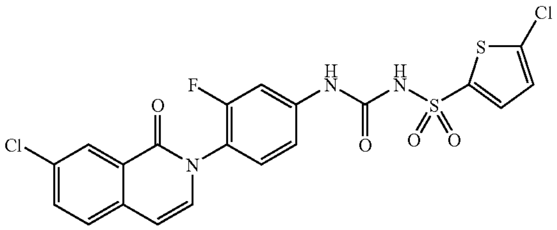
Example 409
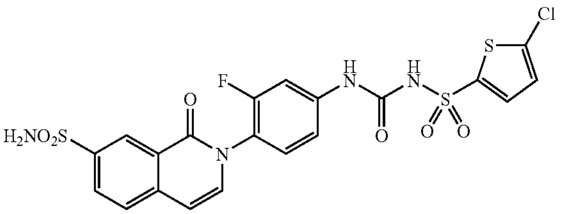
Example 410
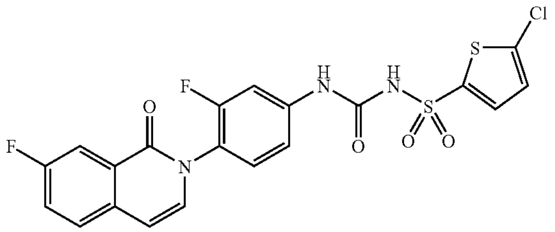
Example 411
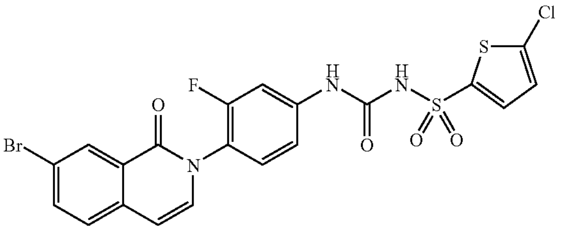
Example 412
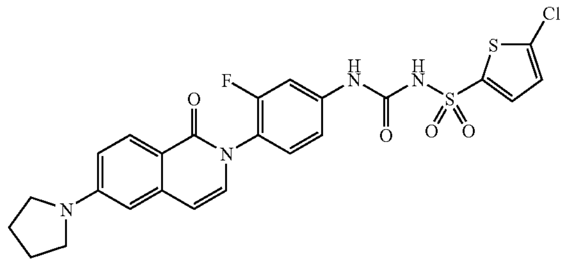

-continued
Example 413
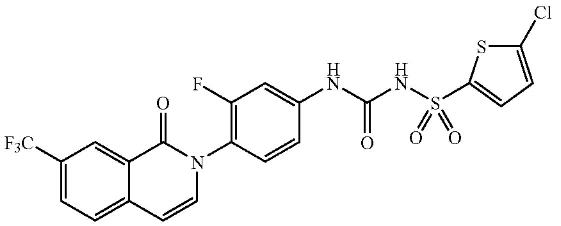
Example 414
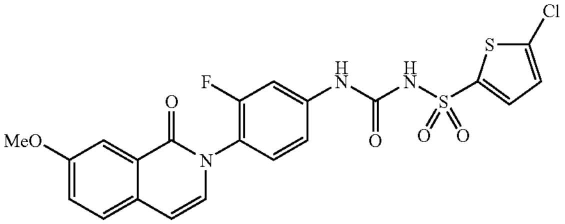
Example 415
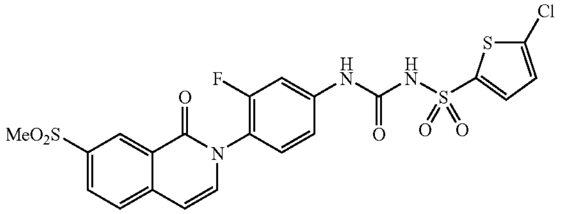
Example 416
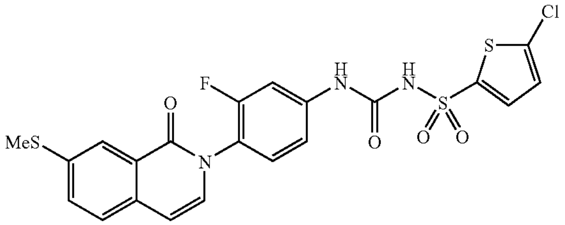
Example 417
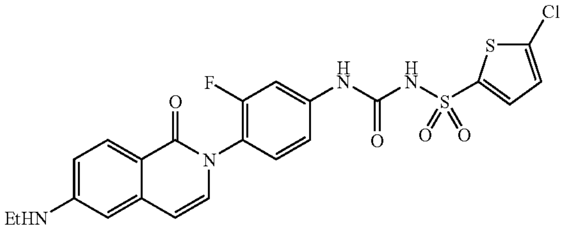
Example 418
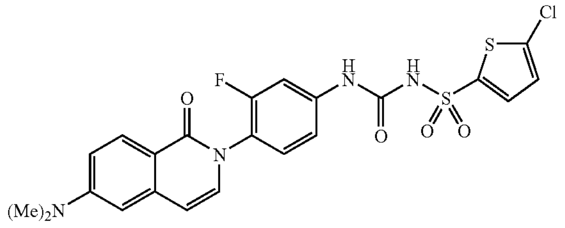
-continued
Example 419
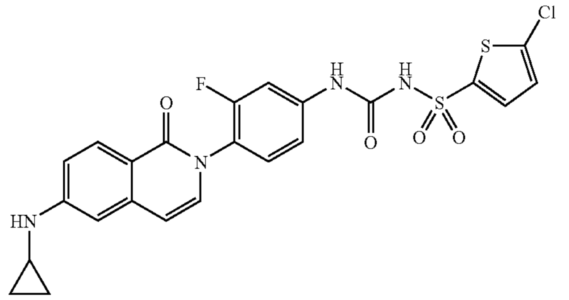
Example 420
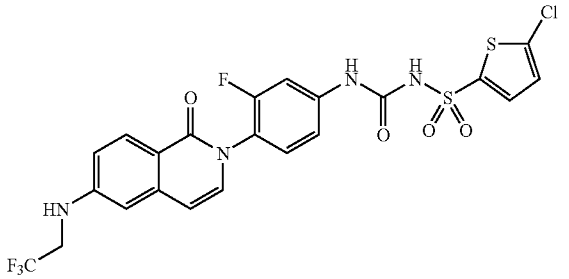
Example 421
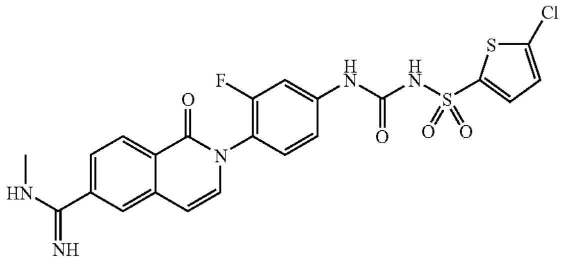
Example 422
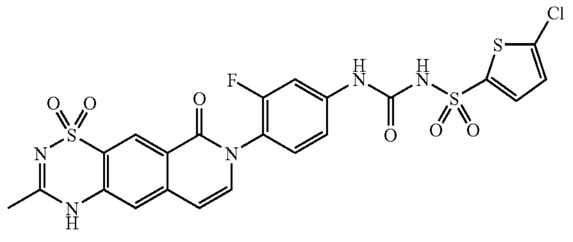
Example 423
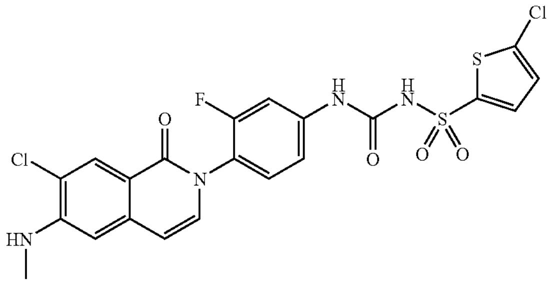

-continued
Example 424
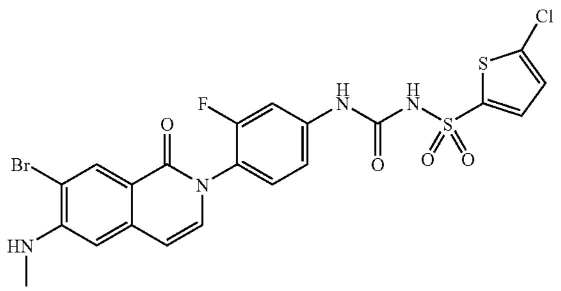
Example 425
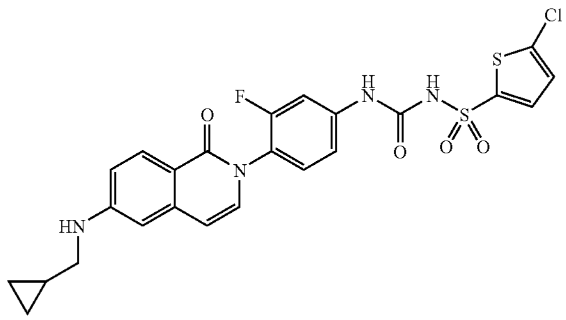
Example 426
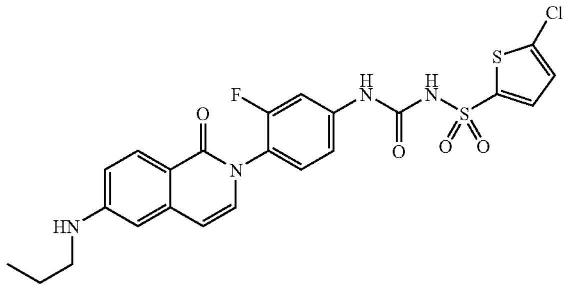
Example 427
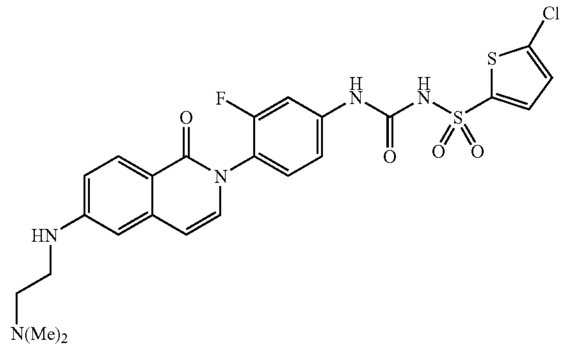
-continued
Example 428
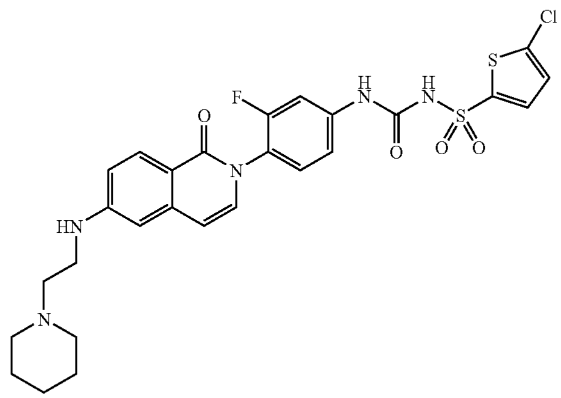
Example 429
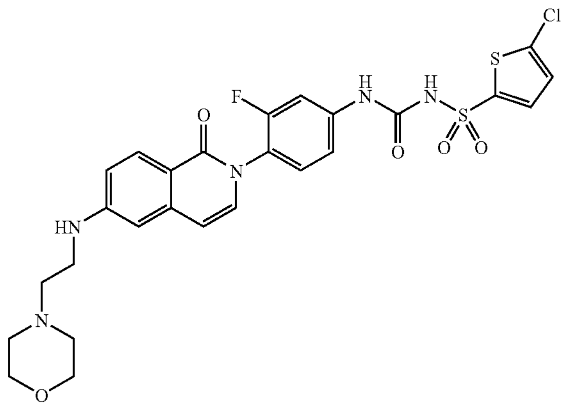
Example 430
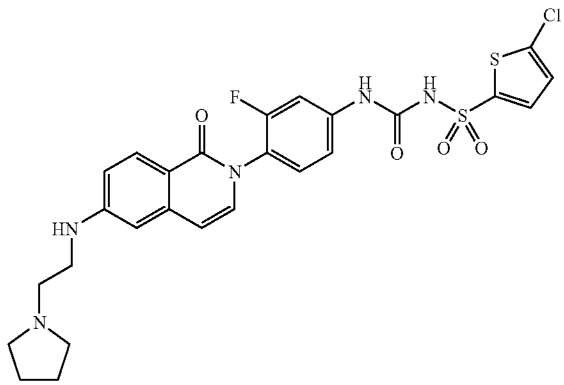
Example 431
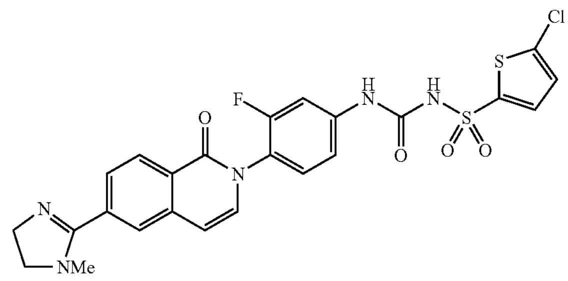

-continued
Example 432
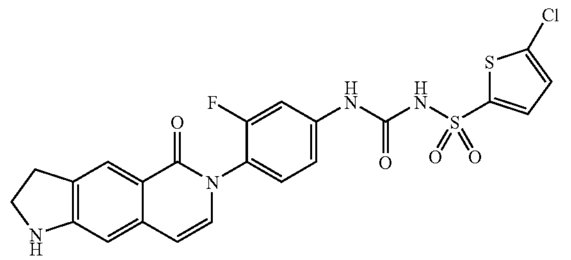
Example 433
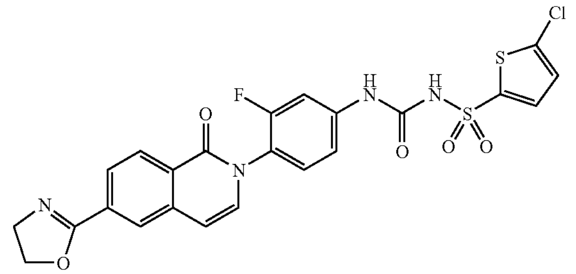
Example 434
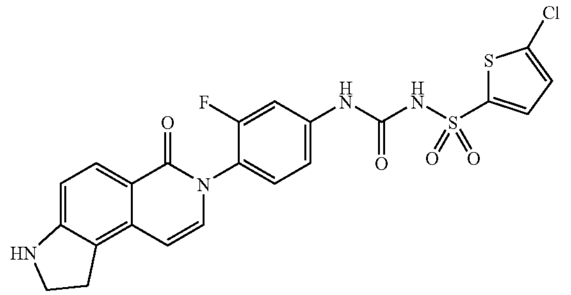
Example 435
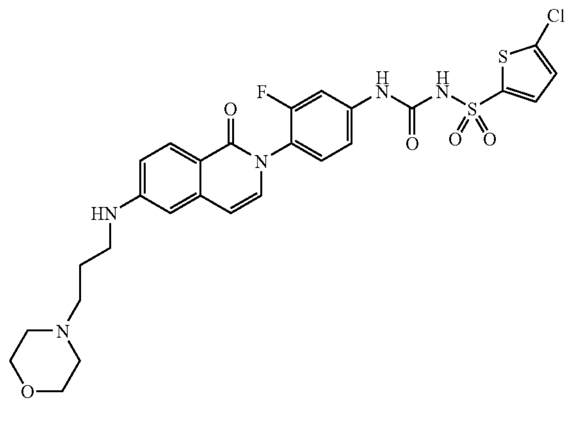
-continued
Example 436
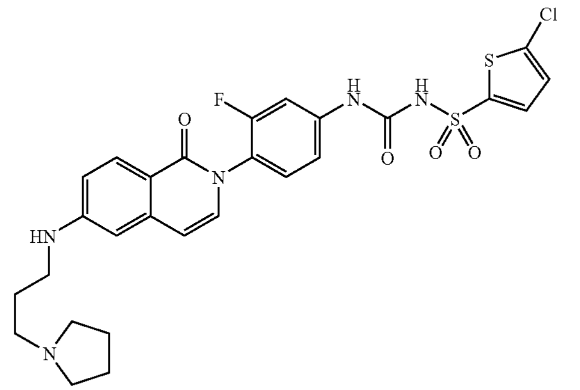
Example 437
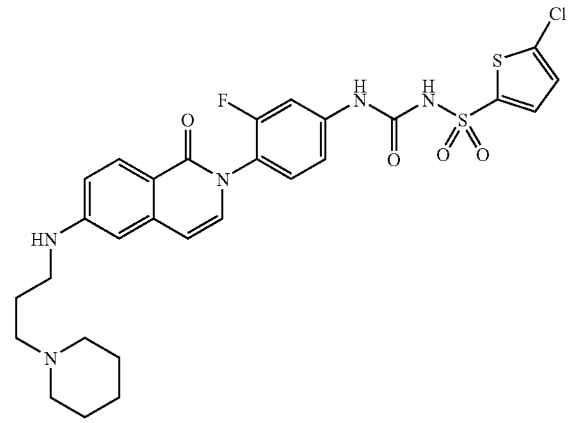
Example 438
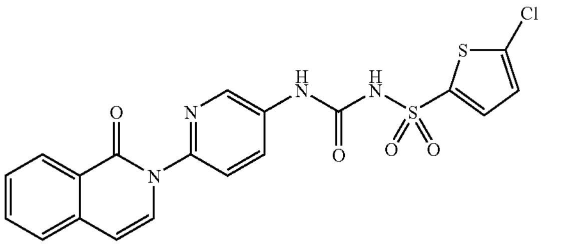
Example 439
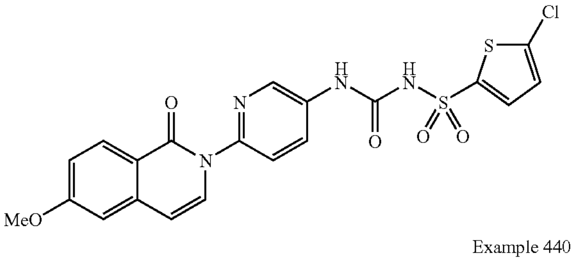
Example 440
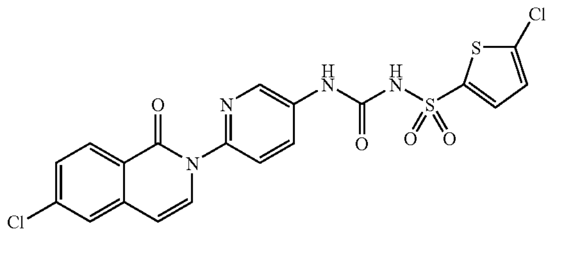

-continued
Example 441
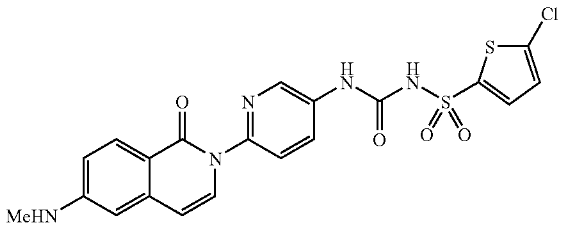
Example 442
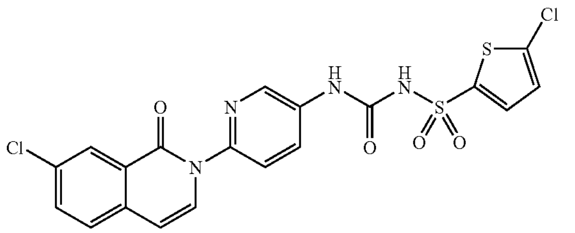
Example 443
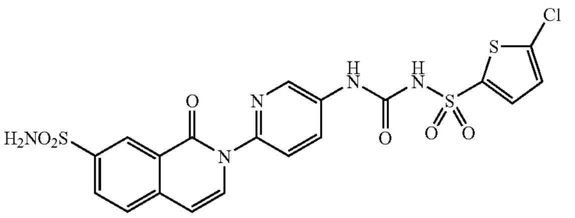
Example 444
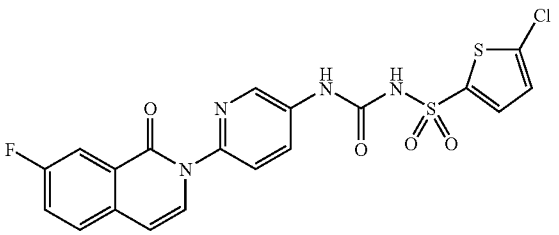
Example 445
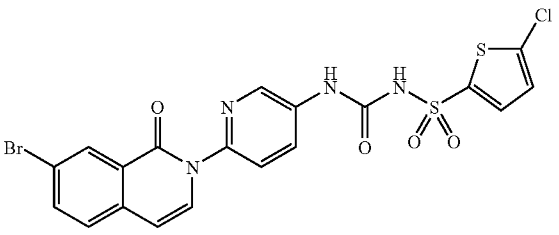
Example 446
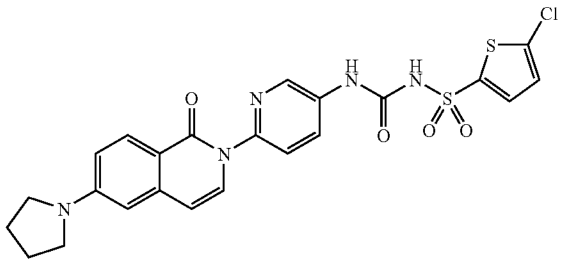
-continued
Example 447
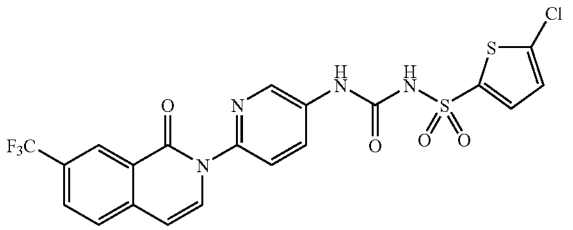
Example 448
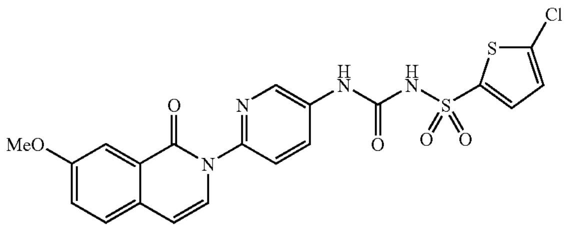
Example 449
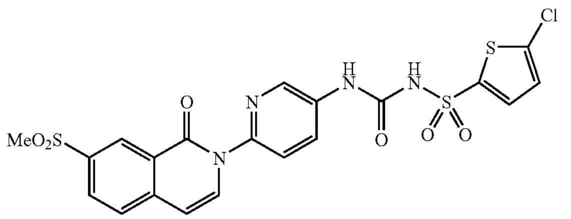
Example 450
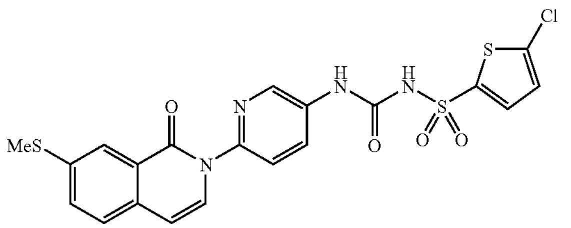
Example 451
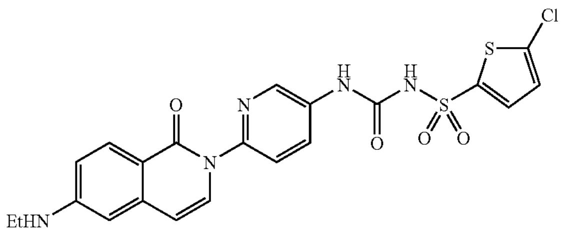
example 452
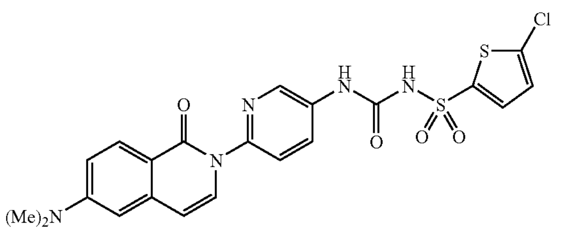

-continued
Example 453
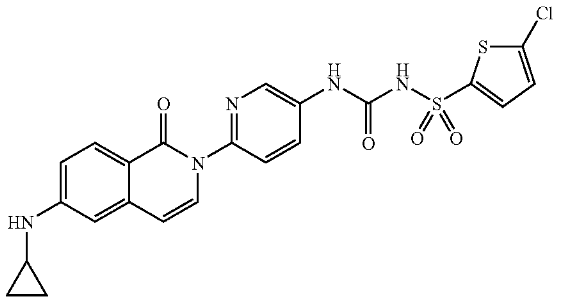
Example 454
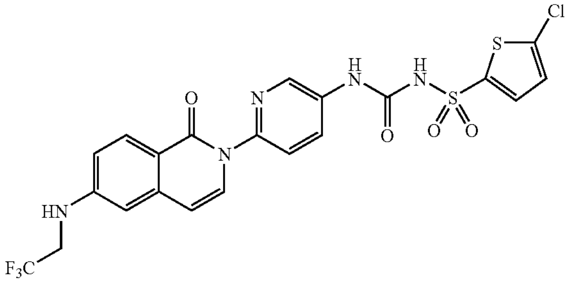
Example 455
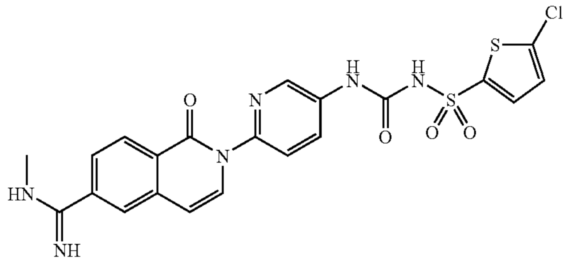
Example 456
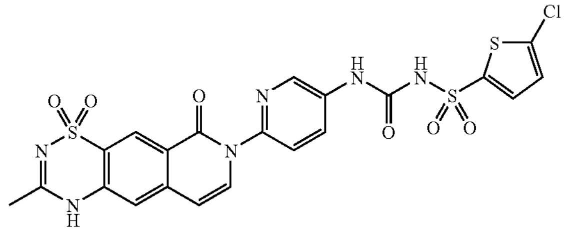
Example 457
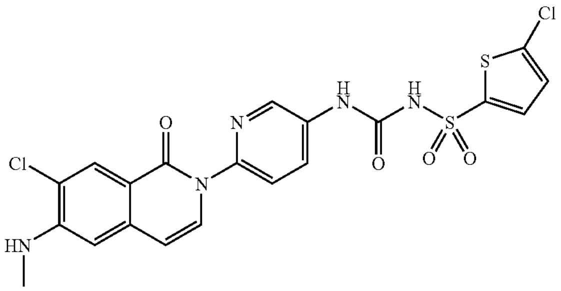
-continued
Example 458
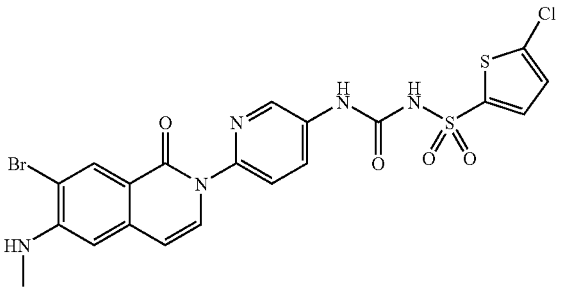
Example 459
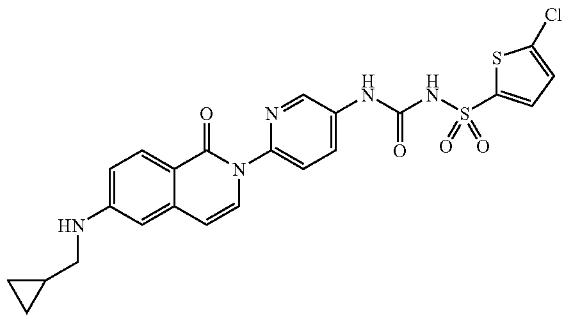
Example 460
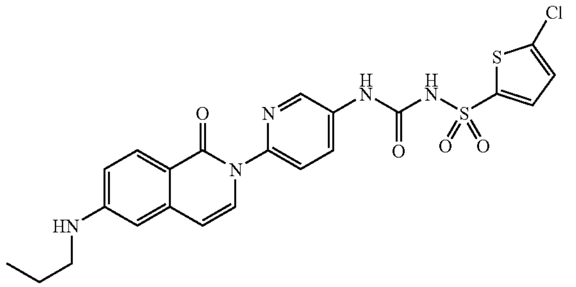
Example 461
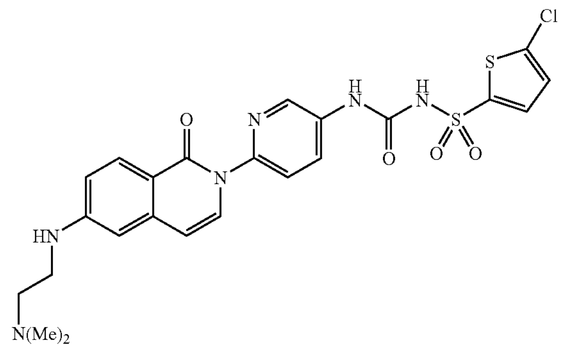

-continued
Example 462
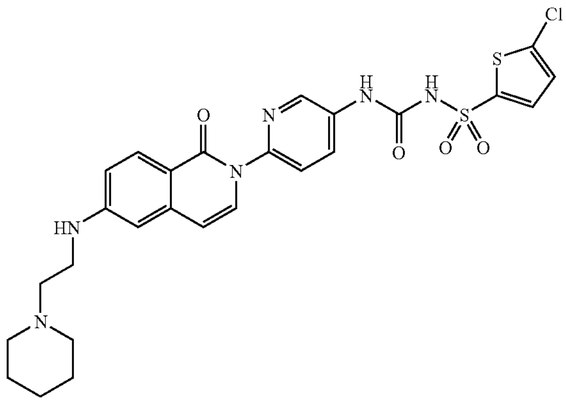
Example 463
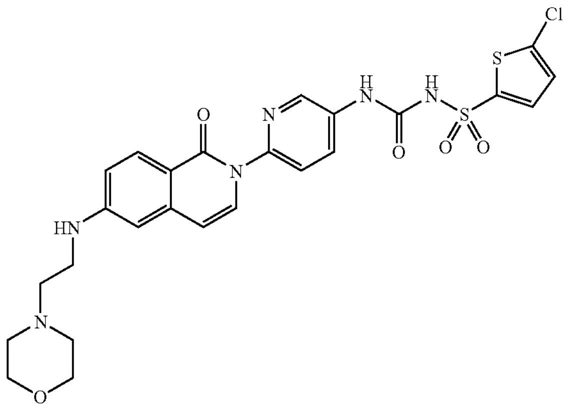
Example 464
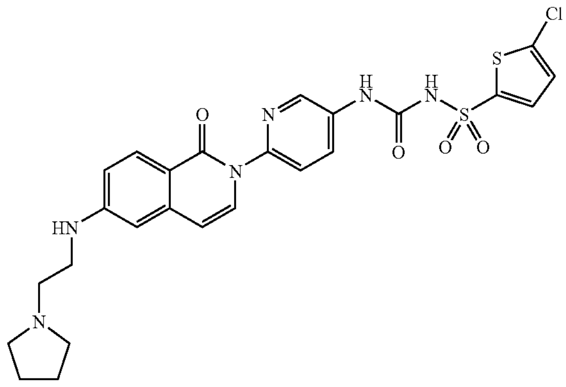
Example 465
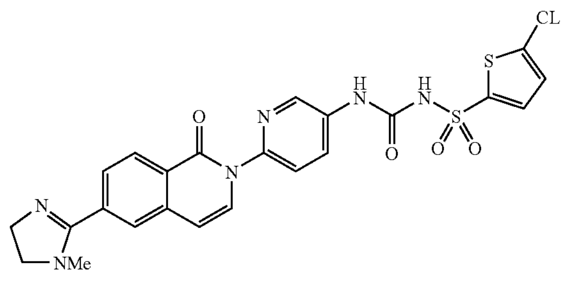
-continued
Example 466
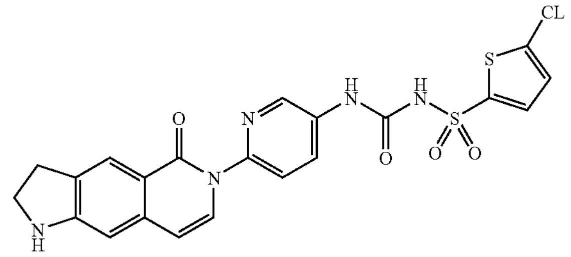
Example 467
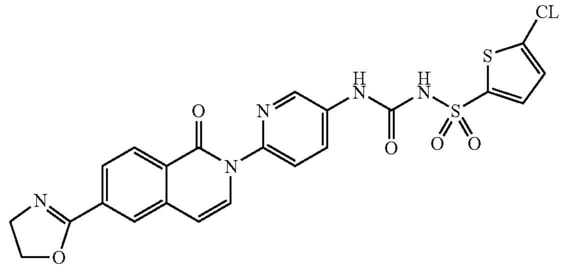
Example 468
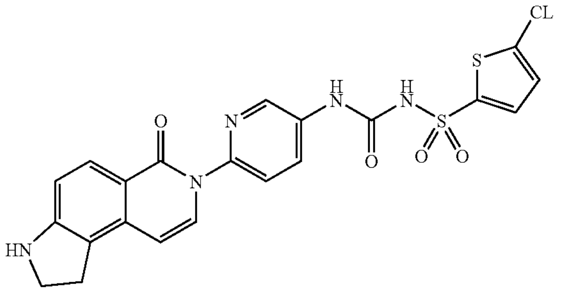
Example 469
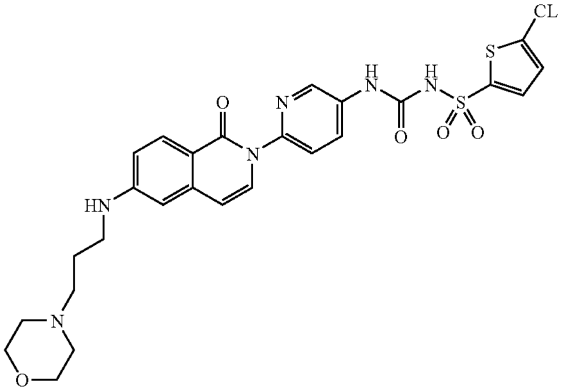

-continued
Example 470
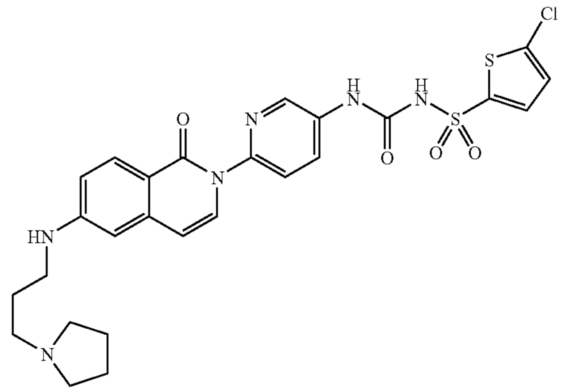
example 471
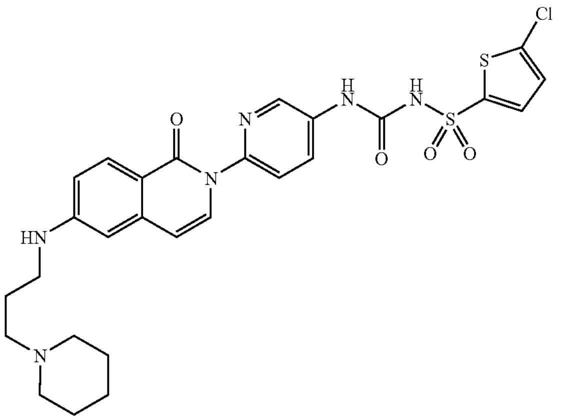
Example 472
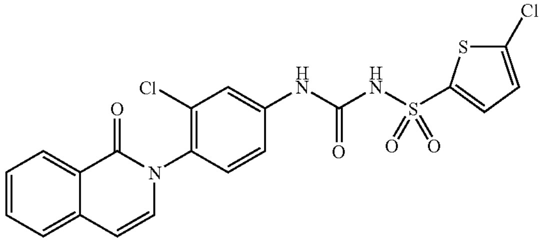
Example 473
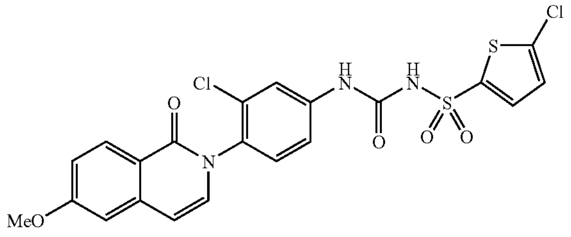
Example 474
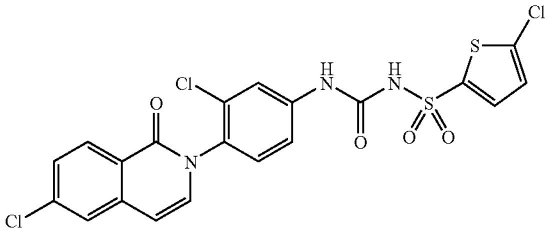
-continued
Example 475
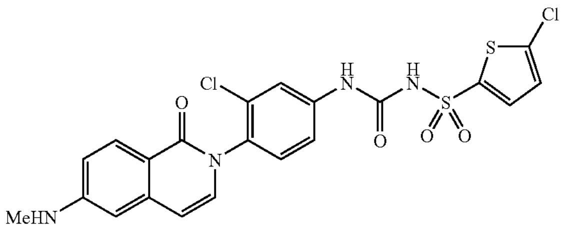
Example 476
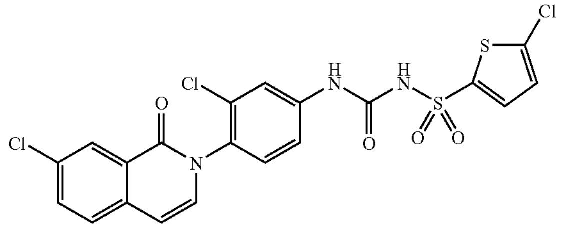
Example 477
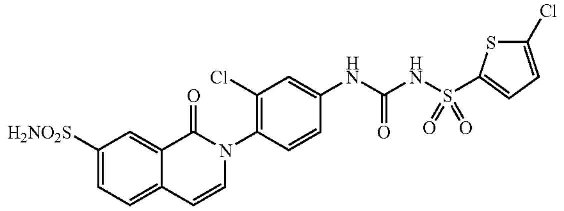
Example 478
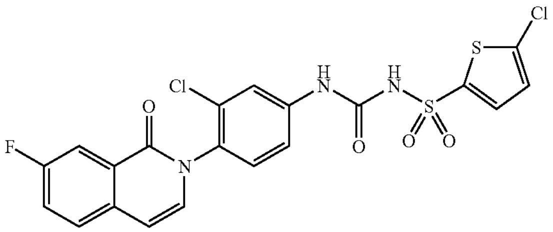
Example 479
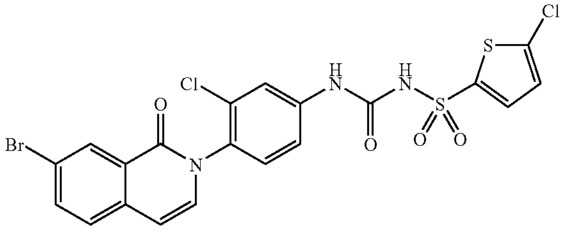
Example 480
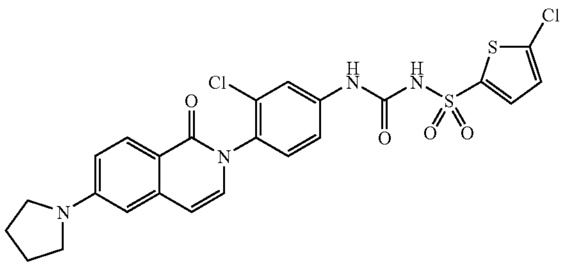

Example 481
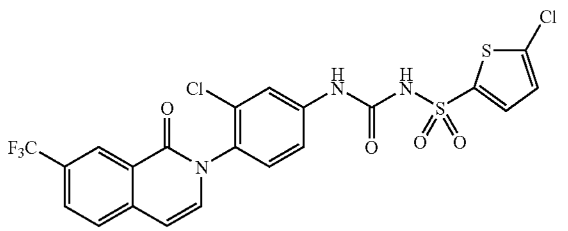
Example 482
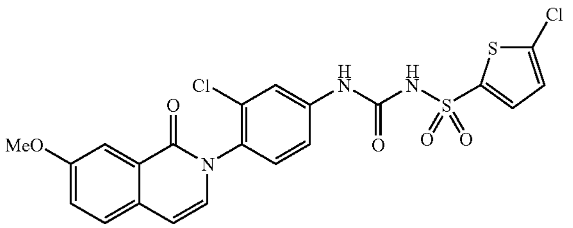
Example 483
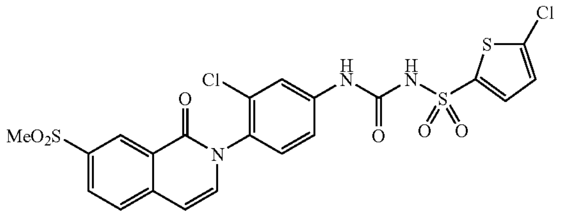
Example 484
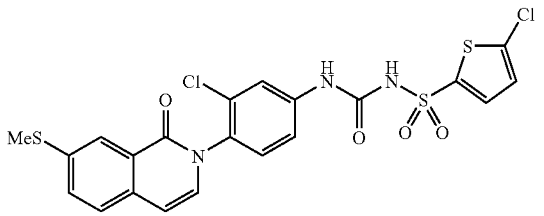
Example 485
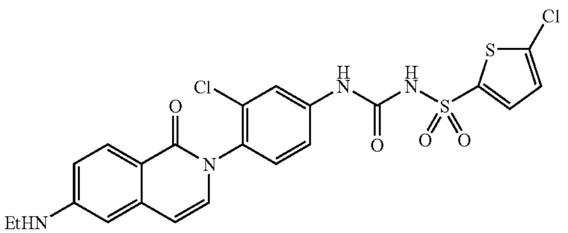
Example 486
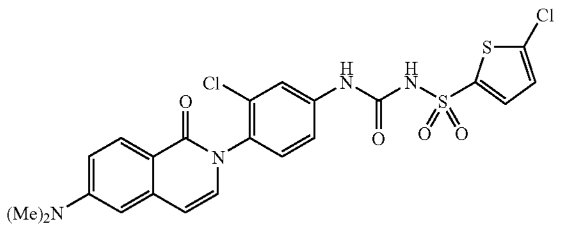
Example 487
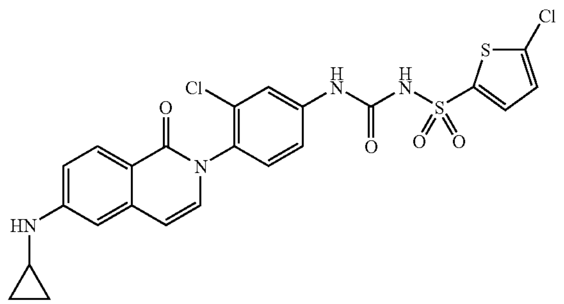
Example 488
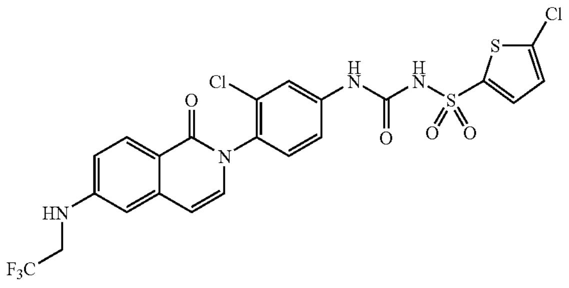
Example 489
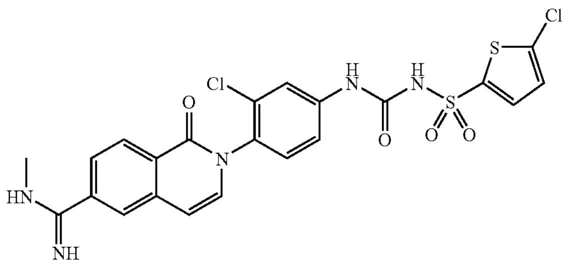
Example 490
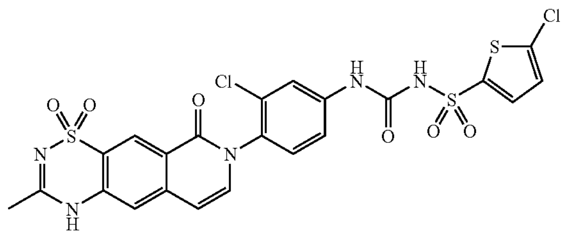
Example 491
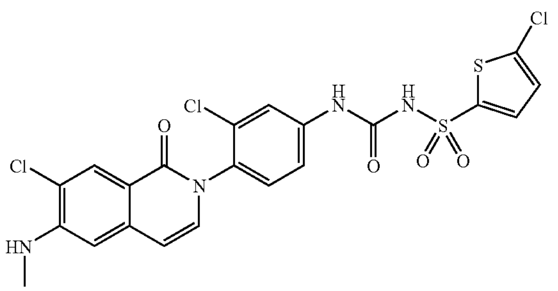

Example 492
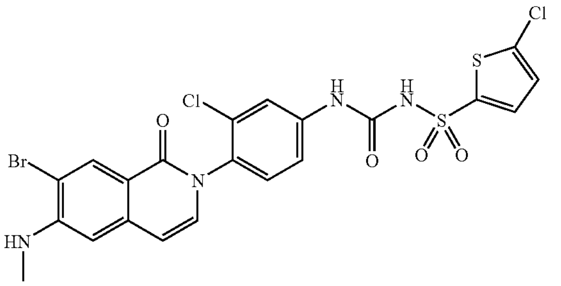
Example 493
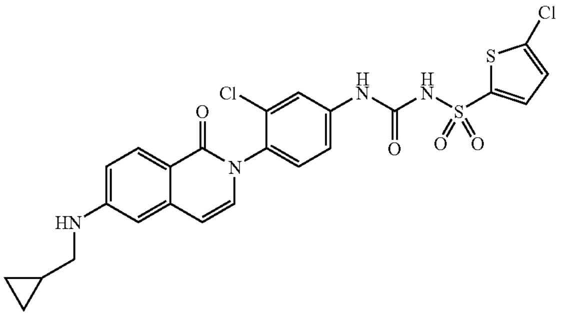
Example 494
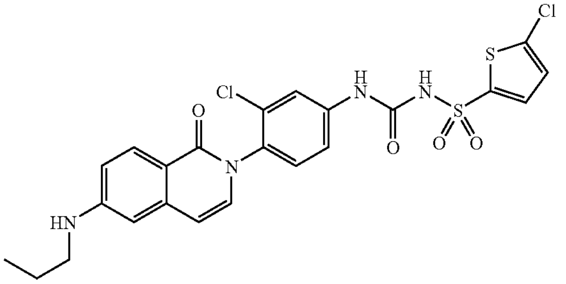
Example 495
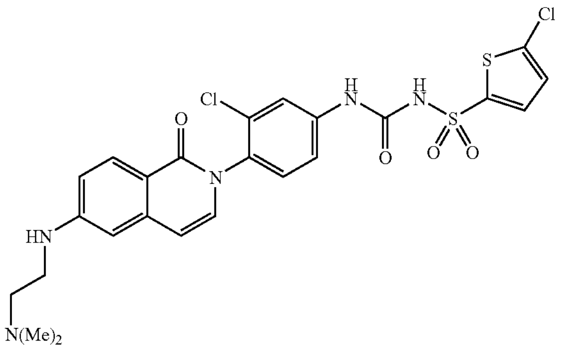
Example 496
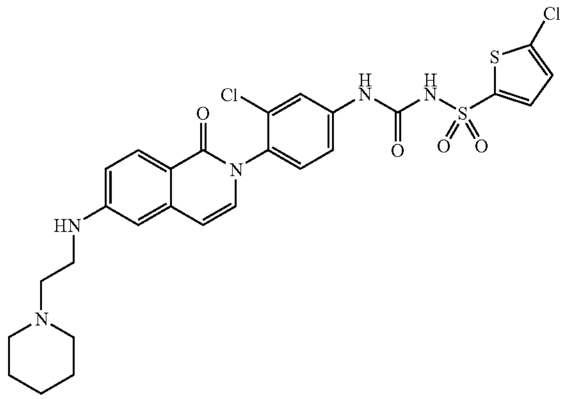
Example 497
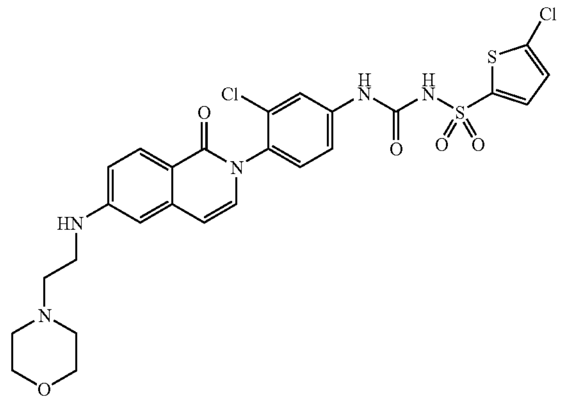
Example 498
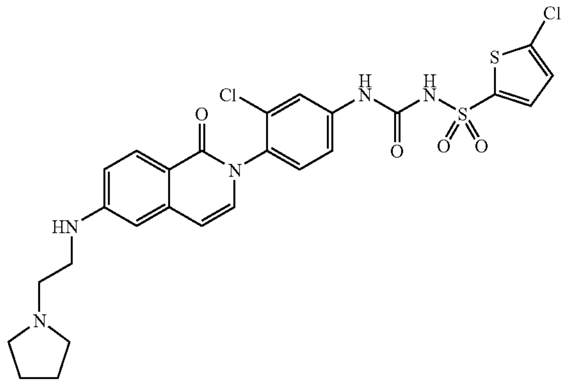
Example 499
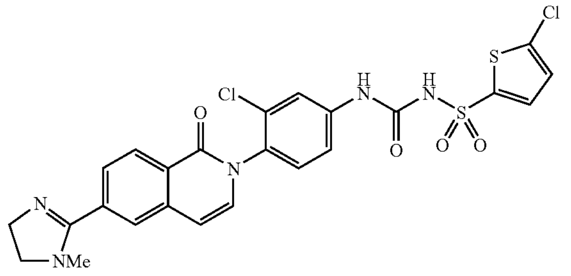

-continued
Example 500
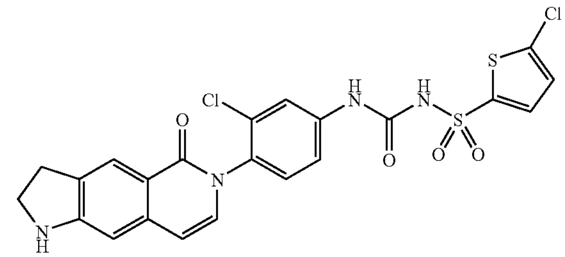
Example 501
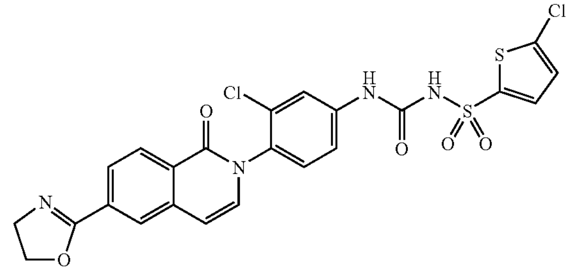
Example 502
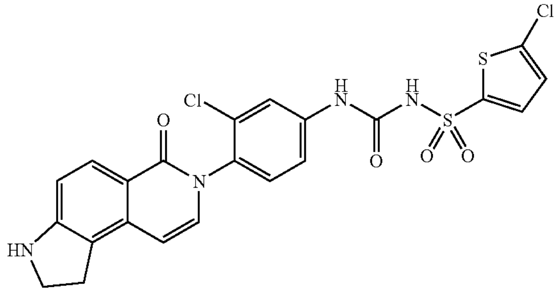
Example 503
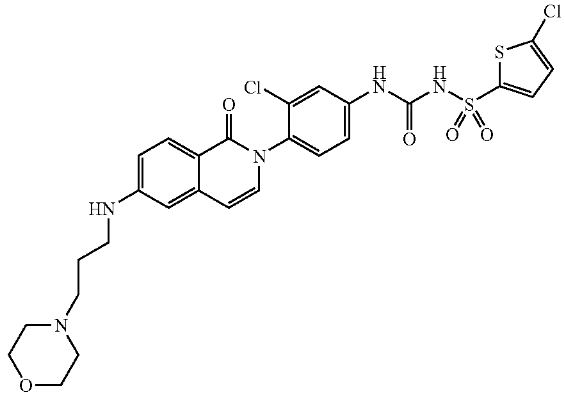
-continued
Example 504
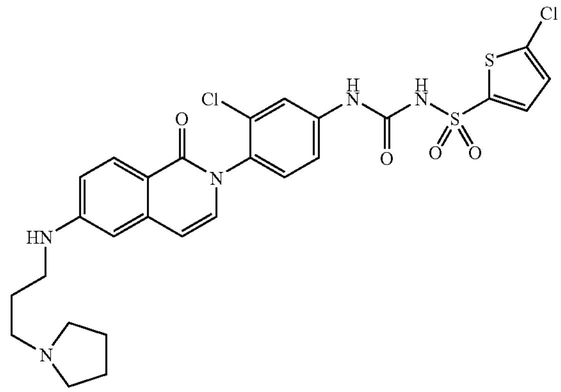
Example 505
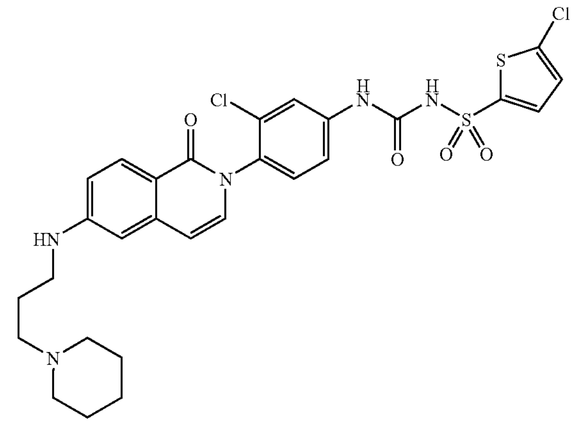
Example 506
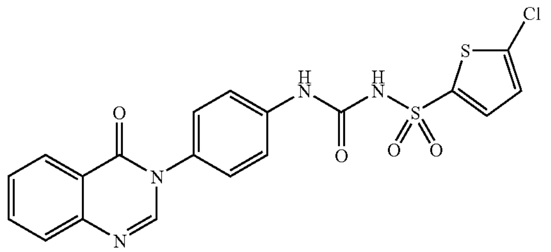
Example 507
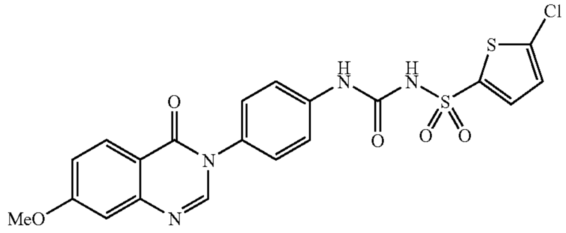
Example 508
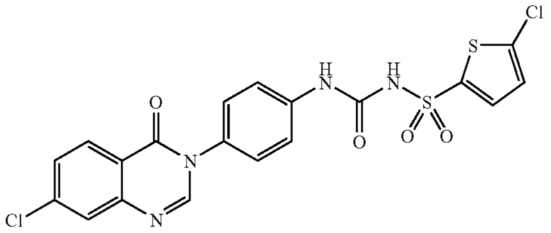

-continued
Example 509
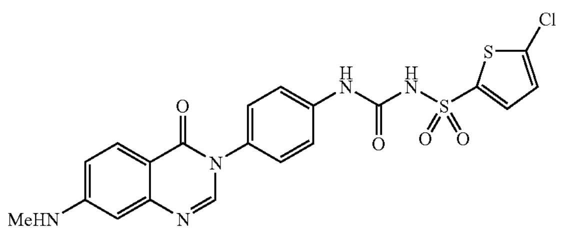
Example 510
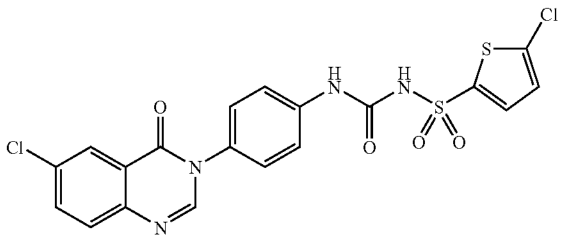
Example 511
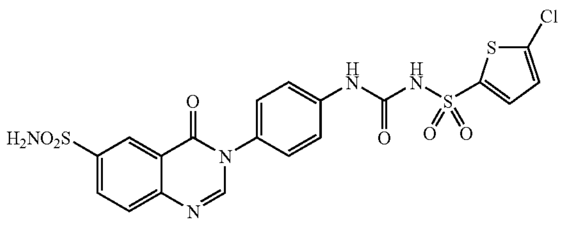
Example 512
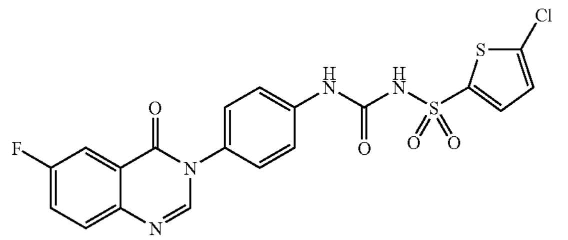
Example 513
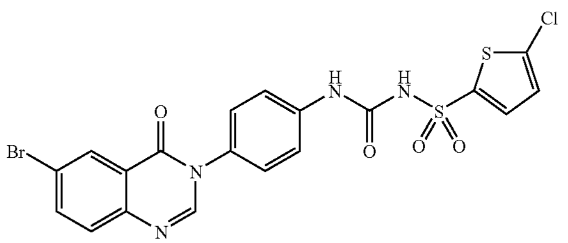
Example 514
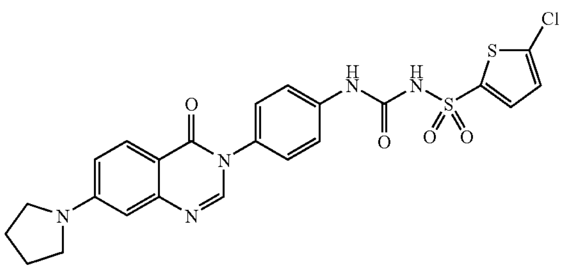
-continued
Example 515
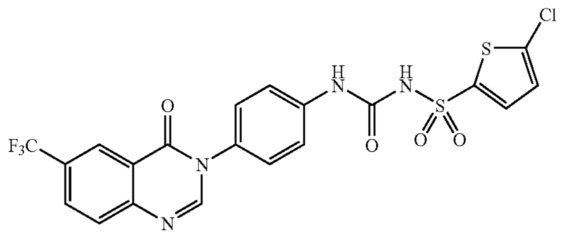
Example 516
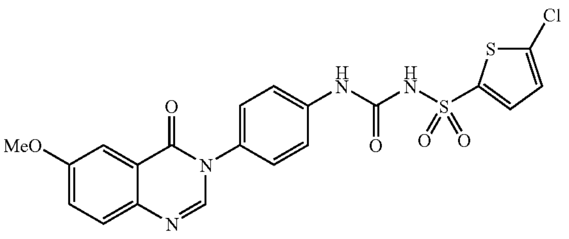
Example 517
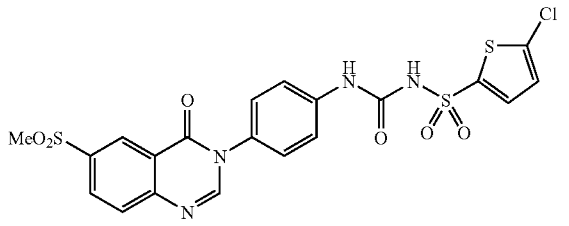
Example 518
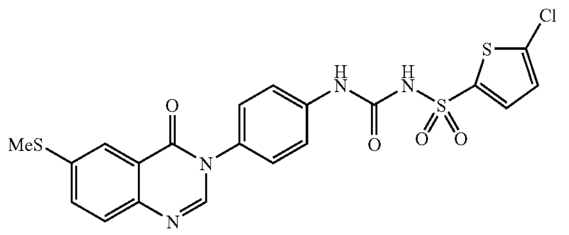
Example 519
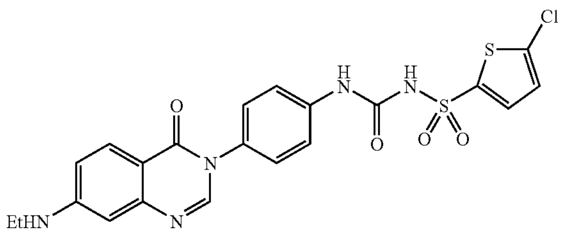
Example 520
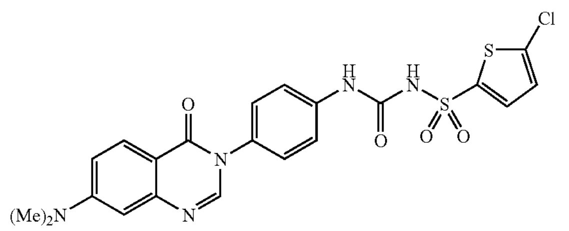

Example 521
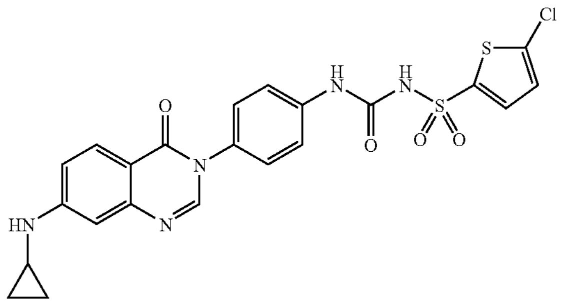
Example 522
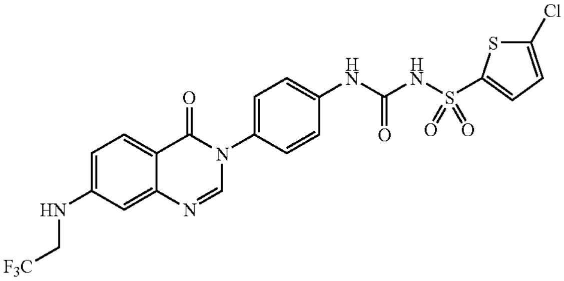
Example 523
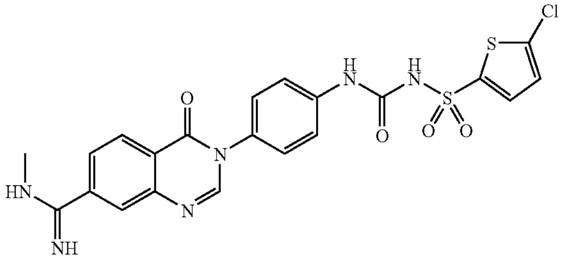
Example 524
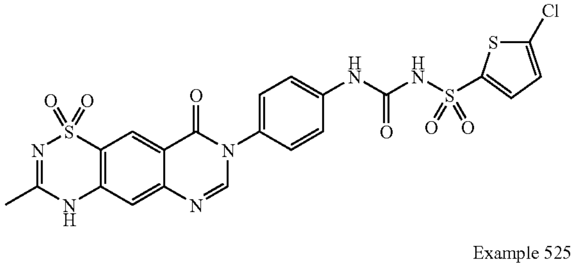
Example 525
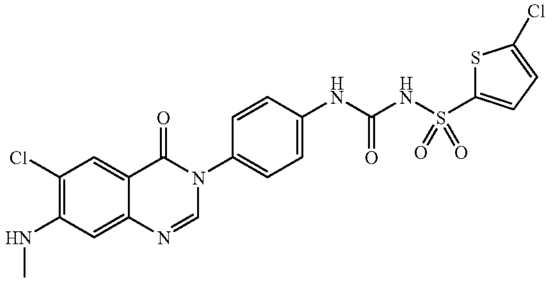
Example 526
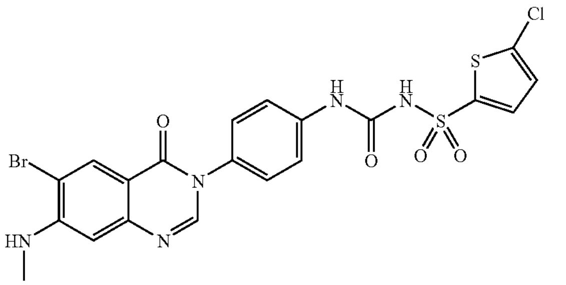
Example 527
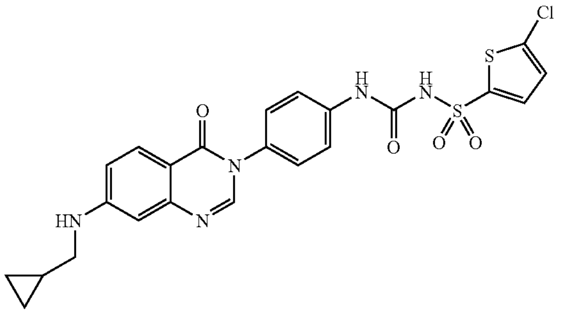
Example 528
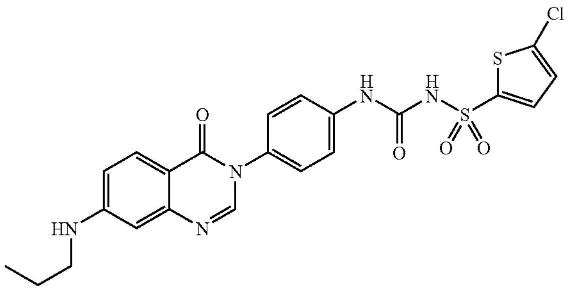
Example 529
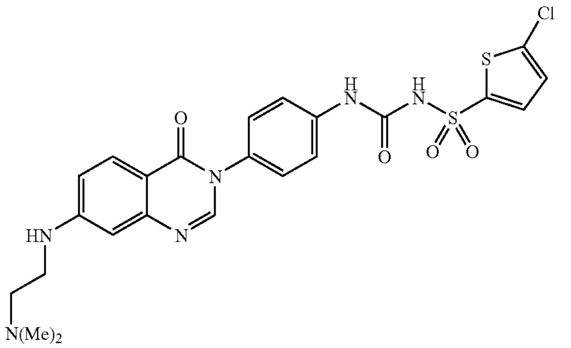

-continued
Example 530
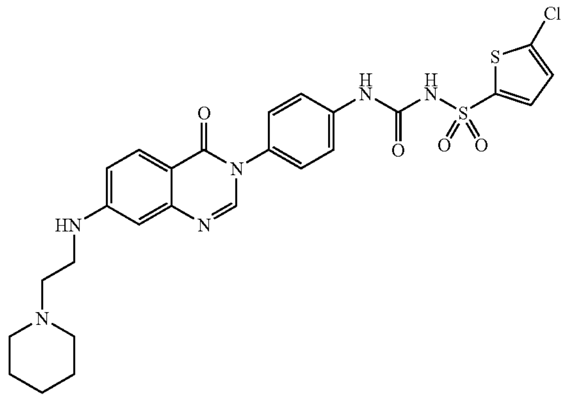
Example 531
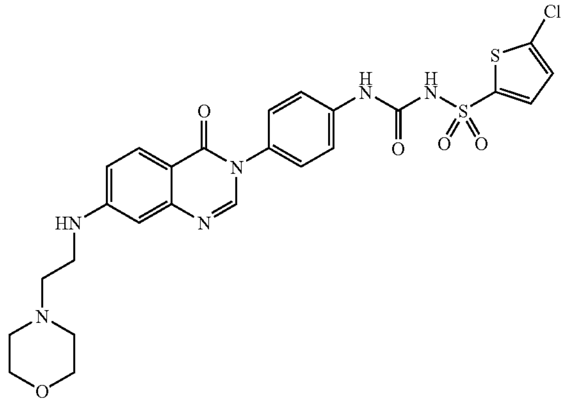
Example 532
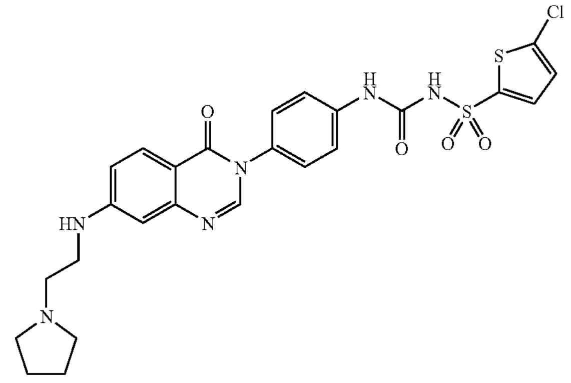
Example 533
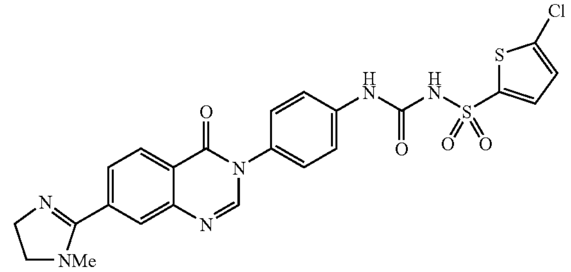
-continued
Example 534
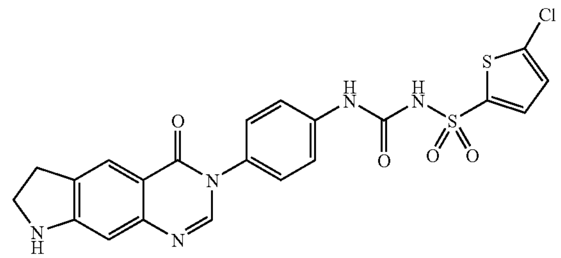
Example 535
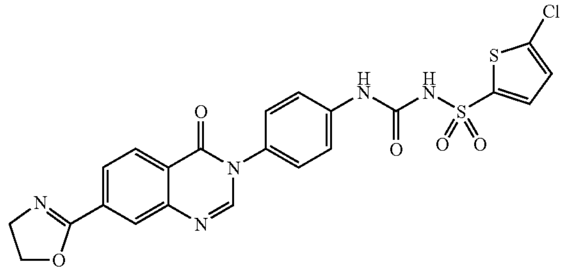
Example 536
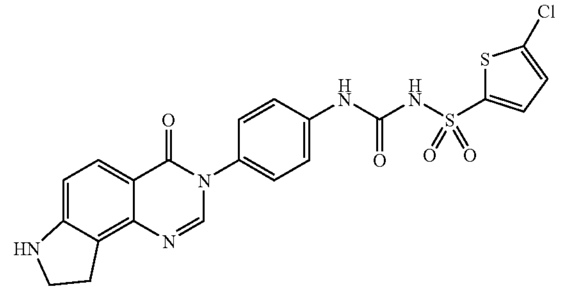
Example 537
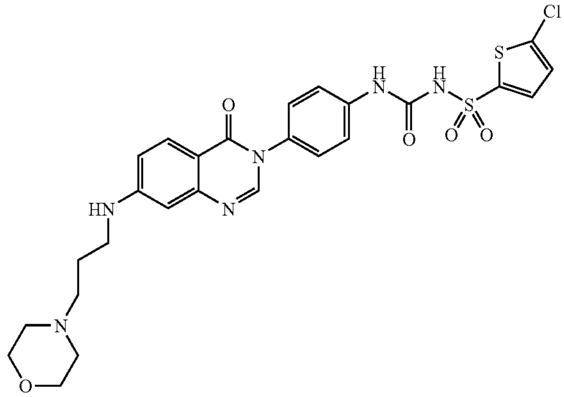

-continued
Example 538
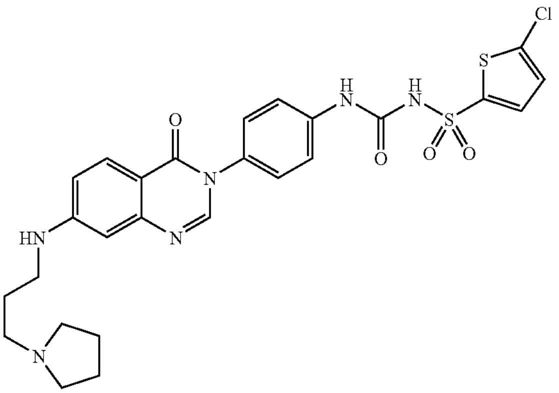
Example 539
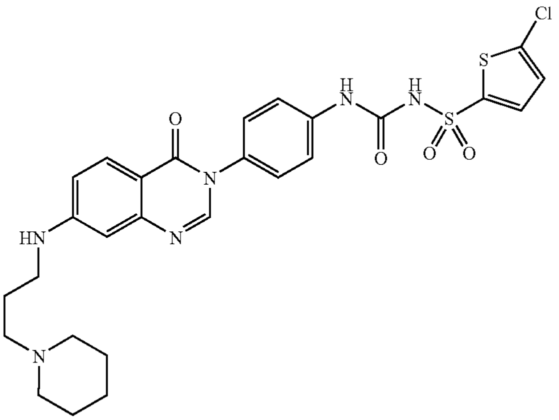
Example 540
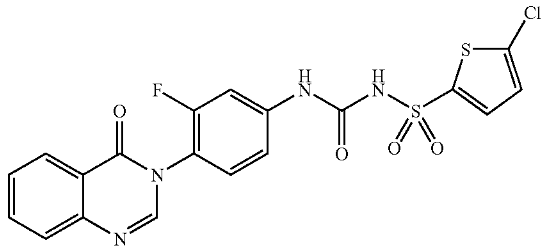
Example 541
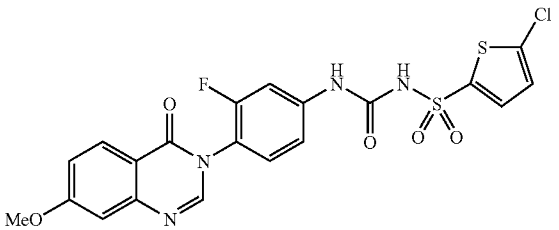
Example 542
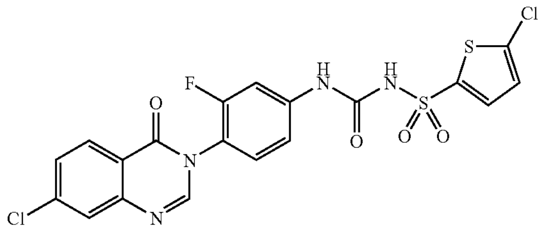
-continued
Example 543
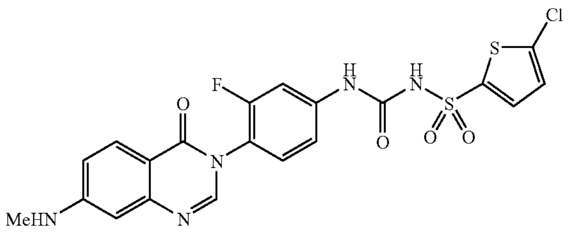
Example 544
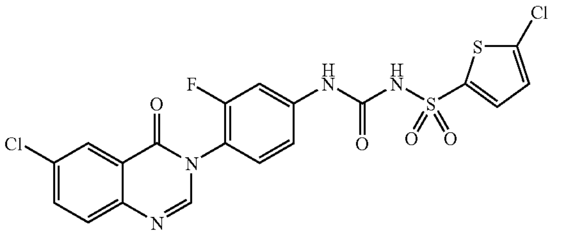
Example 545
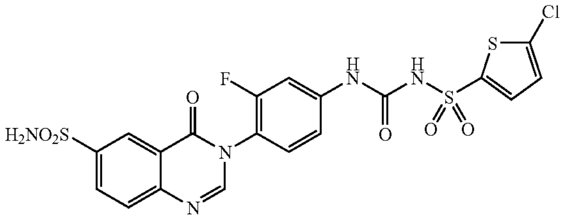
Example 546
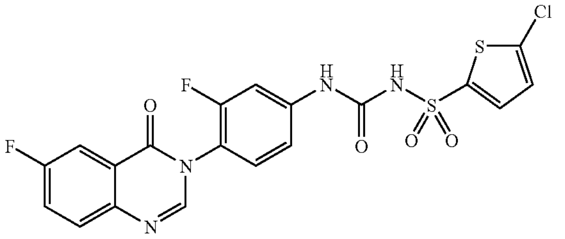
Example 547
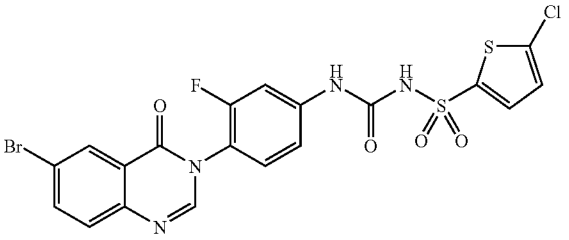
Example 548
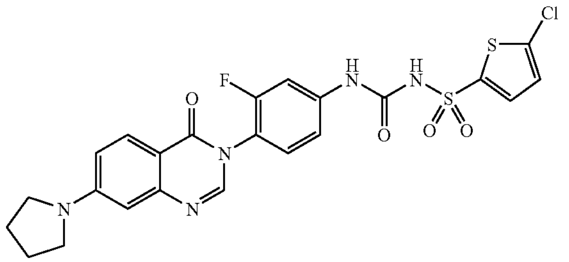

-continued
Example 549
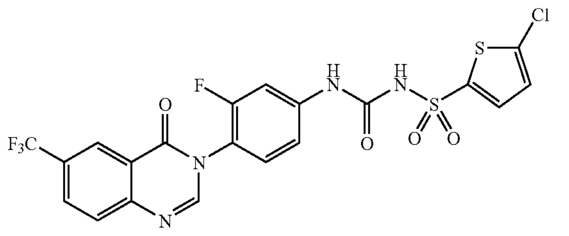
Example 550
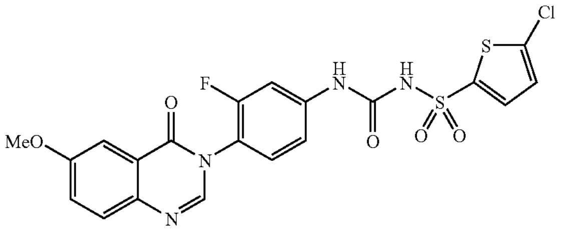
Example 551
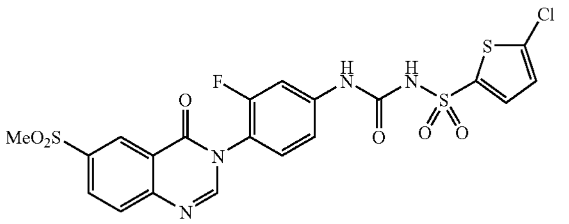
Example 552
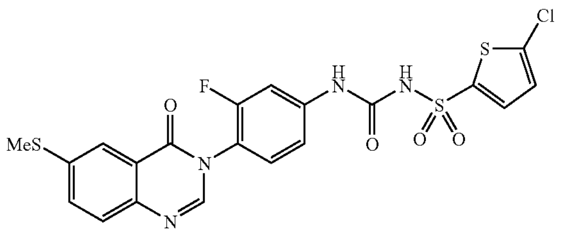
Example 553
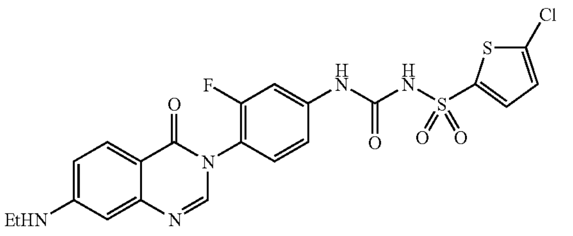
Example 554
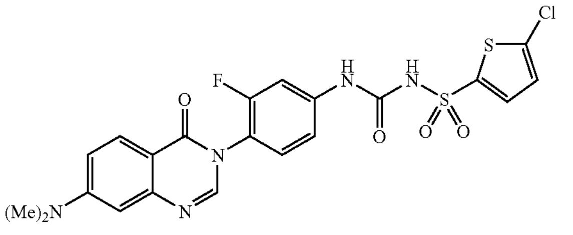
-continued
Example 555
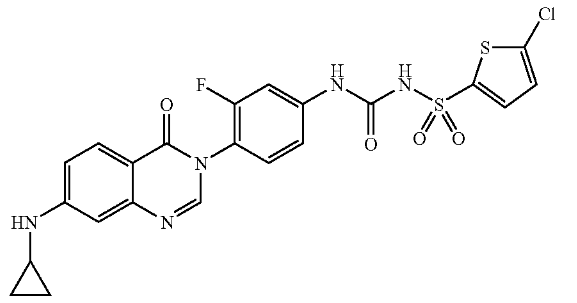
Example 556
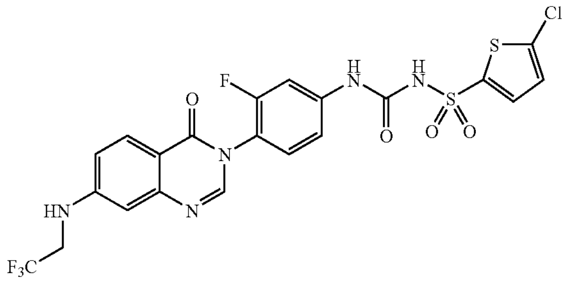
Example 557
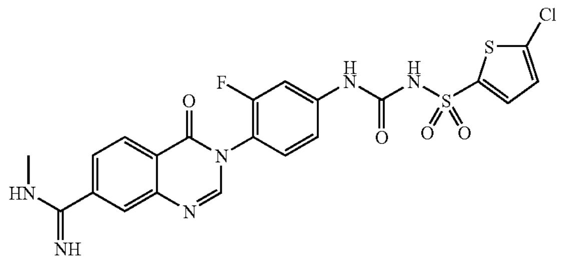
Example 558
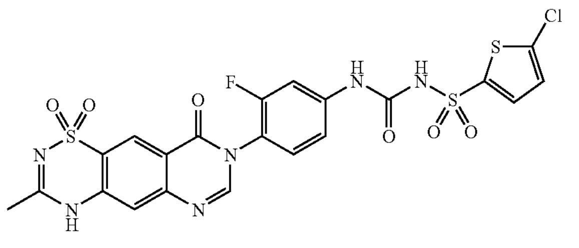
Example 559
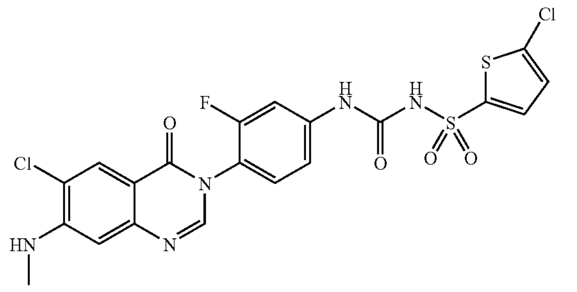

-continued
Example 560
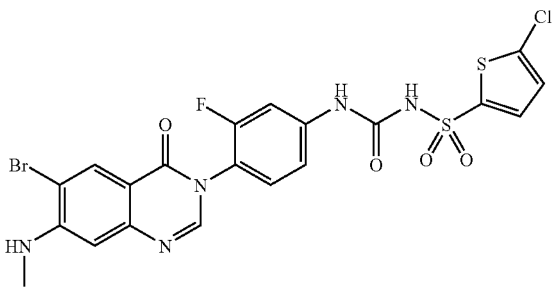
Example 561
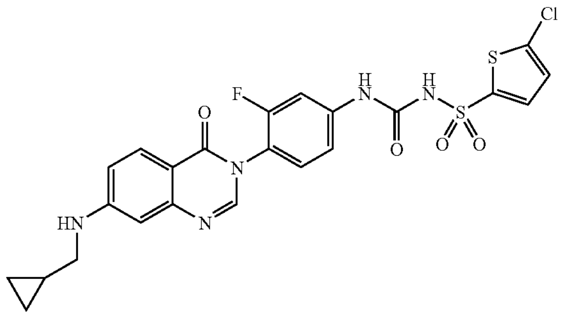
Example 562
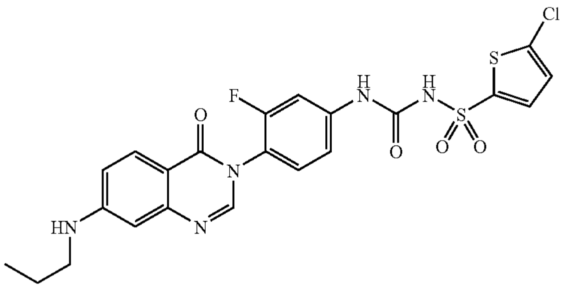
Example 563
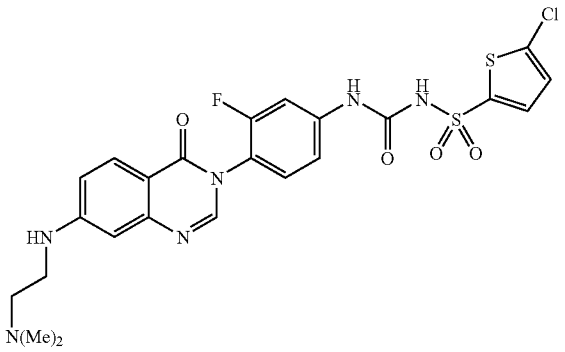
-continued
Example 564
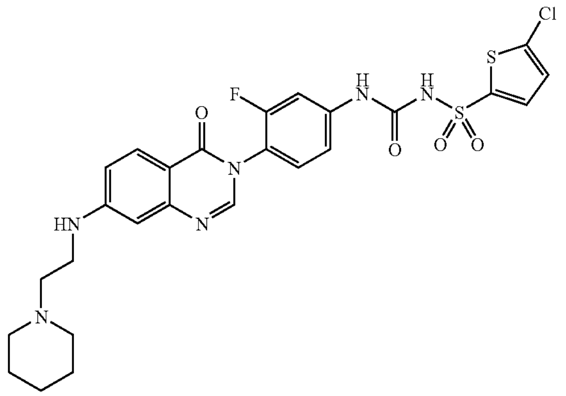
Example 565
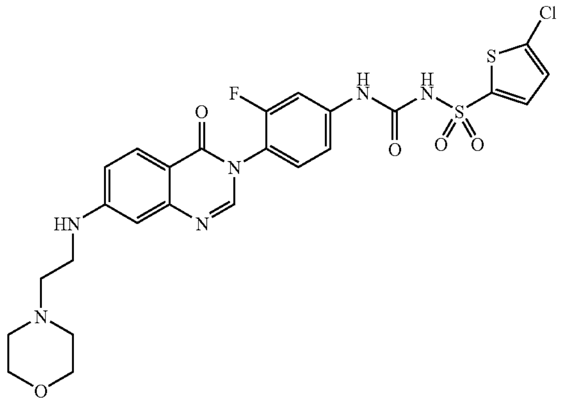
Example 566
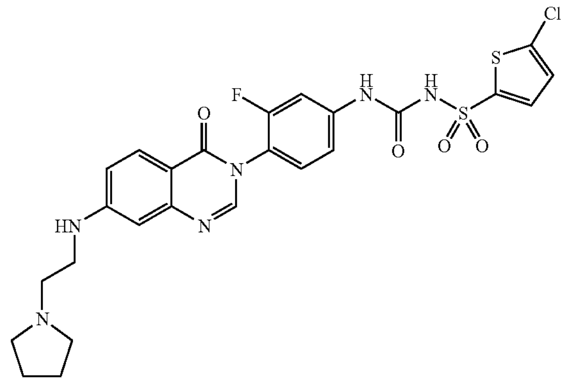
Example 567
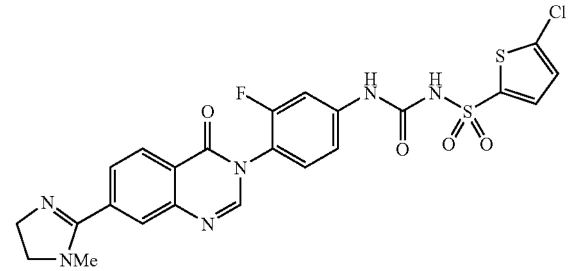

-continued
Example 568
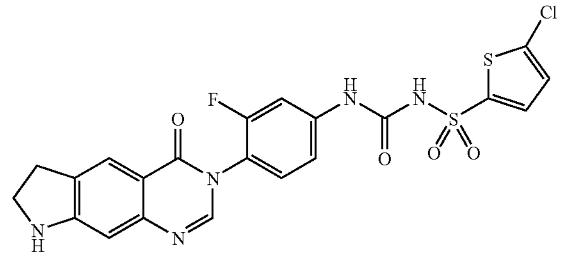
Example 569
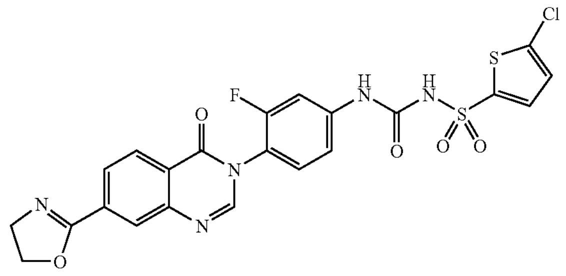
Example 570
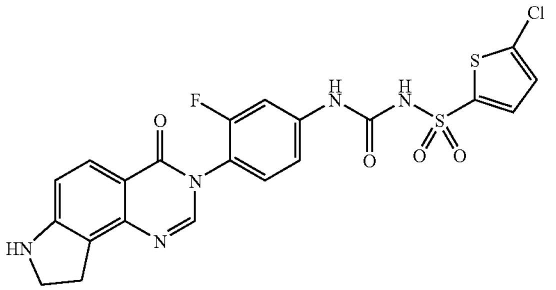
Example 571
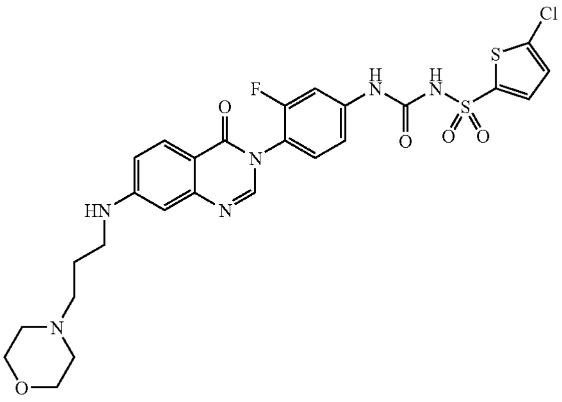
-continued
Example 572
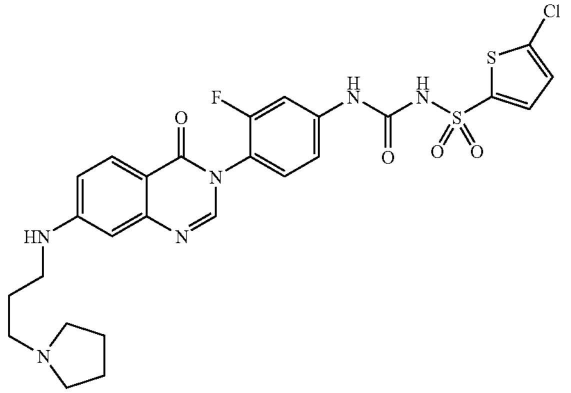
Example 573
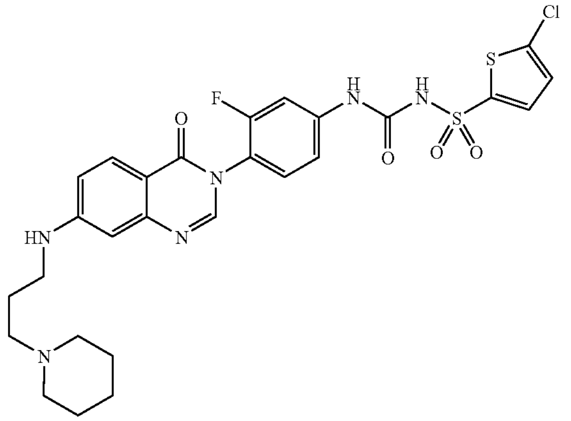
Example 574
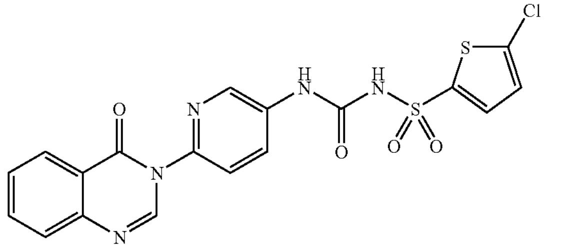
Example 575
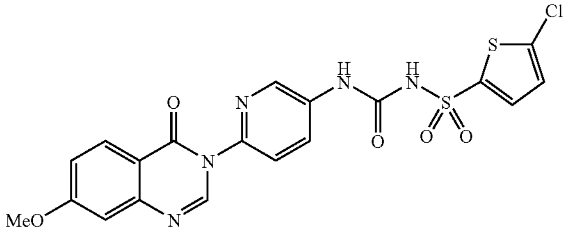
Example 576
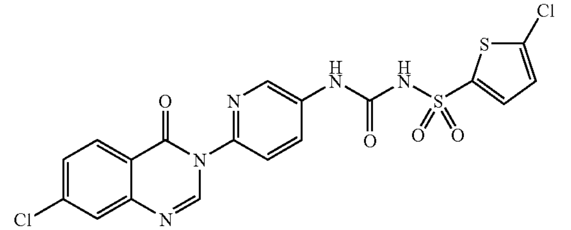

-continued
Example 577
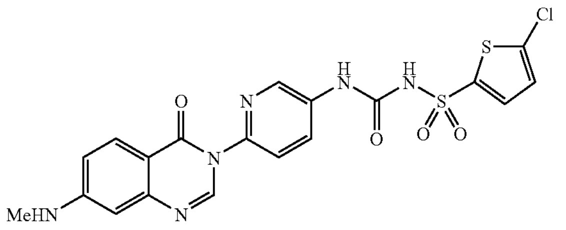
Example 578
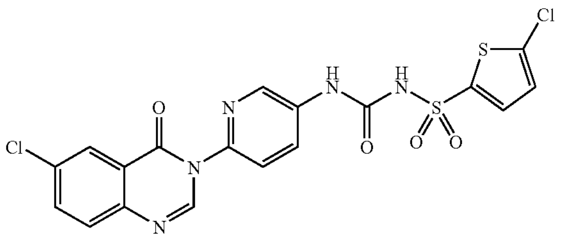
Example 579
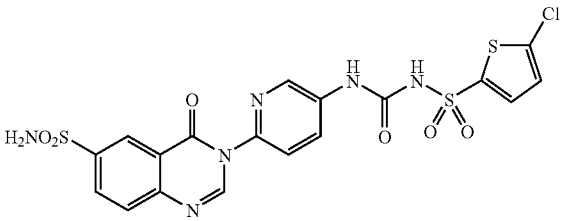
Example 580
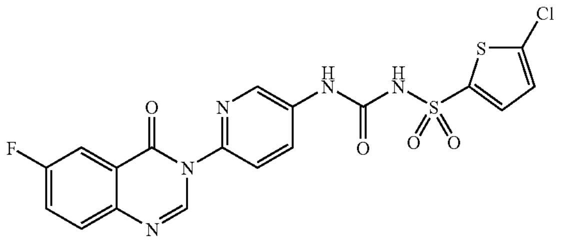
Example 581
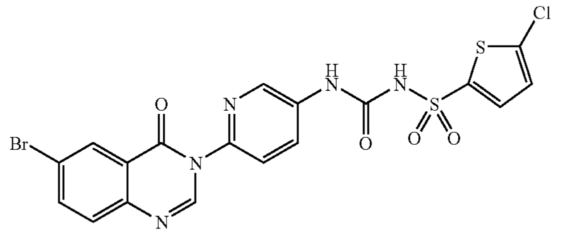
Example 582
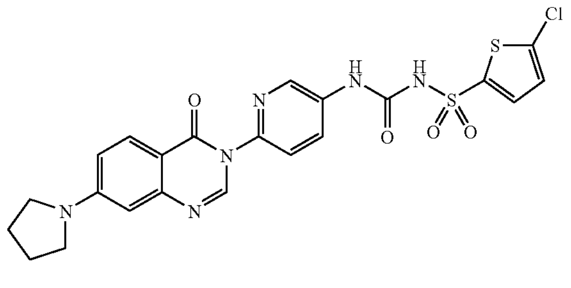
-continued
Example 583
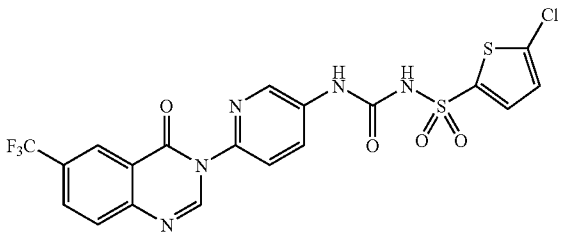
Example 584
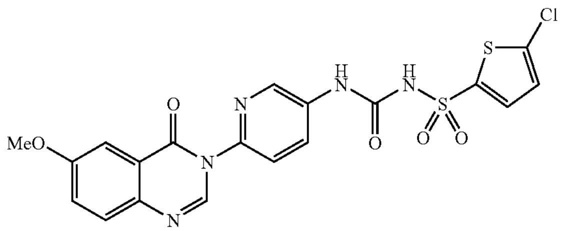
Example 585
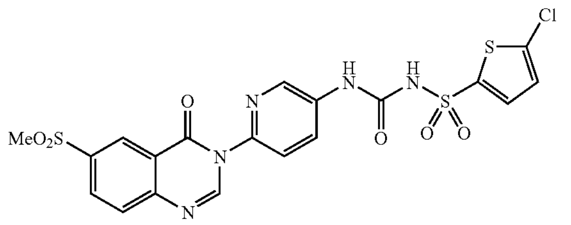
Example 586
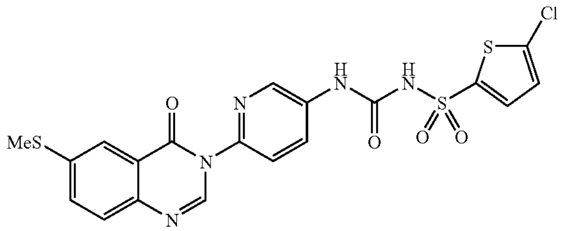
Example 587
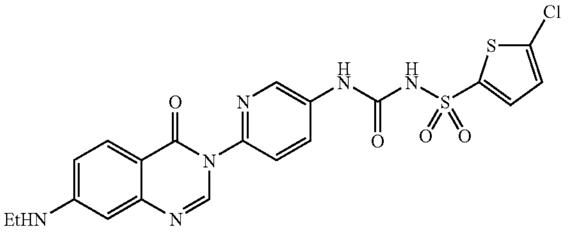
Example 588
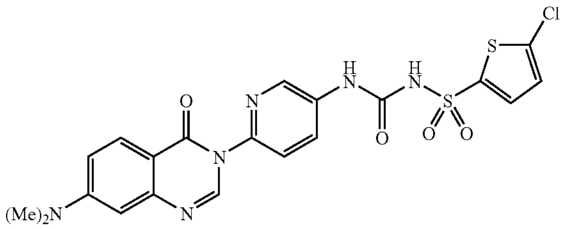

Example 589
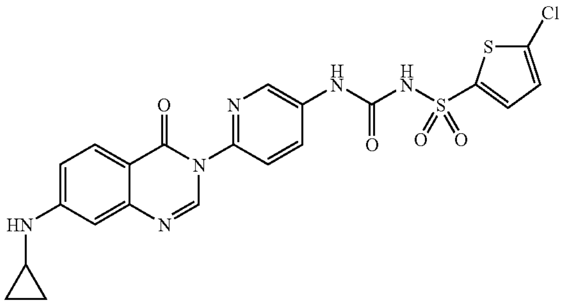
Example 590
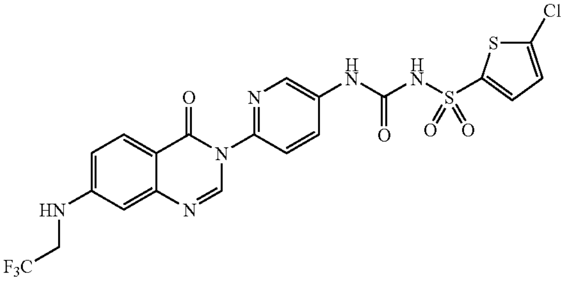
Example 591
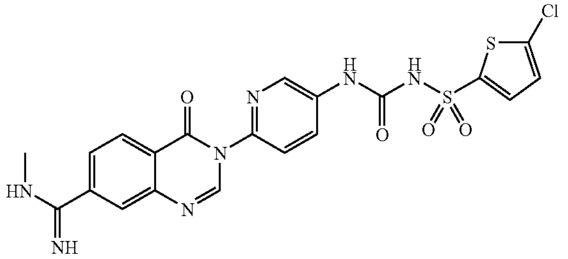
Example 592
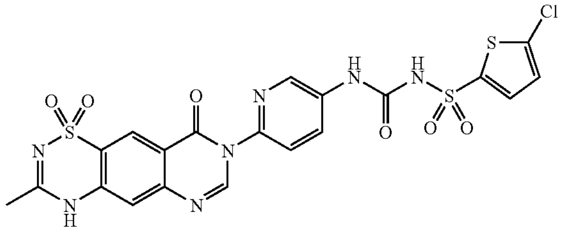
Example 593
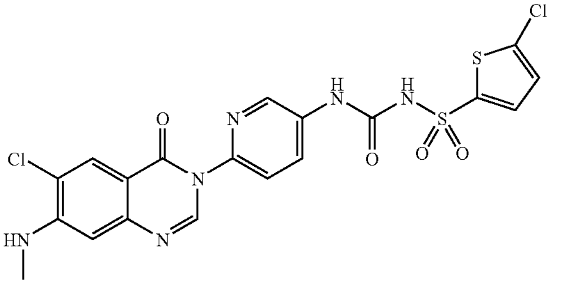
Example 594
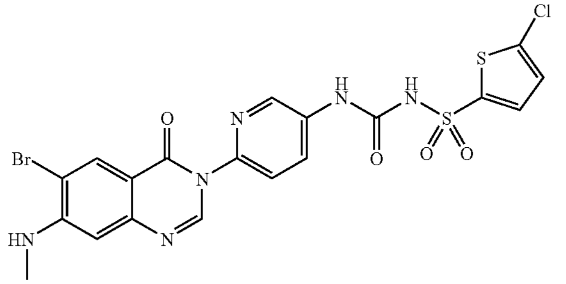
Example 595
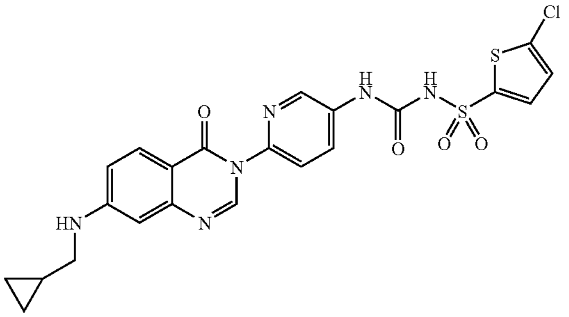
Example 596
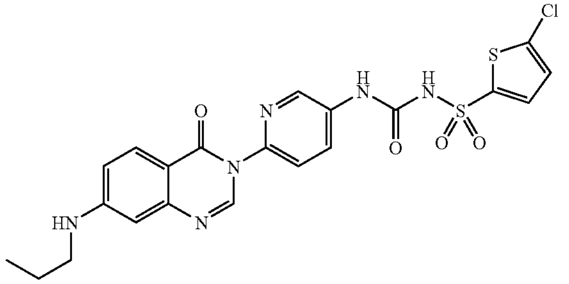
Example 597
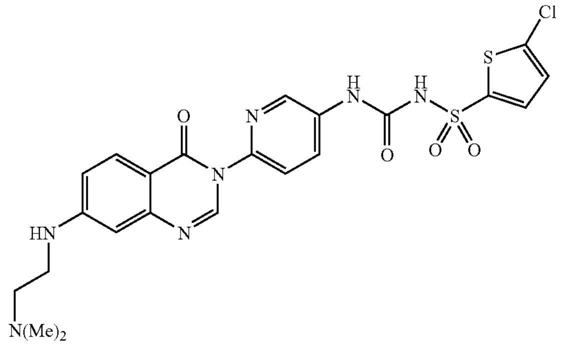

-continued
Example 598
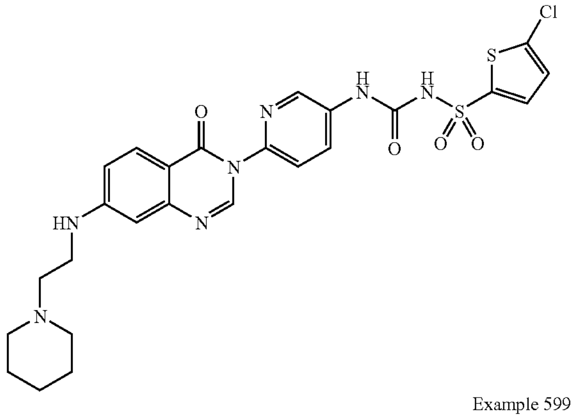
Example 599
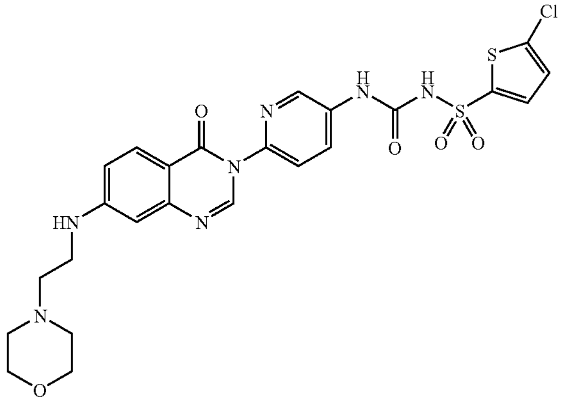
Example 600
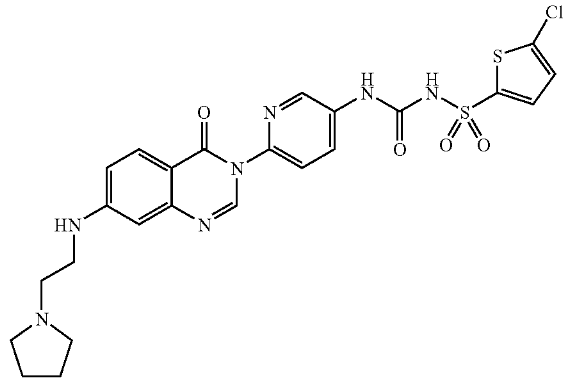
Example 601
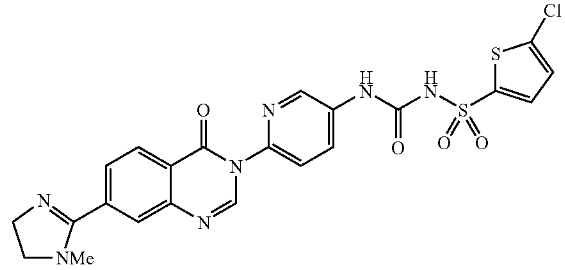
-continued
Example 602
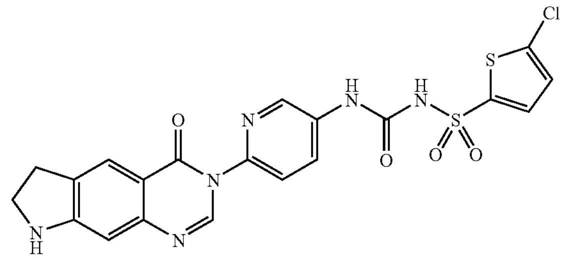
Example 603
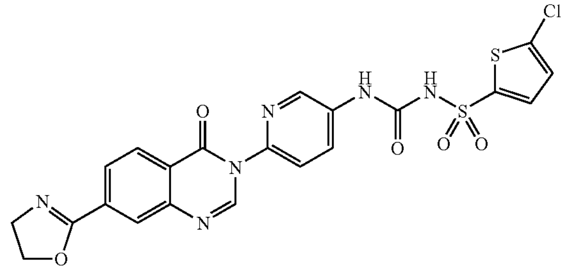
Example 604
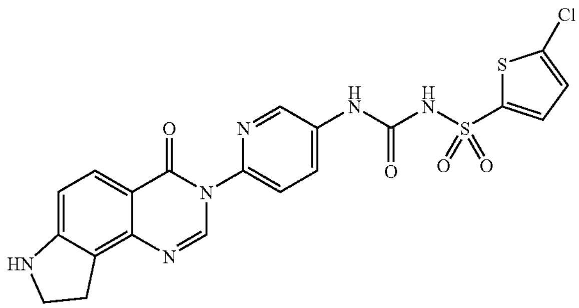
Example 605
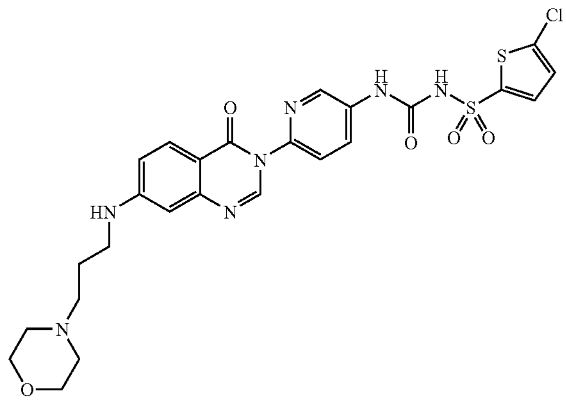

-continued
Example 606
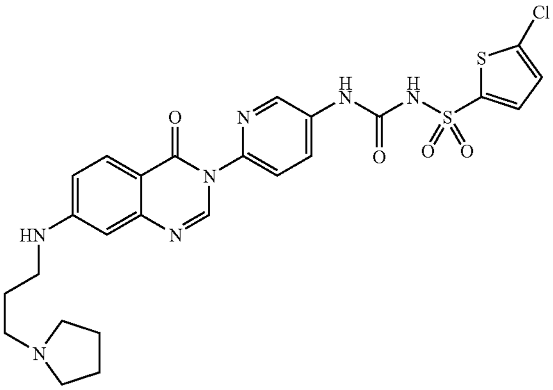
Example 607
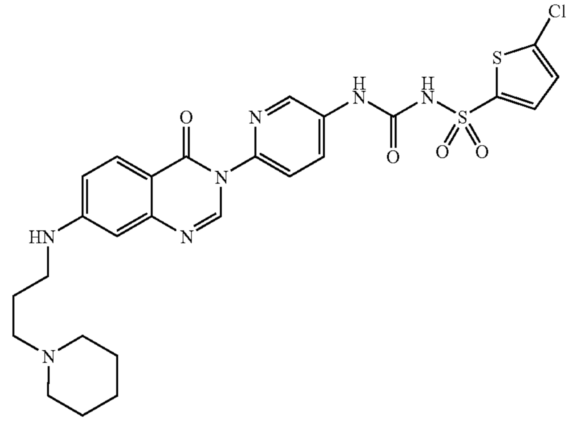
Example 608
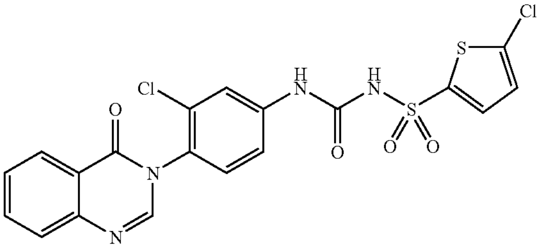
Example 609
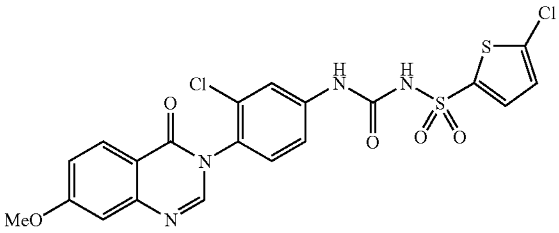
Example 610
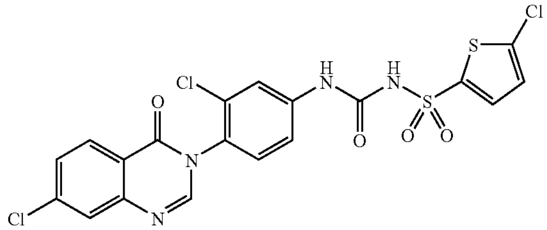
-continued
Example 611
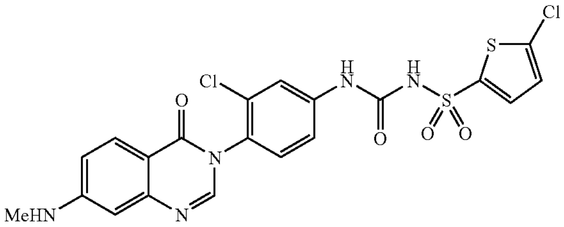
Example 612
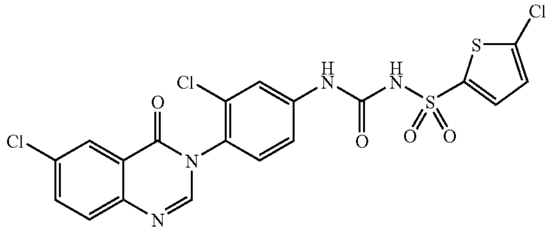
Example 613
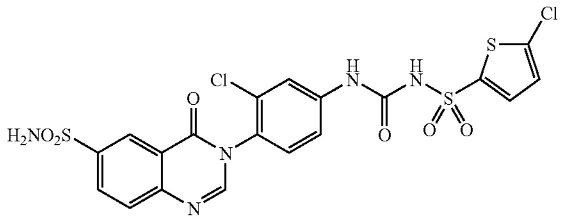
Example 614
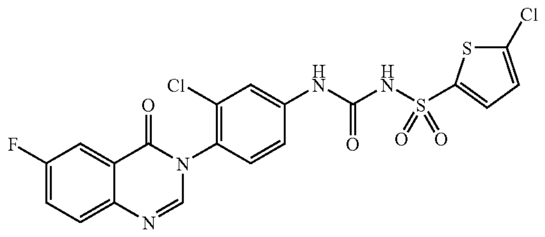
Example 615
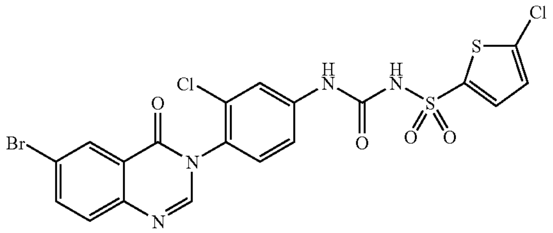
Example 616
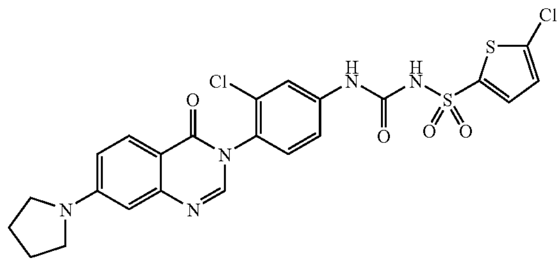

-continued
Example 617
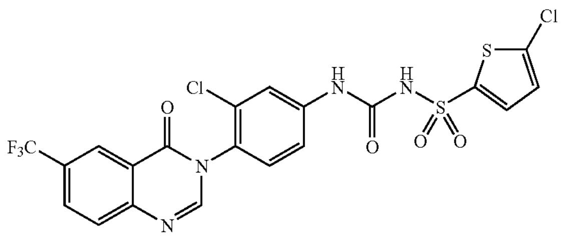
Example 618
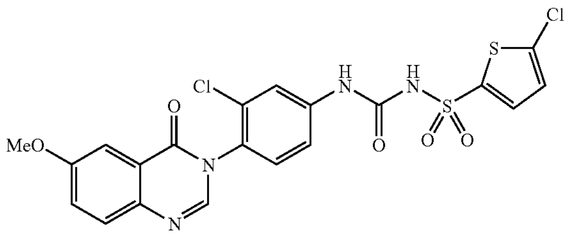
Example 619
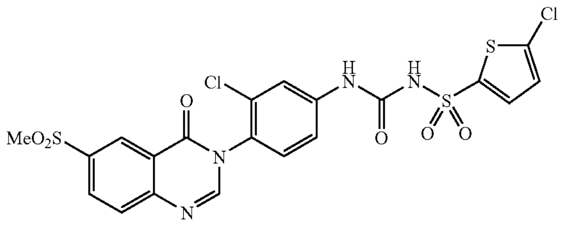
Example 620
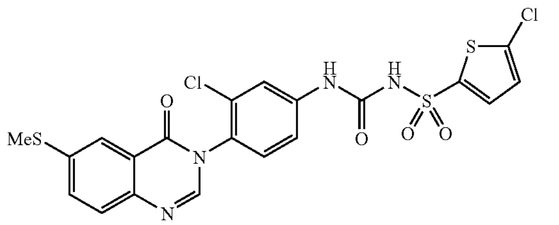
Example 621
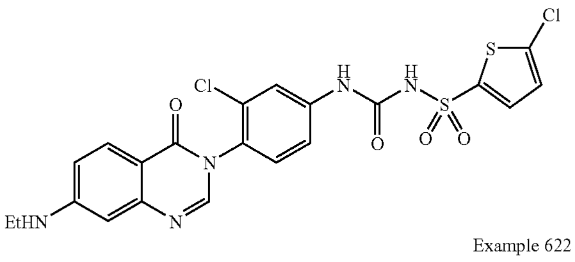
Example 622
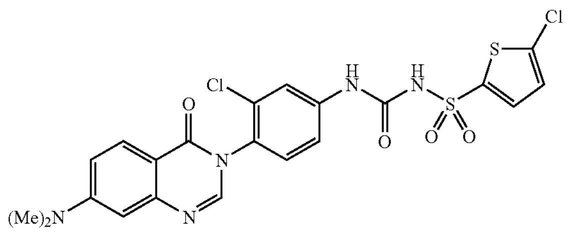
-continued
Example 623
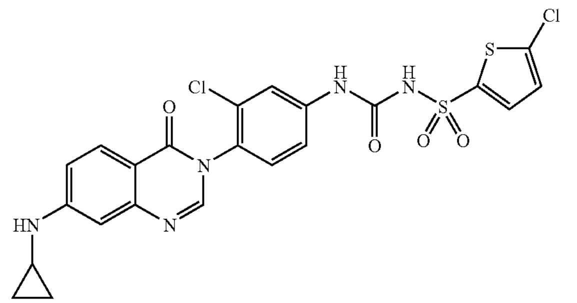
Example 624
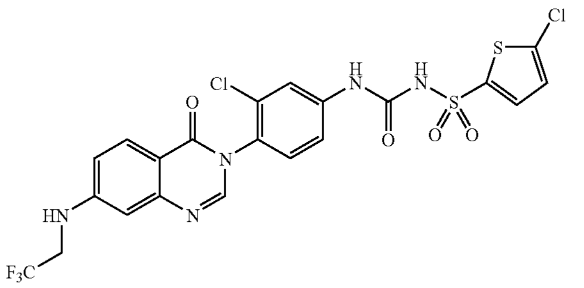
Example 625
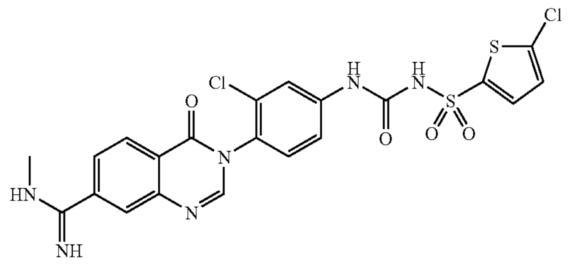
Example 626
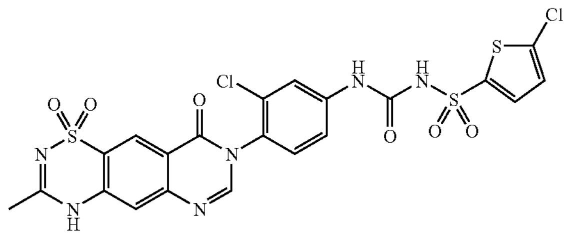
Example 627
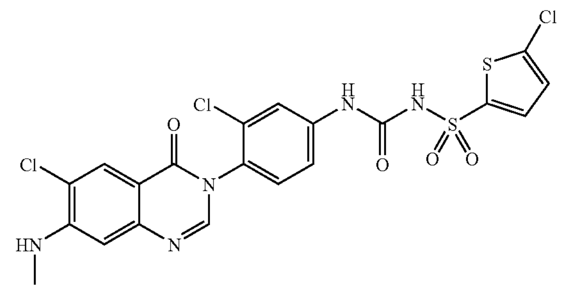

-continued
Example 628
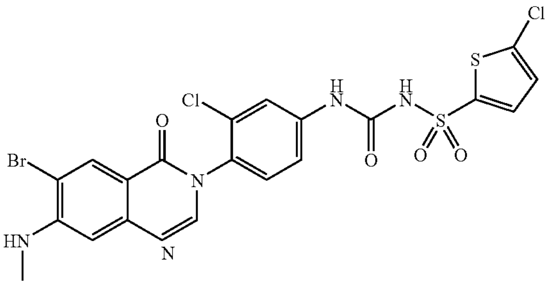
Example 629
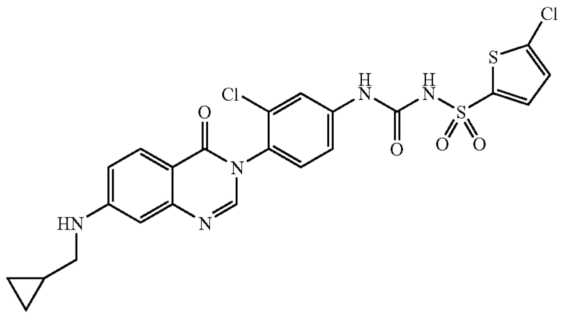
Example 630
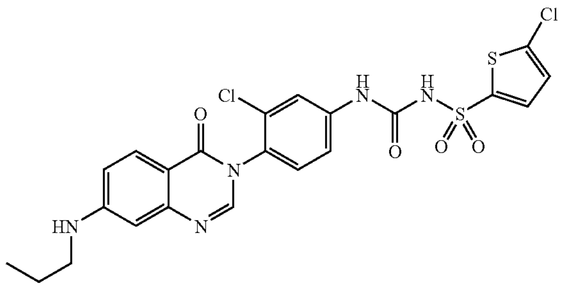
Example 631
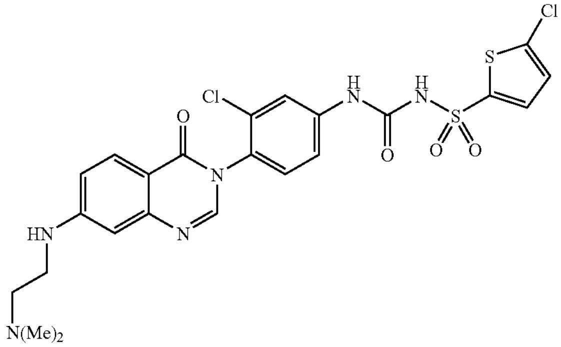
-continued
Example 632
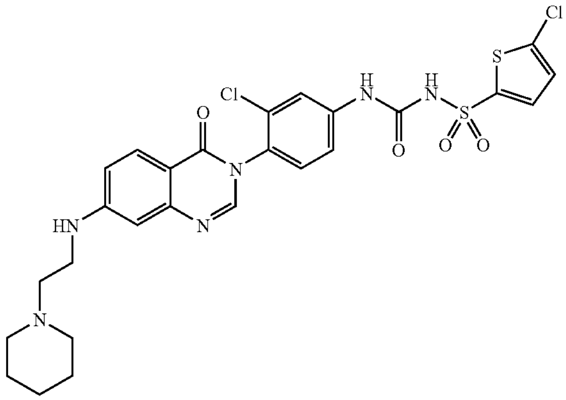
Example 633
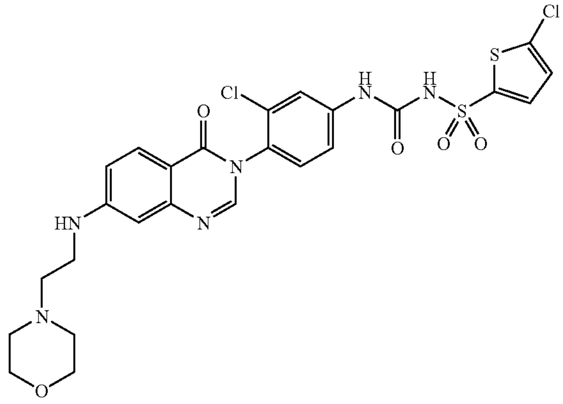
Example 634
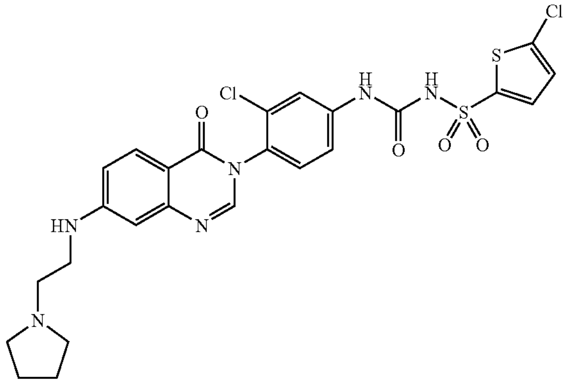
Example 635
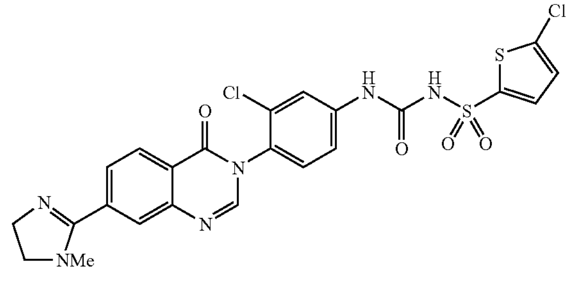

Example 636
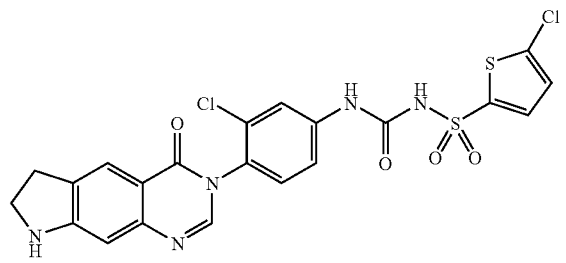
Example 637
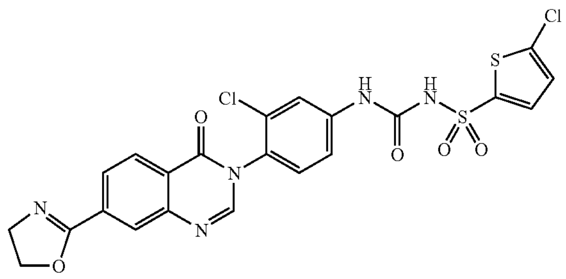
Example 638
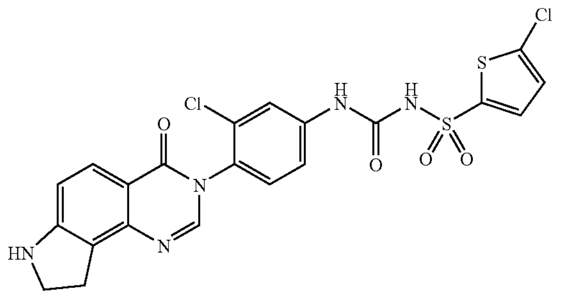
Example 639
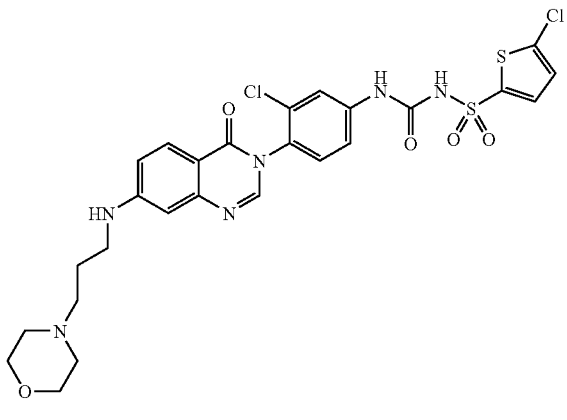
Example 640
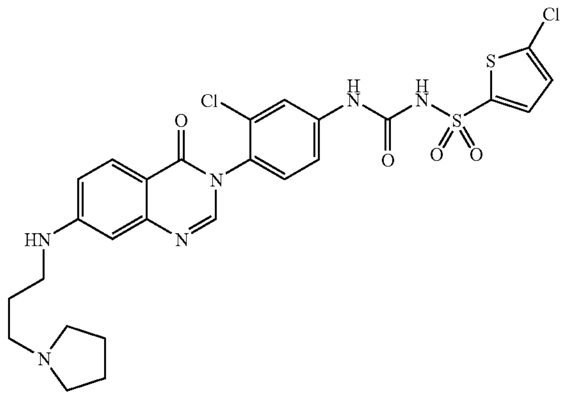
Example 641
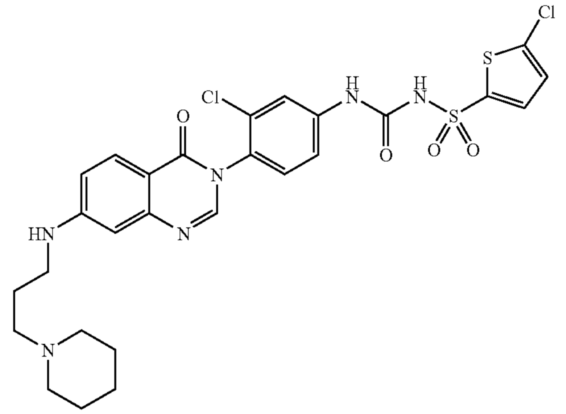
Example 642
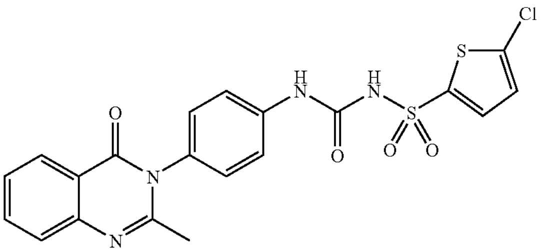
Example 643
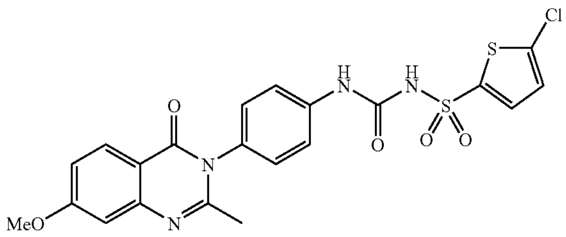
Example 644
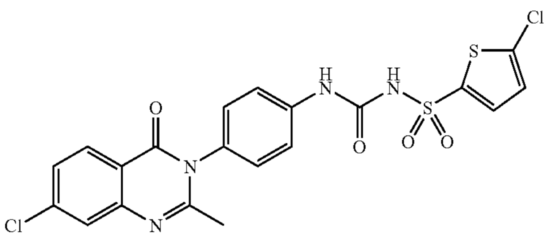

-continued
Example 645
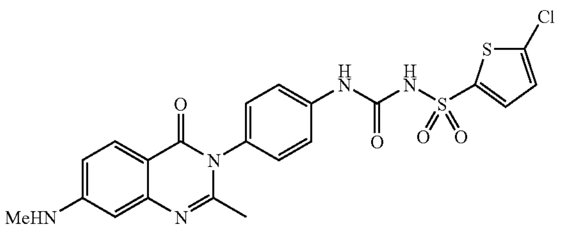
Example 646
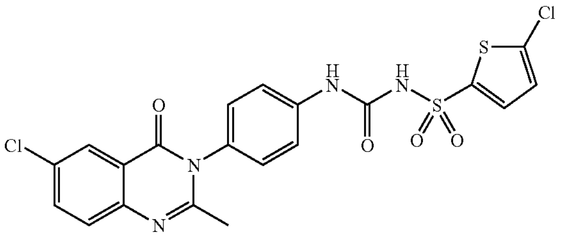
Example 647
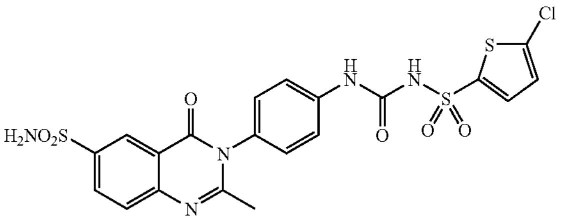
Example 648
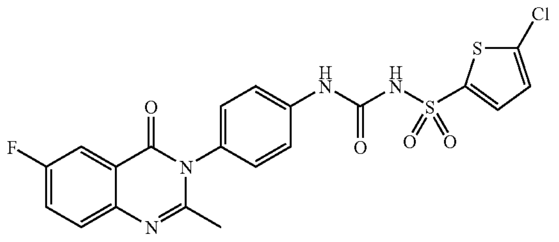
Example 649
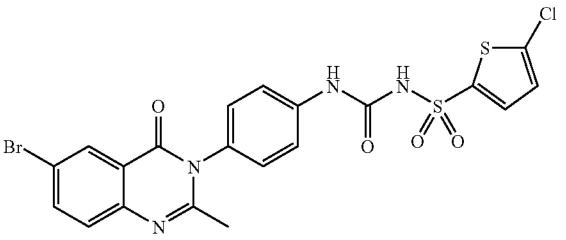
Example 650
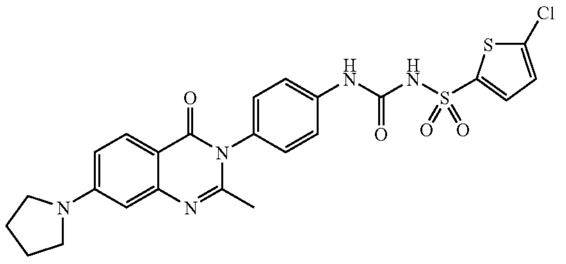
-continued
Example 651
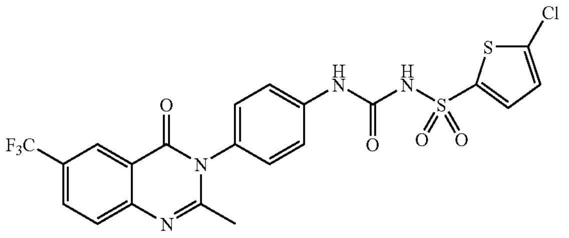
Example 652
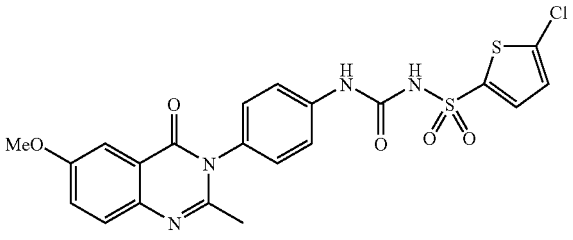
Example 653
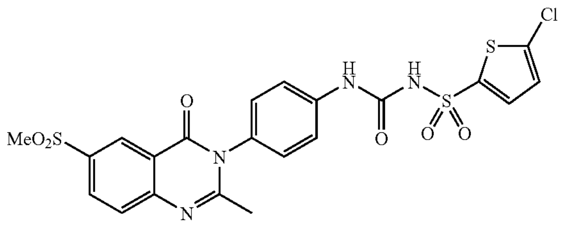
Example 654
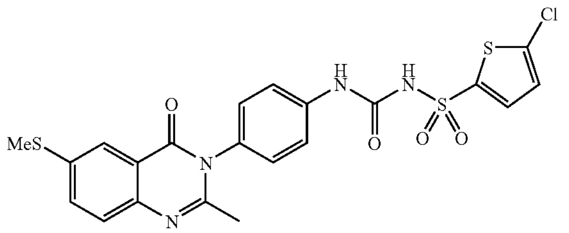
Example 655
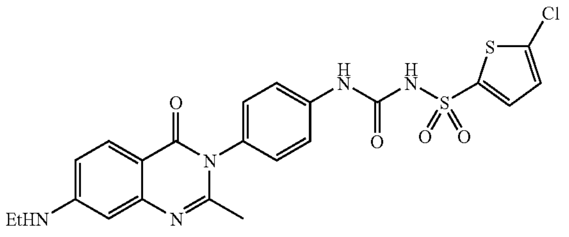
Example 656
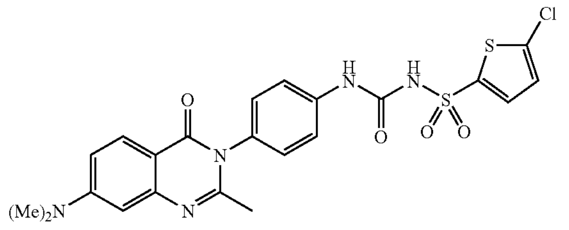

-continued
Example 657
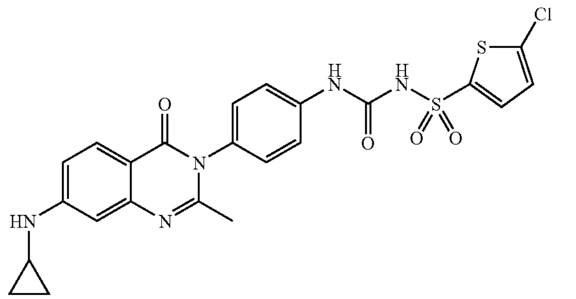
Example 658
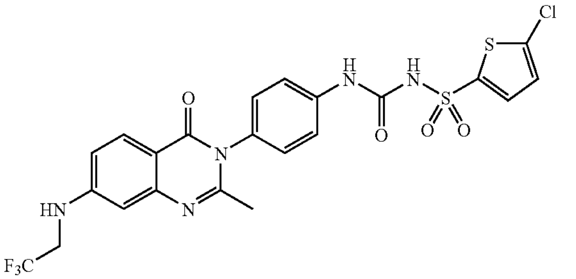
Example 659
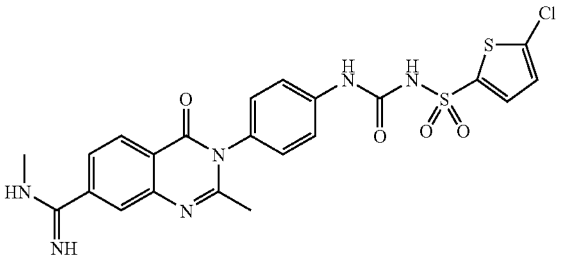
Example 660
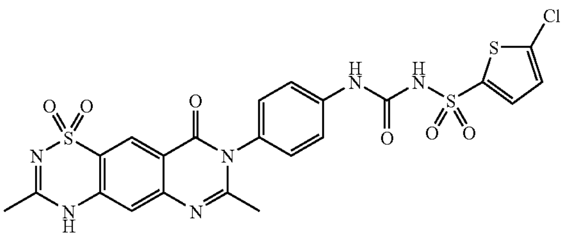
Example 661
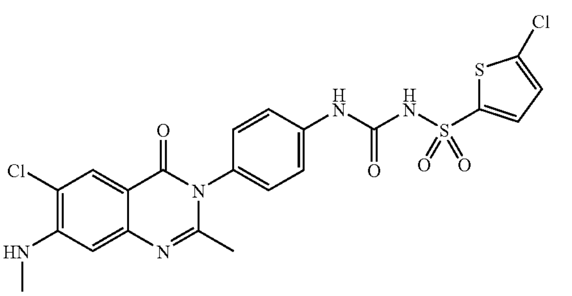
-continued
Example 662
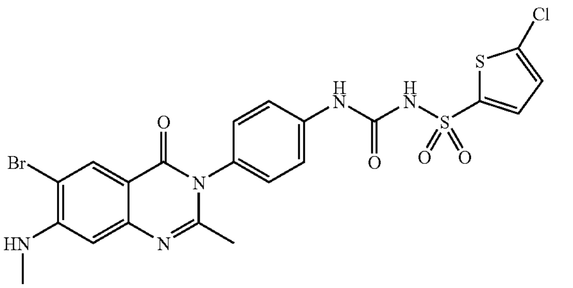
Example 663
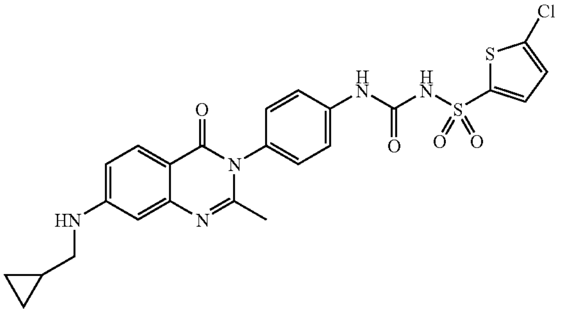
Example 664
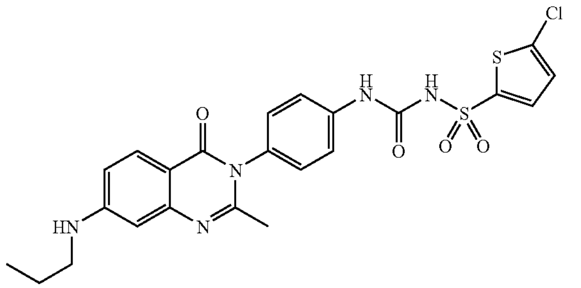
Example 665
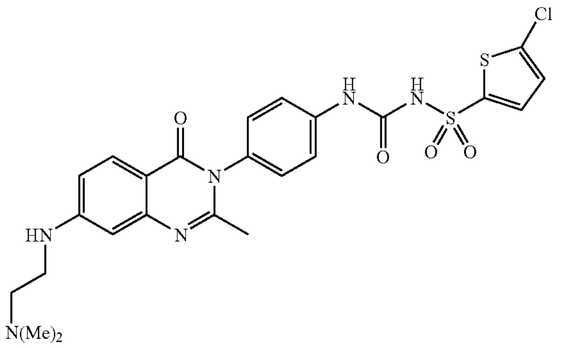

Example 666
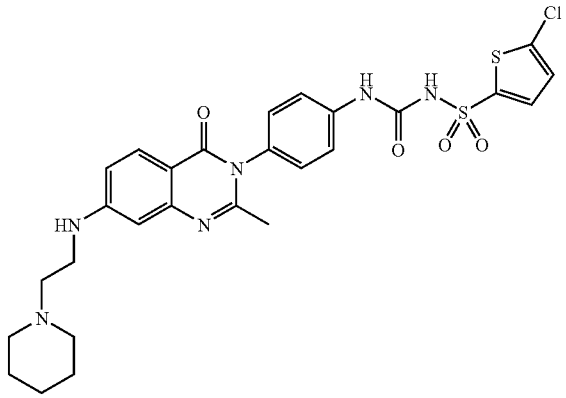
Example 667
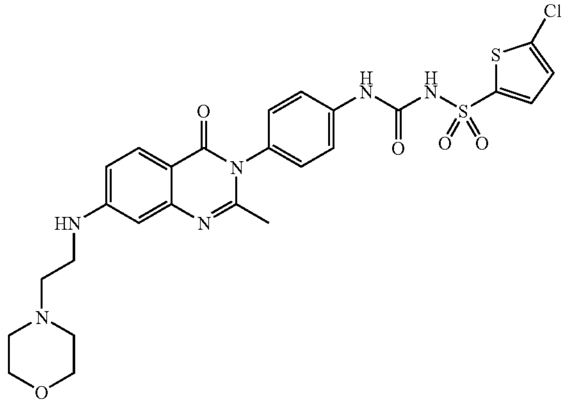
Example 668
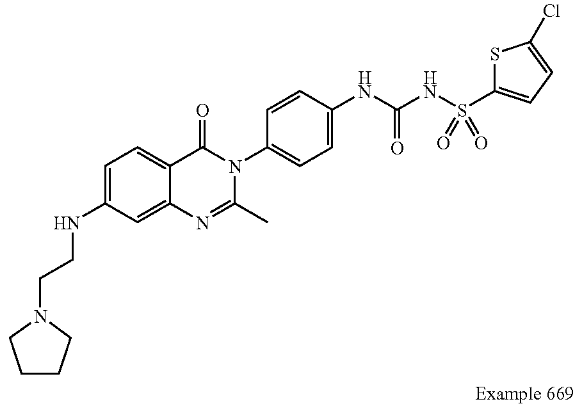
Example 669
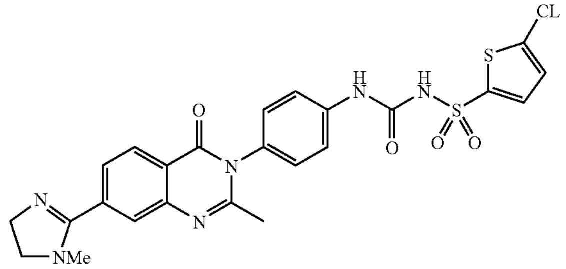
Example 670
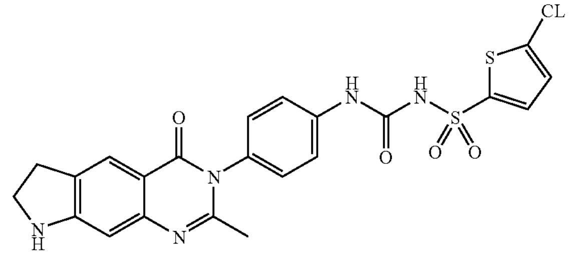
Example 671
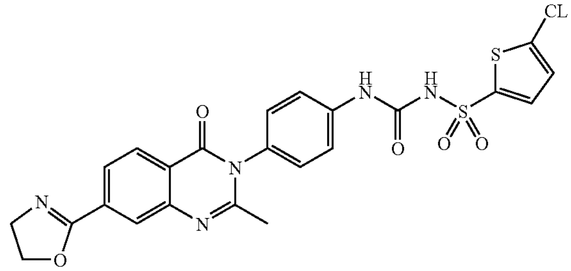
Example 672
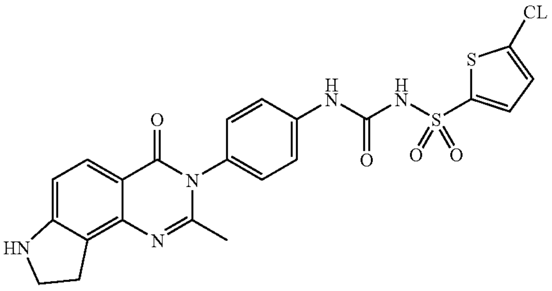
Example 673
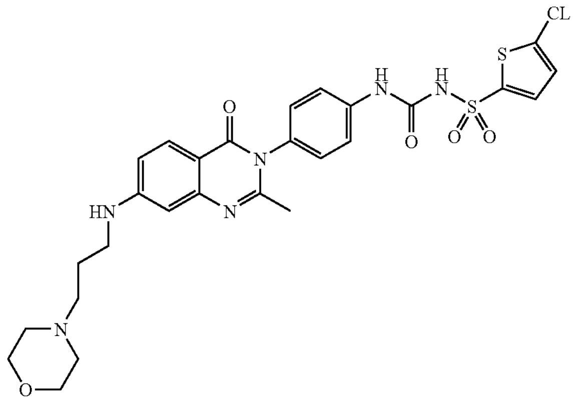

-continued
Example 674
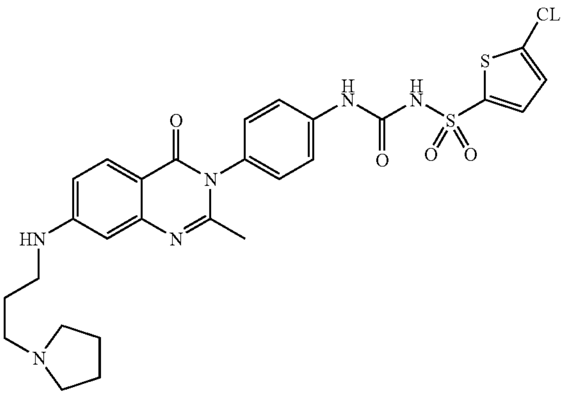
Example 675
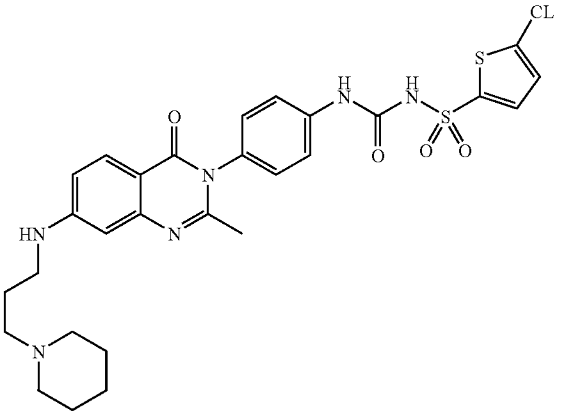
Example 676
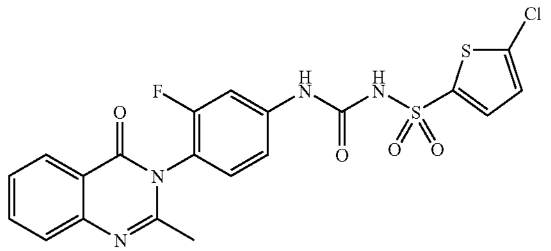
Example 677
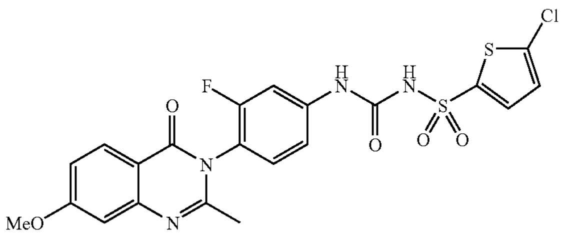
Example 678
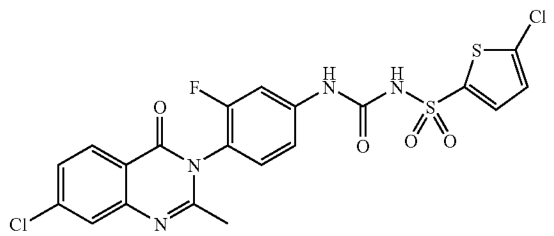
-continued
Example 679
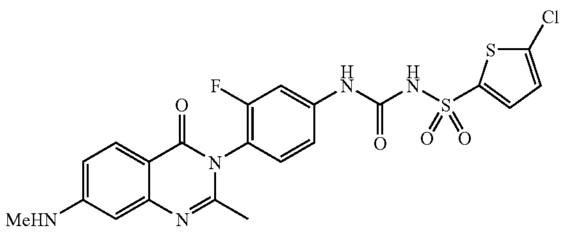
Example 680
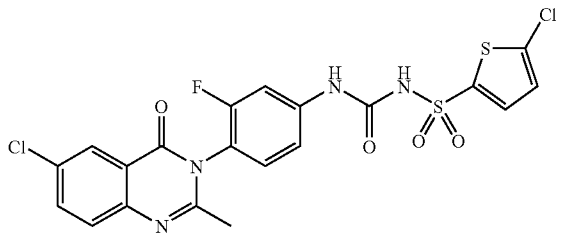
Example 681
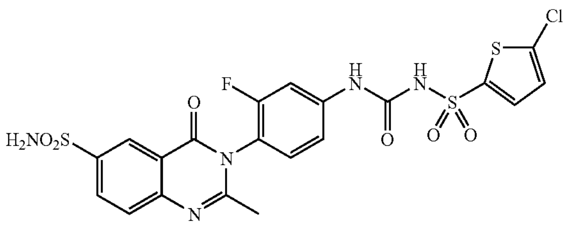
Example 682
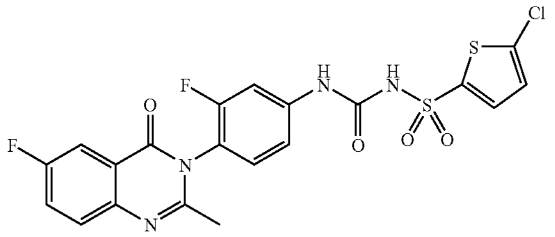
Example 683
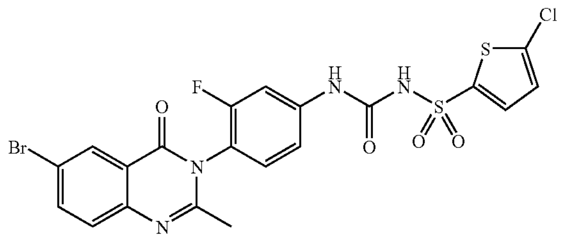
Example 684
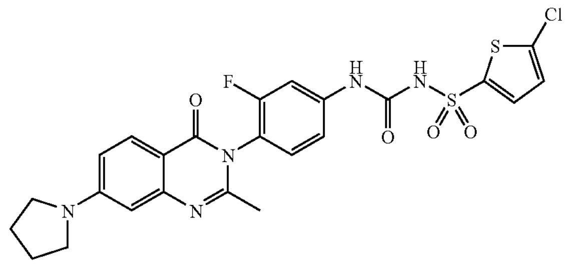

-continued
Example 685
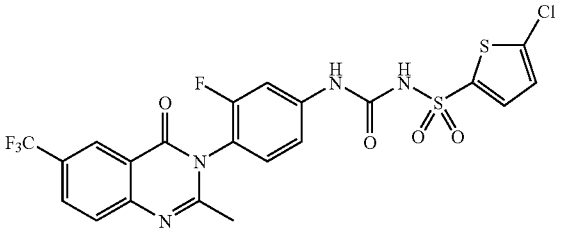
Example 686
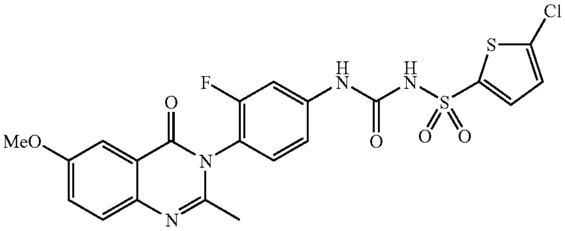
Example 687
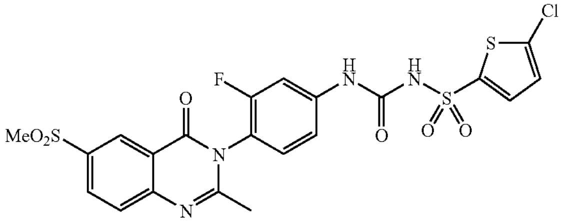
Example 688
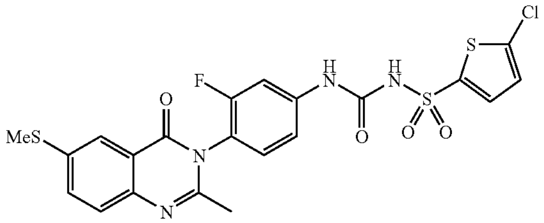
Example 689
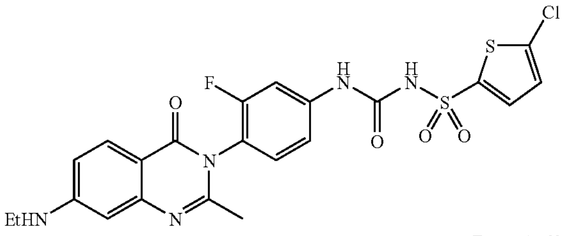
Example 690
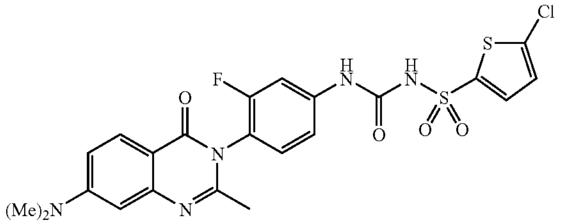
-continued
Example 691
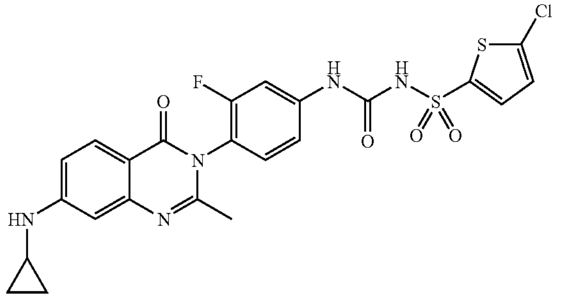
Example 692
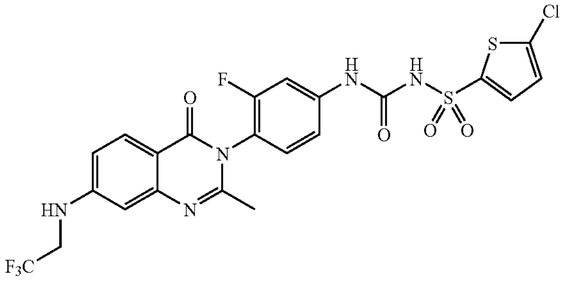
Example 693
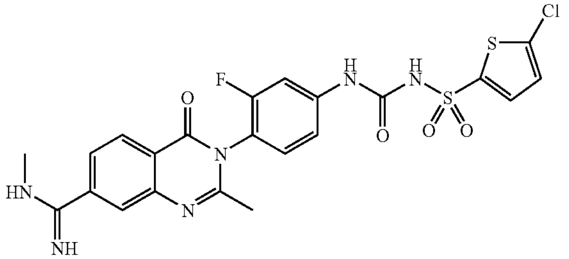
Example 694
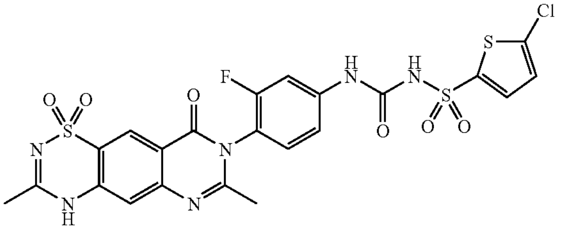
Example 695
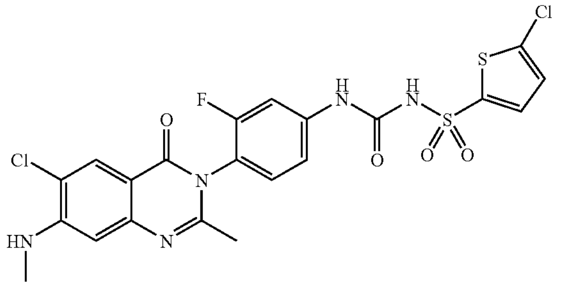

-continued
Example 696
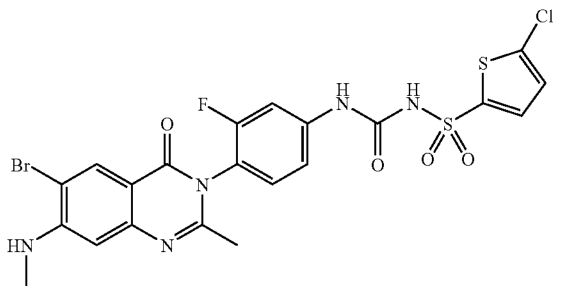
Example 697
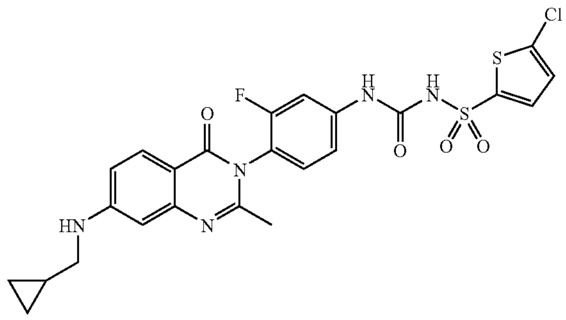
Example 698
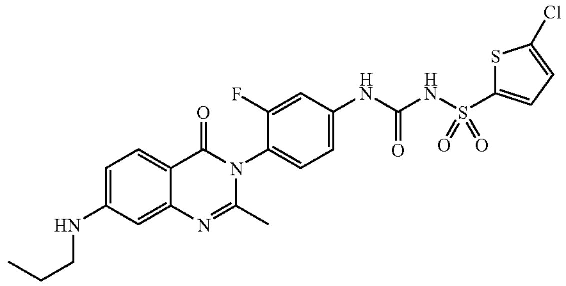
Example 699
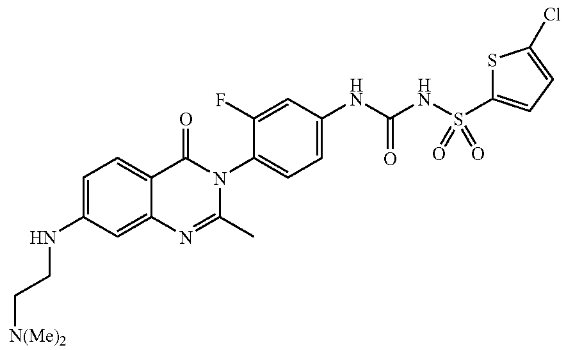
-continued
Example 700
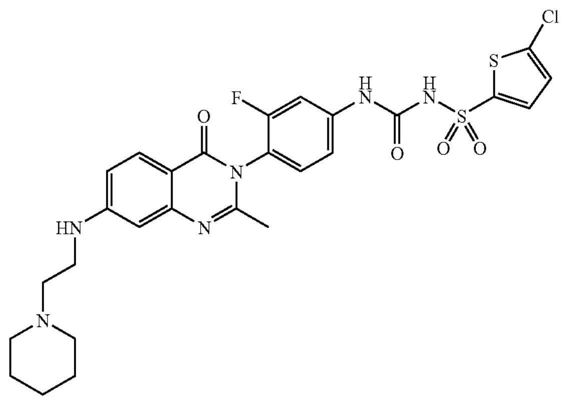
Example 701
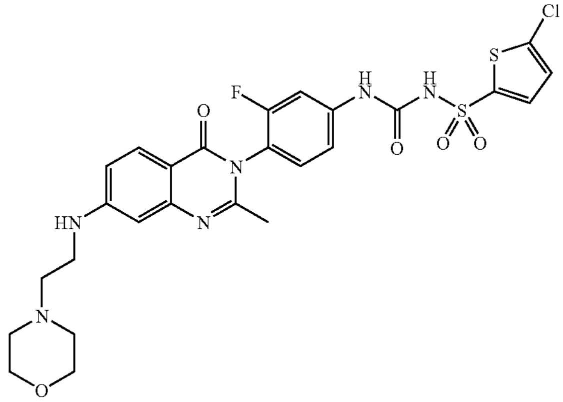
Example 702
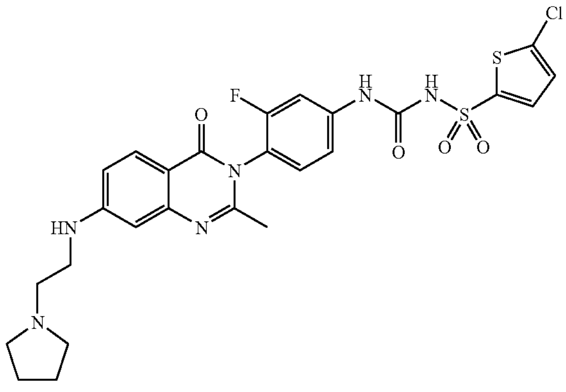
Example 703
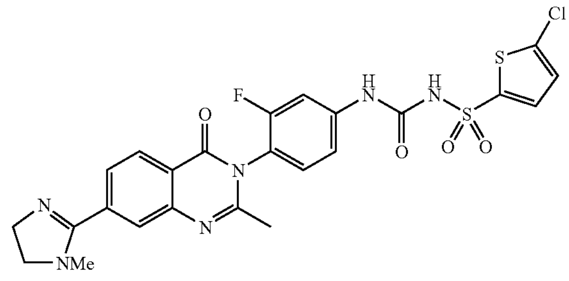

Example 704
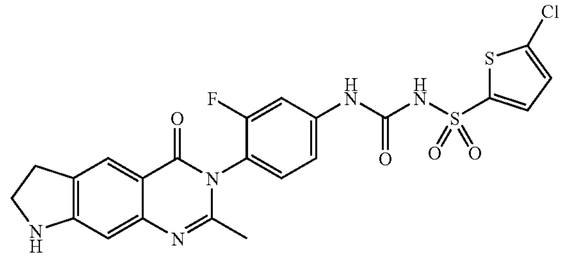
Example 705
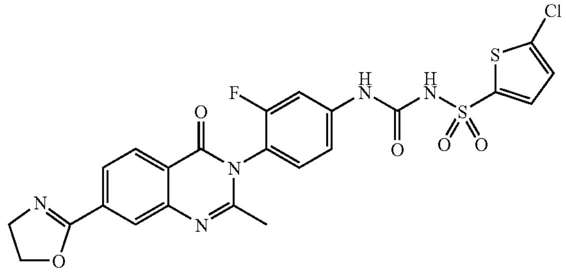
Example 706
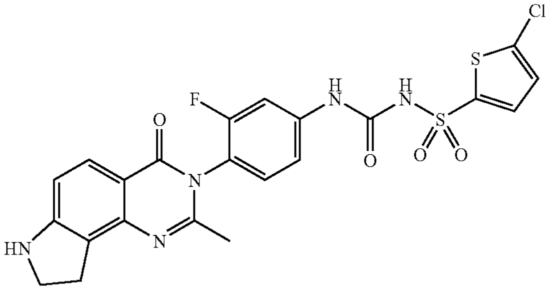
Example 707
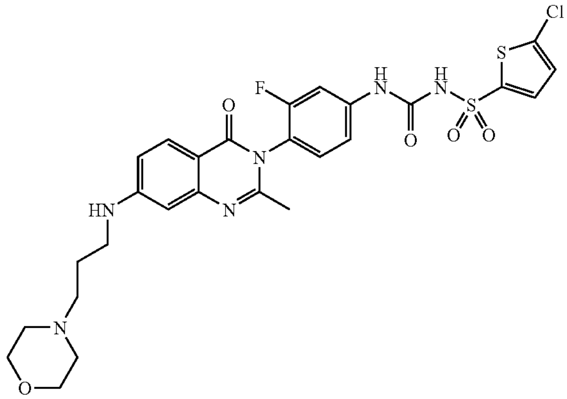
Example 708
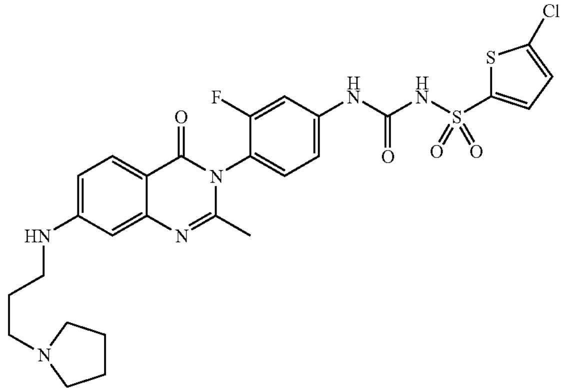
Example 709
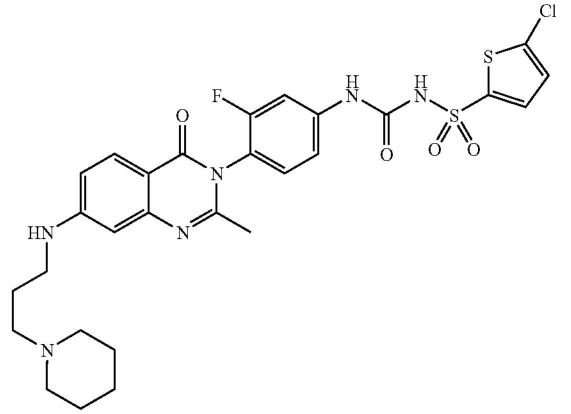
Example 710
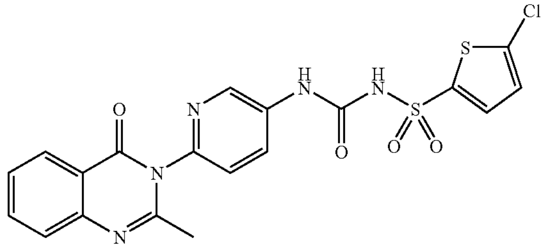
Example 711
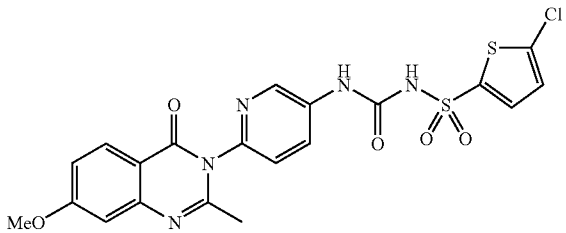
Example 712
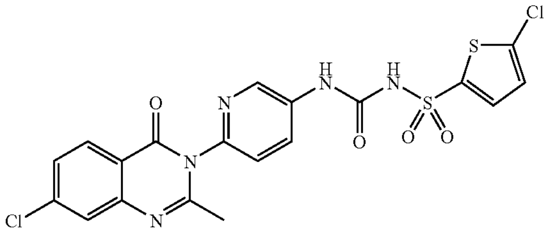

-continued
Example 713
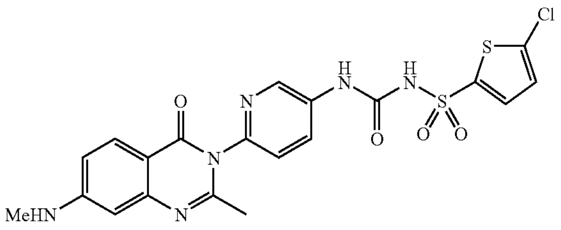
Example 714
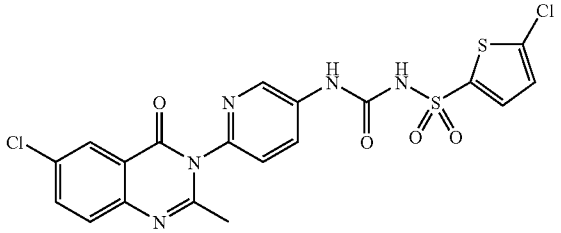
Example 715
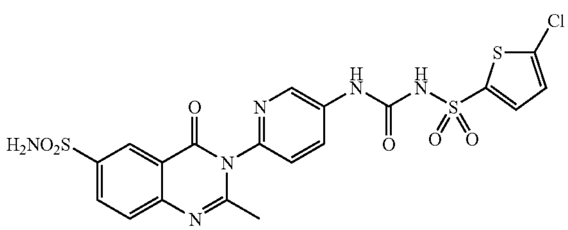
Example 716
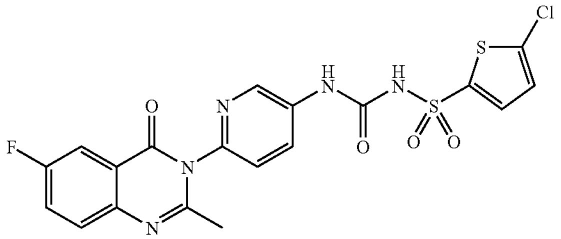
Example 717
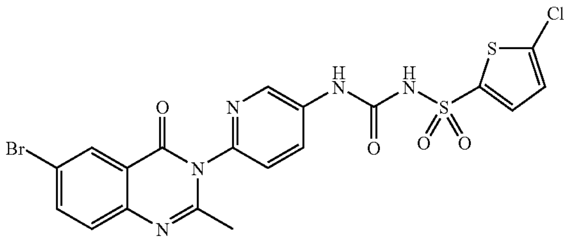
Example 718
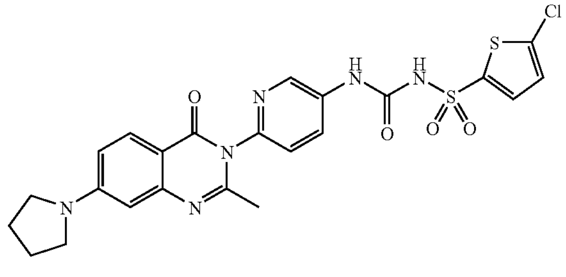
-continued
Example 719
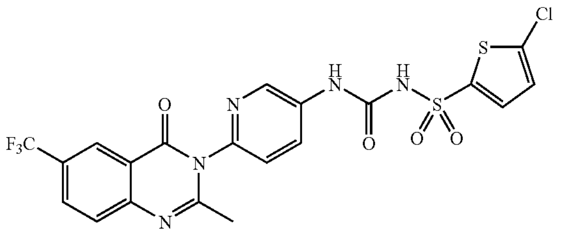
Example 720
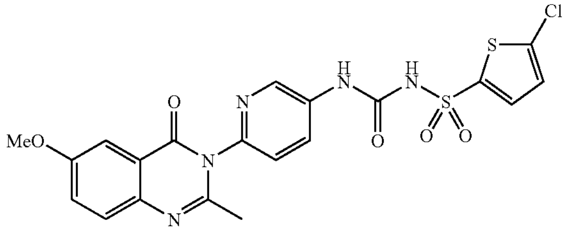
Example 721
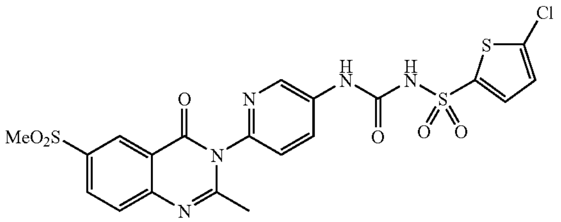
Example 722
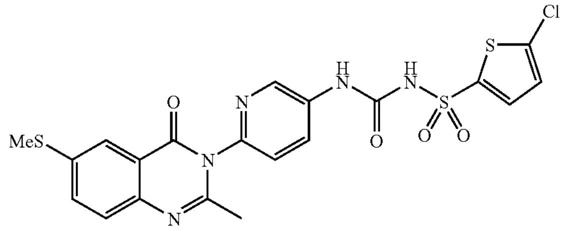
Example 723
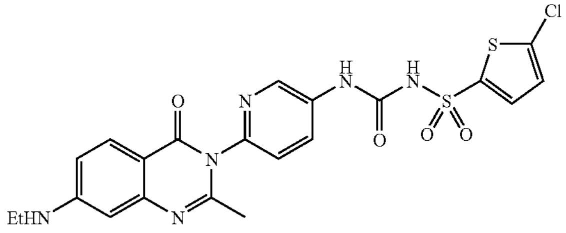
Example 724
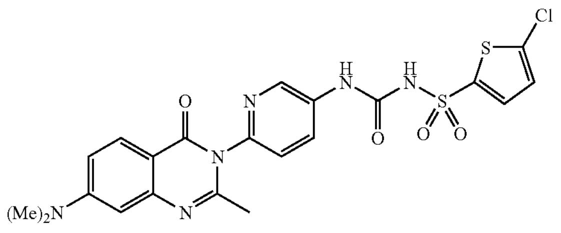

-continued
Example 725
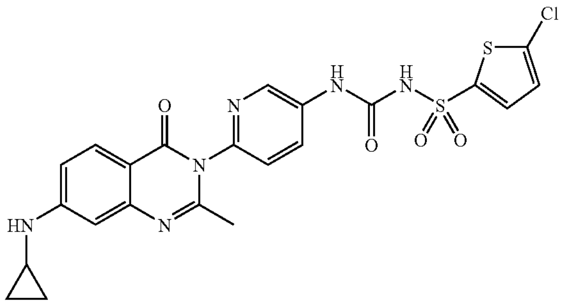
Example 726
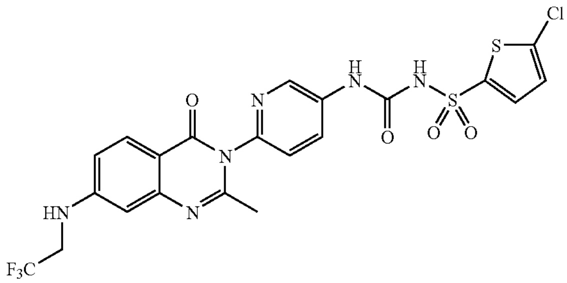
Example 727
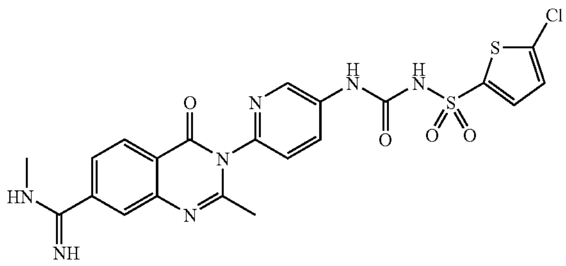
Example 728
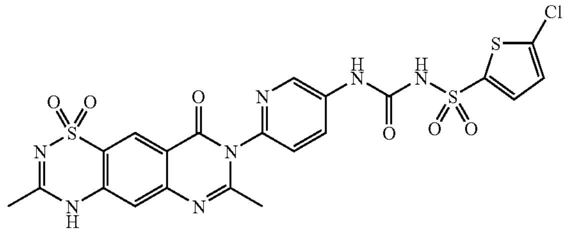
Example 729
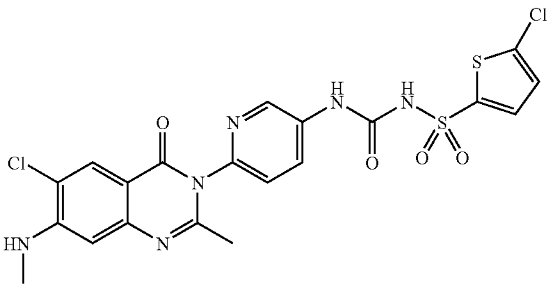
-continued
Example 730
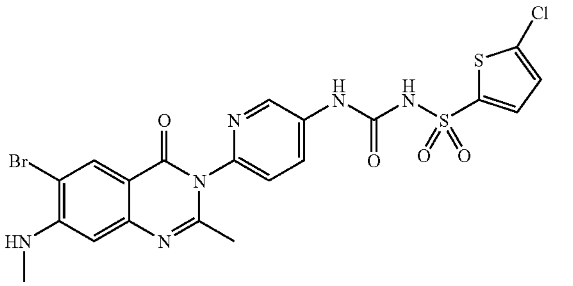
Example 731
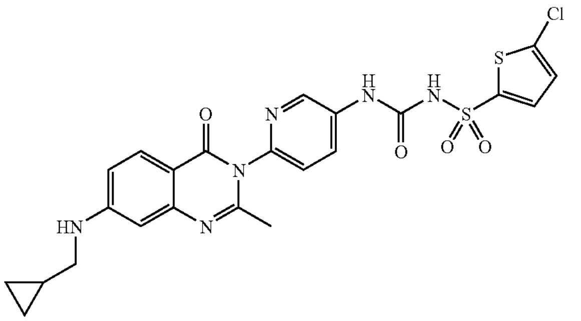
Example 732
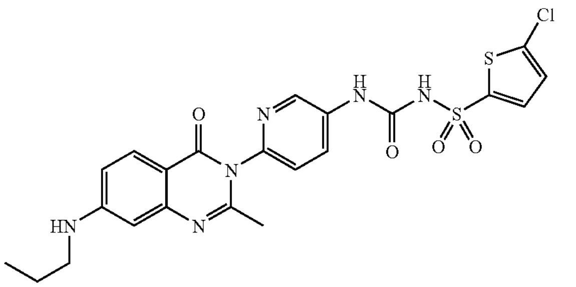
Example 733
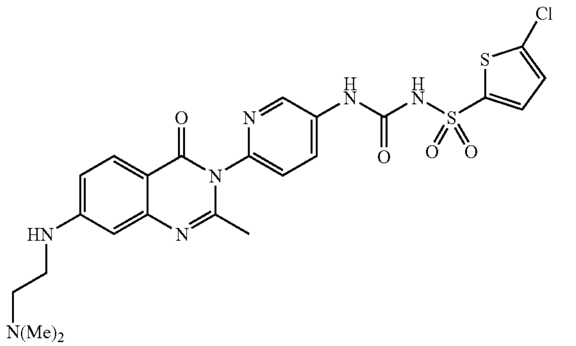

-continued
Example 734
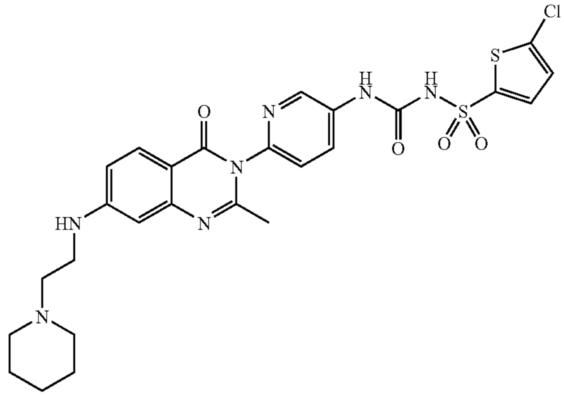
Example 735
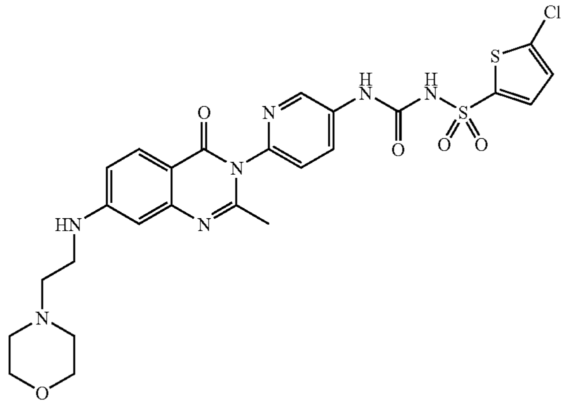
Example 736
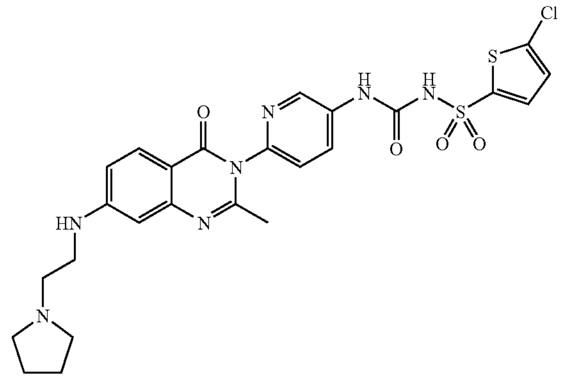
Example 737
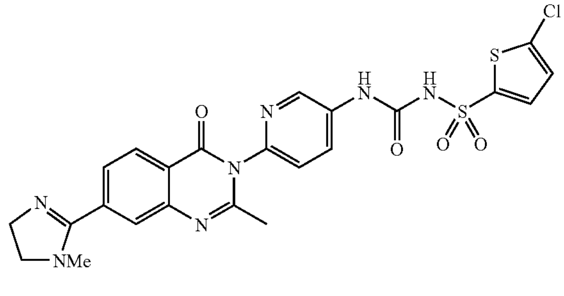
-continued
Example 738
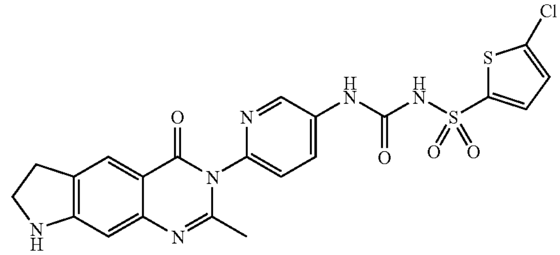
Example 739
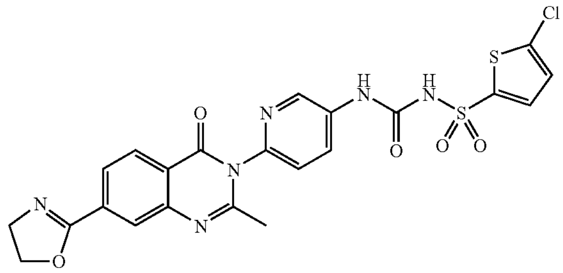
Example 740
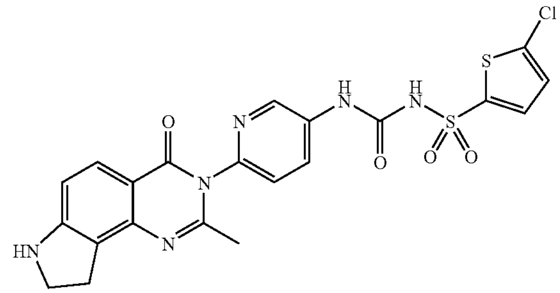
Example 741
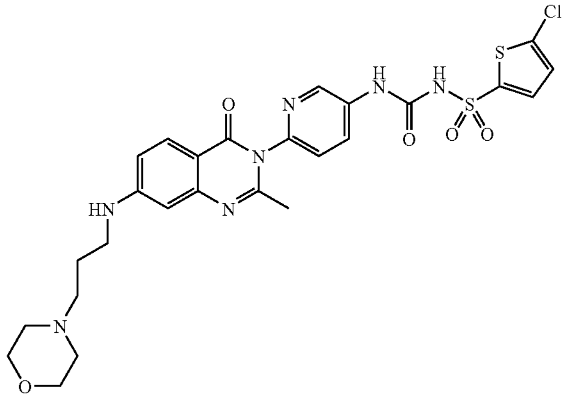

-continued
Example 742
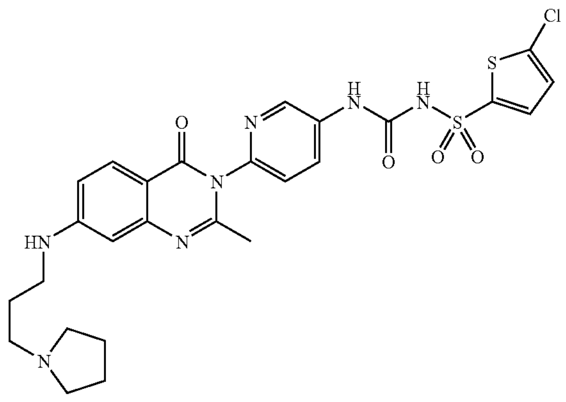
Example 743
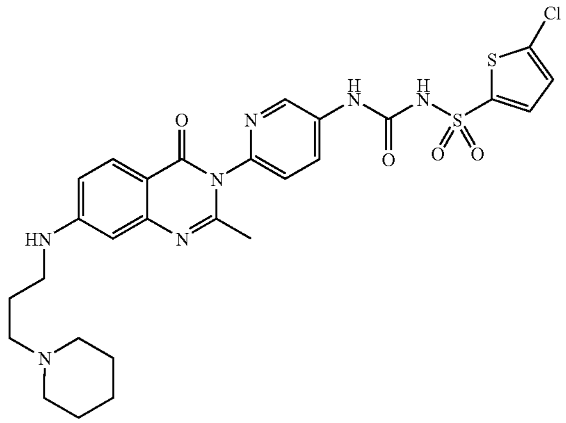
Example 744
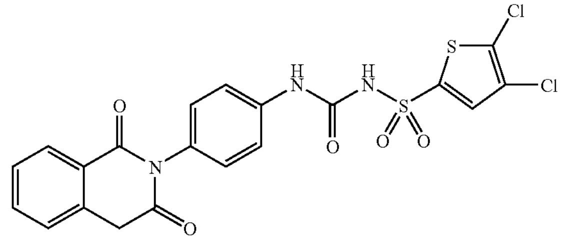
Example 745
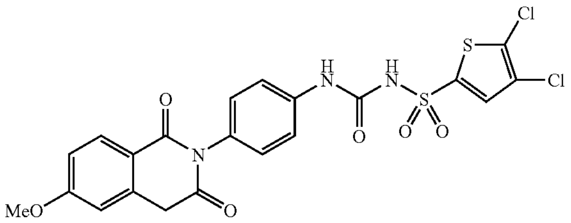
Example 746
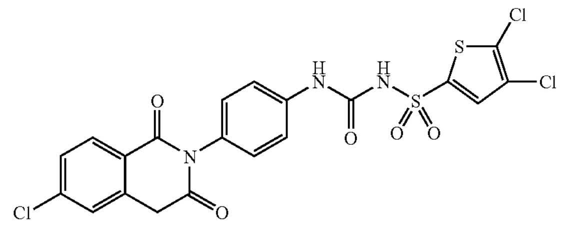
-continued
Example 747
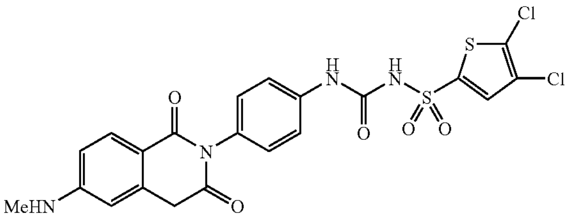
Example 748
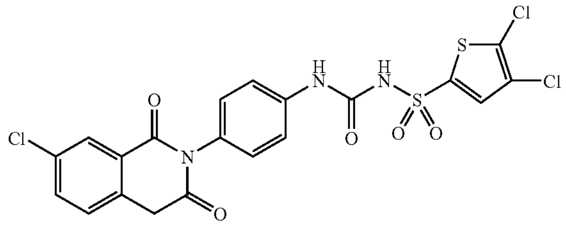
Example 749
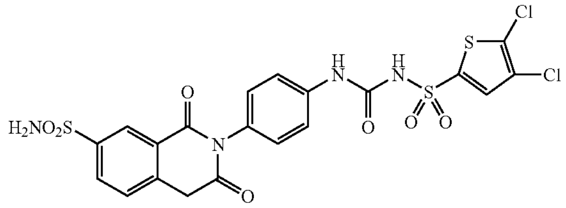
Example 750
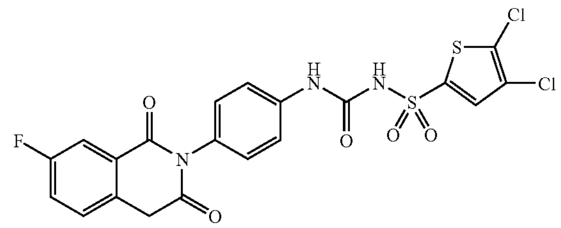
Example 751
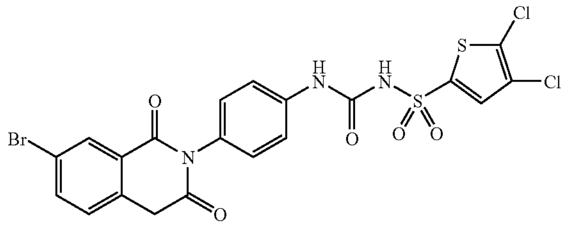
Example 752
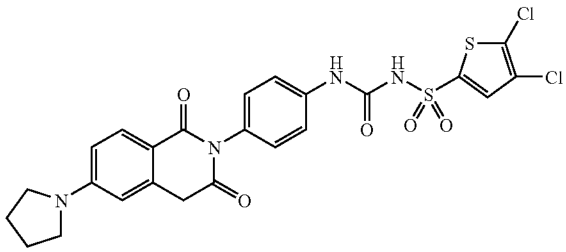

-continued
Example 753
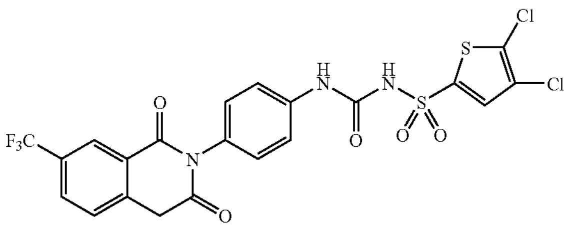
Example 754
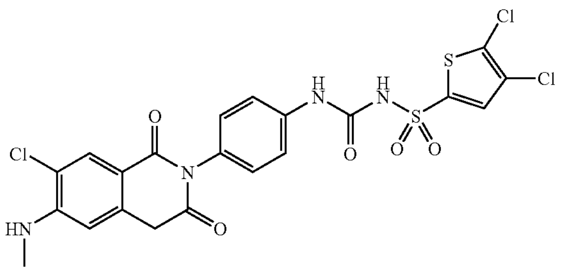
Example 755
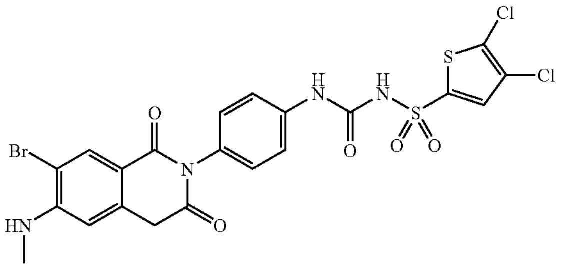
Example 756
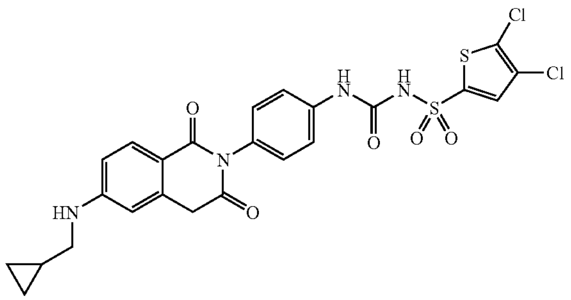
Example 757
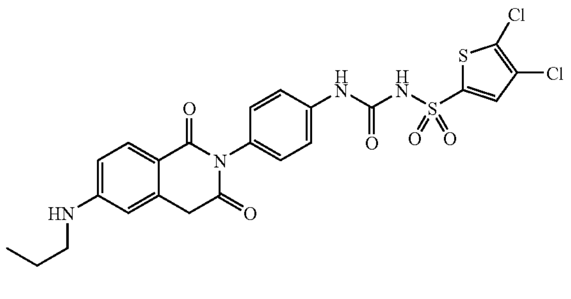
-continued
Example 758
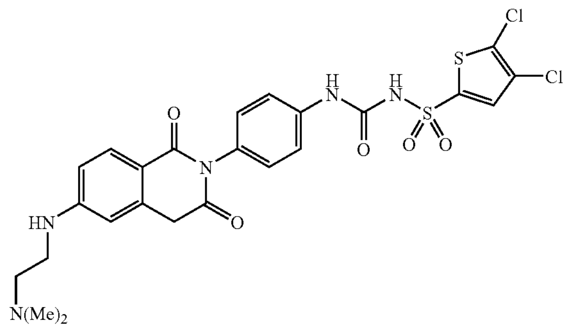
Example 759
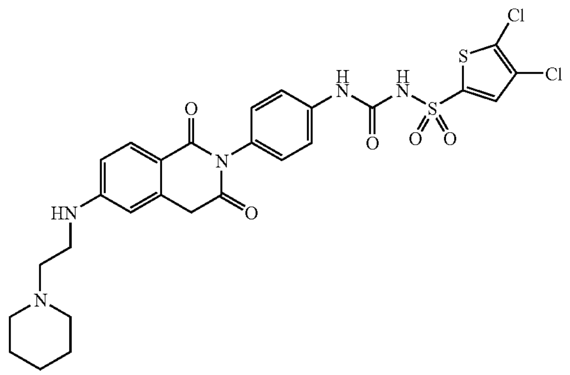
Example 760
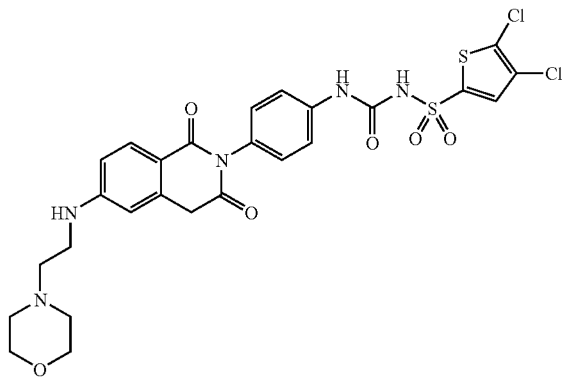
Example 761
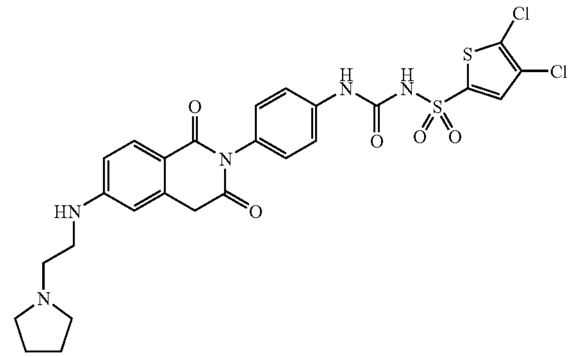

Example 762
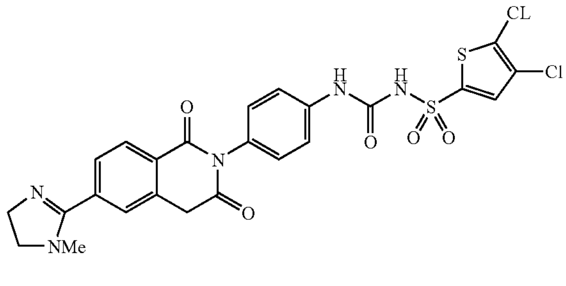
Example 763
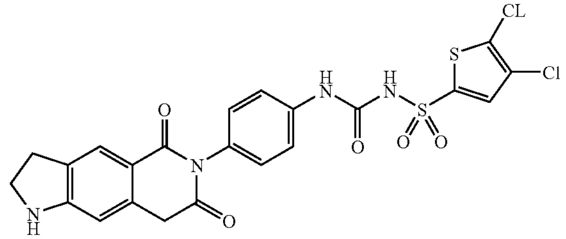
Example 764
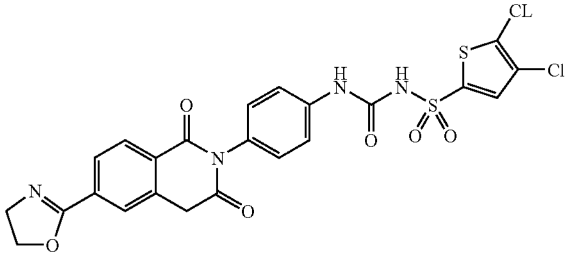
Example 765
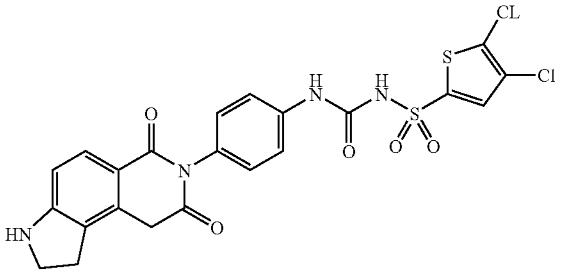
Example 766
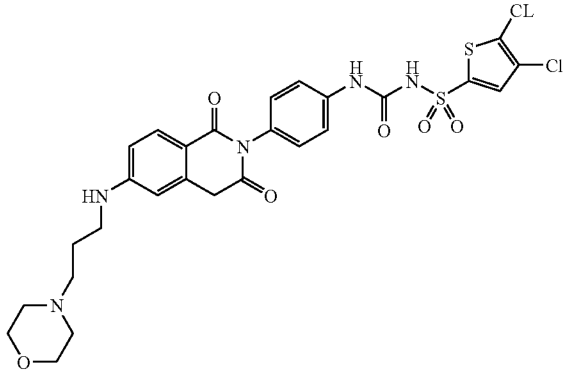
Example 767
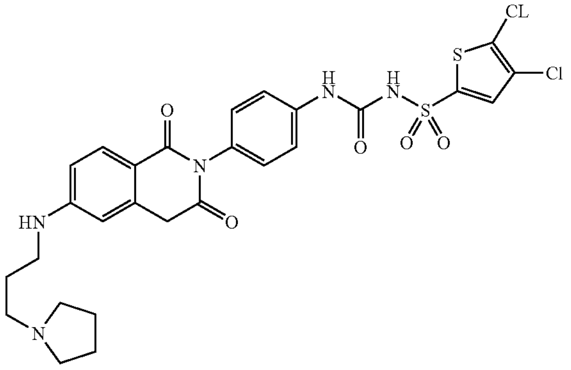
Example 768
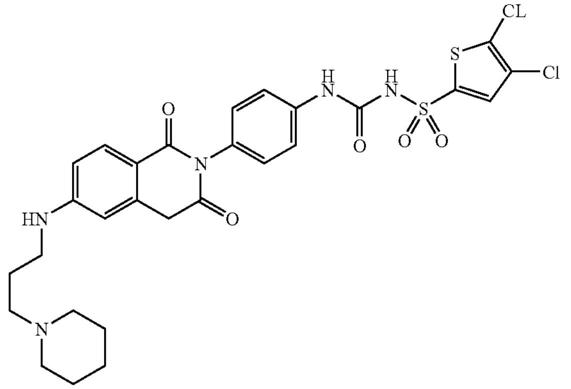
Example 769
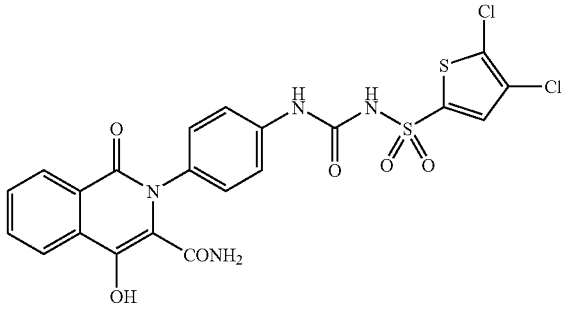
Example 770
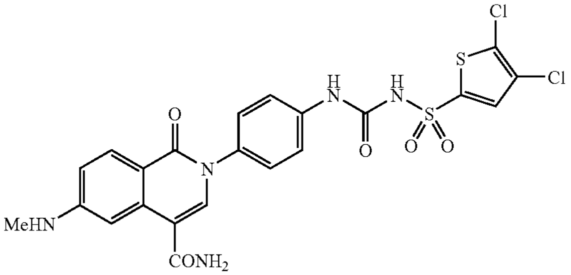

Example 781
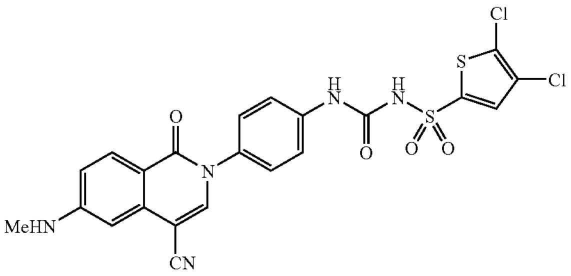
Example 782
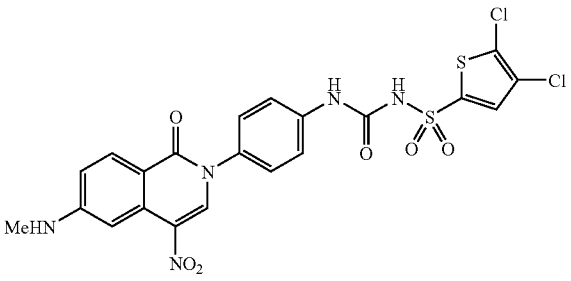
Example 783
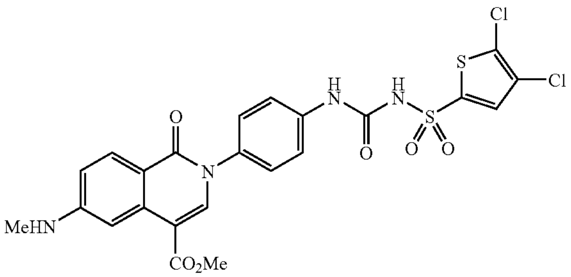
Example 784
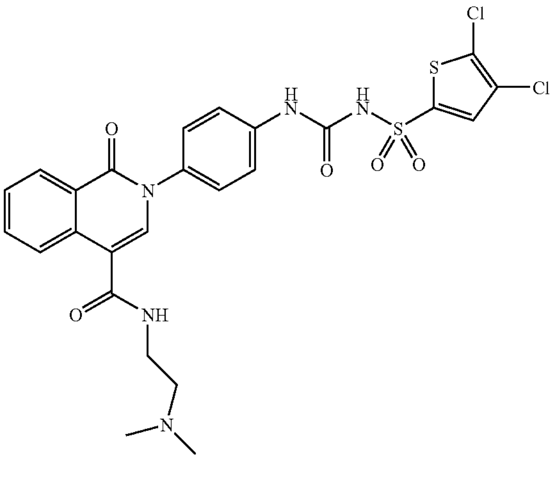
Example 785
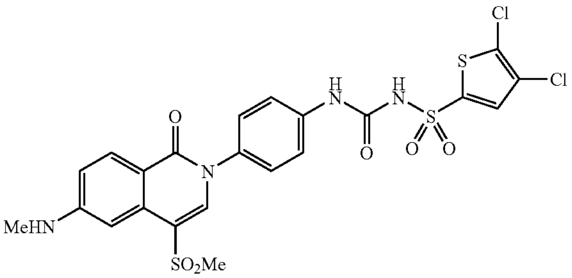
Example 786
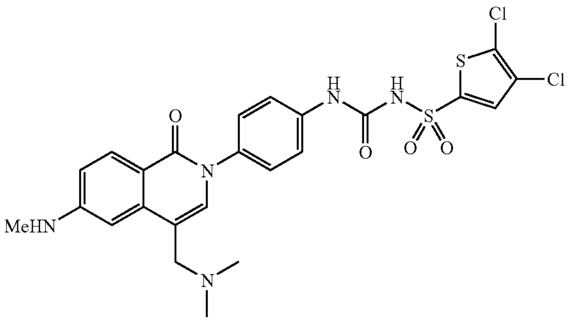
Example 787
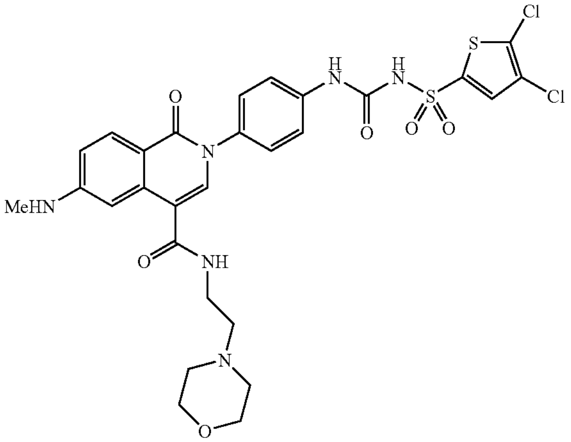
Example 788
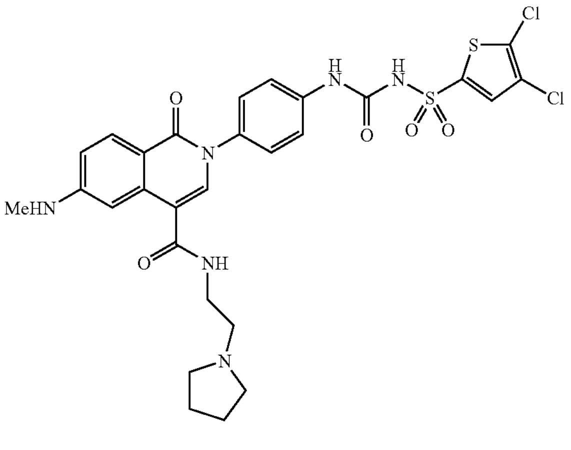

-continued
Example 789
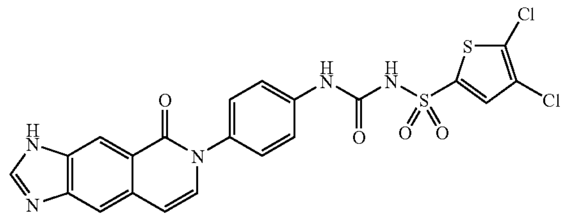
Example 790
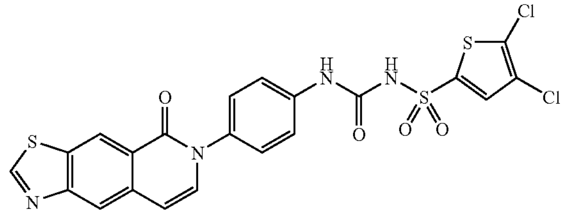
Example 791
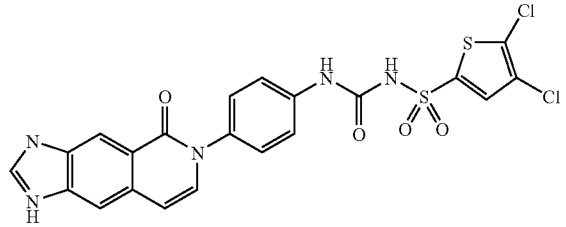
Example 792
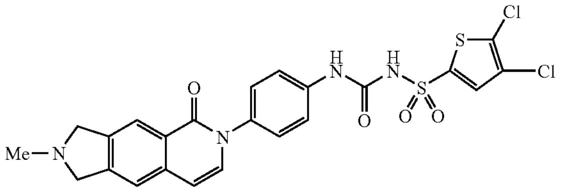
Example 793
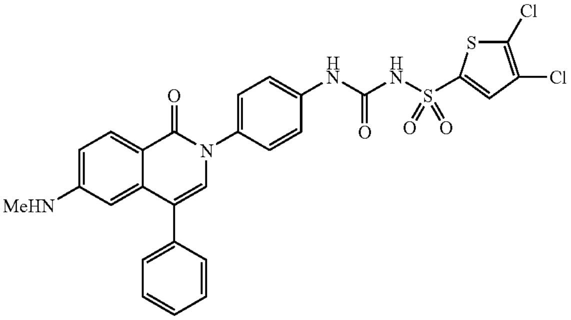
Example 794
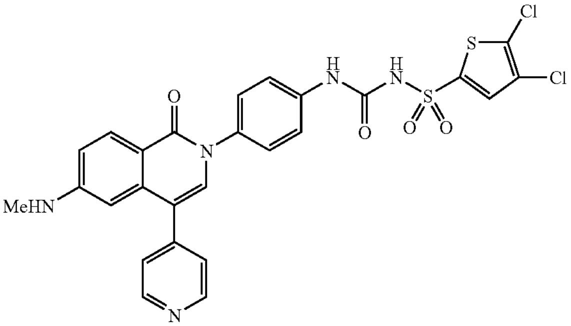
-continued
Example 795
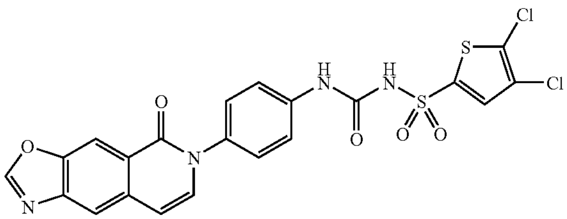
Example 796
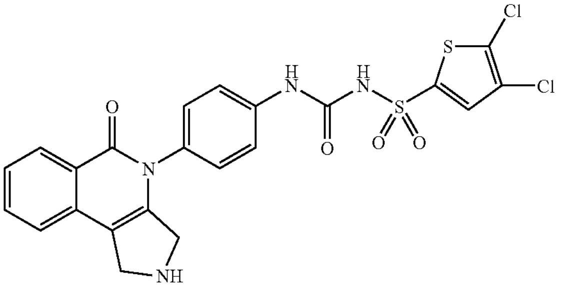
Example 797
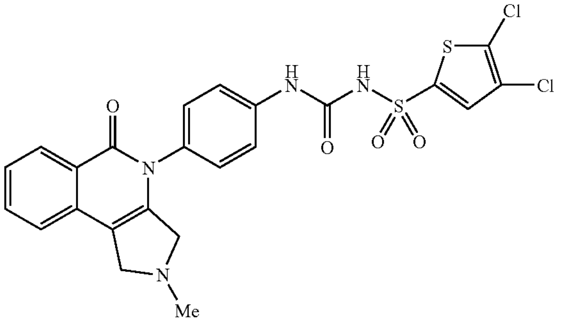
Example 798
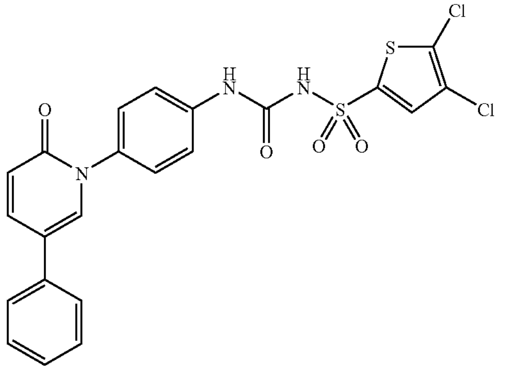
Example 799
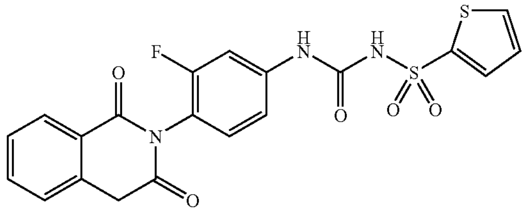

Example 800
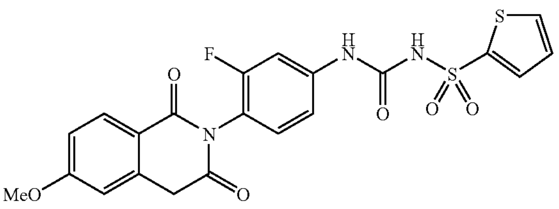
Example 801
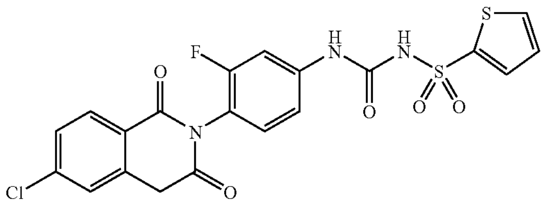
Example 802
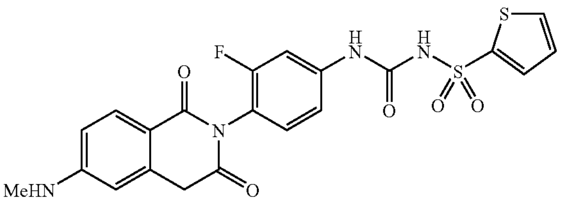
Example 803
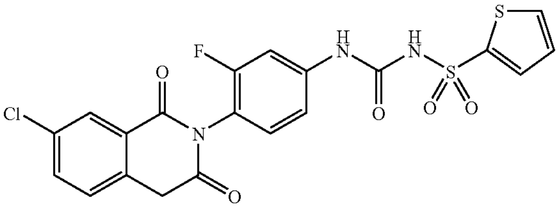
Example 804
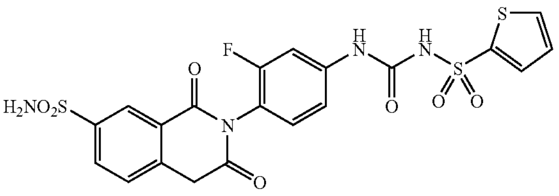
Example 805
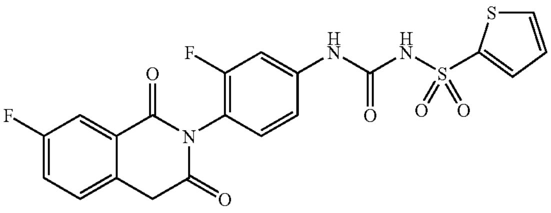
Example 806
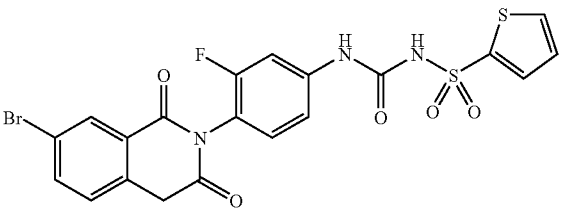
Example 807
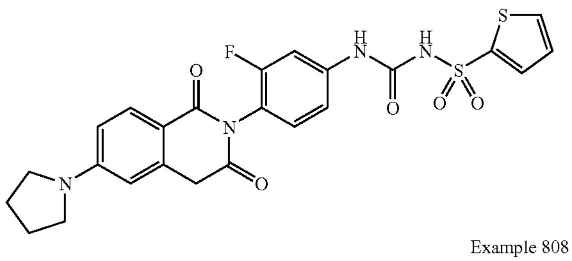
Example 808
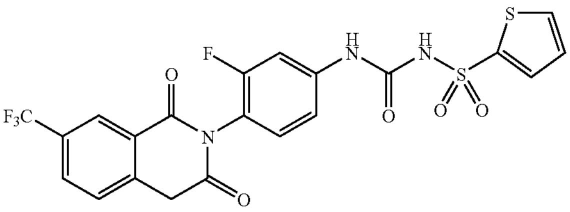
Example 809
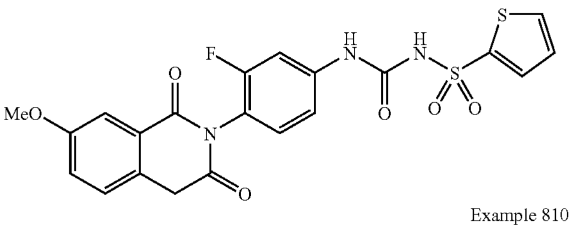
Example 810
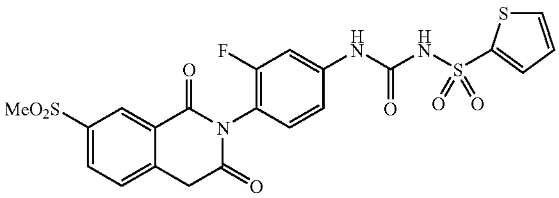
Example 811
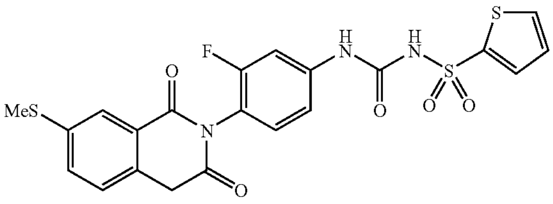
Example 812
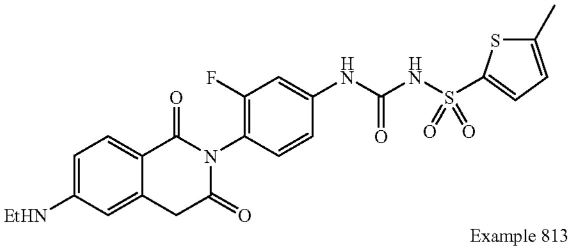
Example 813
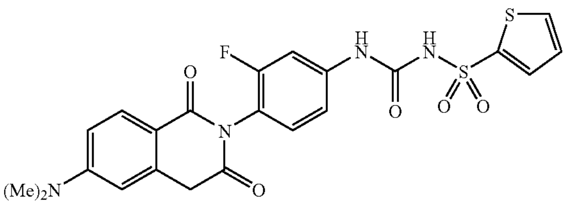

-continued
Example 814
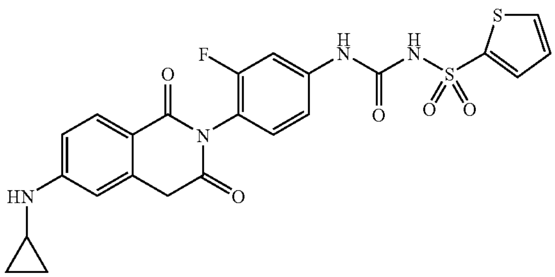
Example 815
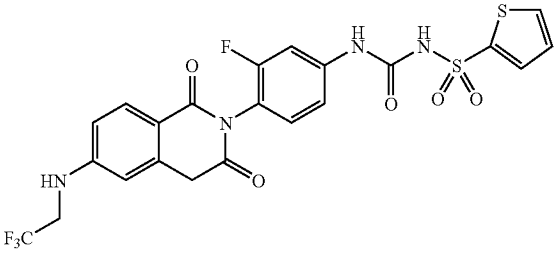
Example 816
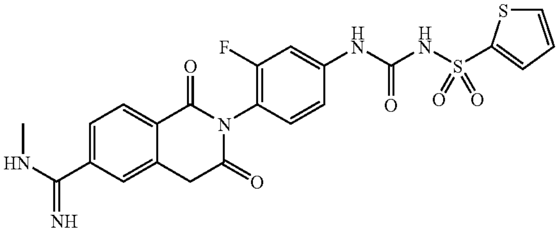
Example 817
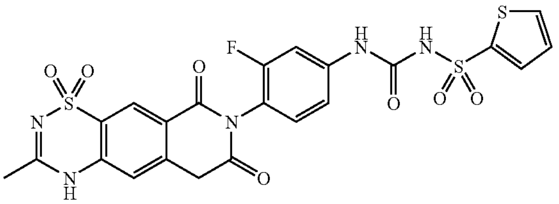
Example 818
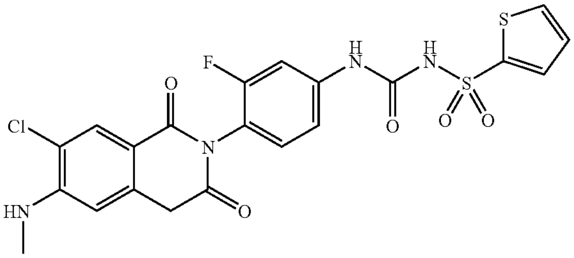
Example 819
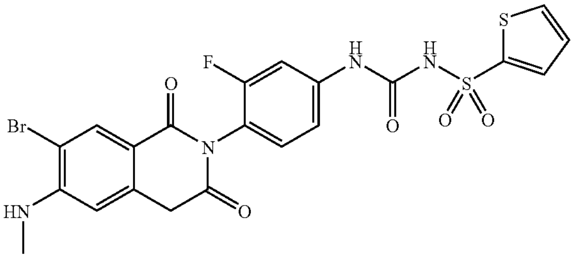
-continued
Example 820
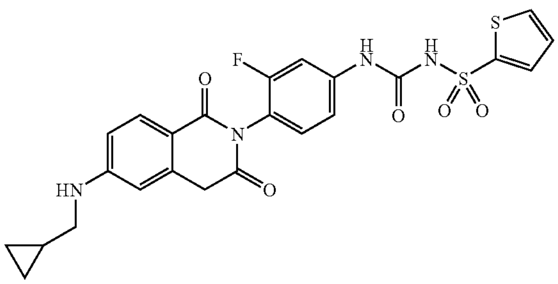
Example 821
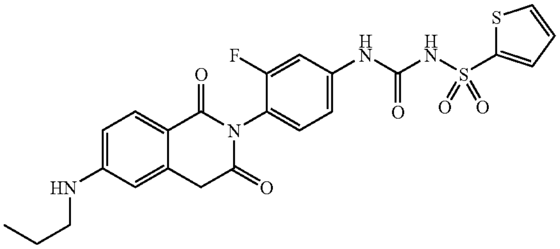
Example 822
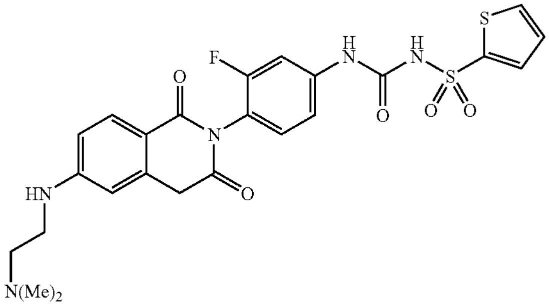
Example 823
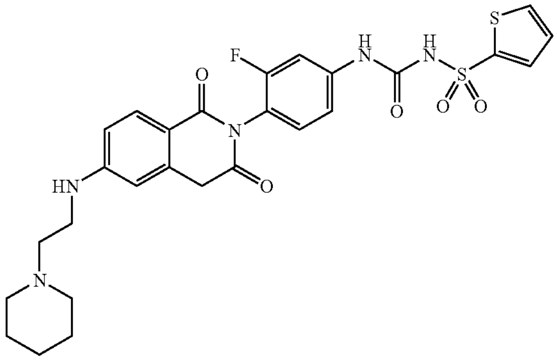

-continued
Example 824
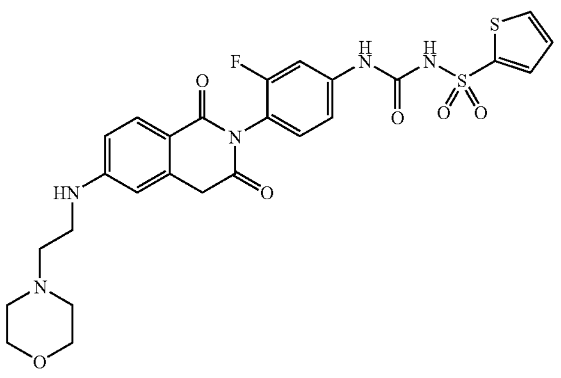
Example 825
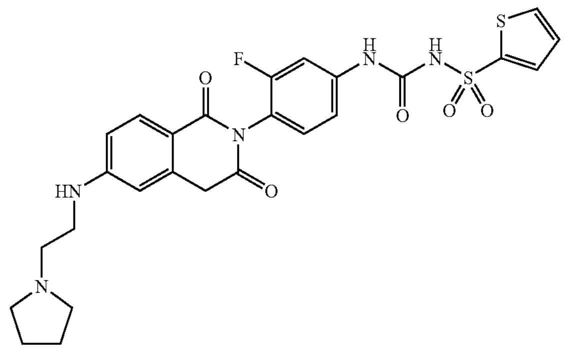
Example 826
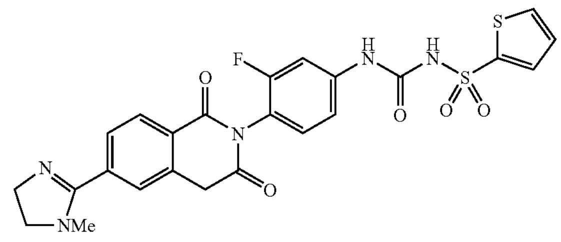
Example 827
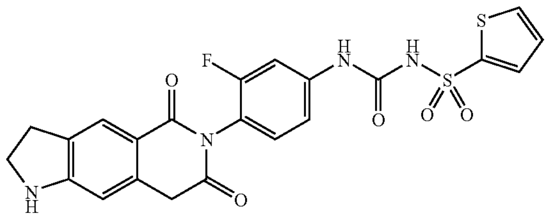
Example 828
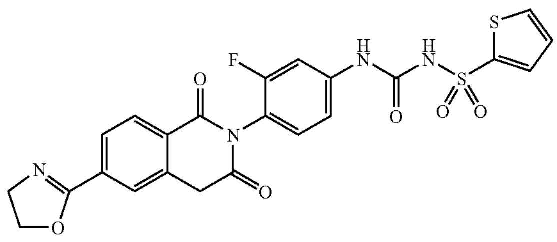
-continued
Example 829
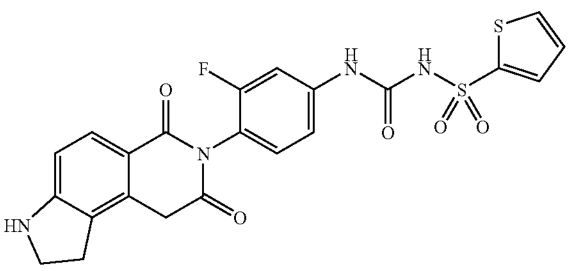
Example 830
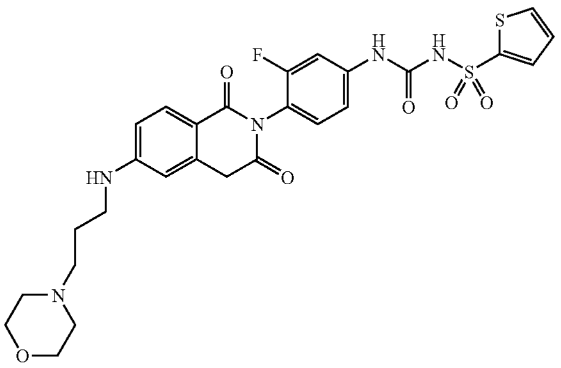
Example 831
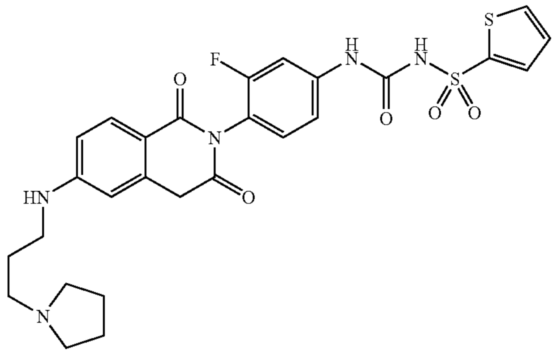
Example 832
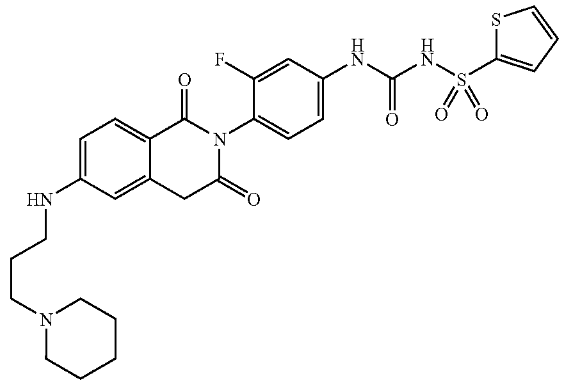

-continued
Example 833
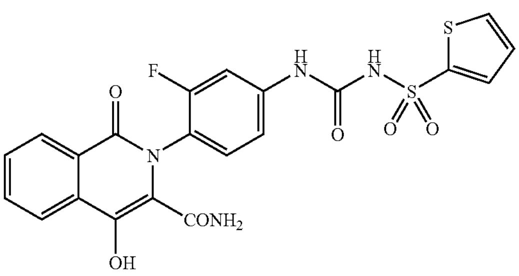
Example 834
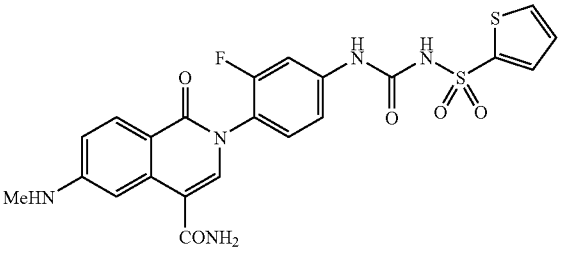
Example 835
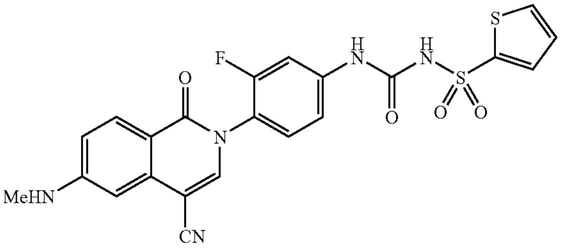
Example 836
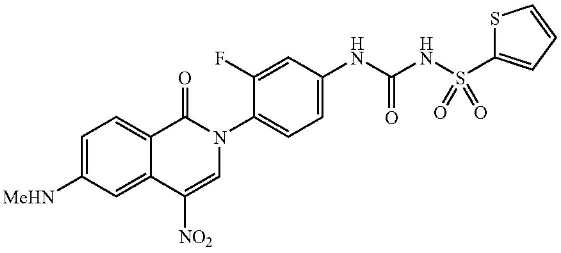
Example 837
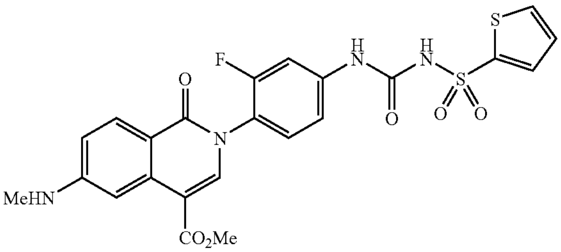
-continued
Example 838
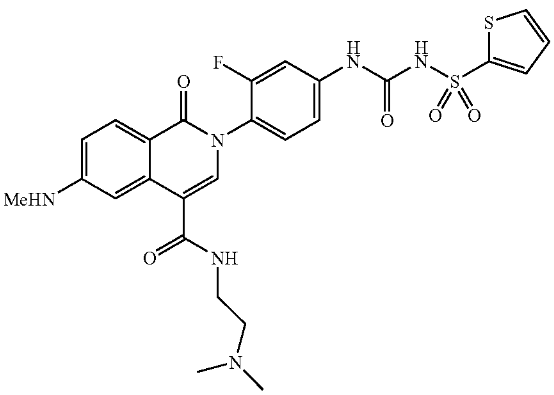
Example 839
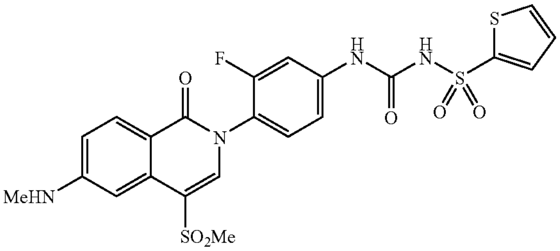
Example 840
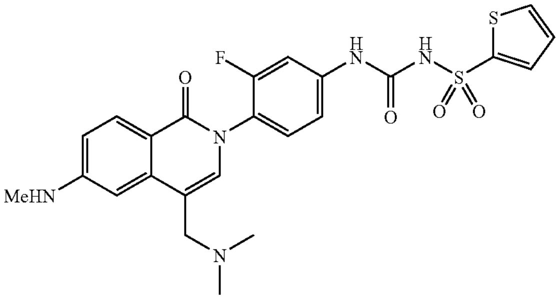
Example 841
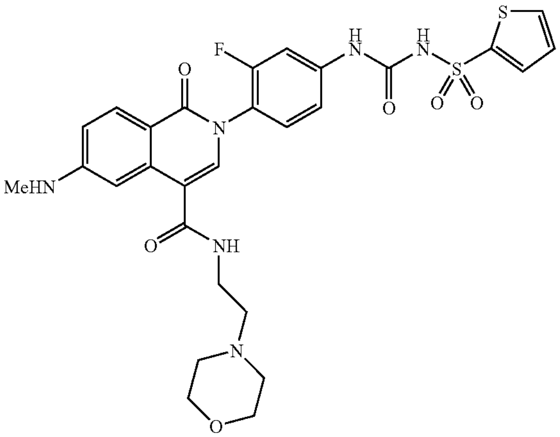

-continued
Example 842
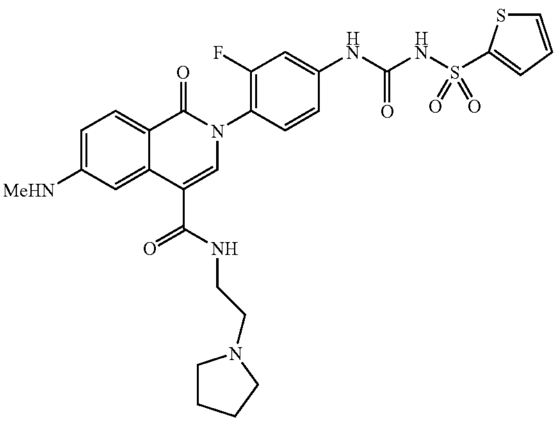
Example 843
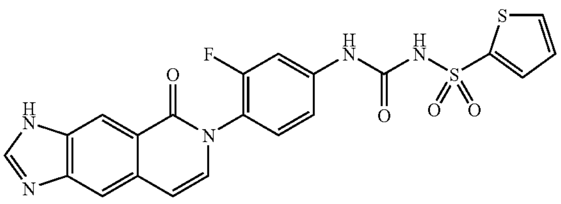
Example 844
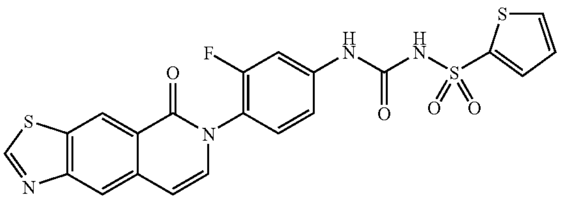
Example 845
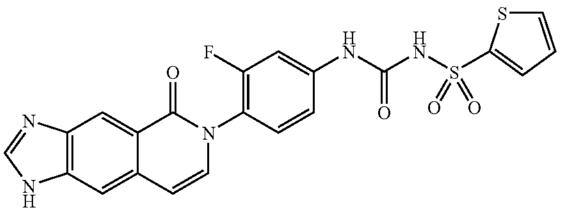
Example 846
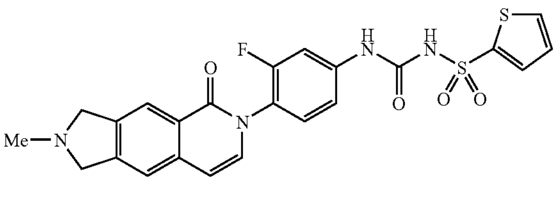
-continued
Example 847
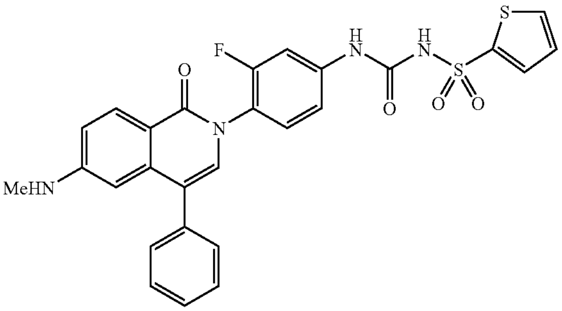
Example 848
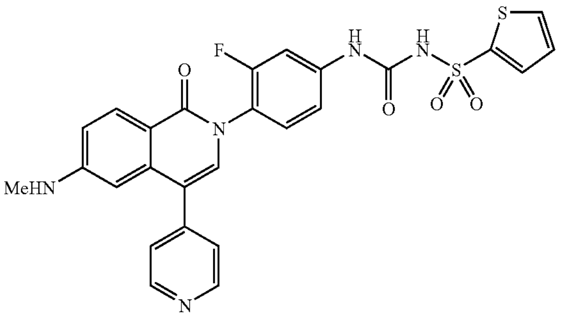
Example 849
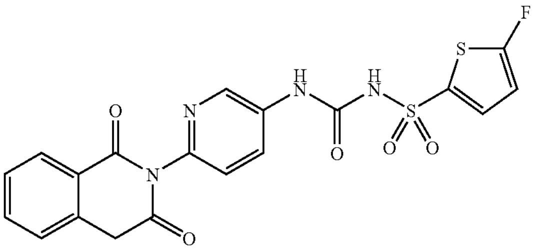
Example 850
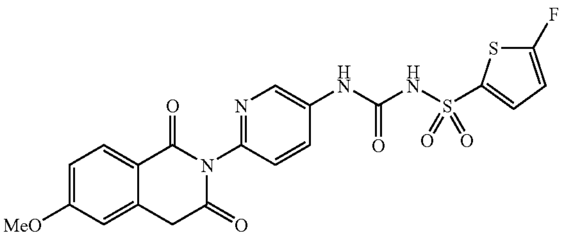
Example 851
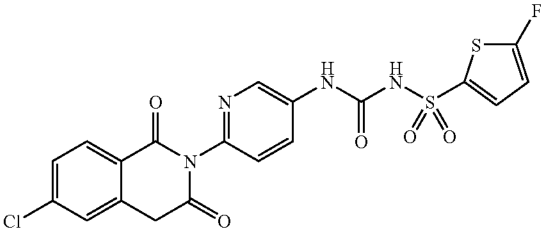

-continued
Example 852
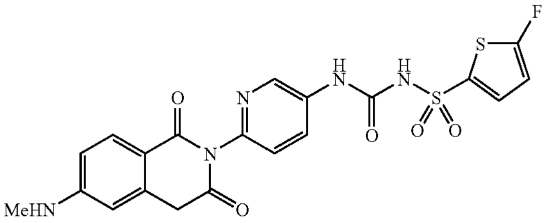
Example 853
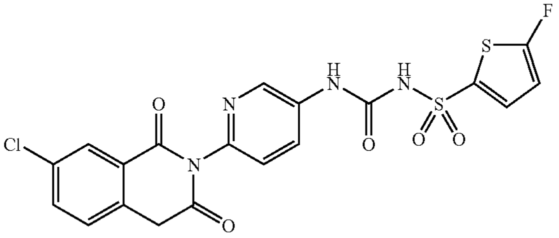
example 854
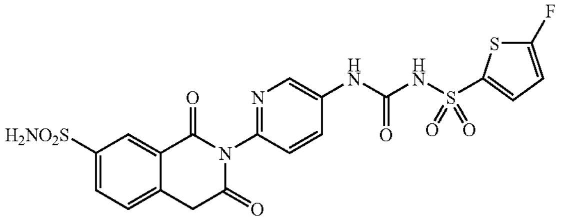
Example 855
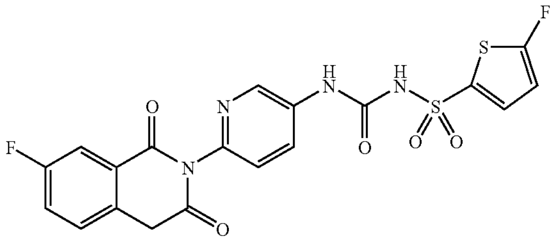
Example 856
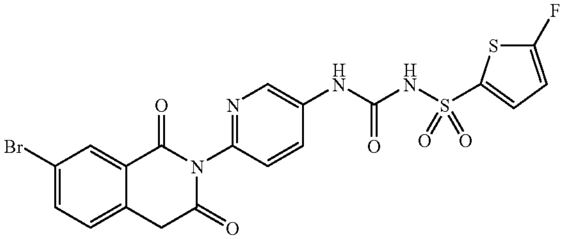
Example 857
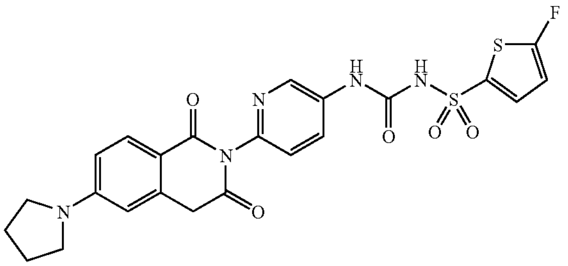
-continued
Example 858
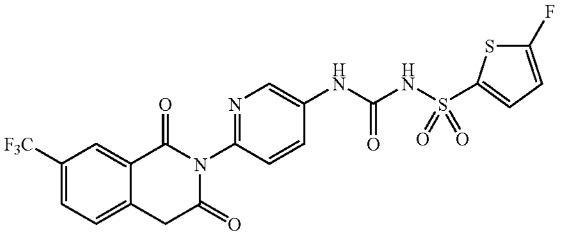
Example 859
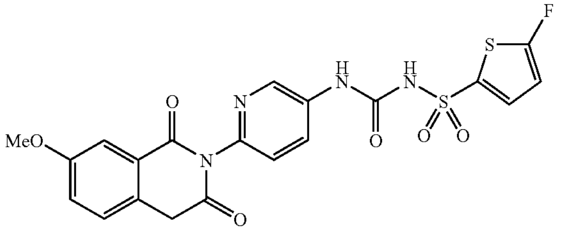
example 860
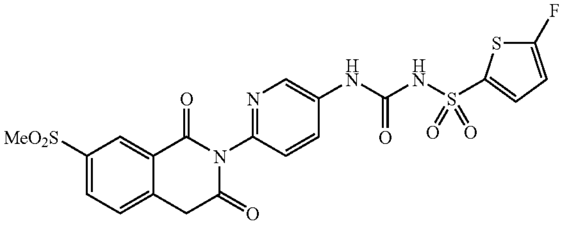
Example 861
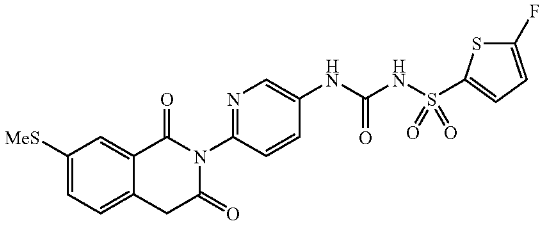
Example 862
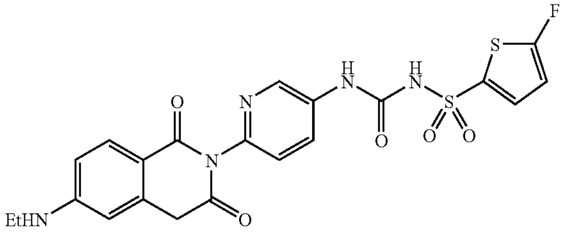
Example 863
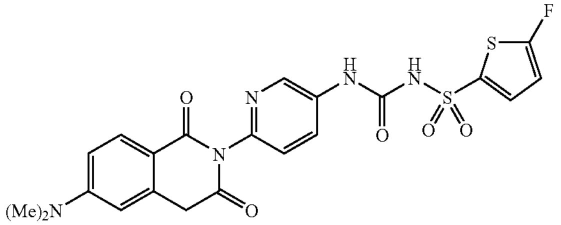

Example 864
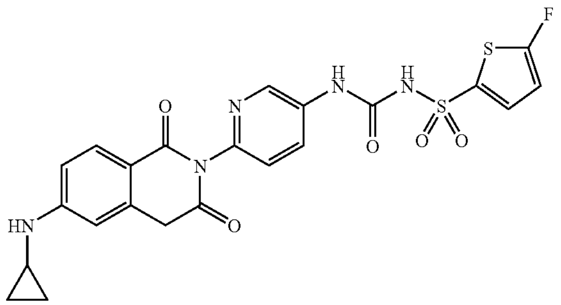
Example 865
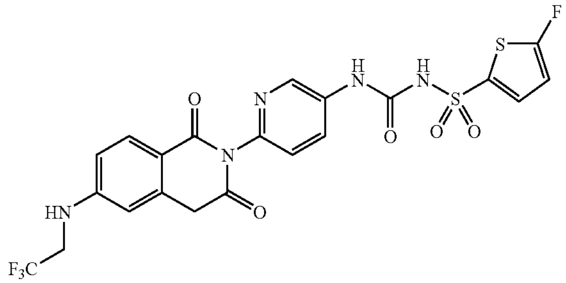
Example 866
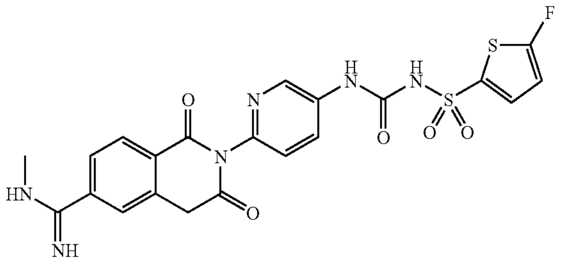
Example 867
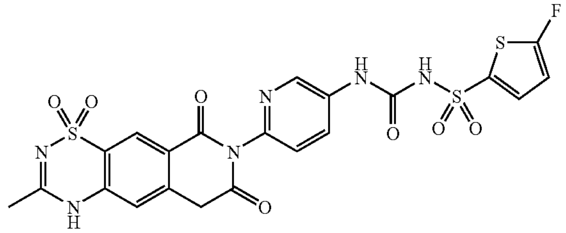
Example 868
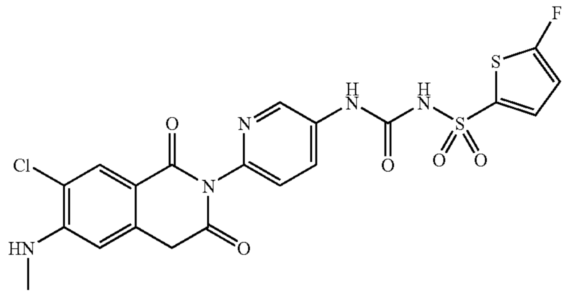
Example 869
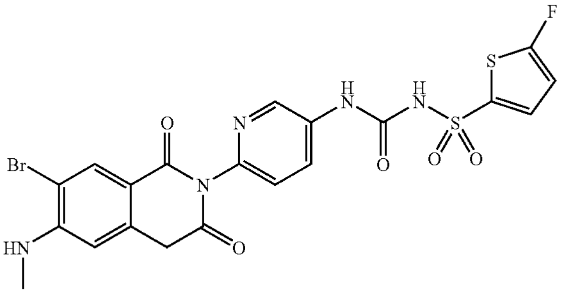
Example 870
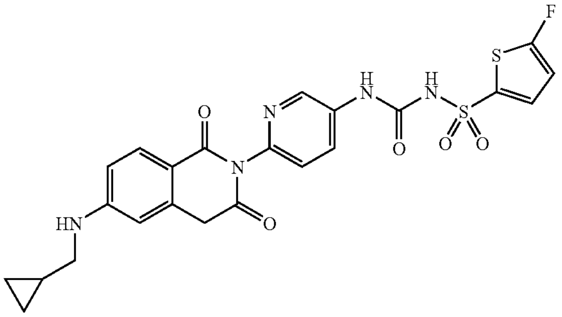
Example 871
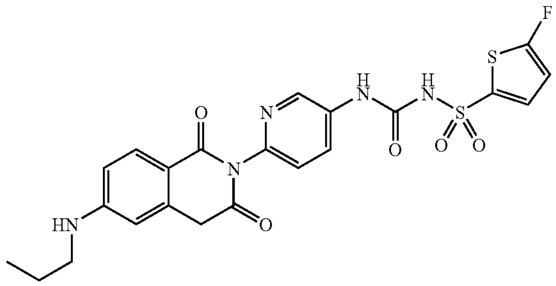
Example 872
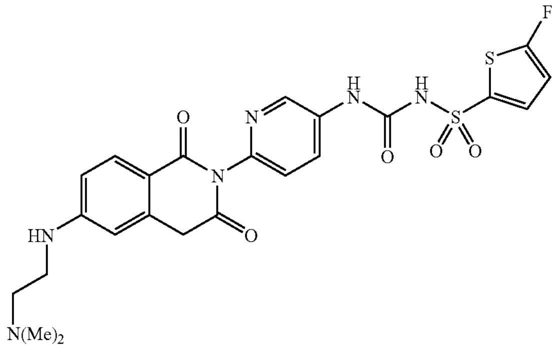

-continued
Example 873
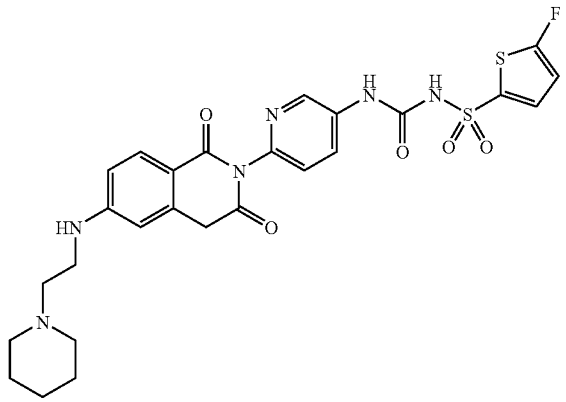
Example 874
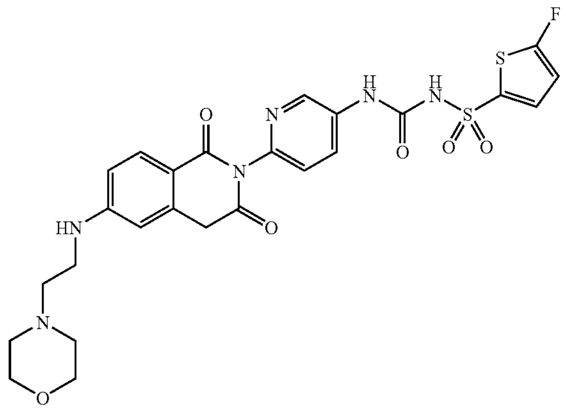
Example 875
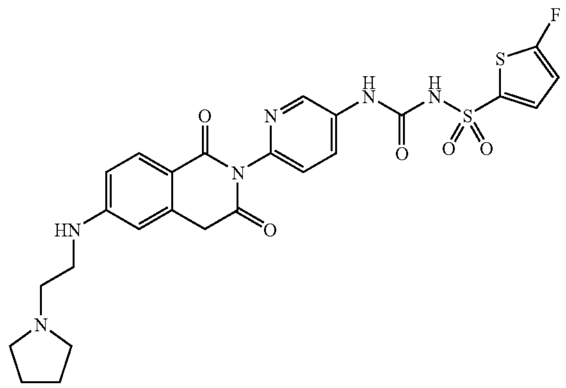
Example 876
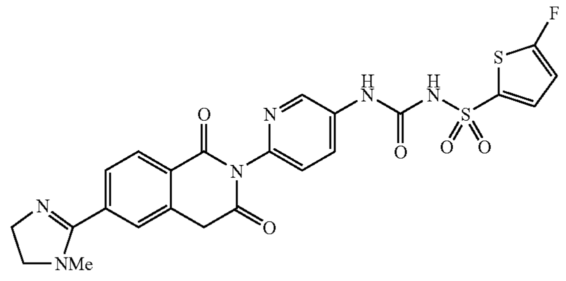
-continued
Example 877
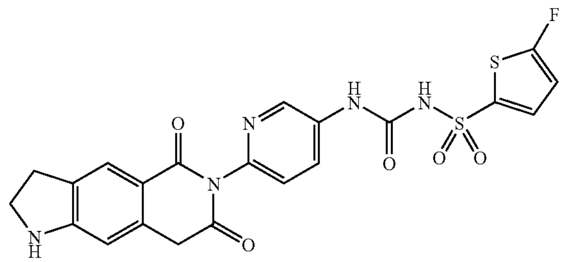
Example 878
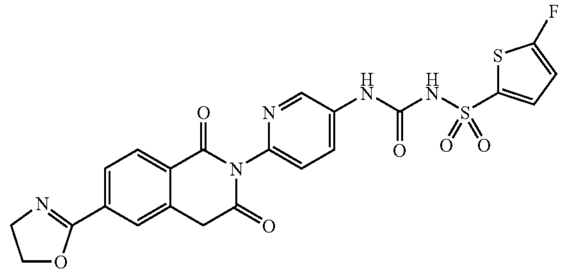
Example 879
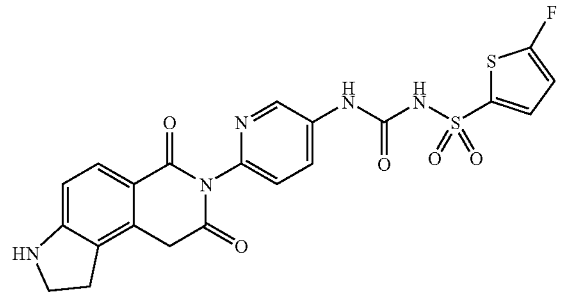
Example 880
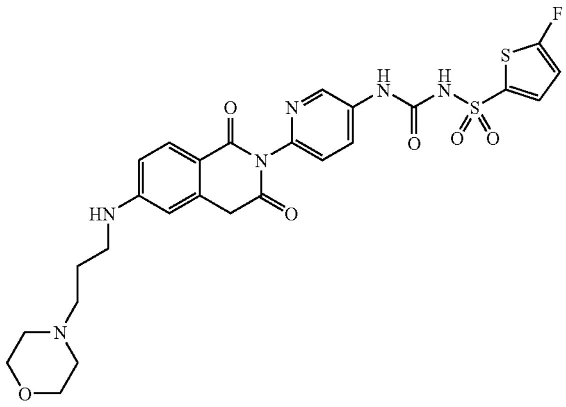

-continued
Example 881
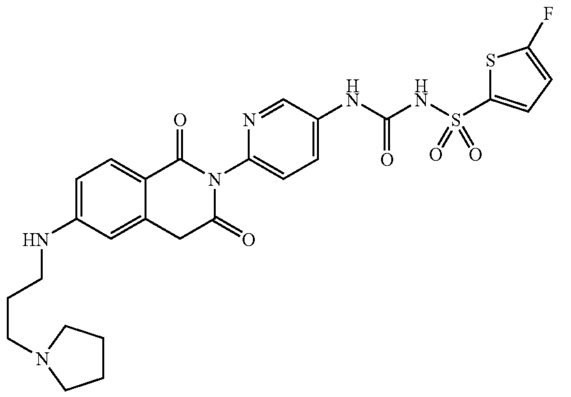
Example 882
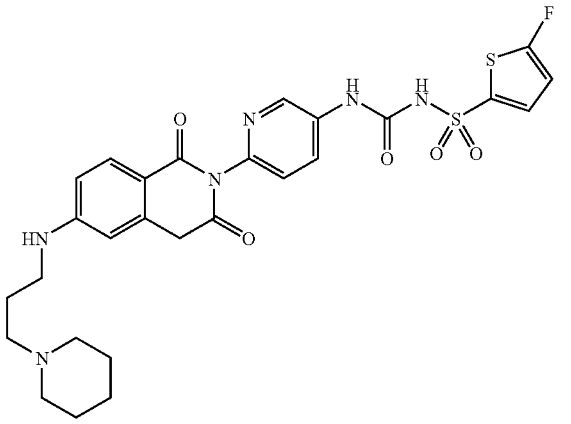
Example 883
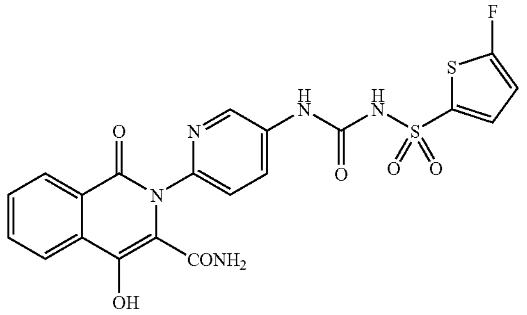
Example 884
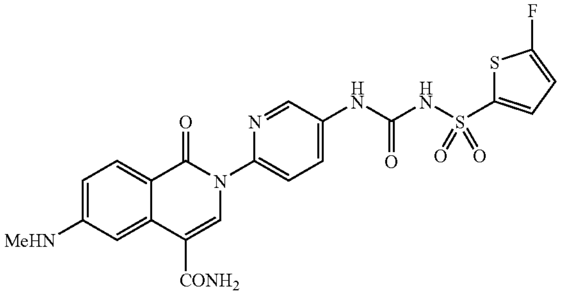
-continued
Example 885
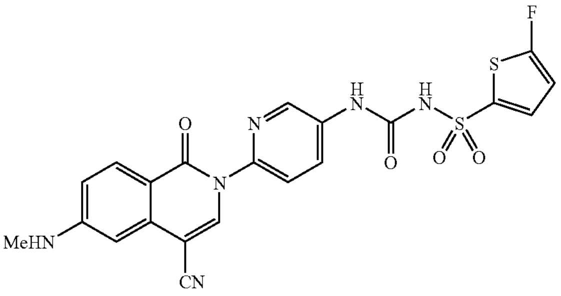
Example 886
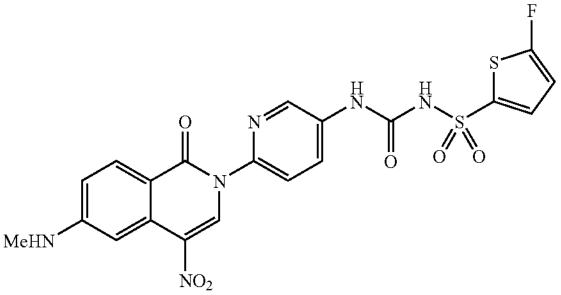
Example 887
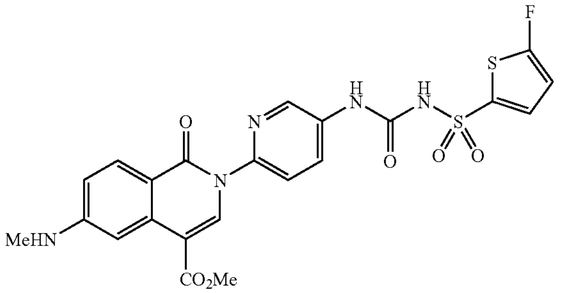
Example 888
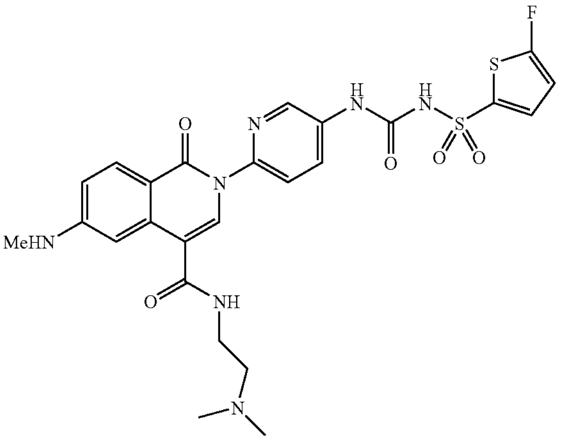

-continued
Example 889
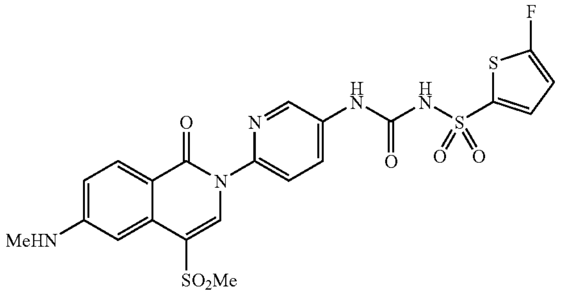
Example 890
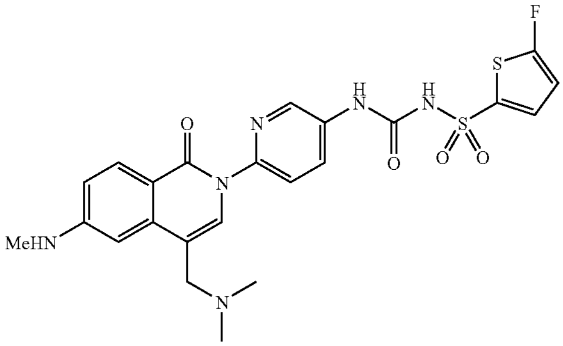
Example 891
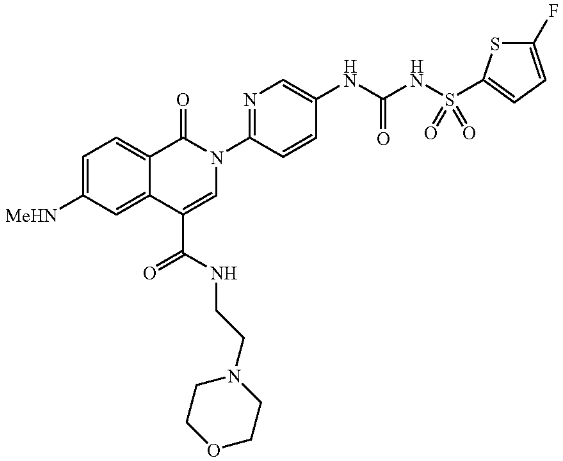
Example 892
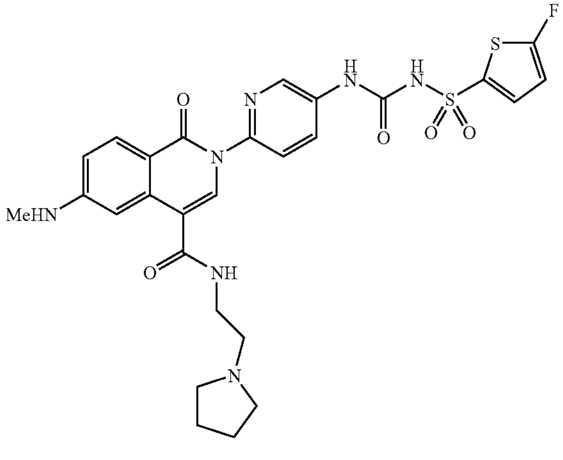
-continued
Example 893
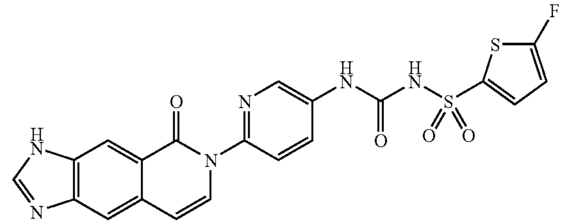
Example 894
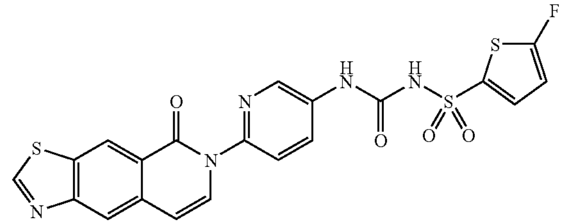
Example 895
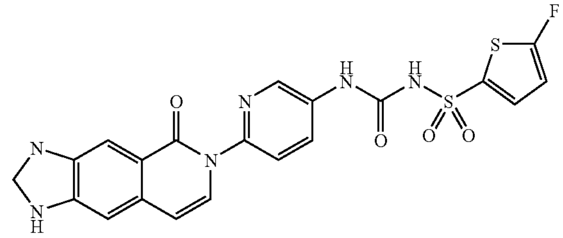
Example 896
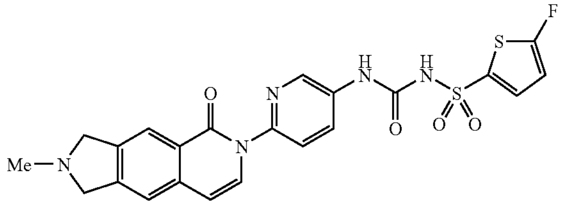
Example 897
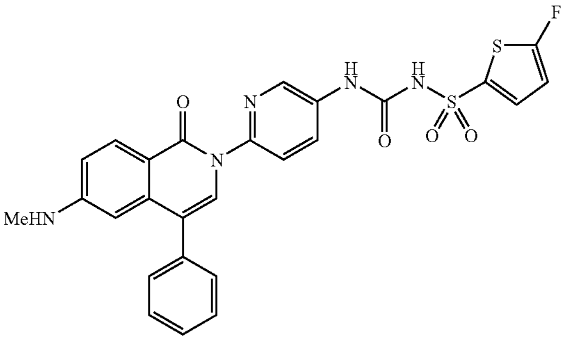

Example 898
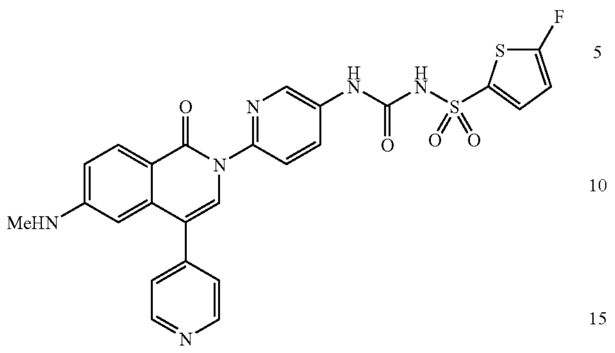
Example 899
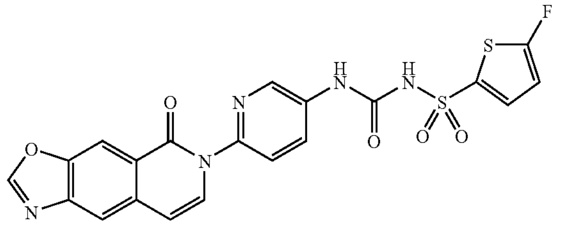
Example 900
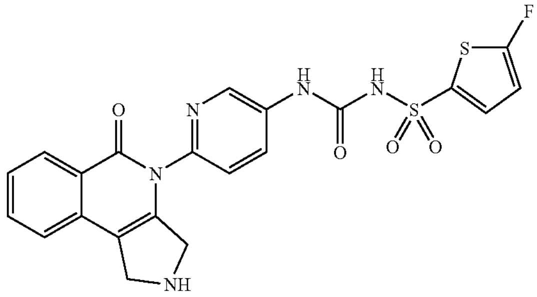
Example 901
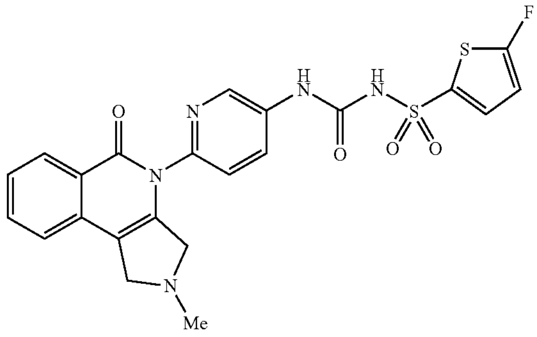
Example 902
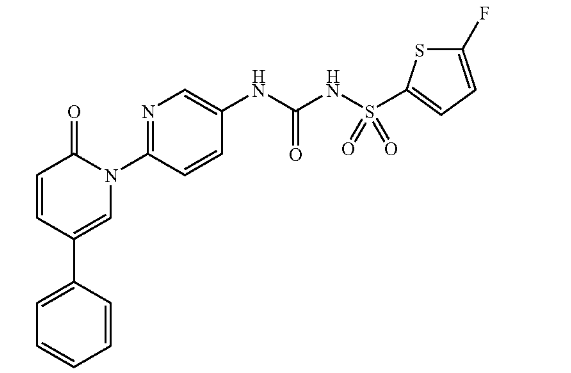
Example 903
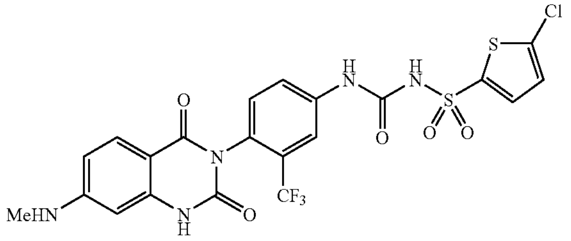
Example 904
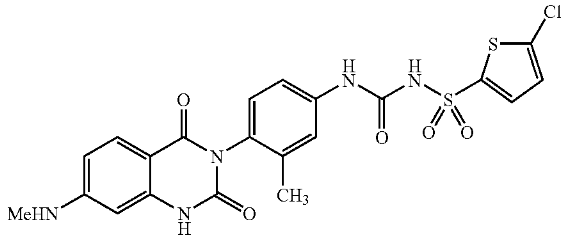
Example 905
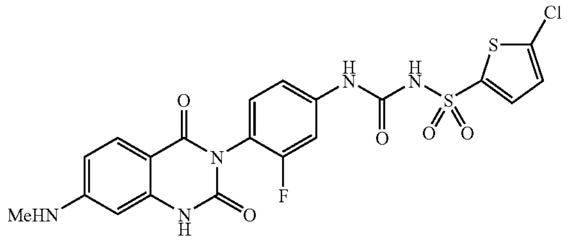
Example 906
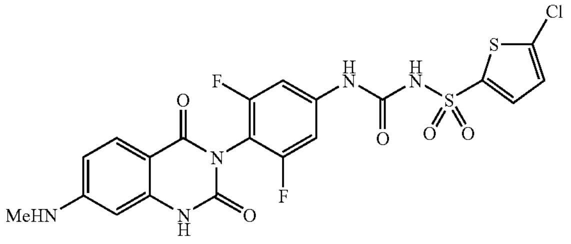

Example 907
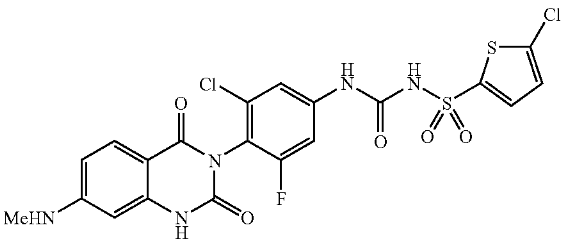
Example 908
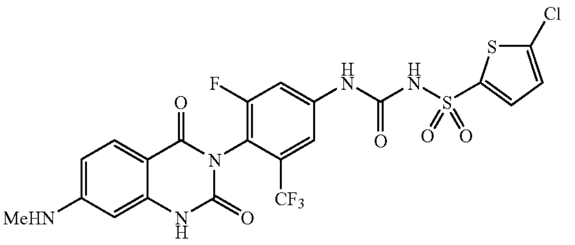
Example 909
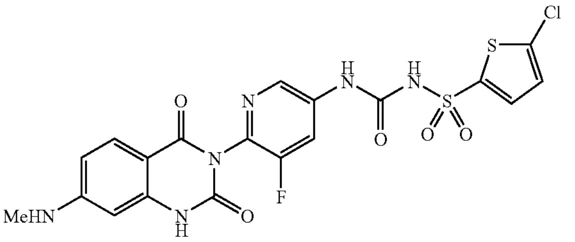
Example 910
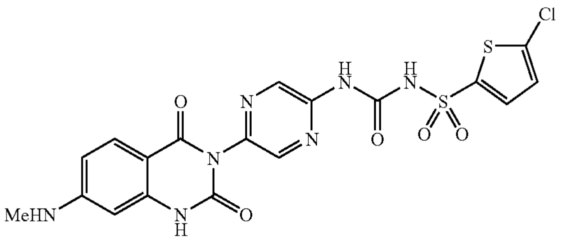
Example 911
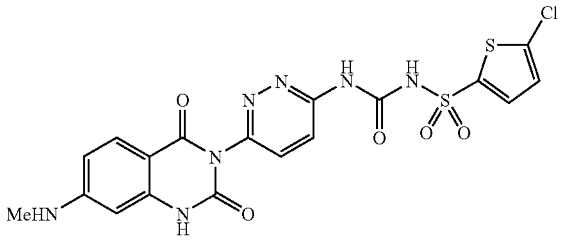
Example 912
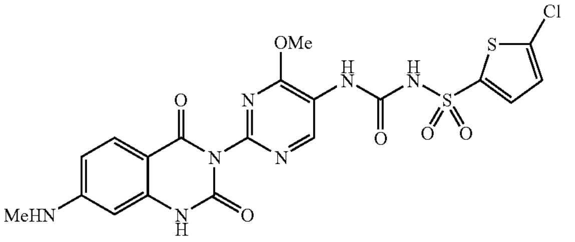
Example 913
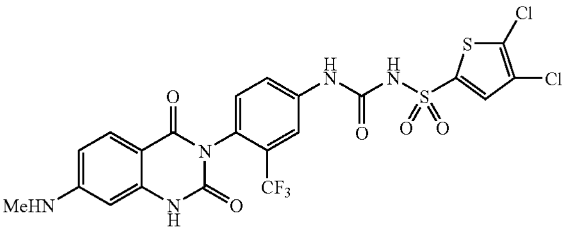
Example 914
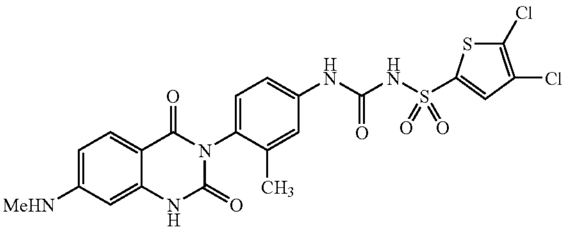
Example 915
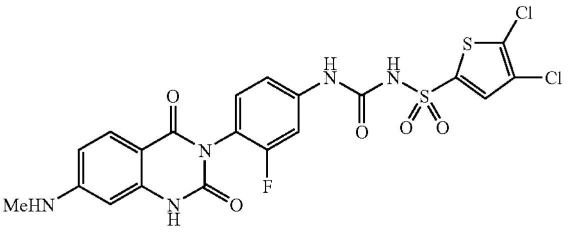
Example 916
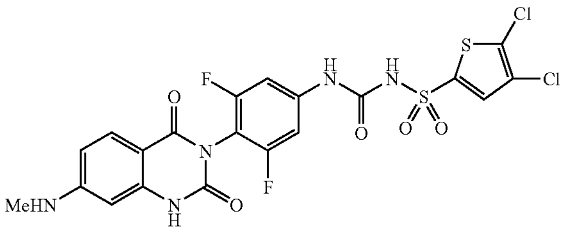
Example 917
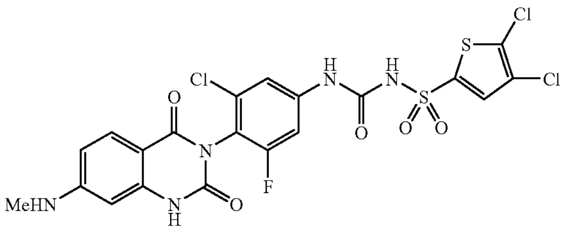
Example 918
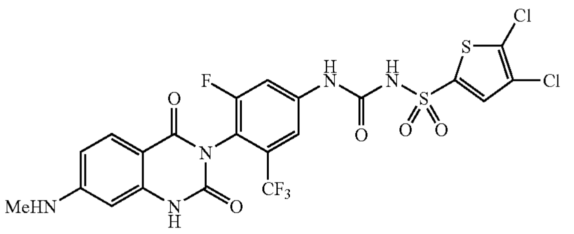

-continued
Example 919
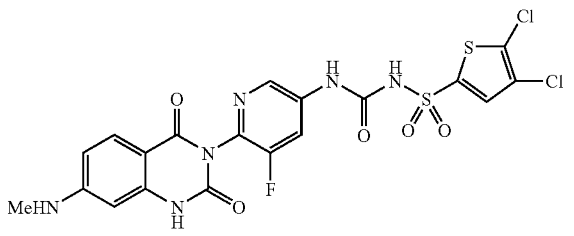
Example 920
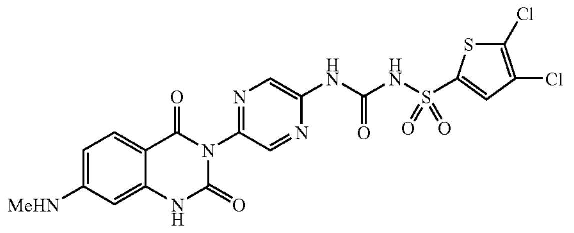
Example 921
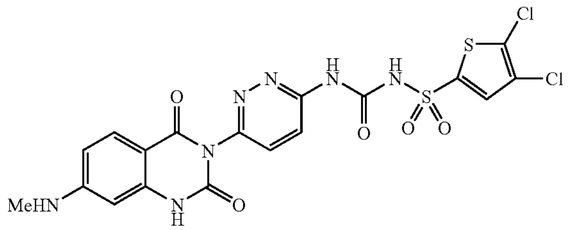
Example 922
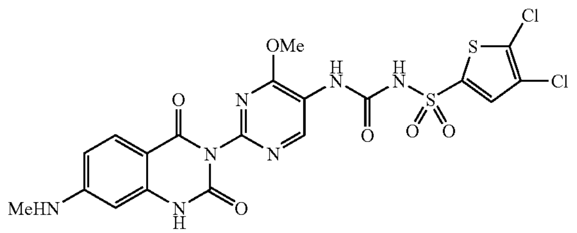
Example 923
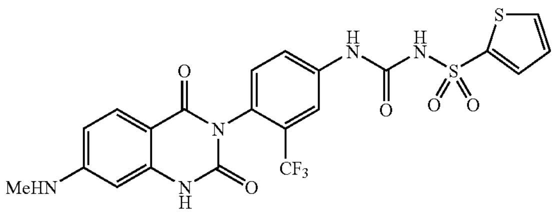
Example 924
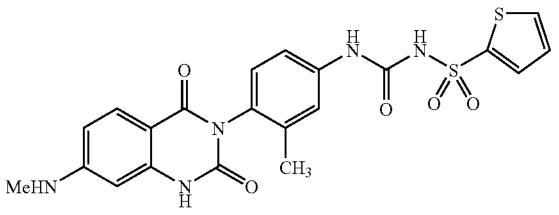
-continued
Example 925
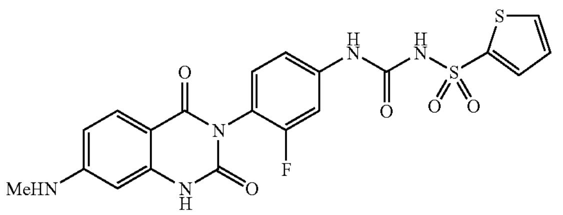
Example 926
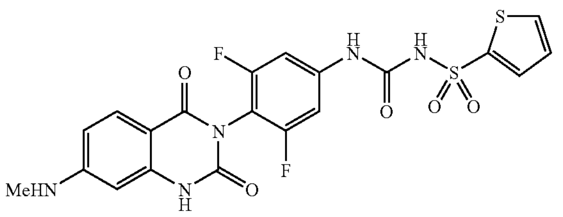
Example 927
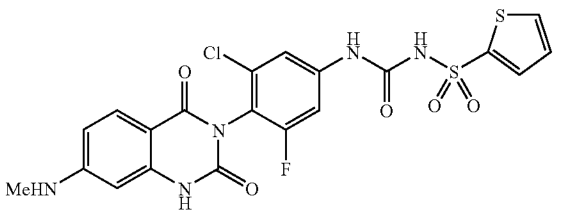
Example 928
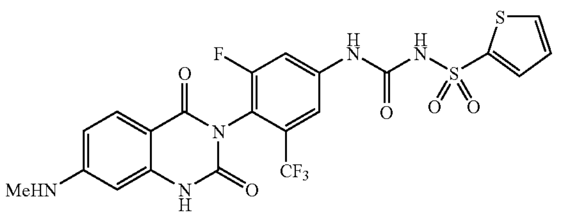
Example 929
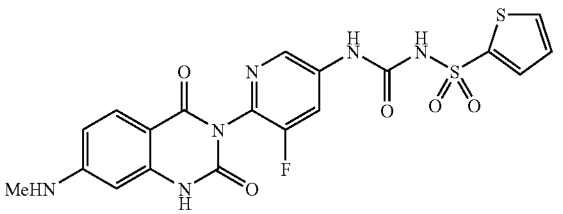
Example 930
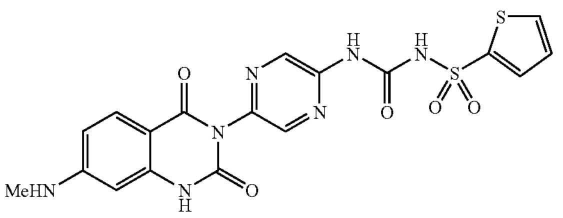

-continued
Example 931
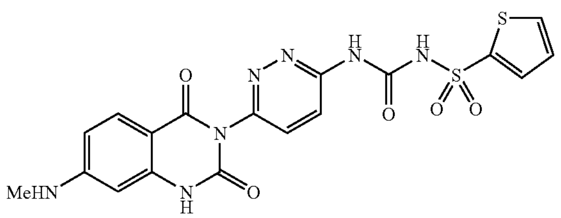
Example 932
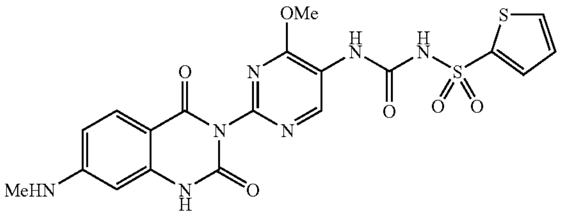
Example 933
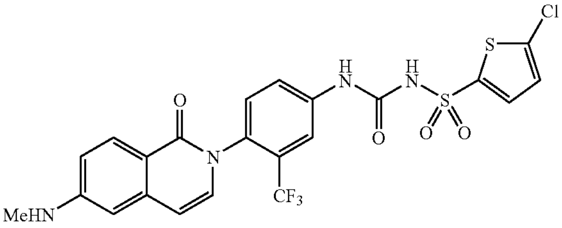
Example 934
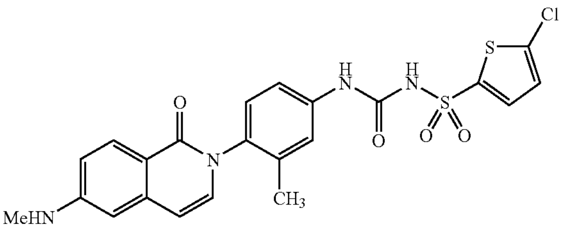
Example 935
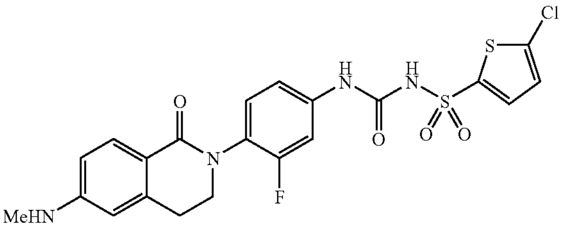
Example 936
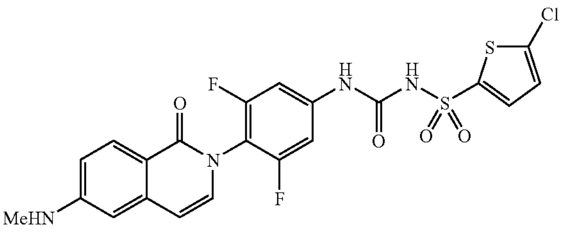
-continued
Example 937
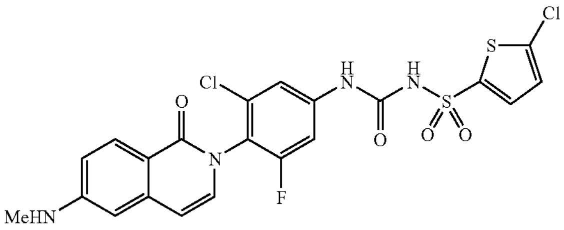
Example 938
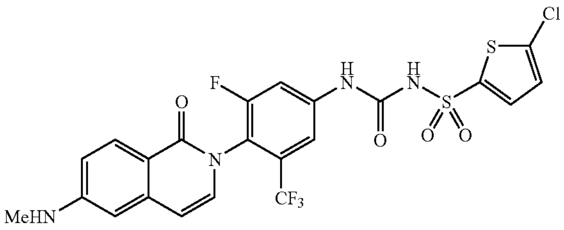
Example 939
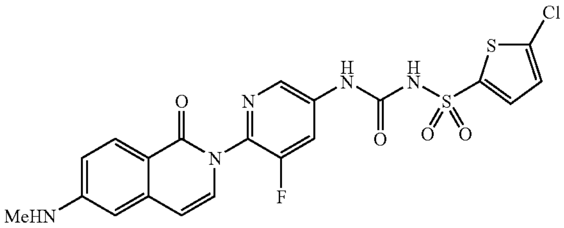
Example 940
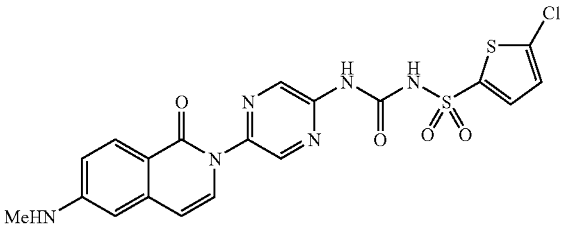
Example 941
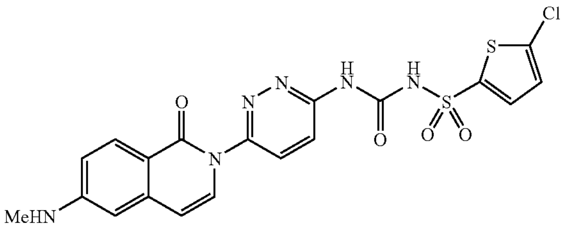
Example 942
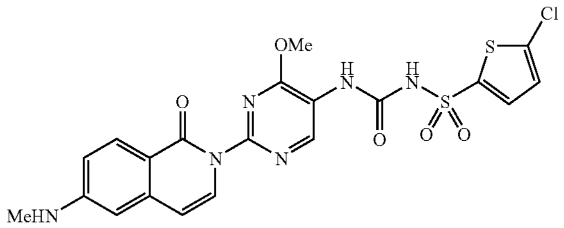

-continued
Example 943
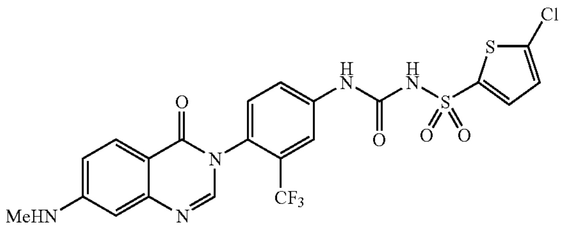
Example 944
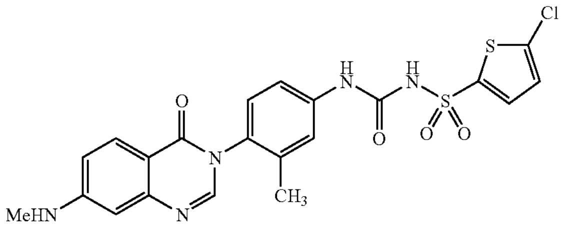
Example 945
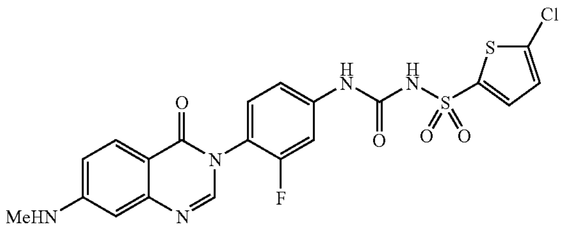
Example 946
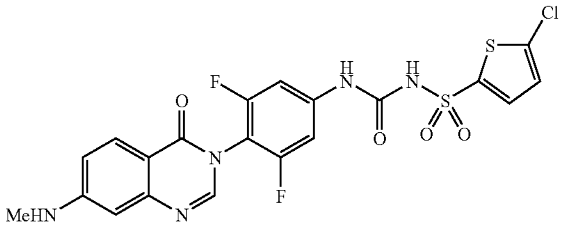
Example 947
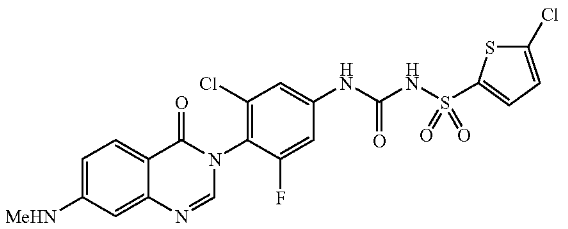
Example 948
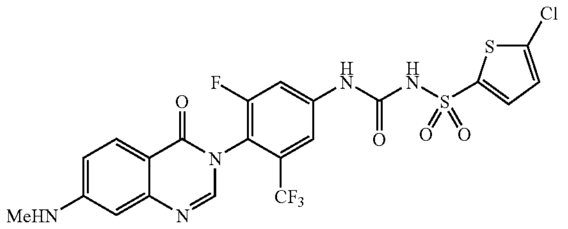
-continued
Example 949
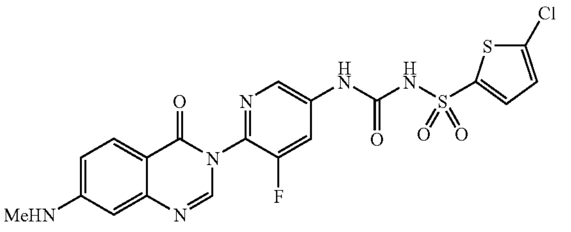
Example 950
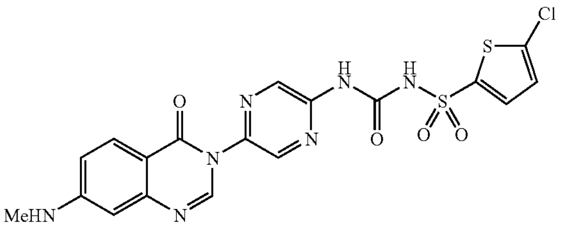
Example 951
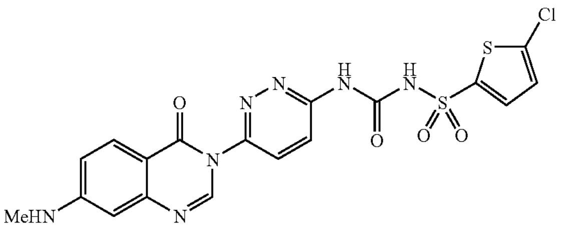
Example 952
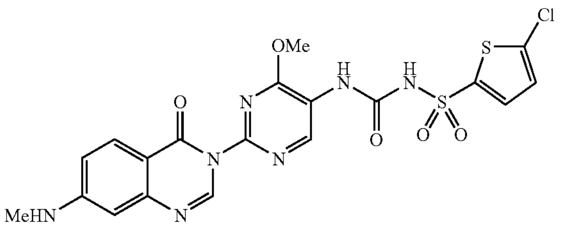
Example 953
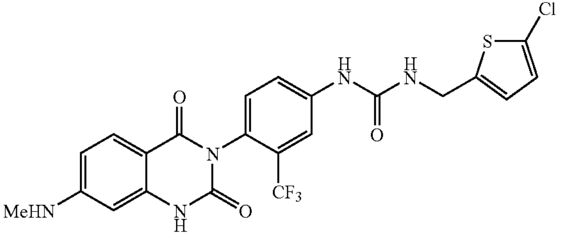
Example 954
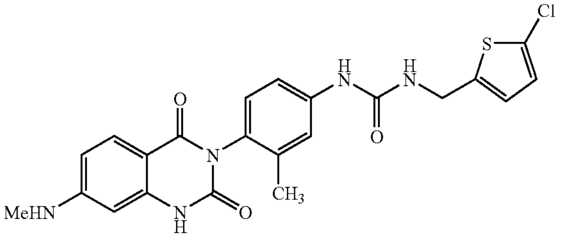

-continued
Example 955
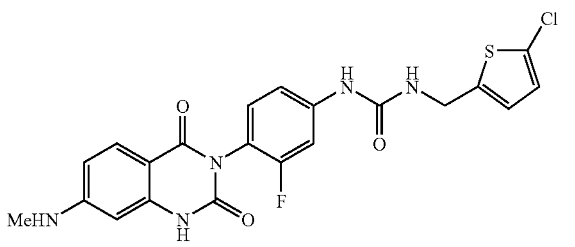
Example 956
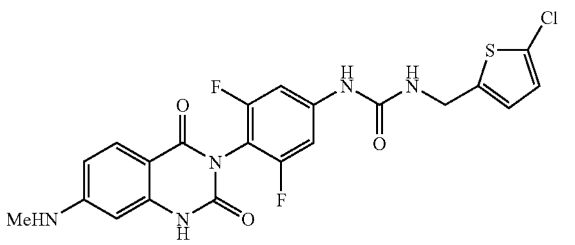
Example 957
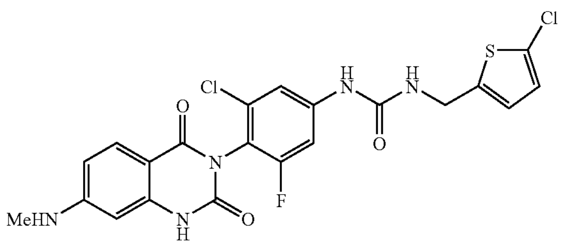
Example 958
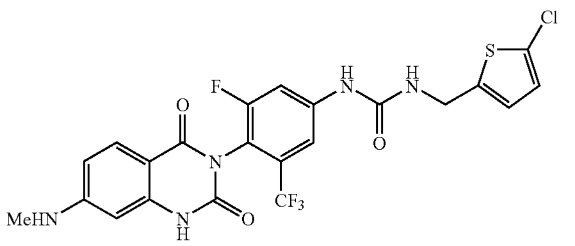
Example 959
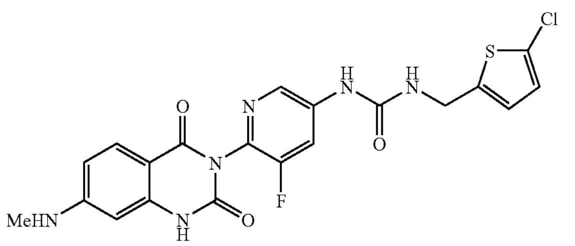
Example 960
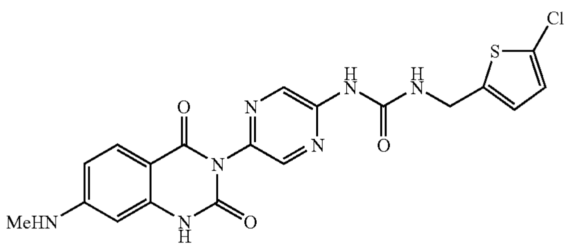
-continued
Example 961
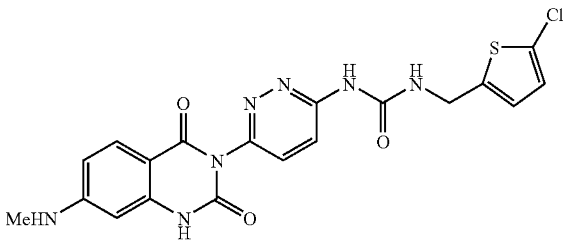
Example 962
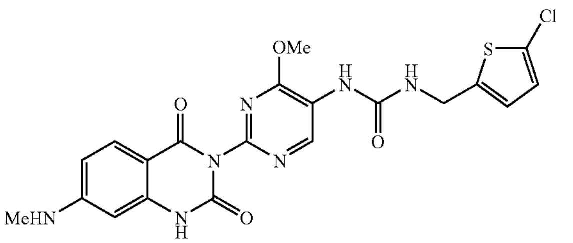
Example 963
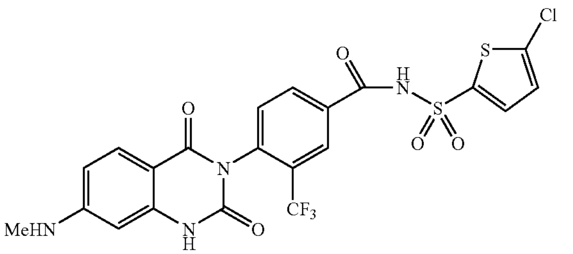
Example 964
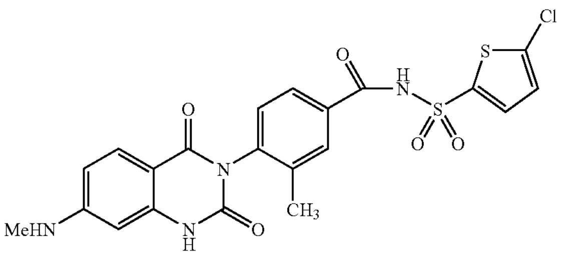
Example 965
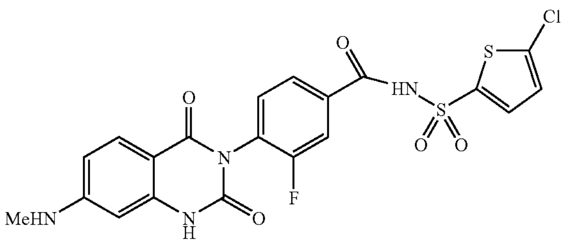
Example 966
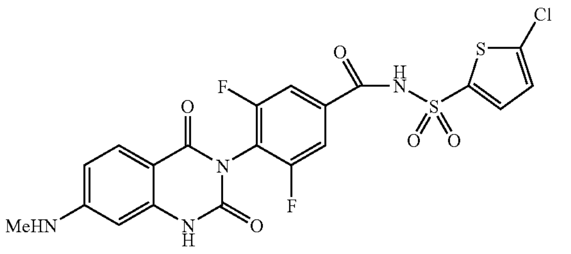

-continued
Example 967
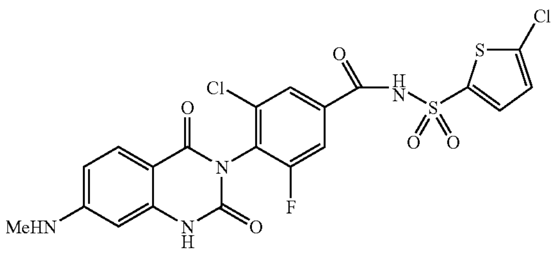
Example 968
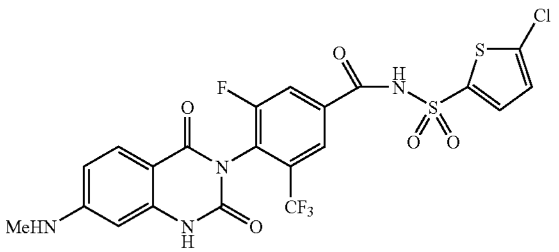
Example 969
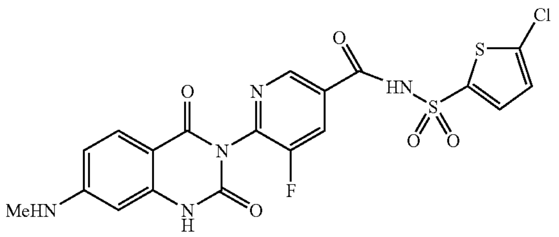
Example 970
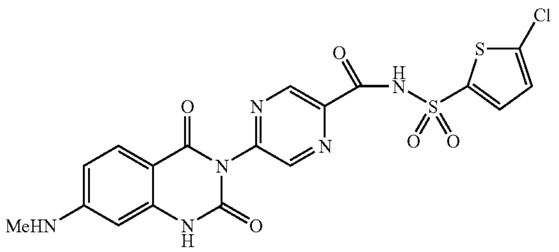
Example 971
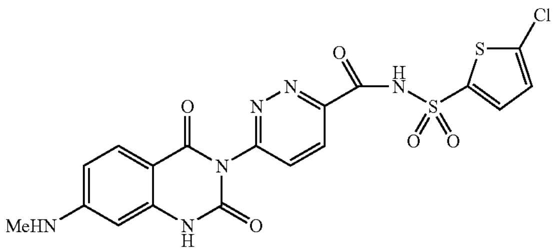
Example 972
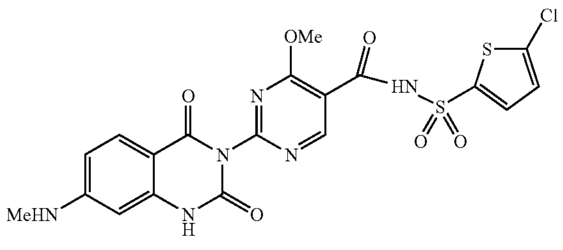
-continued
Example 973
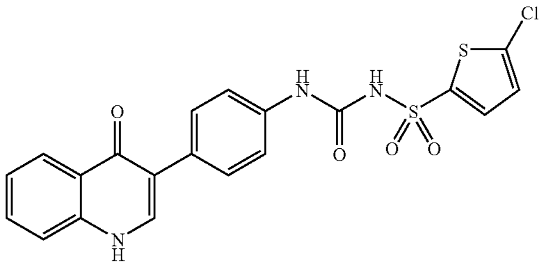
Example 974
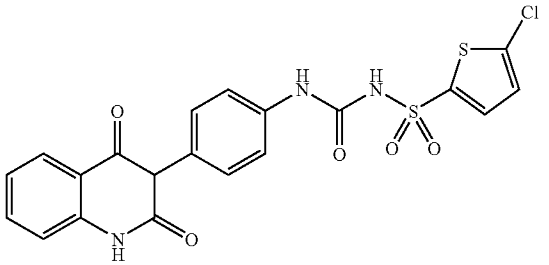
Example 975
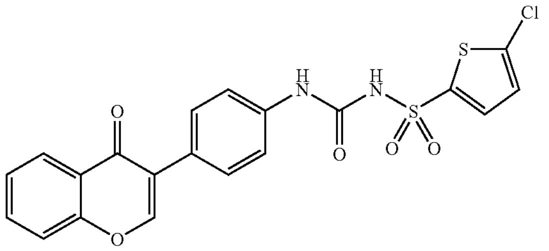
Example 976
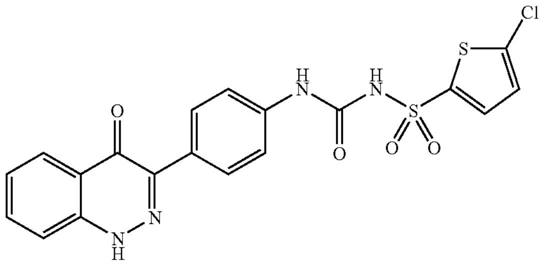
Example 977
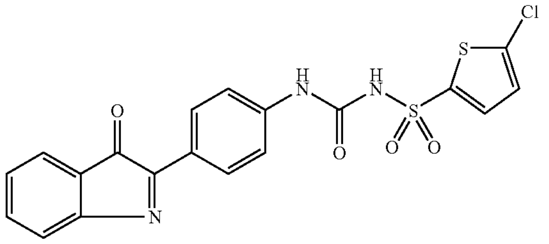

-continued
Example 978
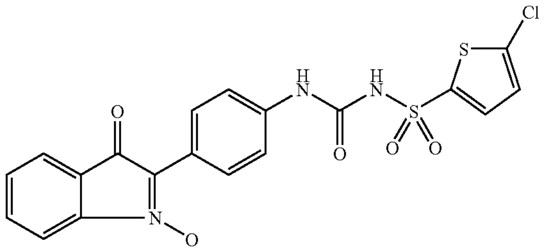
Example 979
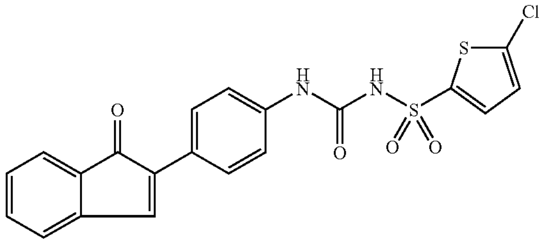
Example 980
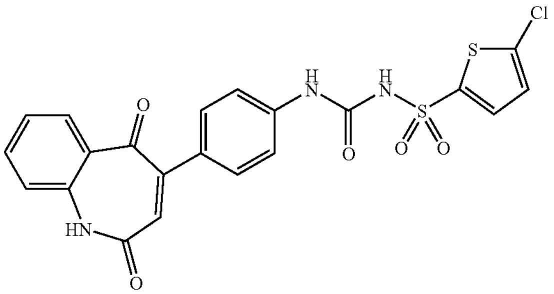
Example 981
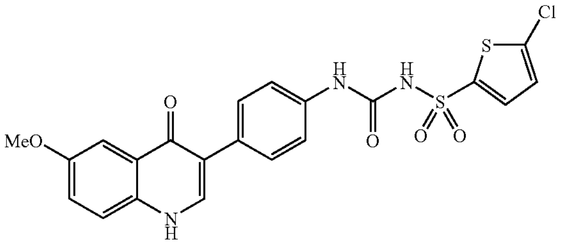
Example 982
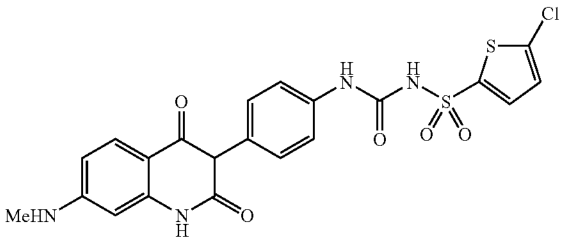
Example 983
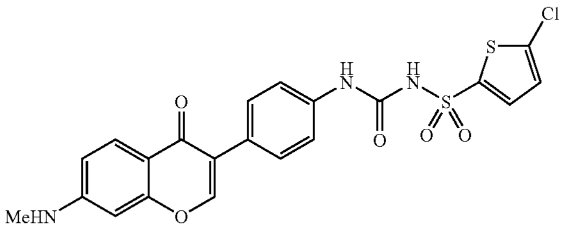
-continued
Example 984
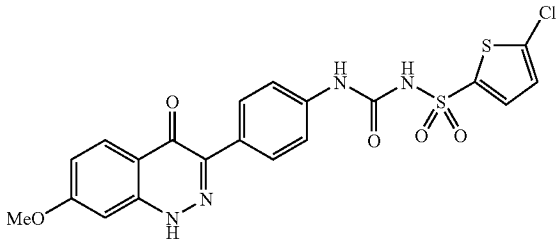
Example 985
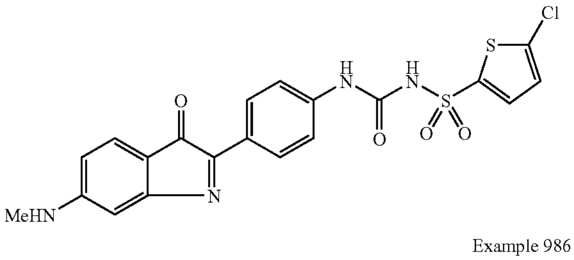
Example 986
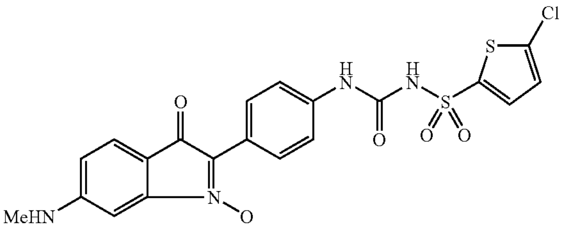
Example 987
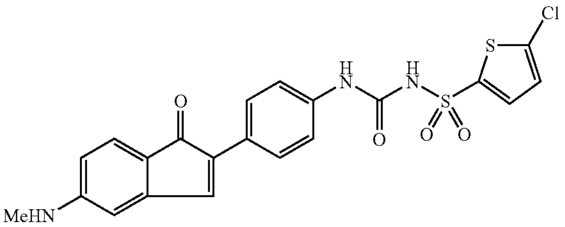
Example 988
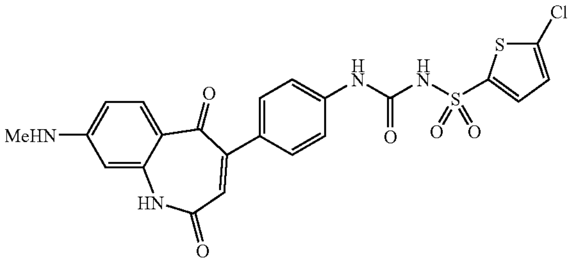
Example 989
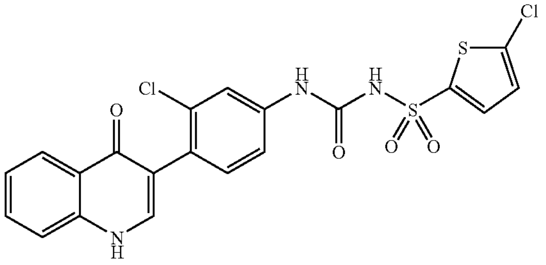

-continued
Example 990
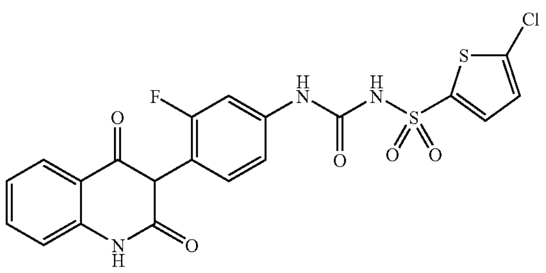
Example 991
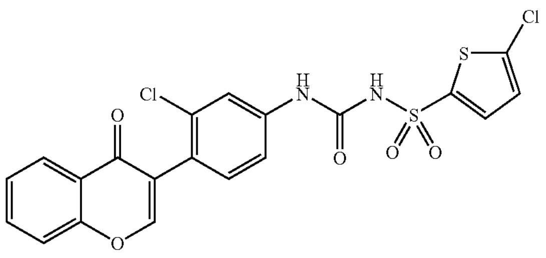
Example 992
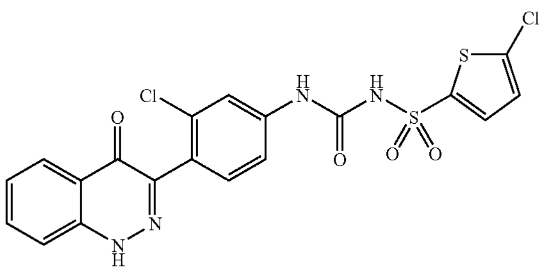
Example 993
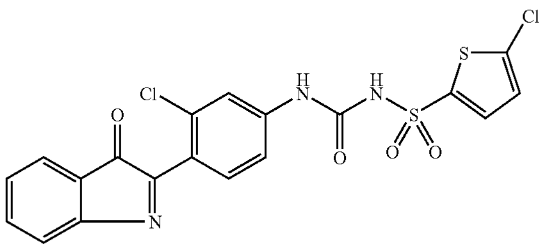
Example 994
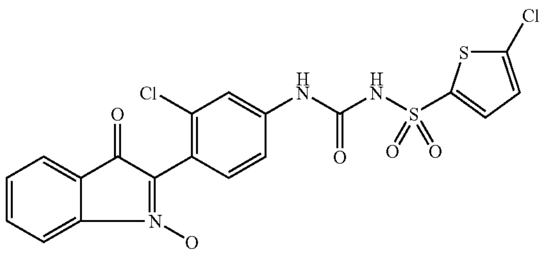
-continued
Example 995
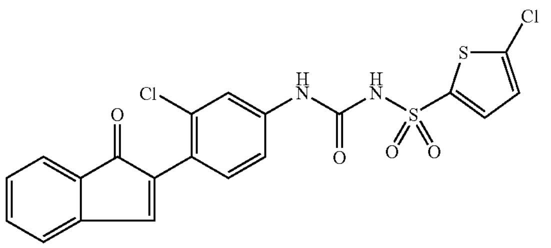
Example 996
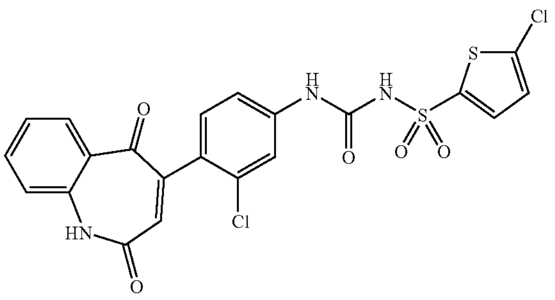
Example 997
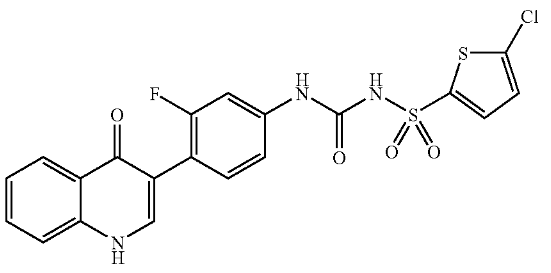
Example 998
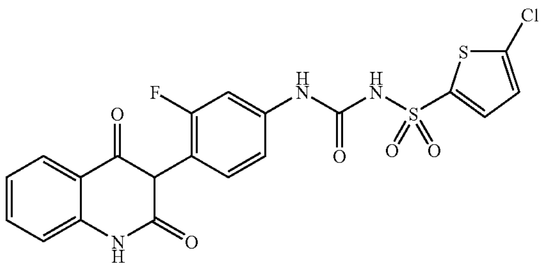
Example 999
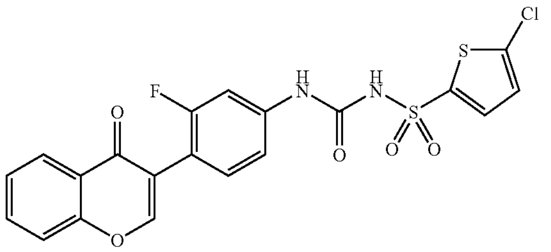

-continued
Example 1000
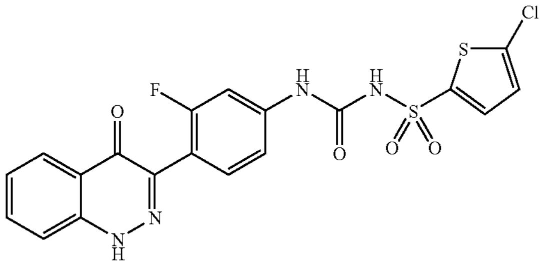
Example 1001
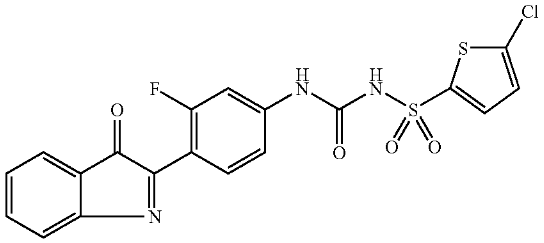
Example 1002
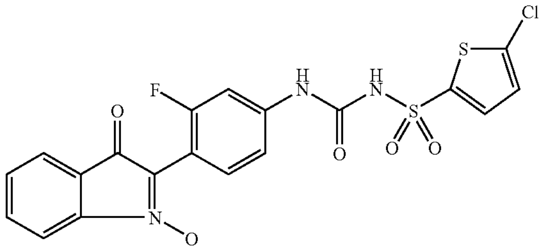
Example 1003
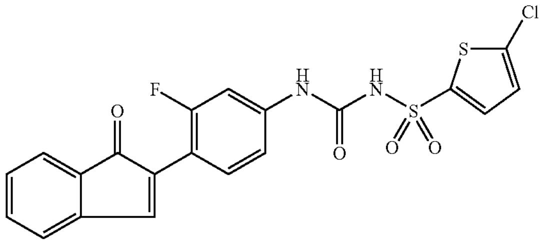
Example 1004
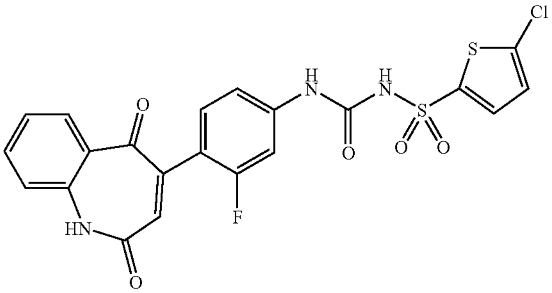
-continued
Example 1005
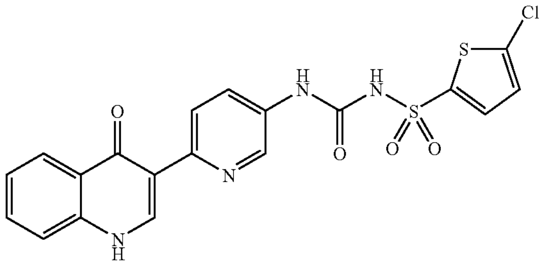
Example 1006
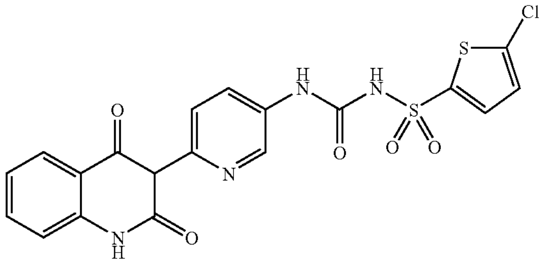
Example 1007
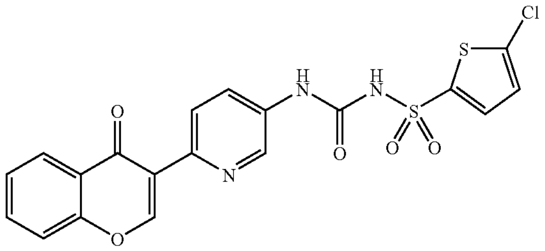
Example 1008
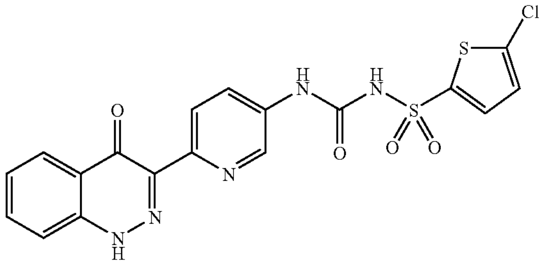
Example 1009
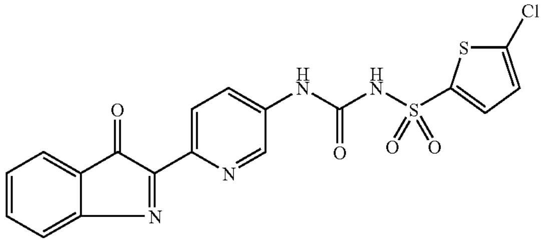

-continued
Example 1010
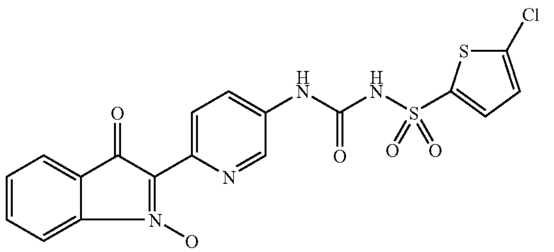
Example 1011
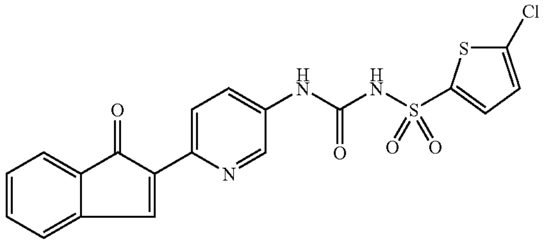
Example 1012
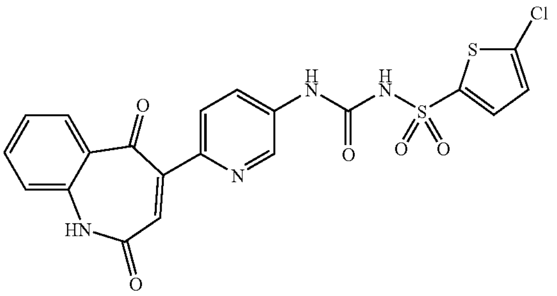
Example 1013
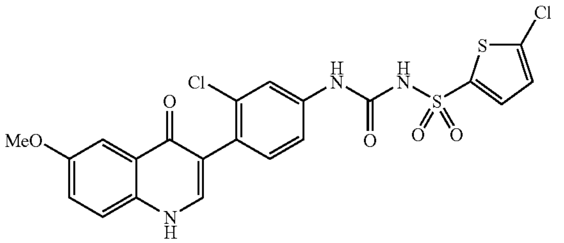
Example 1014
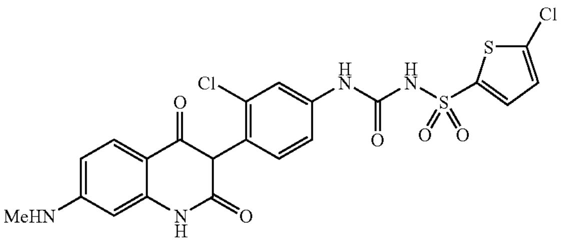
Example 1015
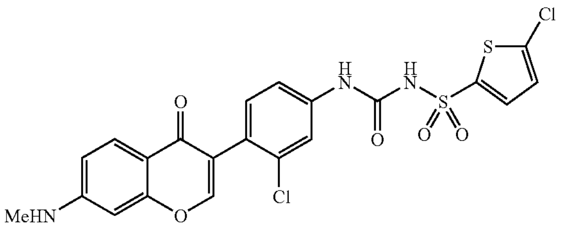
-continued
Example 1016
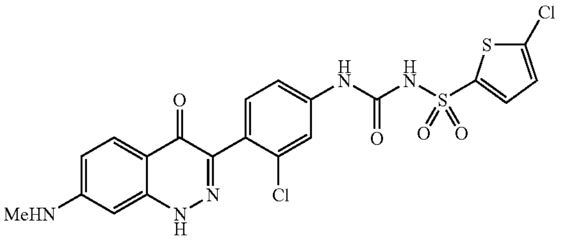
Example 1017
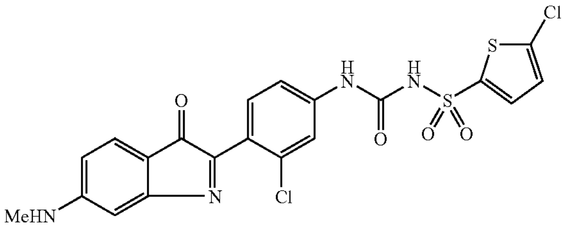
Example 1018
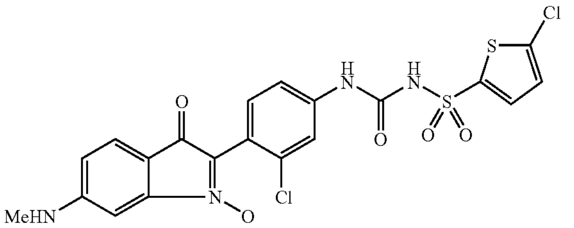
Example 1019
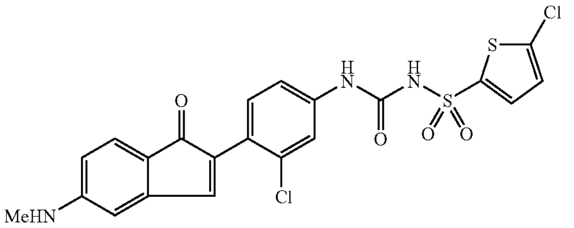
Example 1020
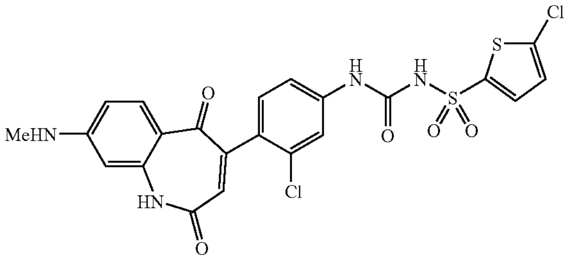
Example 1021
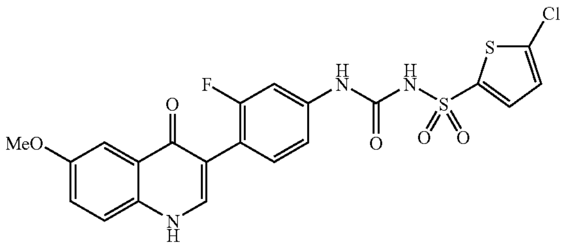

-continued
Example 1022
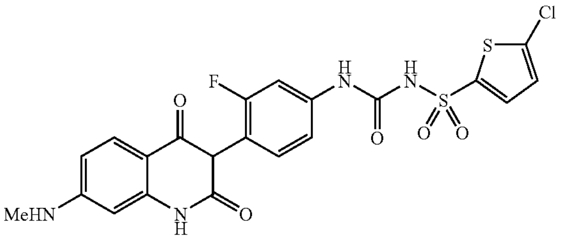
Example 1023
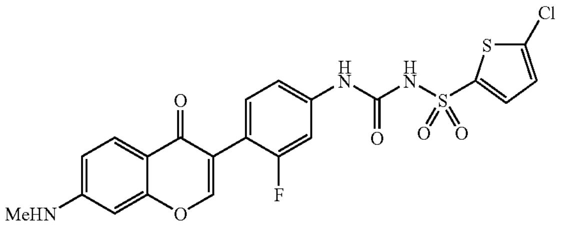
Example 1024
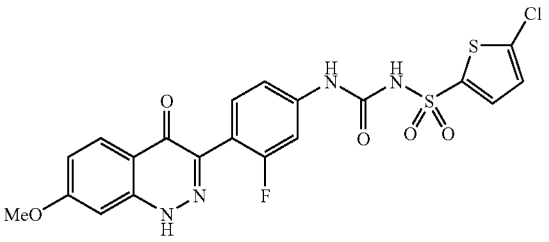
Example 1025
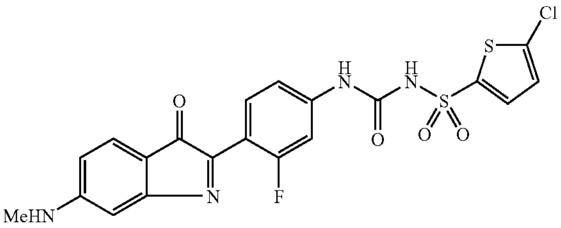
Example 1026
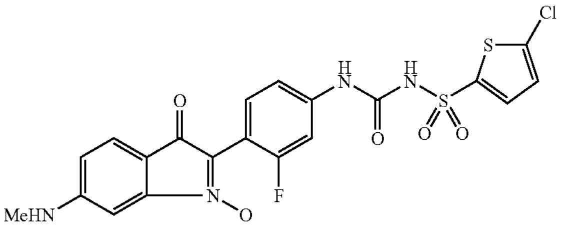
Example 1027
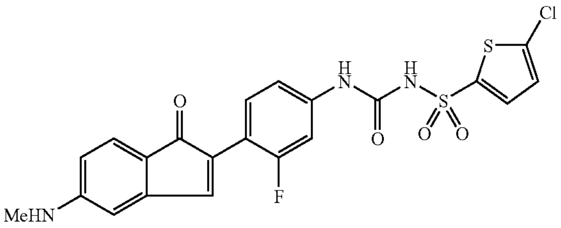
-continued
Example 1028
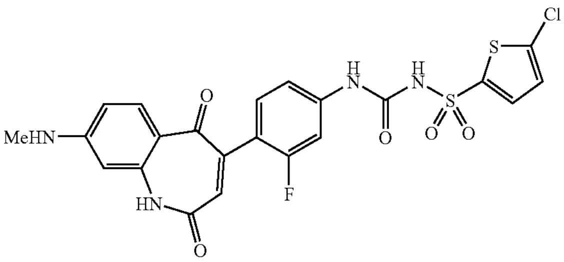
Example 1029
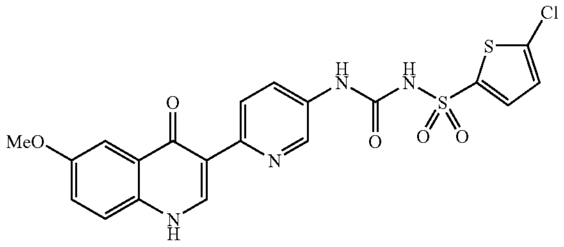
Example 1030
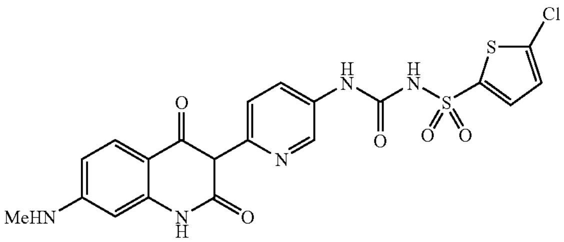
Example 1031
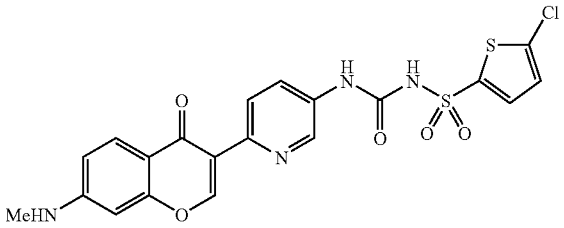
Example 1032
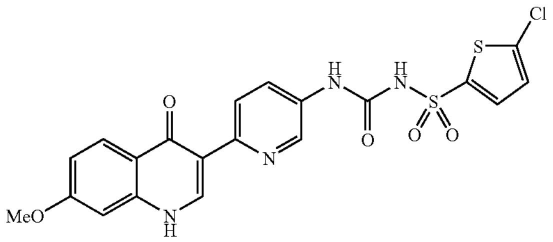
Example 1033
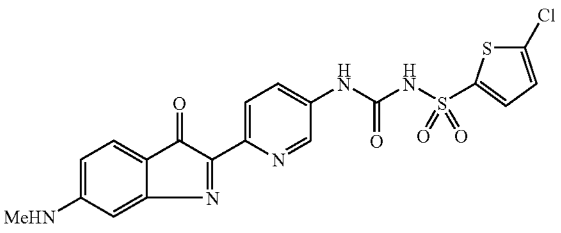

-continued
Example 1034
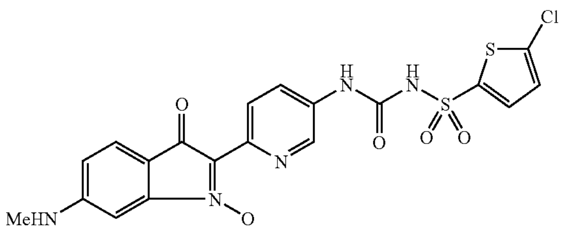
Example 1035
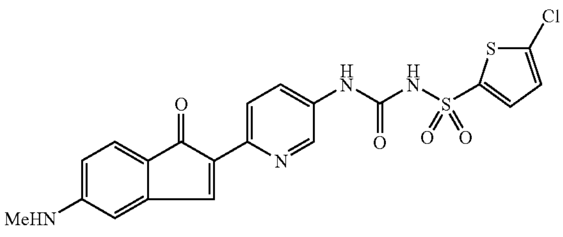
Example 1036
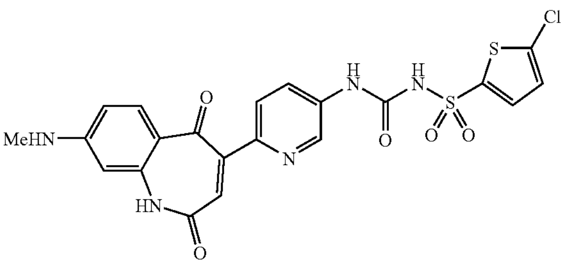
Example 1037
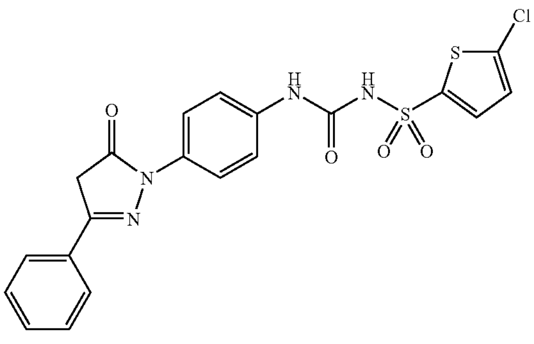
Example 1038
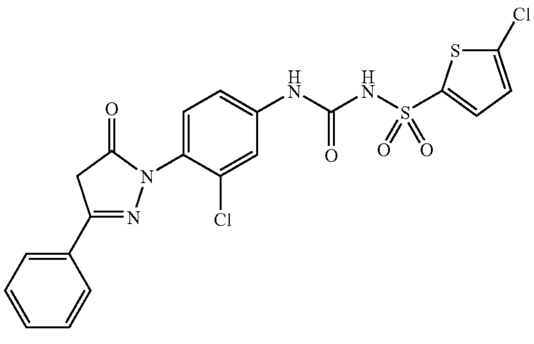
-continued
Example 1039
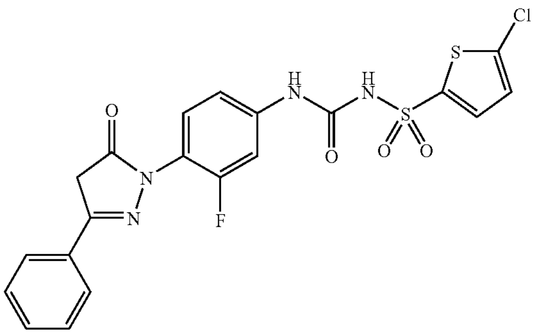
Example 1040
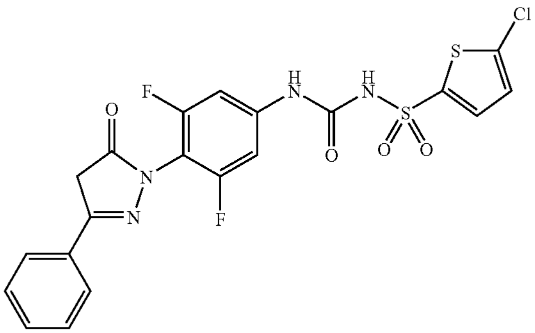
Example 1041
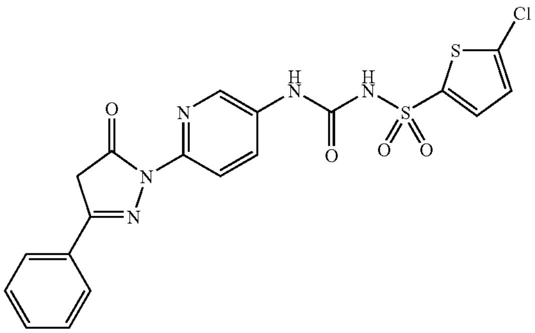
Example 1042
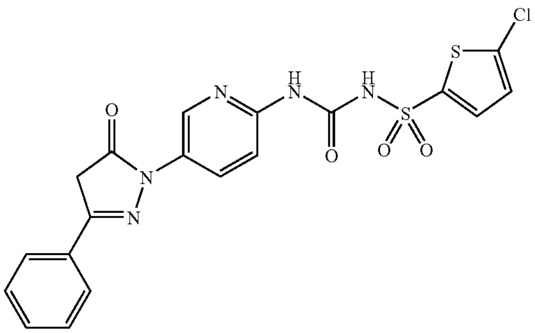

-continued
Example 1043
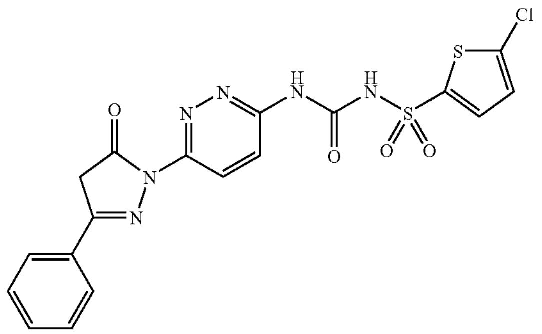
Example 1044
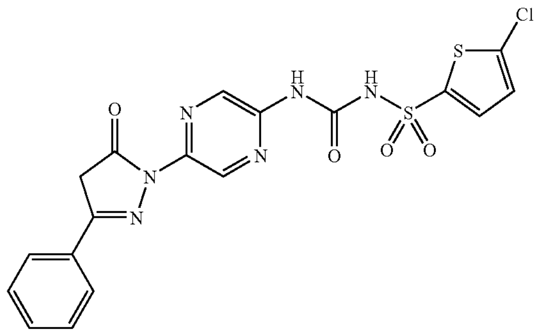
Example 1045
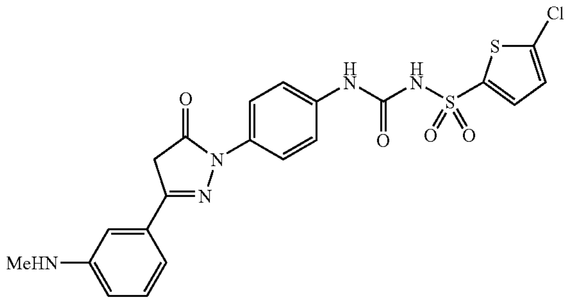
Example 1046
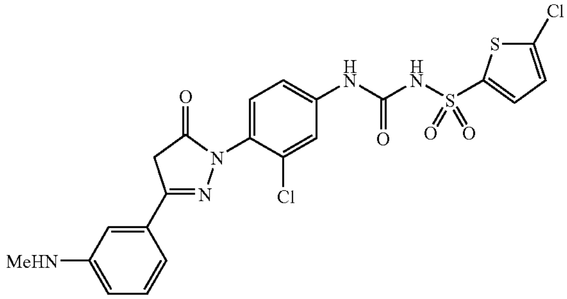
-continued
Example 1047
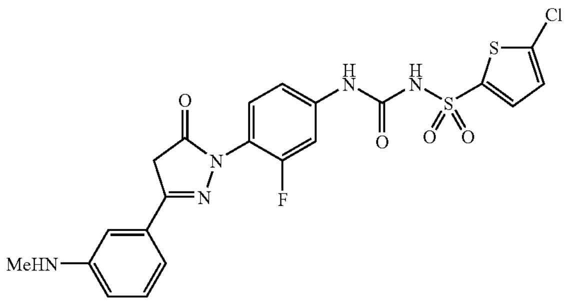
Example 1048
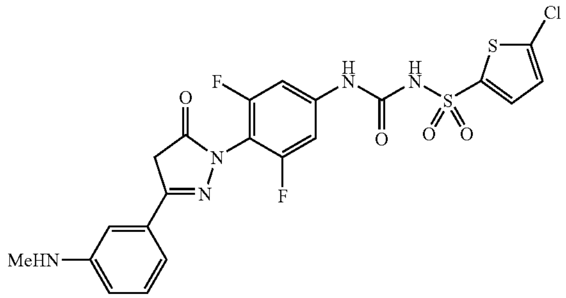
Example 1049
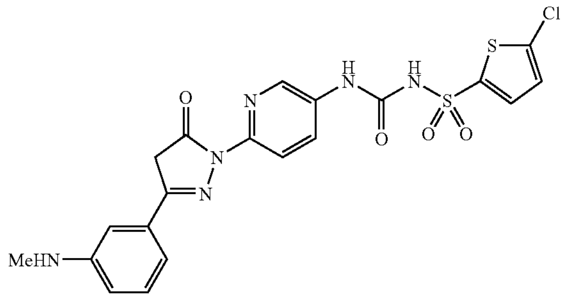
Example 1050
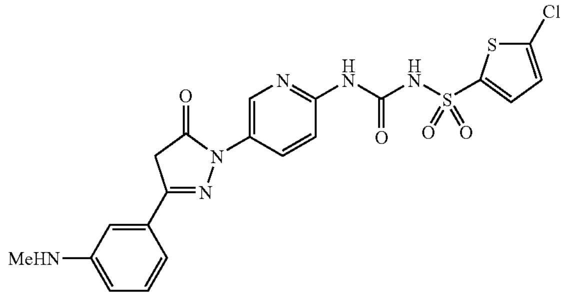
Example 1051
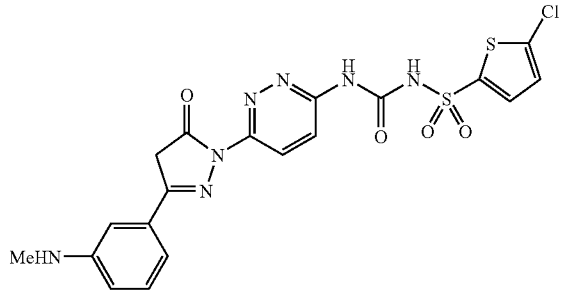

-continued
Example 1052
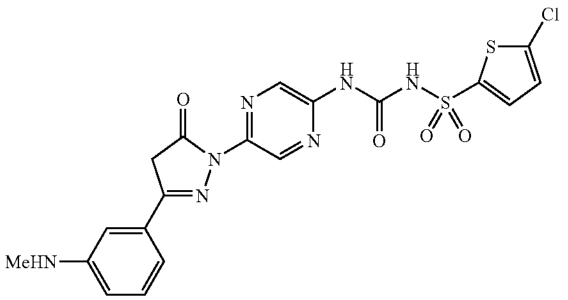
Example 1053
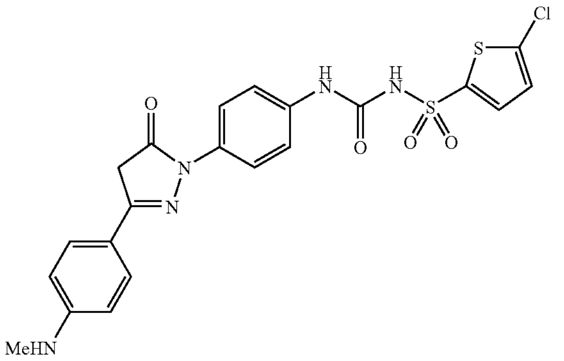
Example 1054
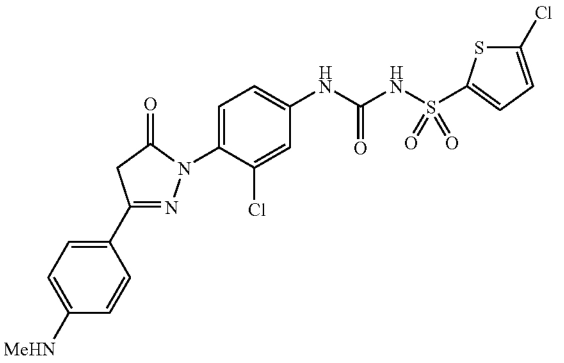
Example 1055
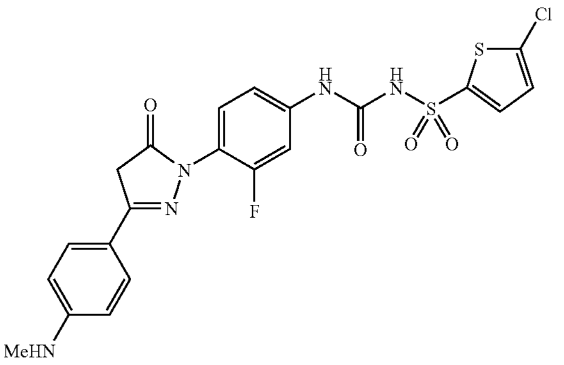
-continued
Example 1056
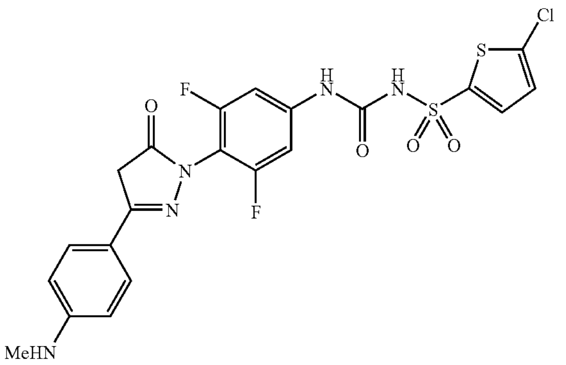
Example 1057
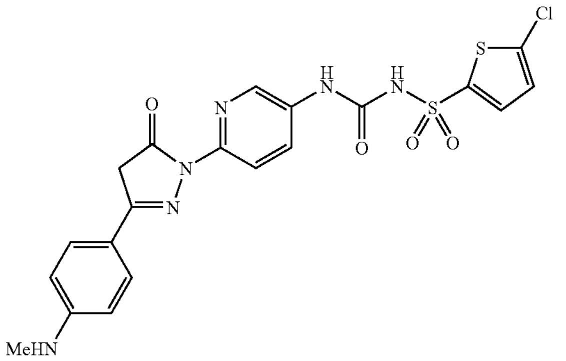
Example 1058
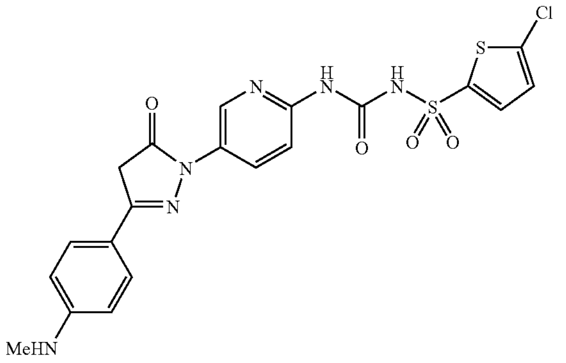
Example 1059
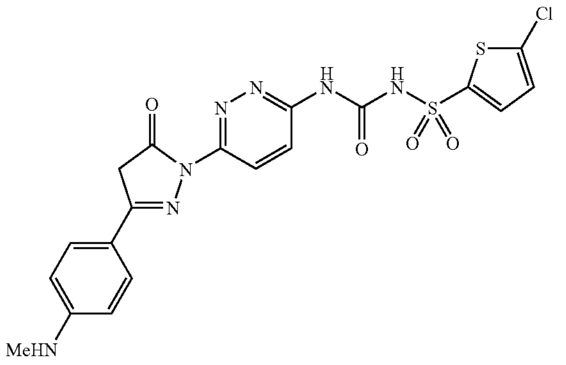

-continued

Example 1060

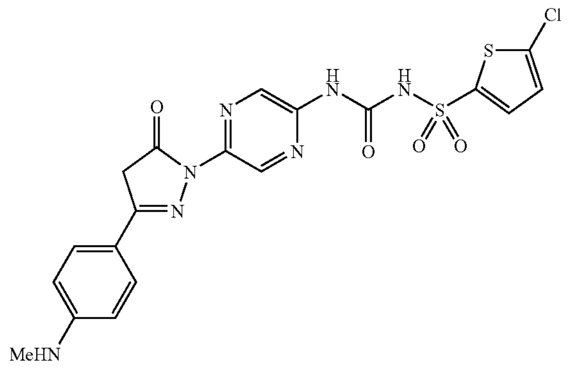

Preparation of Compounds of the Invention

A compound of formulae (I)-(VIII) may be prepared by various methods as outlined in the following documents: J. Med. Chem., 33, 23-93-2407 (1990); Biorg. & Med. Chem. Letts., Vol. 2, No. 9, pp. 987-992 (1992); J. Med. Chem., 35, 3012-3016 (1992); U.S. Pat. No. 5,234,955 (1993), U.S. Pat. No. 5,354,778 (1994); U.S. Pat. No. 5,565,494 (1996); U.S. Pat. No. 5,594,028 (1997); U.S. Pat. No. 5,302,724 (1994); and WO 97/08145, which are incorporated herein in their entirety by reference. Other well-known heterocyclic and carbocyclic synthetic procedures as well as modification of the procedures that are incorporated above may be utilized.

Compounds of formulae (I)-(VIII) may be isolated using typical isolation and purification techniques known in the art, including, for example, chromatographic and recrystallization methods.

In compounds of formula formulae (I)-(VIII) of the invention, carbon atoms to which four non-identical substituents are bonded are asymmetric. Accordingly, a compound of formulae (I)-(VIII) may exist as enantiomers, diastereomers or a mixture thereof. The enantiomers and diastereomers may be separated by chromatographic or crystallization methods, or by other methods known in the art. The asymmetric carbon atom when present in a compound of formulae (I)-(VIII) of the invention, may be in one of two configurations (R or S) and both are within the scope of the invention. The presence of small amounts of the opposing enantiomer or diastereomer in the final purified product does not affect the therapeutic or diagnostic application of such compounds.

According to the invention, compounds of formulae (I)-(VIII) may be further treated to form pharmaceutically acceptable salts. Treatment of a compound of the invention with an acid or base may form, respectively, a pharmaceutically acceptable acid addition salt and a pharmaceutically acceptable base addition salt, each as defined above. Various inorganic and organic acids and bases known in the art including those defined herein may be used to effect the conversion to the salt.

The invention also relates to pharmaceutically acceptable isomers, hydrates, and solvates of compounds of formulae (I)-(VIII). Compounds of formulae (I)-(VIII) may also exist in various isomeric and tautomeric forms including pharmaceutically acceptable salts, hydrates and solvates of such isomers and tautomers.

This invention also encompasses prodrug derivatives of the compounds of formulae (I)-(VIII). The term "prodrug" refers to a pharmacologically inactive derivative of a parent drug molecule that requires biotransformation, either spontaneous or enzymatic, within the organism to release the active drug. Prodrugs are variations or derivatives of the compounds of formulae (I)-(VIII) of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple, etc., depending on the number of biotransformation steps required to release the active drug within the organism, and indicating the number of functionalities present in a precursor-type form. Prodrug forms often offer advantages of solubility, tissue compatibility, or delayed release in the mammalian organism (Bundgard, *Design of Prodrugs*, pp. 7-9, 21-24, Elsevier, Amsterdam (1985); Silverman, *The Organic Chemistry of Drug Design and Drug Action*, pp. 352-401, Academic Press, San Diego, Calif. (1992)). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

Example 1

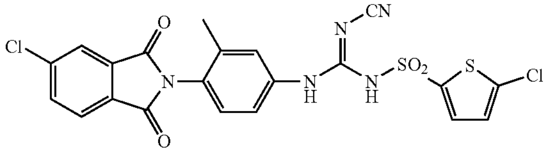

Preparation of 5-chloro-2-{4-[({[(5-chloro(2-thienyl))sulfonyl]amino}(cyanoimino)methyl)amino]-2-methylphenyl}benzo[c]azolidine-1,3-dione A solution of N-(4-amino-2-methylphenyl)-4-chlorophthalimide (0.14 g, 0.5 mmol) and dimethyl N-cyanodithioiminocarbonate (0.13 g, 1 mmol) in pyridine (1.3 mL) was stirred at 115° C. for 8 hr. The reaction mixture was then cooled and concentrated in vacuo. To a solution of this crude intermediate (56 mg, 0.11 mol) in pyridine (0.7 mL) was added DBU (33 μL, 0.22 mmol) and 5-chlorothiophene-2-sulfonamide (44 mg, 0.22 mmol). The reaction mixture was heated at 115° C. for 23 hr with addition of DMAP (10 mg) after 2 hr. Acidification and HPLC purification yielded (2Z)-2-aza-3-{[(5-chloro(2-thienyl))sulfonyl]amino}-3-{[4-(5-chloro-1,3-dioxobenzo[c]azolidin-2-yl)-3-methylphenyl]amino}prop-2-enenitrile (14 mg, 24%). ES-MS (M+H)+= 534, 536 (Cl). $^1$H-NMR (DMSO-$d_6$): δ 2.03 (s, 3H), 7.06-7.07 (d, 1H), 7.18-7.20 (d, 1H), 7.30-7.31 (d, 1H), 7.37 (s, 2H), 7.93-7.94 (2H), 8.03 (d, 1H), 8.84 (s, 1H).

Example 1061

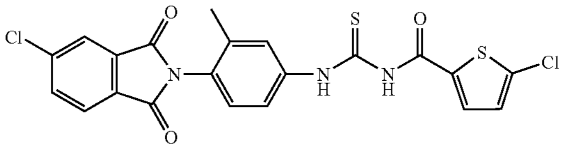

Preparation of (5-chloro(2-thienyl))-N-({[4-(5-chloro-1,3-dioxobenzo[c]azolin-2-yl)-3-methylphenyl]amino}thioxomethyl)carboxamide A. Synthesis of 5-chlorothiophene-2-carbonyl chloride To a chilled solution of 5-chlorothiophene-2-carboxylic acid (0.16 g, 1.0 mmol) in EtOAc (3 mL) and DMF (1 drop) was added neat oxalyl chloride (92 μL, 1.05 mmol). The reaction mixture was stirred cold for 2 hr and concentrated in vacuo to give crude 5-chlorothiophene-2-carbonyl chloride.

B. Synthesis of (5-chloro(2-thienyl))-N-({[4-(5-chloro-1,3-dioxobenzo[c]azolin-2-yl)-3-methylphenyl]amino}thioxomethyl)carboxamide To a suspension of KSCN (29 mg, 0.3 mmol) in dry acetonitrile (0.2 mL) was added a solution of the crude acid chloride (36 mg, 0.2 mmol) in $CH_3CN$ (0.2 mL). The resulting suspension was stirred at room temp for 30 min. This acylthioisocyanate in situ was added to a suspension of N-(4-amino-2-methylphenyl)-4-chlorophthalimide (58 mg, 0.2 mmol) in $CH_3CN$. The reaction mixture was stirred at room temp for 1 hr, filtered and dried to give pure (5-chloro-(2-thienyl))-N-({[4-(5-chloro-1,3-dioxobenzo[c]azolin-2-yl)-3-methylphenyl]amino}thioxomethyl)carboxamide (66 mg, 70%). ES-MS (M+H)+=490, 492 (Cl).

Example 1062

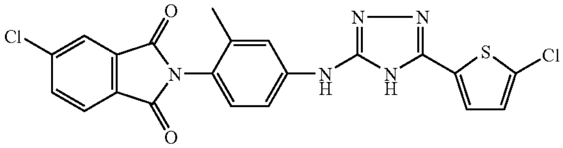

Preparation of 5-chloro-2-(4-{[5-(5-chloro(2-thienyl))(4H-1,2,4-triazol-3-yl)]amino}-2-methylphenyl)benzo[c]azoline-1,3-dione To a suspension of (5-chloro(2-thienyl))-N-({[4-(5-chloro-1,3-dioxobenzo[c]azolin-2-yl)-3-methylphenyl]amino}thioxomethyl)carboxamide (15 mg, 0.030 mmol) and hydrazine dihydrochloride (4 mg, 0.038 mmol) in DMF (0.3 mL) was added HgO (7 mg, 0.032 mmol). The reaction was stirred at room temp for 17 hr, and HPLC purified to give the desired product 5-chloro-2-(4-{[5-(5-chloro(2-thienyl))(4H-1,2,4-triazol-3-yl)]amino}-2-methylphenyl)benzo[c]azoline-1,3-dione (2 mg) (ES-MS (M+H)+=470, 472) and the aminoguanidine intermediate N-((1E)-2-aza-1-{[4-(5-chloro-1,3-dioxobenzo[c]azolidin-2-yl)-3-methylphenyl]amino}-2-aminovinyl)(5-chloro(2-thienyl))carboxamide (2 mg) ES-MS (M+H)+=488, 490 (2Cl).

Example 1063

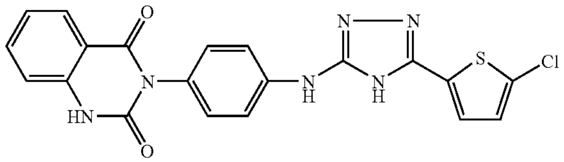

Preparation of 3-(4-{[5-(5-chloro-2-thienyl)-4H-1,2,4-triazol-3-yl]amino}phenyl)-1,3-dihydroquinazoline-2,4-dione was executed using the same methodology as shown in Examples 1061 and 1062, using 3-(4-aminophenyl)-1,3-dihydroquinazoline-2,4-dione as the aniline in step B from Example 1061. ES-MS (M+H)+=437, 439 (Cl).

Example 1064

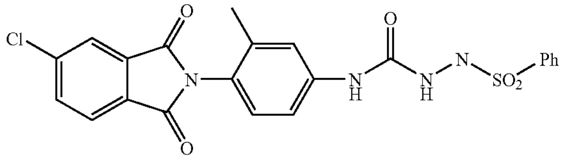

To a solution of triphosgene (22 mg, 0.074 mmol) in $CH_2Cl_2$ (1 mL) was added a suspension of N-(4-amino-2-methylphenyl)-4-chlorophthalimide (57 mg, 0.2 mmol) in $CH_2Cl_2$ (1.5 mL) and diethylisopropylamine (70 μL) dropwise over 10 min. The reaction mixture was stirred for 10 min, then a suspension of benzenesulfonylhydrazide (52 mg, 0.3 mmol) in $CH_2Cl_2$ (1.5 mL) and DIEA (35 μL) was added. The mixture was stirred at room temp for 17 hr, acidified and HPLC purified to give N-[4-(5-chloro-1,3-dioxobenzo[c]azolidin-2-yl)-3-methylphenyl][2-(phenylsulfonyl)hydrazino]-carboxamide (43 mg, 46%). ES-MS (M+H)+=485, 487. $^1$H-NMR (DMSO-$d_6$): δ 2.00 (s, 3H), 7.13-7.15 (d, 1H), 7.28-7.31 (d, 1H), 7.34 (s, 1H), 7.55-7.67 (m, 3H), 7.82-7.84 (m, 2H), 7.93 (s, 2H), 8.02 (s, 1H).

Example 1065

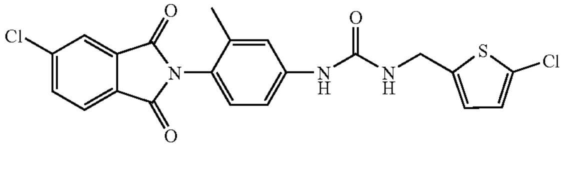

Preparation of {[(5-chloro(2-thienyl))methyl]amino}-N-[4-(5-chloro-1,3-dioxobenzo[c]azolidin-2-yl)-3-methylphenyl]carboxamide A. Synthesis of 5-chloro-2-[(1,3,5,7-tetraazatricyclo[3.3.1.1(3,7)]decyl)methyl]thiophene To a suspension of hexamethylenetetramine (HMTA) (3.12 g, 22.2 mmol) in $CHCl_3$ (35 mL) was added 2-chloro- 5-chloromethylthiophene (1.02 mL, 8.46 mmol). The reaction mixture was heated at reflux for 4 hr, cooled, and filtered to give white solid 5-chloro-2-[(1,3,5,7-tetraazatricyclo-[3.3.1.1(3,7)]decyl)methyl]thiophene (2.28 g, 88%). ES-MS (M)+=271, 273 (Cl). $^1$H-NMR (DMSO-$d_6$): δ 4.27 (s, 2H), 4.39-4.57 (ABq, 6H), 5.06 (s, 6H), 7.21-7.24 (ABq, 2H).

B. Synthesis of (5-chloro-2-thienyl)methylamine

To a solution of 5-chloro-2-[(1,3,5,7-tetraazatricyclo[3.3.1.1(3,7)]decyl)methyl]thiophene (2.15 g, 7 mmol) in methanol (10 mL) and water (5 mL) was added conc. HCl (5 mL). The reaction mixture was refluxed for 3 hr, poured onto water and washed with ethyl ether. The aqueous layer was basified with 4N NaOH and extracted into ethyl ether, washed with brine, dried and concentrated in vacuo to give (5-chloro-2-thienyl)methylamine (0.8 g, 78%).

C. Synthesis of {[(5-chloro(2-thienyl))methyl]amino}-N-[4-(5-chloro-1,3-dioxobenzo[c]azolidin-2-yl)-3-methylphenyl]carboxamide To a solution of triphosgene (22 mg, 0.074 mmol) in $CH_2Cl_2$ (1 mL) was added a suspension of N-(4-amino-2-methylphenyl)-4-chlorophthalimide (57 mg, 0.2 mmol) in $CH_2Cl_2$ (1.5 mL) and diethylisopropylamine (70 μL) dropwise over 10 min. The reaction mixture was stirred for 10 min, then a solution (5-chloro-2-thienyl)methylamine from step B (47 mg, 0.32 mmol) in $CH_2Cl_2$ (1 mL) and DMA (35 μL) was added. The mixture was stirred at room temp for 17 hr, acidified and HPLC purified to give {[(5-chloro(2-thienyl))methyl]amino}-N-[4-(5-chloro-1,3-dioxobenzo[c]azolidin-2-yl)-3-methylphenyl]carboxamide (18 mg, 20%). ES-MS (M+H)+=460, 462 (Cl). $^1$H-NMR (DMSO-$d_6$): δ 2.02 (s, 3H), 4.34-4.36 (d, 2H), 6.77-6.80 (t, 1H), 6.82-6.93 (2d, 2H), 7.14-7.16 (d, 1H), 7.29-7.32 (dd, 1H), 7.41 (d, 1H), 7.93 (ABq, 2H), 8.02 (s, 1H), 8.77 (s, 1H).

Example 1066

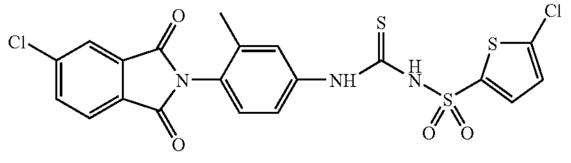

Preparation of 5-chloro-2-{4-[({[(5-chloro(2-thienyl))sulfonyl]amino}thioxomethyl)amino]-2-methylphenyl}benzo[c]azolidine-1,3-dione A. Synthesis of 4-(5-chloro-1,3-dioxobenzo[c]azolidin-2-yl)-3-methylbenzenisothiocyanate To a slurry of 150 mg (0.52 mmol) of 2-(4-amino-2-methylphenyl)-5-chlorobenzo[c]azoline-1,3-dione in 2 mL of acetone, was added 41 uL (0.54 mmol) of thiophosgene. The yellow slurry dissolved whereupon a white precipitate formed. After 1 h, this solid was collected by filtration and dried to give 127 mg (74%) of the desired product.

B. Synthesis of 5-chloro-2-{4-[({[5-chloro(2-thienyl)sulfonyl]amino}thioxomethyl)amino]-2-methylphenyl}benzo[c]azolidine-1,3-dione To a slurry of 51 mg (0.156 mmol) of the isothiocyanate prepared above and 31 mg (0.156 mmol) of 5-chlorothiophenesulfonamide in 300 μL of DMSO was added 26 μL of 1,8-diazabicyclo[5.4.0]undec-7-ene (DBU). After a few minutes the reaction mixture was diluted with 1.2 mL of water and acidified with acetic acid to pH 4 when a precipitate was formed, collected, and dried to give 77 mg (94%) of the titled compound. ES-MS (M+H)+=525.8 (2Cl).

Example 1067

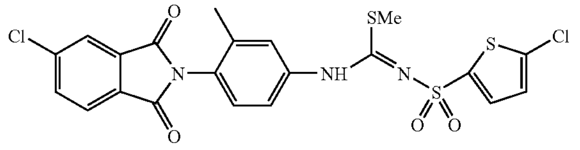

Preparation of 2-[4-({(1Z)-2-aza-2-[(5-chloro(2-thienyl))sulfonyl]-1-methylthiovinyl}amino)-2-methylphenyl]-5-chlorobenzo[c]azolidine-1,3-dione To a solution of 20 mg (0.038 mmol) 5-chloro-2-{4-[({[(5-chloro(2-thienyl))sulfonyl]amino}thioxomethyl)amino]-2-methylphenyl}benzo[c]azolidine-1,3-dione in 780 μL of acetone and 63 μL of 0.6M $NaHCO_3$ was added 5.9 μL of methyl iodide. After 2 h, the reaction mixture was acidified with acetic acid and the precipitate was collected and dried to give 13 mg (63%) of the titled compound.

Example 1068

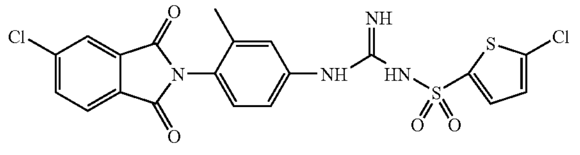

Preparation of 5-chloro-2-{4-[({[(5-chloro(2-thienyl))sulfonyl]amino}iminomethyl)amino]-2-methylphenyl}benzo[c]azolidine-1,3-dione A 15 mg portion of the 5-chloro-2-{4-[({[(5-chloro(2-thienyl))sulfonyl]amino}thioxomethyl)-amino]-2-methylphenyl}benzo[c]azolidine-1,3-dione was dissolved in 120 μL of DMF containing 6.6 mg of conc. ammonium hydroxide and 6 mg of mercuric oxide was added. After stirring for 18 h, the mercuric sulfide was filtered off and the solution was purified by reversed phase HPLC to give 1 mg (7%) of a white solid. ES-MS (M+H)+=509 (2Cl).

Example 1069

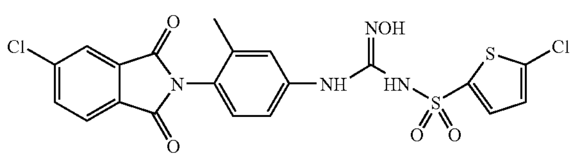

Preparation of 5-chloro-2-{4-[({[(5-chloro(2-thienyl))sulfonyl]amino}(hydroxyimino)methyl)amino]-2-methylphenyl}benzo[c]azolidine-1,3-dione The titled compound was prepared in a similar fashion as for Example 1068 with a 10% yield after purification. ES-MS (M+H)+=525 (2Cl).

Example 1070

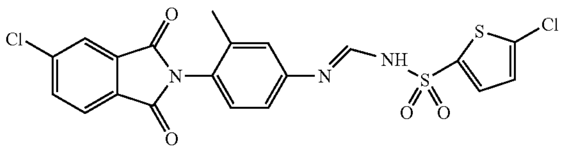

Preparation of 5-chloro-2-{4-[({[(5-chloro(2-thienyl))sulfonyl]amino}methyl)amino]-2-methylphenyl}benzo[c]azolidine-1,3-dione A. Synthesis of 2-[4-((1E)-1-aza-2-ethoxyvinyl)-2-methylphenyl]-5-chlorobenzo[c]azolidine-1,3-dione A 50 mg (0.175 mmol) portion of 2-(4-amino-2-methylphenyl)-5-chlorobenzo[c]azoline-1,3-dione in 2 mL of triethylorthoformate was heated to reflux for 1 h then distilled to leave a solid, 598 mg (100%).

B. Synthesis of 5-chloro-2-{4-[({[(5-chloro(2-thienyl))sulfonyl]amino}methyl)amino]-2-methylphenyl}benzo[c]azolidine-1,3-dione A 100 mg sample of 2-[4-((1E)-1-aza-2-ethoxyvinyl)-2-methylphenyl]-5-chlorobenzo[c]-azolidine-1,3-dione plus 58 mg (0.29 mmol) of 5-chlorothiophenesulfonamide was slurried in 1.2 mL of MeOH, heated to reflux for 2 h, and the methanol was distilled off. The remaining solid was triturated with ACN/MeOH, filtered, and concentrated to afford 104 mg (87%) of the titled compound. ES-MS (M+H)+=494.

Example 1071

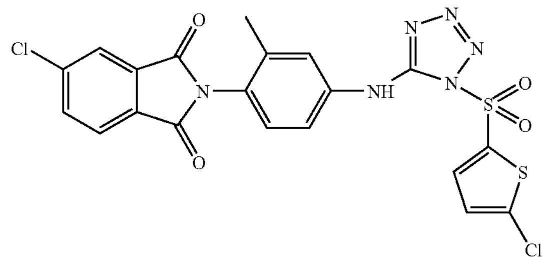

Preparation of 5-chloro-2-[4-({1-[(5-chloro(2-thienyl))sulfonyl](1,2,3,4-tetraazol-5-yl)}amino)-2-methylphenyl]benzo[c]azolidine-1,3-dione The titled compound was prepared in a similar fashion as for Example 1068 to yield a 18% yield after RP-HPLC purification. ES-MS (M+H)+=535 (2Cl).

Example 1072

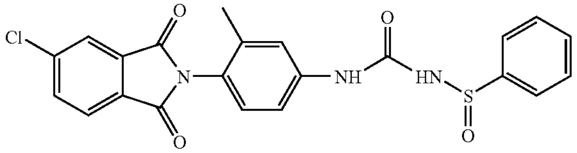

5-chloro-2-[4-({1-[(5-chloro(2-thienyl))sulfonyl](1,2,3,4-tetraazol-5-yl)}amino)-2-methylphenyl]benzo[c]azolidine-1,3-dione A. Synthesis of chlorophenylsulfoxide To 2 g (12 mmol) of sodium benzenesulfinic acid was added 5 mL of thionyl chloride and stirred at 0° C. for 4 h. The product was isolated by bulb-to-bulb distillation (180° C. @ 4 mmHg) to afford 1.25 g (64%) of the liquid benzenesulfinic chloride.

B. Synthesis of benzenesulfinamide

The chlorophenylsulfoxide (500 mg, 3.2 mmol) was dissolved in 5 mL of diethyl ether at 0° C. and anhydrous ammonia was bubbled through until no more precipitate is formed. The solution was filtered and concentrated to afford a solid which was recrystallized from water to afford 152 mg (35%) of benzenesulfinamide.

C. Synthesis of 5-chloro-2-[4-({1-[(5-chloro(2-thienyl))sulfonyl](1,2,3,4-tetraazol-5-yl)}amino)-2-methylphenyl]benzo[c]azolidine-1,3-dione A 16 mg portion of benzenesulfinamide and 47 mg of 2-(4-amino-2-methylphenyl)-5-chlorobenzo[c]azoline-1,3-dione was dissolved in 232 uL of CAN followed by 18 μL of DBU. The reaction was stirred at 23° C. for 1 h and purified by RP-HPLC to give 20 mg (38%) of the desired material. ES-MS (M+H)+=454 (2Cl).

Example 1073

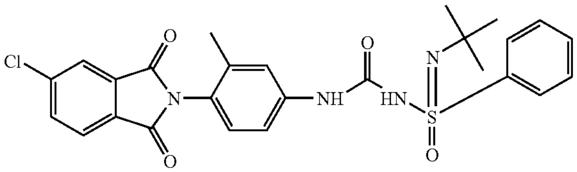

Preparation of {[4-(5-chloro-1,3-dioxobenzo[c]azolidin-2-yl)-3-methylphenyl]amino}-N-(N-t-butylphenylsulfonimidoyl)carboxamide A. Synthesis of (tert-butyl)(phenylsulfonyl)amine In a similar fashion for the preparation of Example 1072 B, tert-butyl amine (5 equivalents) was used to prepare the named compound in 75% yield. $^1$H-NMR (DMSO-$d_6$): δ 7.67 (m, 2); 7.45 (m, 3) 4.83 (br s, 1); 1.39 (s, 9).

B. Synthesis of (tert-butyl)(phenyliminosulfonyl)amine

To a 50 mg-portion (0.25 mmol) of (tert-butyl)(phenylsulfonyl)amine in 5 mL of anhydrous THF was added 58 mg (0.26 mmol) of N-chlorosaccharin under an argon atmosphere. After a few minutes the reaction mixture was cooled to −78° C., and anhydrous ammonia was bubbled through. After warming to 23° C. the solvent was evaporated, the residue was dissolved in water, extracted 3 times with EtOAc. The combined organic layers were washed with 5% $NaHCO_3$, dried ($Na_2SO_4$), and concentrated to afford 37 mg (68%) of the titled compound. ES-MS (M+H)+=236.

C. Synthesis of {[4-(5-chloro-1,3-dioxobenzo[c]azolidin-2-yl)-3-methylphenyl]amino}-N-(N-t-butylphenylsulfonimidoyl)carboxamide In a similar fashion for preparation of Example 1072C, the titled compound was prepared in 2% yield after RP-HPLC purification. ES-MS (M+H)+=525.

Example 1074

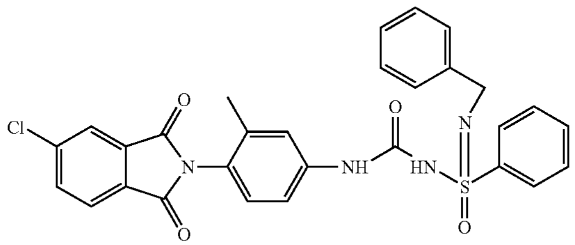

Preparation of {[4-(5-chloro-1,3-dioxobenzo[c]azolidin-2-yl)-3-methylphenyl]amino}-N-(N-benzylphenylsulfonimidoyl)carboxamide A. Synthesis of (benzyl)(phenylsulfonyl)amine In a similar fashion for the preparation of Example 1072 Step B, benzylamine (5 equivalents) was used to prepare the named compound in 74% yield. ES-MS (M+H)+=232.1. $^1$H-NMR ($CDCl_3$) δ 7.67 (m, 2); 7.51 (m, 3); 7.28 (m, 5); 4.28 (ABX, 1); 4.23 (ABX, 1); 3.89 (X, 1).

B. Synthesis of (benzyl)(phenyliminosulfonyl)amine

In a similar fashion as for the preparation of Example 1072 Step C, the titled compound was prepared in quantitative yield.

C. {[4-(5-chloro-1,3-dioxobenzo[c]azolidin-2-yl)-3-methylphenyl]amino}-N-(N-benzylphenylsulfonimidoyl)carboxamide In a similar fashion for preparation of Example 1072 Step C, the titled compound was prepared in 34% yield after RP-HPLC purification. ES-MS (M+H)+=559.

Example 1075

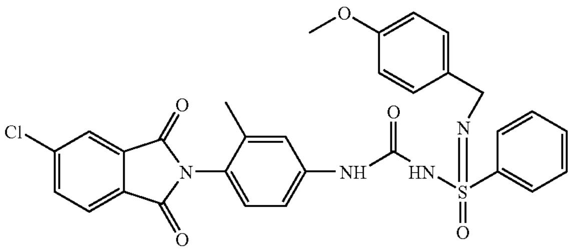

Preparation of {[4-(5-chloro-1,3-dioxobenzo[c]azolidin-2-yl)-3-methylphenyl]amino}-N-(N-p-methoxybenzylphenylsulfonimidoyl)carboxamide A. Synthesis of (p-methoxybenzyl)(phenyliminosulfonyl)amine In a similar fashion for the preparation of Example 1072 Step B, p-methoxybenzylamine (5 equivalents) was used to prepare the named compound in 66% yield. ES-MS (M+H)+=262. $^1$H-NMR ($CDCl_3$): δ 7.97 (m, 2); 7.49 (m, 3); 7.18 (d, 2); 6.81 (d, 2); 4.20 (m, 2); 3.8 (dd, 1); 3.74 (s, 3).

B. Synthesis of (p-methoxybenzyl)(phenyliminosulfonyl)amine

In a similar fashion as for the preparation of Example 1072 Step C, the titled compound was prepared in quantitative yield. Material used in next step without purification.

C. Synthesis of {[4-(5-chloro-1,3-dioxobenzo[c]azolidin-2-yl)-3-methylphenyl]amino}-N-(N-benzylphenylsulfonimidoyl)carboxamide In a similar fashion for preparation of Example 1072 Step C, the titled compound was prepared in 17% yield after RP-HPLC purification. ES-MS (M+H)+=589.

Example 1076

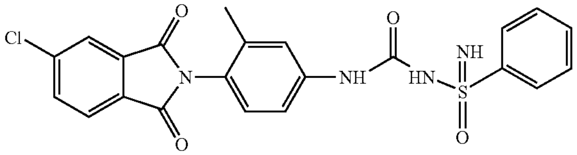

Preparation of {[4-(5-chloro-1,3-dioxobenzo[c]azolidin-2-yl)-3-methylphenyl]amino}-N-(phenylsulfonimidoyl)carboxamide To 10 mg (0.016 mmol) of {[4-(5-chloro-1,3-dioxobenzo[c]azolidin-2-yl)-3-methylphenyl]-amino}-N-(N-p-methoxybenzylphenylsulfonimidoyl)carboxamide dissolved in 380 μL of CAN followed by 96 uL of water was added 70 mg (0.13 mmol) of cerric ammonium nitrate. After 20 m, the reaction was complete and purified by RP-HPLC to give 1.8 mg (23%) after lyophilization. ES-MS (M+H)+=469 (Cl).

Example 1077

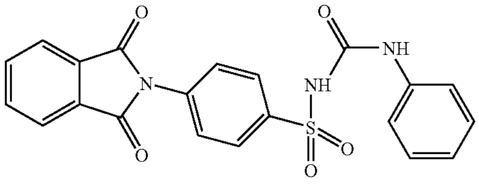

Preparation of N-{[4-(1,3-dioxobenzo[c]azolidin-2-yl)phenyl]sulfonyl(phenylamino)carboxamide A. Synthesis of 4-(1,3-dioxobenzo[c]azolidin-2-yl) benzenesulfonamide A solution of 1.0 g (5.8 mmol) of p-aminophenylsulfonamide in 3.6 ml, of pyridine was added 878 μL (6.1 mmol) of phthalic dichloride. After heating to 60° C. for 18 h, the solution was poured into 1N HCl, cooled to 0° C., the precipitate was collected by filtration, and dried under vacuum to give 1.58 g (90%) of the titled compound.

A. Synthesis of N-{[4-(1,3-dioxobenzo[c]azolidin-2-yl)phenyl]sulfonyl}(phenylamino)carboxamide To a solution of 4-(1,3-dioxobenzo[c]azolidin-2-yl)benzenesulfonamide in 660 uL of DMSO was added 60 mg (0.40 mmol) of DBU followed by 36 μl (0.33 mmol) of phenylsulfonylisocyanate. After stirring for 0.5 h, the mixture was poured into 1N HCl, cooled, and the precipitate was collected by filtration and dried under vacuum to give 137 mg (100%) of the titled compound.

Example 1078

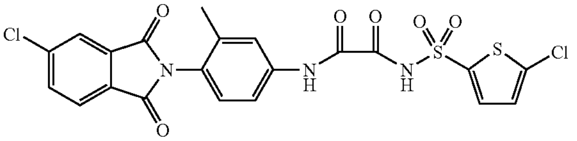

Preparation of N-[(5-chloro(2-thienyl))sulfonyl]-N'-[4-(5-chloro-1,3-dioxobenzo[c]azolidin-2-yl)-3-methylphenyl]ethane-1,2-diamide A 200 mg (1.0 mmol) of 5-chlorothiophenesulfonamide was slurried in 0.5 mL of oxalyl chloride and refluxed for 6 h. The solvent was removed in vacuo and 36 mg of the resulting solid was dissolved in 240 μl, acetonitrile and treated with 40 mg (0.14 mmol) 2-(4-amino-2-methylphenyl)-5-chlorobenzo[c]azoline-1,3-dione. After stirring for 1 h, the solvent was removed and the residue was purified by RP-HPLC to give 33 mg (44%) of the titled compound. ES-MS (M+H)+= 538(2Cl).

Example 1079

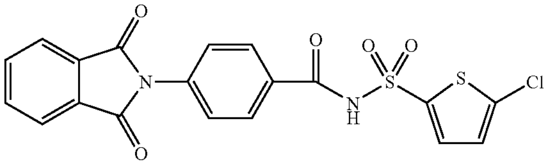

Preparation of [4-(1,3-dioxobenzo[c]azolidin-2-yl)phenyl]-N-[(5-chloro(2-thienyl))sulfonyl]-carboxamide A. Synthesis of N-[(5-chloro(2-thienyl))sulfonyl](4-nitrophenyl)carboxamide A 85 mg portion (0.43 mmol) of 5-chlorothiophenesulfonamide dissolved in 2 mL of acetone was treated with 110 μL of 4N NaOH (0.43 mmol) followed by addition of 80 mg (0.43 mmol) of 4-nitrobenzoyl chloride. After stirring for 12 h, the solution was acidified 1N HCl and the precipitate was collected by filtration and dried. Recrystallization from EtOAc/hexane afforded 120 mg (81%) of the titled compound. ES-MS (M+H)+=347 (Cl).

B. Synthesis of (4-aminophenyl)-N-[(5-chloro(2-thienyl))sulfonyl]carboxamide

A 74 mg portion (0.21 mmol) of [4-(1,3-dioxobenzo[c]azolidin-2-yl)phenyl]-N-[(5-chloro(2-thienyl))sulfonyl]-carboxamide, 192 mg (0.84 mmol) of tin dichloride dihydrate were combined and dissolved in 1.4 mL of EtOAc. The mixture was refluxed for 4 h, filtered through celite, and concentrated in vacuo to afford a solid which was purified on silica gel eluting with 10% $MeOH/CH_2Cl_2$ to give a quantitative yield of the titled compound. ES-MS (M+H)+=317 (Cl).

C. Synthesis of [4-(1,3-dioxobenzo[c]azolidin-2-yl)phenyl]-N-[(5-chloro(2-thienyl))sulfonyl]carboxamide A 22 mg portion (0.070) of (4-aminophenyl)-N-[(5-chloro(2-thienyl))sulfonyl]carboxamide was combined with 15 mg (0.10 mmol) of phthalic anhydride in 140 μL of DMF. After 18 h of heating at 110° C., the mixture was cooled and purified by RP-HPLC, to give 20 mg (55%) of the desired compound. ES-MS $(M+H)^+=447$ (Cl).

Example 1080

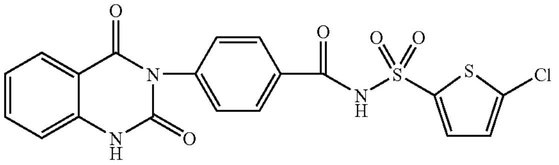

[4-(2,4-dioxo(1,3-dihydroquinazolin-3-yl))phenyl]-N-[(5-chloro(2-thienyl))sulfonyl]carboxamide A 44 mg portion (0.14) of (4-aminophenyl)-N-[(5-chloro(2-thienyl))sulfonyl]carboxamide was combined with 25 mg (0.14 mmol) of methyl 2-isocyanatobenzoate in 500 uL of THF followed by the addition of 1 equivalent of TEA (24 μL) and 1 equivalent of DBU. After 18 h, the mixture was purified by RP-HPLC, to give 21 mg (34%) of the desired compound. ES-MS $(M+H)^+=462$ (Cl).

Scheme 1 General Synthesis of Phthalimide Compounds:

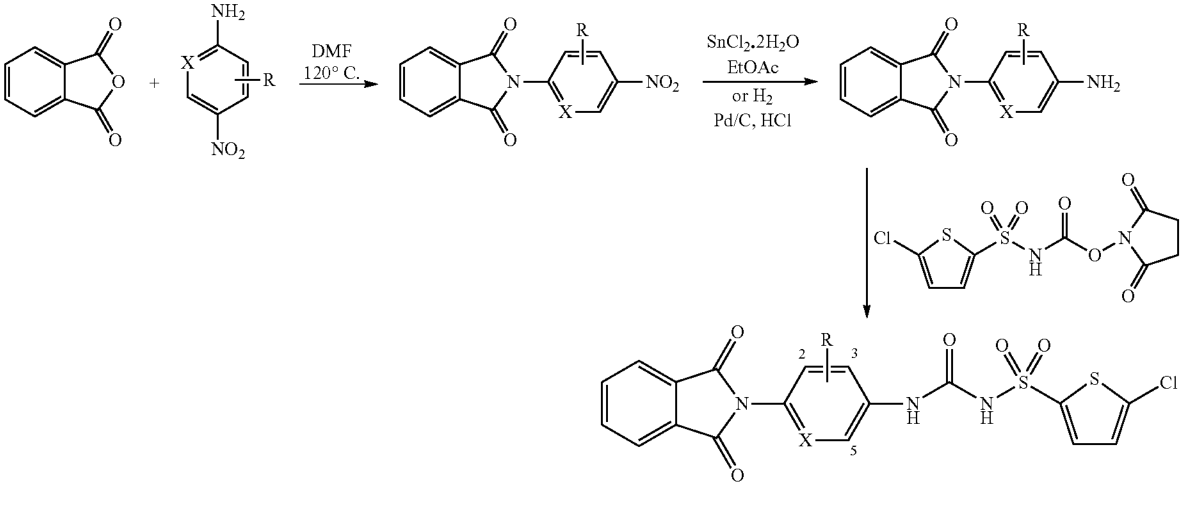

General Procedure for Synthesizing Phthalimide Targets

A. General Procedure for Phthalic Anhydride Reaction

A mixture of phthalic anhydride (0.96 g, 6.5 mmol) and the substituted nitroaniline (5 mmol) in DMF (10 ml.) was heated to 120° C. for 22 hr. The reaction was then concentrated and chromatographed on silica gel using $CH_2Cl_2$/hexane mixtures as eluent to give pure product in 35-65% yields, depending on the substituents.

A-1. General Reduction Procedure 1

A suspension of the nitrophenyl intermediate (0.75 mmol) and tin(II) chloride dihydrate (3 mmol) in ethyl acetate (4.5 mL) was heated at 70° C. for 2 hr. The reaction mixture was then poured onto ice (25 mL), basified with 5% $NaHCO_3$ (13 mL), extracted with EtOAc, washed with brine, dried and concentrated in vacuo to give pure aniline product in very good yields, typically >90%.

B-2. General Reduction Procedure 2

To a suspension of the nitrophenyl intermediate (0.8 mmol) in methanol (3 mL), ethyl acetate (2 mL) and 2 N HCl (0.4 mL, 0.8 mmol) was added 10% Pd/C (43 mg, 0.04 mmol) under argon. The reaction mixture was hydrogenated under 1 atm $H_2$ for 2 hr, filtered through Celite and concentrated in vacuo to give the aniline hydrochloride salt in very good yields.

C. General Procedure for Coupling the Aniline Intermediate with 5-chlorothiophenesulfonamides to Form Sulfonyl Ureas To a suspension of 5-chlorothiophene-2-sulfonamide (40 mg, 0.2 mmol) and DSC (61 mg, 0.24 mmol) in dry acetonitrile (1 mL) was added DBU (60 μL, 0.4 mmol). The resulting solution was stirred at room temp for 16 hr. The aniline from step B (0.2 mmol) was then added as a solid with additional acetonitrile (1 mL), and the reaction was heated to 70° C. and stirred for another 17 hr. Acidification and HPLC purification of the crude reaction product gave the final compounds in varying yields (20-70%).

Example 7 and Examples 1081-1093

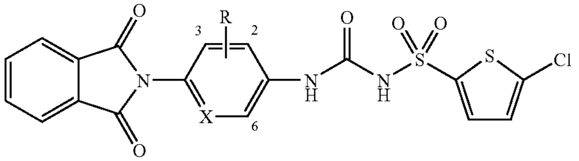

The targets above were prepared using the procedures outlined in Scheme 1, steps A-C using a variety of substituted nitroanilines, where R=3-Cl; 3-CN; 3-$CF_3$; 3-F; 3-Br; 3-OMe; 3-iPr; 2-$CF_3$; 2-Cl, 5-Me; 2-$NMe_2$, 5-Cl; 2,5-diMe; 3,5-diMe; 3,5-diCl; 2-OMe, 5-Me; and X═N, R═H.

Example 7

N-[4-(1,3-dioxobenzo[c]azolidin-2-yl)-3-chlorophenyl]{[(5-chloro(2-thienyl))sulfonyl]amino}-carboxamide. ES-MS (M+H)+=496, 498 (2Cl).

Example 1081

N-[4-(1,3-dioxobenzo[c]azolidin-2-yl)-3-cyanophenyl]{[(5-chloro(2-thienyl))sulfonyl]amino}-carboxamide. ES-MS (M+H)+=487, 489 (Cl).

Example 1082

N-[4-(1,3-dioxobenzo[c]azolidin-2-yl)-3-(trifluoromethyl)phenyl]{[(5-chloro(2-thienyl))sulfonyl]-amino}carboxamide. ES-MS (M+H)+=530, 532 (Cl).

Example 1083

N-[4-(1,3-dioxobenzo[c]azolidin-2-yl)-3-fluorophenyl]{[(5-chloro(2-thienyl))sulfonyl]amino}-carboxamide. ES-MS (M+H)+=530, 532 (Cl).

Example 1084

N-[4-(1,3-dioxobenzo[c]azolidin-2-yl)-3-bromophenyl]{[(5-chloro(2-thienyl))sulfonyl]amino}-carboxamide. ES-MS (M+H)+=540, 542 (Cl, Br).

Example 1085

N-[4-(1,3-dioxobenzo[c]azolidin-2-yl)-3-methoxyphenyl]{[(5-chloro(2-thienyl))sulfonyl]amino}-carboxamide. ES-MS (M+H)+=492.0 (Cl).

Example 1086

N-[4-(1,3-dioxobenzo[c]azolidin-2-yl)-3-(methylethyl)phenyl]{[(5-chloro(2-thienyl))sulfonyl]amino}-carboxamide. ES-MS (M+H)+=490.9 (Cl).

Example 1087

N-[4-(1,3-dioxobenzo[c]azolidin-2-yl)-2-(trifluoromethyl)phenyl]{[(5-chloro(2-thienyl))sulfonyl]-amino}carboxamide. ES-MS (M+H)+=463, 465 (Cl).

Example 1088

N-[4-(1,3-dioxobenzo[c]azolidin-2-yl)-2-chloro-5-methylphenyl]{[(5-chloro(2-thienyl))sulfonyl]-amino}carboxamide. ES-MS (M+H)+=510, 512 (2Cl).

Example 1089

N-[2-(dimethylamino)-4-(1,3-dioxobenzo[c]azolidin-2-yl)-5-chlorophenyl]{[(5-chloro(2-thienyl))-sulfonyl]amino}carboxamide. ES-MS (M+H)+=539, 541 (2Cl).

Example 1090

N-[4-(1,3-dioxobenzo[c]azolidin-2-yl)-2,5-dimethylphenyl]{[(5-chloro(2-thienyl))sulfonyl]amino}-carboxamide. ES-MS (M+H)+=490.0 (Cl).

Example 1091

N-[4-(1,3-dioxobenzo[c]azolidin-2-yl)-3,5-dimethylphenyl]{[(5-chloro(2-thienyl))sulfonyl]amino}-carboxamide. ES-MS (M+H)+=490.0 (Cl).

Example 1092

N-[4-(1,3-dioxobenzo[c]azolidin-2-yl)-3,5-dichlorophenyl]{[(5-chloro(2-thienyl))sulfonyl]amino}-carboxamide. ES-MS (M+H)+=529.9, 532.0 (2Cl)

Example 1093

N-[4-(1,3-dioxobenzo[c]azolidin-2-yl)-5-methyl-2-methoxyphenyl]{[(5-chloro(2-thienyl))sulfonyl]-amino}carboxamide. ES-MS (M+H)+=506, 507 (Cl).

Example 1094

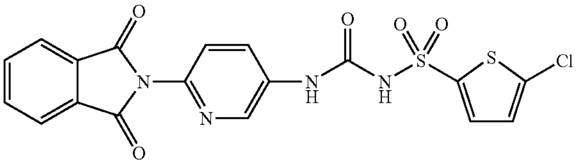

Preparation of N-[6-(1,3-dioxobenzo[c]azolidin-2-yl)(3-pyridyl)]{[(5-chloro(2-thienyl))sulfonyl]-amino}carboxamide was accomplished using the procedures outlined in Scheme 1, steps A-C using 2-amino-5-nitropyridine. ES-MS (M+H)+=463, 465 (Cl).

Example 1095

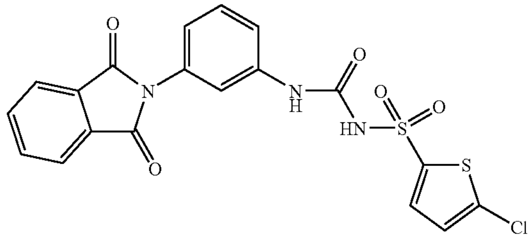

Preparation of N-[6-(1,3-dioxobenzo[c]azolidin-2-yl)(3-phenyl)]{[(5-chloro(2-thienyl))sulfonyl]-amino}carboxamide was accomplished using the procedures outlined in Scheme 1, steps A-C. ES-MS (M+H)+=462.0 (Cl).

Example 1096

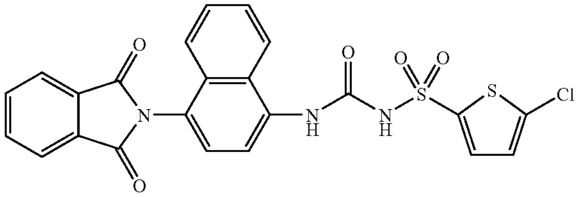

Preparation of N-[4-(1,3-dioxobenzo[c]azolidin-2-yl)-4-napthyl]{[(5-chloro(2-thienyl))sulfonyl]-amino}carboxamide was accomplished using the procedures outlined in Scheme 1, steps A-C. ES-MS (M+H)+=511.9 (Cl).

Scheme 2

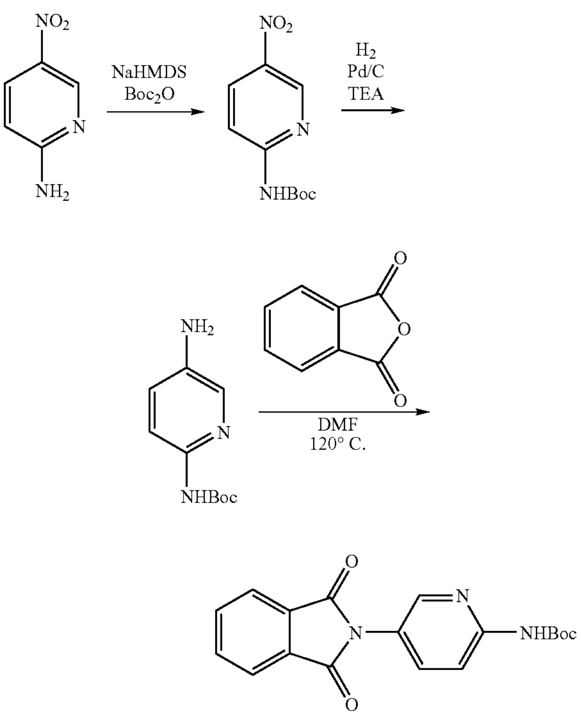

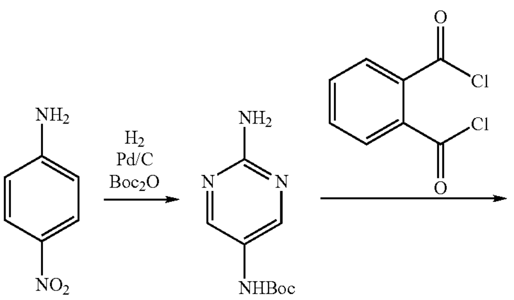

-continued

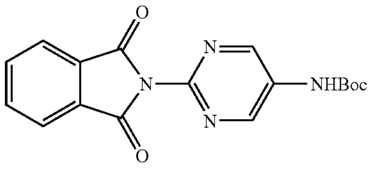

Example 1097

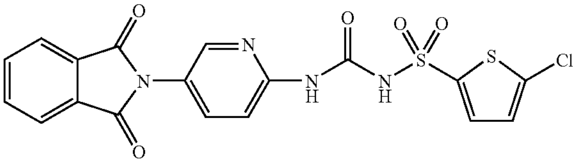

Preparation of N-[5-(1,3-dioxobenzo[c]azolidin-2-yl)(2-pyridyl)]{[(5-chloro(2-thienyl))-sulfonyl]amino}carboxamide A. Synthesis of (tert-butoxy)-N-(5-nitro(2-pyridyl))carboxamide To a solution of 2-amino-5-nitropyridine (0.555 g, 4 mmol) in THF (10 mL) was added 1 M NaHMDS in THF (8 mL, 8 mmol). The resulting dark red suspension was stirred for 15 min, followed by addition of a solution of Boc anhydride (0.87 mL, 3.8 mmol) in THF (5 mL). The reaction mixture was stirred at room temp for 21 hr, dilute with EtOAc, washed with 1 N HCl and brine, dried and concentrated in vacuo to give (tert-butoxy)-N-(5-nitro(2-pyridyl))carboxamide (0.63 g, 70%). ES-MS (M+H-tBu)+=184.

B. Synthesis of N-(5-amino(2-pyridyl))(tert-butoxy)carboxamide

To a suspension of (tert-butoxy)-N-(5-nitro(2-pyridyl))carboxamide (0.27 g, 1.13 mmol) in methanol (2 mL), ethyl acetate (4 mL) and TEA (0.16 mL) was added 10% Pd/C (60 mg, 0.056 mmol) under argon. The reaction mixture was hydrogenated under 1 atm $H_2$ for 20 hr, filtered through Celite and concentrated in vacuo to give N-(5-amino(2-pyridyl))(tert-butoxy)carboxamide (0.226 g, 97%). $^1$H-NMR. (DMSO-$d_6$): δ 1.40 (s, 9H), 4.92 (br s, 2H), 6.89-6.91 (dd, 1H), 7.35-7.37 (d, 1H), 7.58 (d, 1H), 9.06 (s, 1H).

C. Synthesis of N-[5-(1,3-dioxobenzo[c]azolidin-2-yl)(2-pyridyl)]{[(5-chloro(2-thienyl)-sulfonyl]amino}carboxamide N-[5-(1,3-dioxobenzo[c]azolidin-2-yl)(2-pyridyl)]{[(5-chloro(2-thienyl))-sulfonyl]amino}carboxamide was prepared by following the procedure in Scheme 1 step A, followed by TFA deprotection, followed by the coupling procedure outlines in Scheme 1 step C. ES-MS (M+H)+=463, 465 (Cl).

Example 1098

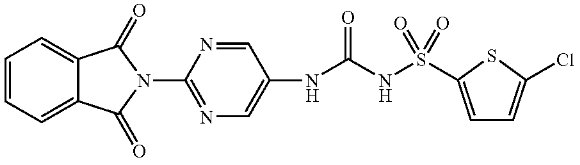

Preparation of N-[2-(1,3-dioxobenzo[c]azolidin-2-yl)pyrimidin-5-yl]{[(5-chloro(2-thienyl))sulfonyl]amino}carboxamide Scheme 3 Benzamide-containg Sulfonylureas

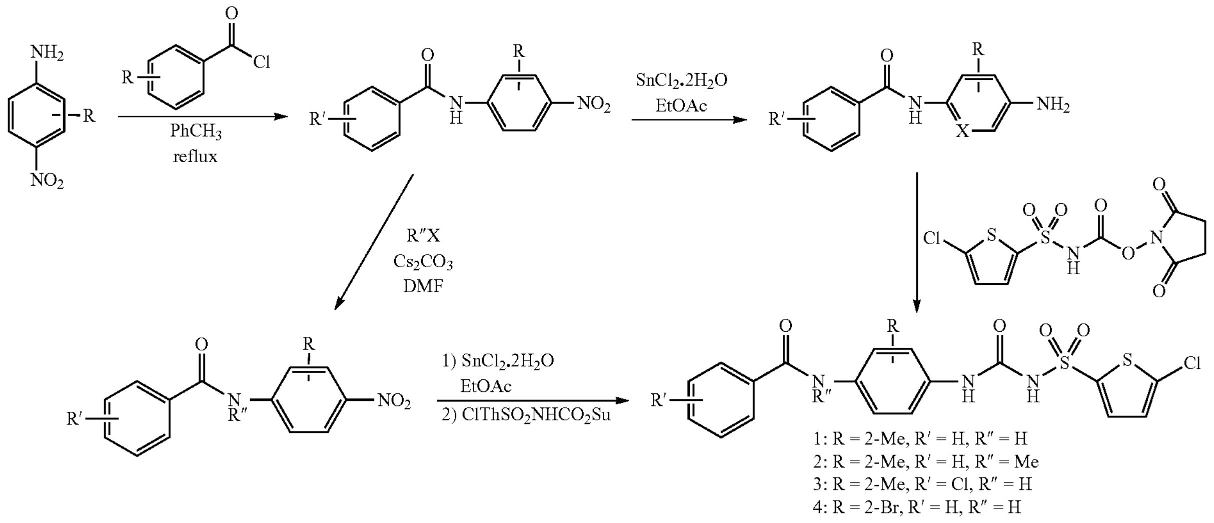

A. Synthesis of N-(2-aminopyrimidin-5-yl)(tert-butoxy)carboxamide

To a suspension of 2-amino-5-nitropyrimidine (0.25 g, 1.78 mmol) in methanol (4 mL) was added tert-butyl (tert-butoxycarbonyloxy) formate (0.5 mL, 2.18 mmol) and 10% Pd/C (96 mg, 0.090 mmol) under argon. The reaction mixture was hydrogenated under 1 atm $H_2$ for 5 hr, filtered through Celite and concentrated in vacuo to give crude N-(2-aminopyrimidin-5-yl)(tert-butoxy)carboxamide (0.435 g). ES-MS (M+H)+=211.

B. Synthesis of (tert-butoxy)-N-[2-(1,3-dioxobenzo[c]azolidin-2-yl)pyrimidin-5-yl]carboxamide To a solution of N-(2-aminopyrimidin-5-yl)(tert-butoxy)carboxamide (0.237 g, 1.0 mmol) in pyridine (1 mL) was added phthaloyl dichloride (0.144 mL, 1.0 mmol). The resulting suspension was stirred at 45° C. for 2 hr, diluted with EtOAc, washed with water and brine, dried and concentrated in vacuo to give crude (tert-butoxy)-N-[2-(1,3-dioxobenzo[c]azolidin-2-yl)pyrimidin-5-yl]carboxamide (0.31 g). ES-MS (M+H)+=341; (M+H-tBu)+=285.

C. Synthesis of N-[2-(1,3-dioxobenzo[c]azolidin-2-yl)pyrimidin-5-yl]{[(5-chloro(2-thienyl))sulfonyl]amino}carboxamide TFA deprotection of (tert-butoxy)-N-[2-(1,3-dioxobenzo[c]azolidin-2-yl)pyrimidin-5-yl]carboxamide and coupling with 5-chlorothiophenesulfonamide (see Scheme 1 step C) gave N-[2-(1,3-dioxobenzo[c]azolidin-2-yl)pyrimidin-5-yl]{[(5-chloro(2-thienyl))sulfonyl]amino}carboxamide in 27% yield. ES-MS (M+H)+=464, 466 (Cl).

Example 1099

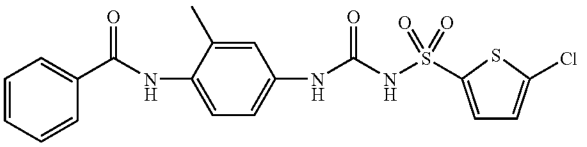

Preparation of N-[4-({[(5-chloro(2-thienyl))sulfonyl]amino}carbonylamino)-2-methylphenyl]-benzamide A. Synthesis of N-(2-methyl-4-nitrophenyl)benzamide To a suspension of 2-methyl-4-nitroaniline (0.76 g, 5 mmol) in toluene (25 mL) was added neat benzoyl chloride (0.59 mL, 5.08 mmol). The reaction mixture was refluxed for 16 hr, cooled and filtered to give N-(2-methyl-4-nitrophenyl)benzamide (1.21 g, 95%) as a beige solid. ES-MS (M+H)+=257.

B. Synthesis of N-(4-amino-2-methylphenyl)benzamide

A suspension of N-(2-methyl-4-nitrophenyl)benzamide (0.256 g, 1.0 mmol) and tin(II) chloride dihydrate (0.89 g, 3.96 mmol) in ethyl acetate (6 mL) was heated at 70° C. for 19 hr. The reaction mixture was then chilled, poured onto 50 mL ice, basified with 5% $NaHCO_3$ (20 mL), extracted into EtOAc, washed with brine, dried and concentrated in vacuo to give N-(4-amino-2-methylphenyl)-benzamide (0.22 g, 97%). ES-MS (M+H)+=227, (M+Na)+=249.

C. Synthesis of N-[4-({[(5-chloro(2-thienyl))sulfonyl]amino}carbonylamino)-2-methylphenyl]benzamide A solution of 5-chlorothiophene-2-sulfonamide (30 mg, 0.15 mmol) and DSC (46 mg, 0.18 mmol) in $CH_3CN$ (1 mL) and DBU (45 μL) was heated at 40° C. for 1 hr. To this mixture was added N-(4-amino-2-methylphenyl)benzamide (34 mg, 0.15 mmol) with further heating for 3 days. Acidification and HPLC purification gave N-[4-({[(5-chloro(2-thienyl))sulfonyl]amino}carbonyl-amino)-2-methylphenyl]benzamide (24 mg, 35%). ES-MS (M+H)+=450, 452 (Cl).

Example 1100

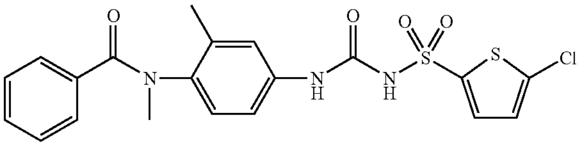

Preparation of N-[4-({[(5-chloro(2-thienyl))sulfonyl]amino}carbonylamino)-2-methylphenyl]-N-methylbenzamide A. Synthesis of N-methyl-N-(2-methyl-4-nitrophenyl)benzamide To a solution of N-(2-methyl-4-nitrophenyl)benzamide (Example 1099A) (0.38 g, 1.48 mmol) in DMF (2 mL) was added cesium carbonate (1.2 g, 3.68 mmol) followed by methyl iodide (0.12 mL, 1.9 mmol). The reaction mixture was stirred at room temp for 2 hr, extracted with EtOAc, washed with water and brine, dried and concentrated in vacuo to give N-methyl-N-(2-methyl-4-nitrophenyl)-benzamide (0.38 g, 95%). ES-MS (M+H)+=271.

B. Synthesis of N-[4-({[(5-chloro(2-thienyl))sulfonyl]amino}carbonylamino)-2-methylphenyl]-N-methylbenzamide N-methyl-N-(2-methyl-4-nitrophenyl)benzamide was reduced and coupled with 5-chloro-thiophenesulfonamide using the same procedure as shown in Example 1099, steps B and C to give N-[4-({[(5-chloro(2-thienyl))sulfonyl]amino}carbonylamino)-2-methylphenyl]-N-methylbenzamide (44 mg, 31%). ES-MS (M+H)+=464, 466 (Cl).

Example 1101

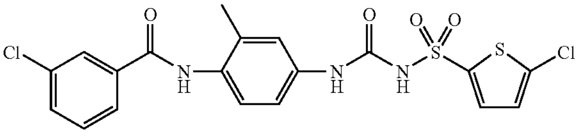

Preparation of N-[4-({[(5-chloro(2-thienyl))sulfonyl]amino}carbonylamino)-2-methylphenyl](3-chlorophenyl)-carboxamide was prepared using a similar procedure as that shown in Example 1099 steps A-C, using 3-chlorobenzoyl chloride in the first step, instead of benzoyl chloride. The final product was obtained in 43% yield. ES-MS (M+H)+=484, 486 (2Cl).

Example 1102

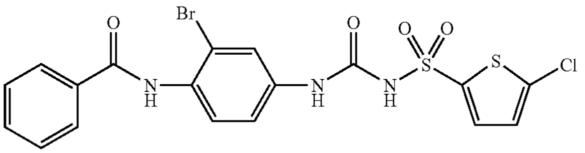

Preparation of N-[2-bromo-4-({[(5-chloro(2-thienyl))sulfonyl]amino}carbonylamino)phenyl]benzamide was prepared using a similar procedure as that shown in Example 1099 steps A-C, using 2-bromo-4-nitro-aniline in the first step, instead of 2-methyl-4-nitroaniline. The final product was obtained in 64% yield. ES-MS (M+H)+=514, 516, 518 (Cl, Br).

Scheme 4

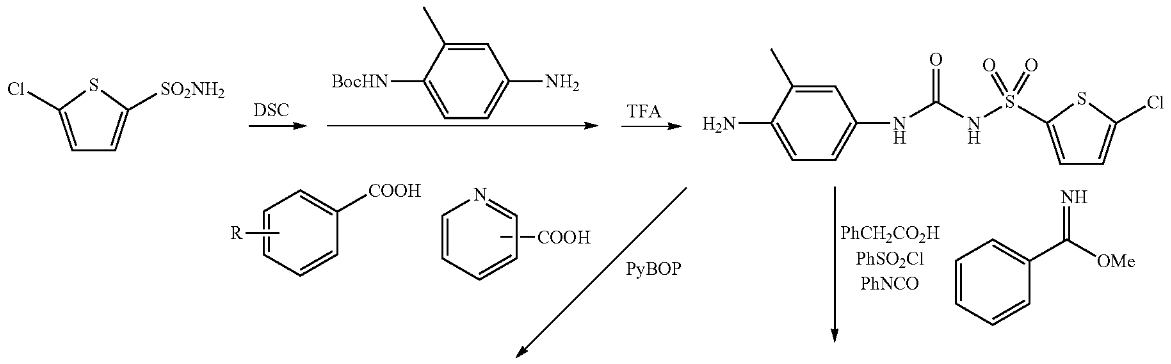

-continued

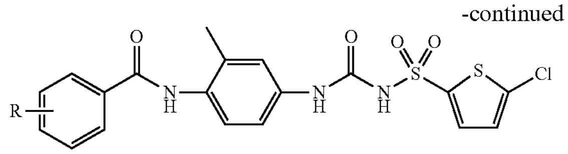

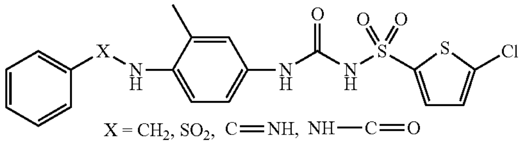

Example 1103

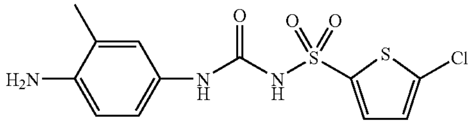

Preparation of N-(4-amino-3-methylphenyl) {[(5-chloro(2-thienyl))sulfonyl]amino}carboxamide A. Synthesis of N-{4-[(tert-butoxy)carbonylamino]-3-methylphenyl}{[(5-chloro(2-thienyl))sulfonyl] amino}carboxamide A solution of 5-chlorothiophene-2-sulfonamide (0.2 g, 1.0 mmol) and DSC (0.307 g, 1.2 mmol) in $CH_2Cl_2$ (5 mL) and DBU (0.3 mL) was stirred at room temp for 16 hr. To this mixture was added N-(4-amino-2-methylphenyl)(tert-butoxy)carboxamide (0.26 g, 1 mmol), followed by heating at 40° C. for 2 hr. Acidification and HPLC purification gave N-{4-[(tert-butoxy)carbonylamino]-3-methyl-phenyl}{[(5-chloro(2-thienyl))sulfonyl]amino}carboxamide (0.28 g, 63%). ES-MS (M+Na)+=468, (M+H−tBu)=390, 392 (Cl).

B. Synthesis of N-(4-amino-3-methylphenyl){[(5-chloro(2-thienyl))sulfonyl]amino}carboxamide To a chilled solution of N-{4-[(tert-butoxy)carbonylamino]-3-methylphenyl}{[(5-chloro(2-thienyl))sulfonyl] amino}carboxamide (0.246 g, 0.55 mmol) in $CH_2Cl_2$ (5 mL) was added neat TFA (1.1 mL). The reaction mixture was stirred cold for 1.5 hr, concentrated in vacuo, azeotroped with heptane and dried to give N-(4-amino-3-methylphenyl){[(5-chloro(2-thienyl))sulfonyl]amino}-carboxamide (0.26 g) as the mono TFA salt. ES-MS (M+H)+=346.

Examples 1104-1116

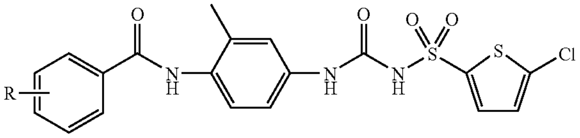

The compounds above were prepared according to Scheme 4 using the following general synthetic procedure: 1.1 equivalent of the benzoic acid and 1 equivalent of N-(4-amino-3-methylphenyl) {[(5-chloro(2-thienyl))sulfonyl] amino}carboxamide were dissolved in DMF (0.5 M) and 1.2 equivalent of PyBOP was added. After 2 h, the reaction mixture was directly purified by RP-HPLC to give the targets above where R=p-$CH_3$, p-$OCH_3$, p-Cl, o-Cl, o-$NO_2$, o-OBn, o-OH, m-F, m, p-diCl, o-pyr, m-pyr and p-pyr. The o-$NH_2$ analog was obtained by reduction of o-$NO_2$ using $H_2$/Pt/C in methanol.

Example 1104

N-[4-({[(5-chloro(2-thienyl))sulfonyl] amino}carbonylamino)-2-methylphenyl](4-methylphenyl)-carboxamide. ES-MS (M+H)+=464, 466 (Cl).

Example 1105

N-[4-({[(5-chloro(2-thienyl))sulfonyl] amino}carbonylamino)-2-methylphenyl](4-methoxyphenyl)-carboxamide. ES-MS (M+H)+=480, 482 (Cl).

Example 1106

N-[4-({[(5-chloro(2-thienyl))sulfonyl] amino}carbonylamino)-2-methylphenyl](4-chlorophenyl)-carboxamide. ES-MS (M+H)+=483.9, 485.9, 487.9 (2Cl).

Example 1107

N-[4-({[(5-chloro(2-thienyl))sulfonyl] amino}carbonylamino)-2-methylphenyl](2-chlorophenyl)-carboxamide. ES-MS (M+H)+=484, 486 (2Cl).

Example 1108

N-[4-({[(5-chloro(2-thienyl))sulfonyl] amino}carbonylamino)-2-methylphenyl](2-nitrophenyl)-carboxamide. ES-MS (M+H)+=495, 497 (Cl).

Example 1109

N-[4-({[(5-chloro(2-thienyl))sulfonyl] amino}carbonylamino)-2-methylphenyl][2-(phenylmethoxy)-phenyl]carboxamide. ES-MS (M+H)+=556, 558 (Cl).

Example 1110

N-[4-({[(5-chloro(2-thienyl))sulfonyl] amino}carbonylamino)-2-methylphenyl][2-hydroxyphenyl]-carboxamide. ES-MS (M+H)+=466, 468 (Cl).

Example 1111

N-[4-({[(5-chloro(2-thienyl))sulfonyl] amino}carbonylamino)-2-methylphenyl](3-fluorophenyl)-carboxamide. ES-MS (M+H)+=468, 470 (Cl).

Example 1112

N-[4-({[(5-chloro(2-thienyl))sulfonyl] amino}carbonylamino)-2-methylphenyl](3,4-dichlorophenyl)-carboxamide. ES-MS (M+H)+=517.9, 519.9, 521.9 (3Cl).

Example 1113

N-[4-({[(5-chloro(2-thienyl))sulfonyl]amino}carbonylamino)-2-methylphenyl]-2-pyridylcarboxamide. ES-MS (M+H)+=451, 453 (Cl).

Example 1114

N-[4-({[(5-chloro(2-thienyl))sulfonyl]amino}carbonylamino)-2-methylphenyl]-3-pyridylcarboxamide. ES-MS (M+H)+=451, 453 (Cl).

Example 1115

N-[4-({[(5-chloro(2-thienyl))sulfonyl]amino}carbonylamino)-2-methylphenyl]-4-pyridylcarboxamide. ES-MS (M+H)+=451, 453 (Cl).

Example 1116

N-[4-({[(5-chloro(2-thienyl))sulfonyl]amino}carbonylamino)-2-methylphenyl](2-aminophenyl)-carboxamide. ES-MS (M+H)+=465, 467 (Cl).

Example 1117-1120

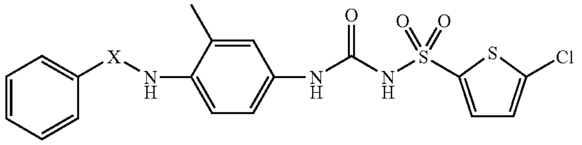

Example 1117

1.0 equivalent of N-(4-amino-3-methylphenyl){[(5-chloro(2-thienyl))sulfonyl]amino}-carboxamide was treated with 1.0 equivalent of $PhCH_2COOH$/PyBOP to give X═$CH_2$, {[(5-chloro(2-thienyl))sulfonyl]amino}-N-{3-methyl-4-[benzylamino]phenyl}carboxamide. ES-MS (M+H)+=464, 466 (Cl).

Example 1118

Alternatively (for X═$SO_2$), the compounds above were prepared according to Scheme 4 using the following general synthetic procedure: 1.0 equivalents of N-(4-amino-3-methylphenyl){[(5-chloro(2-thienyl))sulfonyl]amino}-carboxamide dissolved in DMF (0.5 M) was treated with 1.0 equivalent of $PhSO_2Cl$ and 1.2 equivalents of DIEA to give, after RP-HPLC purification, X═$SO_2$, {[(5-chloro(2-thienyl))sulfonyl]amino}-N-{3-methyl-4-[(phenylsulfonyl)amino]phenyl}carboxamide. ES-MS (M+H)+=486, 488 (Cl).

Example 1119

For X═C═NH: Treatment with methyl benzimidate.HCl (1.4 eq) in DMF gave the amidine X═C═NH, {[(5-chloro(2-thienyl))sulfonyl]amino}-N-{4-[(iminophenylmethyl)amino]-3-methylphenyl}carboxamide. ES-MS (M+H)+=449, 451 (Cl).

Example 1120

For X═NH—C═O: Treatment with phenyl isocyanate (1.07 eq) in DMF to give the urea X═NH—C═O, {[(5-chloro(2-thienyl))sulfonyl]amino}-N-{3-methyl-4-[(phenylamino)carbonylamino]phenyl}carboxamide. ES-MS (M+H)+=465, 467 (Cl).

Scheme 5

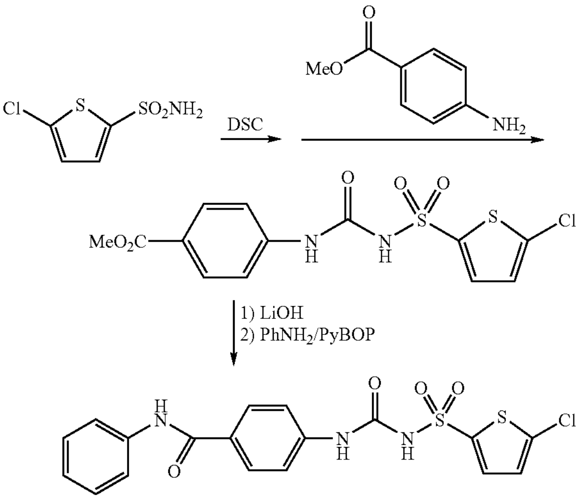

Example 1121

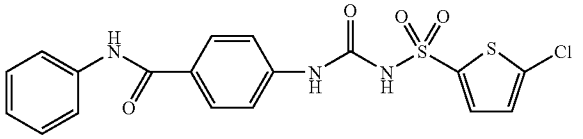

Preparation of {[(5-chloro(2-thienyl))sulfonyl]amino}-N-[4-(N-phenylcarbamoyl)phenyl]carboxamide

A. Synthesis of methyl 4-({[(5-chloro-2-thienyl)sulfonyl]amino}carbonylamino)benzoate A solution of 5-chlorothiophene-2-sulfonamide (0.2 g, 1.0 mmol) and DSC (0.307 g, 1.2 mmol) in $CH_2Cl_2$ (5 mL) and DBU (0.3 mL) was stirred at room temp overnight. To this mixture was added methyl 4-aminobenzoate (0.15 g, 1.0 mmol). The reaction was then stirred at room temp for 17 hr, acidified and HPLC purified to give methyl 4-({[(5-chloro-2-thienyl)sulfonyl]amino}carbonyl-amino)benzoate (0.23 g, 61%). ES-MS (M+H)+=375, 377 (Cl).

B. Synthesis of 4-({[(5-chloro-2-thienyl)sulfonyl]amino}carbonylamino)benzoic acid To a suspension of methyl 4-({[(5-chloro-2-thienyl)sulfonyl]amino}carbonylamino)benzoate (56 mg, 0.15 mmol) in methanol (1 mL) and acetonitrile (1 mL) was added 1N LiOH (0.16 mL, 0.16 mmol). The resulting solution was stirred at room temp for 21 hr, then an additional 0.32 mL 1N LiOH was added and the reaction was stirred at 40° C. for another 21 hr til complete. Concentration in vacuo gave crude 4-({[(5-chloro-2-thienyl)sulfonyl]amino}carbonylamino)benzoic acid (69 mg). ES-MS (M+H)+=361.

C. Synthesis of {[(5-chloro(2-thienyl))sulfonyl]amino}-N-[4-(N-phenylcarbamoyl)phenyl]-carboxamide To a solution of 4-({[(5-chloro-2-thienyl)sulfonyl]amino}carbonylamino)benzoic acid (69 mg) in DMF (0.7 mL) was added aniline (21 uL, 0.23 mmol), DIEA (3 eq.) then PyBOP (85 mg, 0.16 mmol). The reaction mixture was stirred at room temp for 28 hr, acidified and HPLC purified to give {[(5-chloro(2-thienyl))sulfonyl]amino}-N-[4-(N-phenylcarbamoyl)phenyl]carboxamide (29 mg, 45%). ES-MS (M+H)+= 436, 438 (Cl).

chloride (2.2 mL, 30 mmol). The reaction mixture was stirred at 60° C. for 2 hr, chilled, concentrated in vacuo and dried to give crude acid chloride. To a solution of the acid chloride in 1,2-dichlorobenzene (22 mL) was added $NaN_3$ (2.6 g, 40 mmol). After heating at 140° C. for 6 hr, complete conversion to the isocyanate was observed, catalytic $I_2$ was added and the reaction was heated to 180° C. for 17 hr. Reaction workups included either precipitation of product with hexane or concentration and flash chromatography using $EtOAc/CH_2Cl_2$ eluent. Yields varied widely depending on the substituent (5-80%).

B-2. General Procedure 2 for Cyclization of Cinnamic Acids to Isoquinolinones

To a chilled solution of the cinnamic acid (16 mmol) in dry THF (35 mL) and triethylamine (2.9 mL, 20.8 mmol) was Scheme 6:
General Procedure for the Synthesis of Isoquinolinone-containing Sulfonylureas

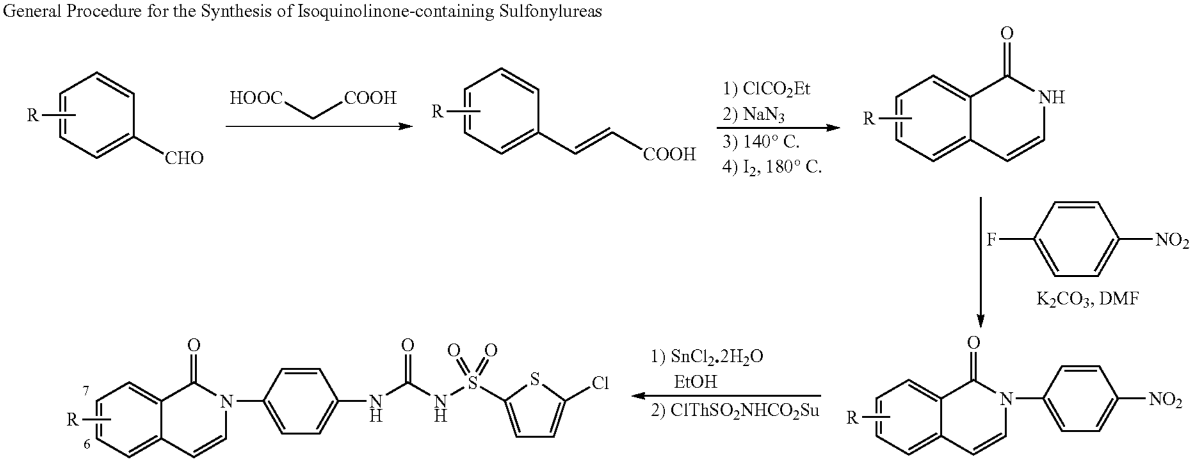

| | | | |
|---|---|---|---|
| R = | 6, 7-diCl | 7-Me | 6-Me, $-CF_3$, -Cl |
| | 7, 8-diCl | 7-Cl | 6-OMe, 6-OH, 6-OiPr, 6-$OCH_2CH_2OMe$ |
| | 7-Cl, 6-OMe | 7-$CF_3$ | 6-$NH_2$, -NHAc, -NHMe, -$NMe_2$ |
| | | 7-F | 6-NHEt, -NHPr, -$NHCH_2cPr$, -$NCH_2CH_2F$, -NHBn |
| | 8-NHMe | 7-SMe | 6-$NHCH_2CH_2OMe$ |
| | 8-CN | 7-OMe | 6-NHPh |
| | | 7-SOMe | 6-F |
| | 4-$CO_2H$ | 7-$SO_2Me$ | 6-$NHNH_2$ |
| | 4-$CONH_2$ | 7-CN | 6-BR, -CN |

General Procedure for Synthesizing Isoquinolinone-Containing Sulfonyl Ureas

A. General Procedure for Synthesis of Cinnamic Acids

To a solution of malonic acid (10.4 g, 0.1 mol) and the benzaldehyde (0.05 mol) in pyridine (20 mL) was added neat piperidine (0.75 mL, 7.6 mmol). The reaction mixture was stirred at 80° C. for 17 hr, chilled, then added to 200 mL cold water. This mixture was acidified with conc. HCl (25 mL) and the white precipitate collected by filtration, washed with 5×10 mL water, and dried to give pure cinnamic acid in typical yields of >95%.

B-1. General Procedure 1 for Cyclization of Cinnamic Acids to Isoquinolinones

To a chilled suspension of the cinnamic acid (25 mmol) in benzene (40 mL) and DMF (5 drops) was added neat thionyl added neat ethyl chloroformate (1.85 mL, 19.4 mmol) dropwise over several minutes. The resulting suspension was stirred cold for 1 hr, then a solution of $NaN_3$ (1.56 g, 24 mmol) in 10 mL water was added. The reaction was stirred at room temp. for 1 hr. Reaction workups included either collection of the reaction precipitate, or extraction of product into $CH_2Cl_2$, giving pure acyl azide in >90% yields. A solution of the acyl azide in 1,2-dichlorobenzene (18 mL) was then heated to 140° C. to form the isocyanate, followed by addition of cat. iodine and heating to 180° C. overnight. Workups were the same as in general procedure B-1.

C. General Procedure for Alkylation of Isoquinolinone with 1-fluoro-4-nitrobenzene To a solution of the isoquinolinone (2.5 mmol) in DMF (5 mL) was added potassium carbonate (0.7 g, 5 mmol), followed by neat fluoro-4-nitrobenzene (0.3 mL, 2.8 mmol). The reaction mixture was stirred at 90° C. for 8 hr, poured onto cold water and filtered to give pure product in typical yields of 85-95%.

D. General Reduction Procedure

A suspension of the nitrophenyl intermediate from C (0.75 mmol) and tin(II) chloride dihydrate (0.68 g, 3 mmol) in ethanol (8 mL) was stirred at 70° C. for 4 hr. The reaction was then chilled, diluted with EtOAc, mixed with Celite, basified with 1M $Na_2CO_3$ (20 mL) then filtered. The organic layer was washed with water and brine, dried with $Na_2SO_4$, concentrated in vacuo to give the product aniline in typical yields of 85-95%.

E. General Procedure for Coupling the Aniline Intermediate with 5-chlorothiophenesulfonamide To a suspension of 5-chlorothiophene-2-sulfonamide (40 mg, 0.2 mmol) and DSC (61 mg, 0.24 mmol) in dry acetonitrile (1 mL) was added DBU (60 μL, 0.4 mmol). The resulting solution was stirred at room temp for 16 hr. The aniline from D (0.2 mmol) was then added as a solid with additional acetonitrile (1 mL), and the reaction was heated to 70° C. and stirred for another 17 hr. Acidification and HPLC purification of the crude reaction gave the final target in varying yields (20-70%) depending on the substituent.

Examples 371, 372, 374, 376, 379, 380 and 1122-1128

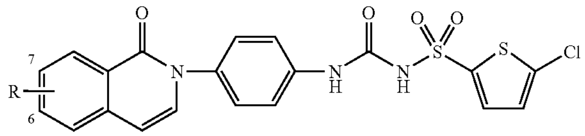

The compounds above where, for example, R=7-$CH_3$, 7-Cl, 7-F, 7-$CF_3$, 7-$OCH_3$, 6-CH3, 6-Cl, 6-F, 6-Br, 6-$CF_3$, 6-$OCH_3$, and 6,7-diCl were synthesized from commercially available benzaldehydes or cinnamic acids using the general procedure outlined in Scheme 6. The 7,8-diCl analog was isolated as a by-product during the synthesis of the 6,7-isomer.

Example 371

{[(5-chloro(2-thienyl))sulfonyl]amino}-N-[4-(6-methoxy-1-oxo(2-2-hydroisoquinolyl))-phenyl]carboxamide. ES-MS (M+H)+=490, 492 (Cl).

Example 372

{[(5-chloro(2-thienyl))sulfonyl]amino}-N-[4-(6-chloro-1-oxo(2-2-hydroisoquinolyl))-phenyl]carboxamide. ES-MS (M+H)+=494, 496, 498 (2Cl).

Example 374

{[(5-chloro(2-thienyl))sulfonyl]amino}-N-[4-(7-chloro-1-oxo(2-2-hydroisoquinolyl))phenyl]-carboxamide. ES-MS (M+H)+=494, 496, 498 (2Cl).

Example 376

{([[(5-chloro(2-thienyl))sulfonyl]amino}-N-[4-(7-fluoro-1-oxo(2-2-hydroisoquinolyl))phenyl]-carboxamide. ES-MS (M+H)+=478.0 (Cl).

Example 379

{[(5-chloro(2-thienyl))sulfonyl]amino}-N-[4-(7-trifluoromethyl-1-oxo(2-2-hydroisoquinolyl))-phenyl]carboxamide. ES-MS (M+H)+=528, 530 (Cl).

Example 380

{[(5-chloro(2-thienyl))sulfonyl]amino}-N-[4-(7-methoxy-1-oxo(2-2-hydroisoquinolyl))-phenyl]carboxamide. ES-MS (M+H)+=490, 492 (Cl).

Example 1122

{[(5-chloro(2-thienyl))sulfonyl]amino}-N-[4-(7-methyl-1-oxo(2-2-hydroisoquinolyl))phenyl]-carboxamide. ES-MS (M+H)+=473.9, 475.9 (Cl).

Example 1123

{[(5-chloro(2-thienyl))sulfonyl]amino}-N-[4-(6-methyl-1-oxo(2-2-hydroisoquinolyl))-phenyl]carboxamide. ES-MS (M+H)+=474, 476 (Cl).

Example 1124

{[(5-chloro(2-thienyl))sulfonyl]amino}-N-[4-(6-fluoro-1-oxo(2-2-hydroisoquinolyl))-phenyl]carboxamide. ES-MS (M+H)+=477.9 (Cl).

Example 1125

{[(5-chloro(2-thienyl))sulfonyl]amino}-N-[4-(6-bromo-1-oxo(2-2-hydroisoquinolyl))-phenyl]carboxamide. ES-MS (M+H)+=537.9 (Cl).

Example 1126

{[(5-chloro(2-thienyl))sulfonyl]amino}-N-[4-(6-trifluoromethyl-1-oxo(2-2-hydroisoquinolyl))-phenyl]carboxamide. ES-MS (M+H)+=528, 530 (Cl).

Example 1127

N-[4-(6,7-dichloro-1-oxo(2-2-hydroisoquinolyl))phenyl]{[(5-chloro(2-thienyl)sulfonyl]-amino}carboxamide. ES-MS (M+H)+=528, 530, 532 (3Cl).

Example 1128

N-[4-(7,8-dichloro-1-oxo(2-2-hydroisoquinolyl))phenyl]{[(5-chloro(2-thienyl))sulfonyl]-amino}carboxamide. ES-MS (M+H)+=528, 530, 532 (3Cl).

Example 1129

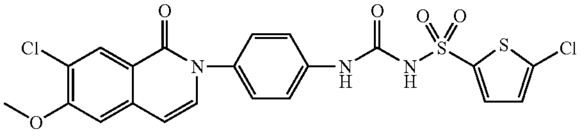

Preparation of {[(5-chloro(2-thienyl))sulfonyl]amino}-N-[4-(7-chloro-6-methoxy-1-oxo(2-2-hydroisoquinolyl))phenyl]carboxamide A. Synthesis of 4-chloro-3-methoxytoluene To a solution of 2-chloro-5-methylphenol (10.7 g, 75 mmol) in DMF (40 mL) was added potassium carbonate (26 g, 188 mmol) followed by neat methyl iodide (4.9 mL, 79 mmol). The reaction mixture was stirred at room temp for 6 hr, extracted with EtOAc, washed with water and brine, dried and concentrated in vacuo to give 4-chloro-3-methoxytoluene (10.8 g, 92%). $^1$H-NMR (DMSO-$d_6$): δ 2.26 (s, 3H), 3.79 (s, 3H), 6.71-6.73 (dd, 1H), 6.94 (s, 1H), 7.22-7.24 (d, 1H).

B. Synthesis of 4-chloro-3-methoxybenzoic acid

To the crude toluene (7.8 g, 50 mmol) was added a solution $KMnO_4$ (19.8 g, 125 mmol) in water (300 mL). The reaction mixture was stirred vigorously at reflux for 17 hr and filtered warm through Celite, washing the cake with 200 mL hot water. The clear filtrate was washed with ethyl ether (2×150 mL), acidified with conc. HCl (9 mL) and filtered to give pure white solid 4-chloro-3-methoxybenzoic acid (5.36 g, 58%). ES-MS (M+H)+=187.

C. Synthesis of (4-chloro-3-methoxyphenyl)methan-1-ol

To a solution of 4-chloro-3-methoxybenzoic acid (4.88 g, 26.2 mmol) in THF (50 mL) was added borane-THF complex (52 mL 1M solution in THF, 52 mmol) via addition funnel over 10 min. The reaction mixture was refluxed for 2 hr, cooled, extracted with EtOAc, washed with water, 5% $Na_2CO_3$ and brine, dried and concentrated in vacuo to give (4-chloro-3-methoxyphenyl)methan-1-ol (4.5 g, 99%). ES-MS (M+H−$H_2O$)+=155, 157 (Cl).

D. Synthesis of 4-chloro-3-methoxybenzaldehyde

To a solution of (4-chloro-3-methoxyphenyl)methan-1-ol (5.08 g, 29.4 mmol) in benzene (120 mL) was added $MnO_2$ (5.65 g, 65 mmol). The reaction mixture was refluxed for 17 hr, chilled, and filtered through Celite, washing the cake with $CH_2Cl_2$ (300 mL). The filtrate was concentrated in vacuo to give 4-chloro-3-methoxybenzaldehyde (4.5 g, 89%).

E. Synthesis of {[(5-chloro(2-thienyl))sulfonyl]amino}-N-[4-(7-chloro-6-methoxy-1-oxo(2-2-hydroisoquinolyl))phenyl]carboxamide {[(5-chloro(2-thienyl))sulfonyl]amino}-N-[4-(7-chloro-6-methoxy-1-oxo(2-2-hydroisoquinolyl))phenyl]carboxamide was synthesized from the benzaldehyde using the general procedure outlined in Scheme 6, steps A-E. ES-MS (M+H)+=489, 491 (Cl).

Example 1130

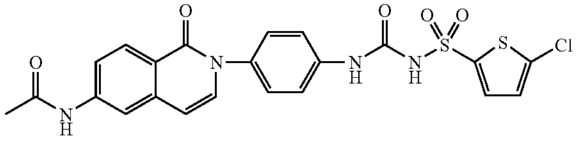

Preparation of N-{2-[4({[(5-chloro(2-thienyl))sulfonyl]amino}carbonylamino)phenyl]-1-oxo-6-2-hydroisoquinolyl}acetamide A. Synthesis of N-(3-formylphenyl)acetamide To a chilled suspension of 3-aminobenzyl alcohol (9.24 g, 75 mmol) in THF (50 mL) was added neat acetic anhydride (8.1 mL, 86 mmol). The reaction mixture was stirred cold for 1 hr, diluted with EtOAc, washed with aq. NaOH and brine, and concentrated in vacuo to give N-[3-(hydroxymethyl)phenyl]acetamide (10.5 g, 85%).

A mixture of N-[3-(hydroxymethyl)phenyl]acetamide (10 g, 60.6 mmol) and $MnO_2$ (7.8 g, 90 mmol) in toluene (250 mL) was refluxed for 29 hr, with addition of more $MnO_2$ (0.7 g, 9 mmol) at 24 hr. The reaction was cooled, filtered through Celite and concentrated in vacuo to give N-(3-formylphenyl)acetamide (9.2 g, 75%). ES-MS (M+H)+=164.

B. Synthesis of N-{2-[4-({[(5-chloro(2-thienyl))sulfonyl]amino}carbonylamino)phenyl]-1-oxo-6-2-hydroisoquinolyl}acetamide N-{2-[4-({[(5-chloro(2-thienyl))sulfonyl]amino}carbonylamino)phenyl]-1-oxo-6-2-hydroisoquinolyl}acetamide was synthesized from N-(3-formylphenyl)acetamide using the general procedure outlined in Scheme 6, steps A-E. ES-MS (M+H)+=517, 519 (Cl).

Example 1131

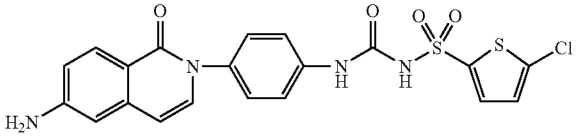

Preparation of N-[4-(6-amino-1-oxo(2-2-hydroisoquinolyl))phenyl]{[(5-chloro(2-thienyl))sulfonyl]amino}-carboxamide: This compound was synthesized by treating N-{2-[4-({[(5-chloro(2-thienyl))sulfonyl]amino}carbonylamino)phenyl]-1-oxo-6-2-hydroisoquinolyl}acetamide with 30 equiv. NaOMe in MeOH and refluxing overnight. It was also synthesized by treatment with neat hydrazine hydrate at 70° C. ES-MS (M+H)+=475, 477 (Cl).

Example 373

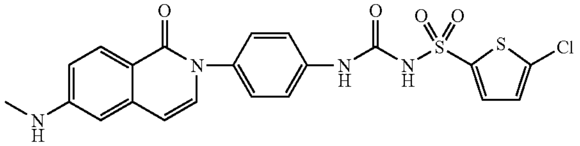

Preparation of {[(5-chloro(2-thienyl))sulfonyl] amino}-N-{4-[6-(methylamino)-1-oxo(2-2-hydroisoquinolyl)]phenyl}carboxamide A. Synthesis of N-methyl-N-[2-(4-nitrophenyl)-1-oxo(6-2-hydroisoquinolyl)]acetamide To a solution of crude N-[2-(4-nitrophenyl)-1-oxo-6-2-hydroisoquinolyl]acetamide (0.26 g, 0.8 mmol) in DMF (2 mL) was added cesium carbonate (0.645 g, 2 mmol) followed by neat methyl iodide (75 μL, 1.2 mmol). The reaction mixture was stirred at room temp for 17 hr, precipitated with addition of water and filtered to give N-methyl-N-[2-(4-nitrophenyl)-1-oxo(6-2-hydroisoquinolyl)]acetamide (75 mg, 25%). ES-MS (M+H)+=338.

B. Synthesis of N-{2-[4-({[(5-chloro(2-thienyl))sulfonyl]amino}carbonylamino)phenyl]-1-oxo(6-2-hydroisoquinolyl)}-N-methylacetamide The reduction and coupling steps were performed using the procedures outlined in Scheme 6, steps D and E. ES-MS (M+H)+=531, 533 (Cl).

C. Synthesis of {[(5-chloro(2-thienyl))sulfonyl] amino}-N-{4-[6-(methylamino)-1-oxo(2-2-hydroisoquinolyl)]phenyl}carboxamide To a solution of N-{2-[4-({[(5-chloro(2-thienyl))sulfonyl] amino}carbonylamino)phenyl]-1-oxo(6-2-hydroisoquinolyl)}-N-methylacetamide (35 mg, 0.072 mmol) in methanol (1.2 mL) was added 0.5 M NaOMe (0.44 mL, 0.22 mmol) in methanol. The reaction mixture was stirred at 60° C. overnight, acidified and HPLC purified to give {[(5-chloro(2-thienyl))sulfonyl]amino}-N-{4-[6-(methylamino)-1-oxo(2-2-hydroisoquinolyl)]phenyl}carboxamide (22 mg, 63%). ES-MS (M+H)+=489, 491 (Cl).

Examples 383 and 1132-1135

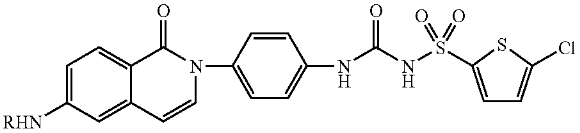

The compounds above where, for example, R=Et, n-Pr, $CH_2$-c-Pr, $CH_2CH_2F$ and benzyl were synthesized using the procedure outlined in Example 373 for R=Me, varying the alkylating agent in step A.

Example 383

{[(5-chloro(2-thienyl))sulfonyl]amino}-N-{-[6-(ethylamino)-1-oxo(2-2-hydroisoquinolyl)]-phenyl}carboxamide. ES-MS (M+H)+=503, 505 (Cl).

Example 1132

{[(5-chloro(2-thienyl))sulfonyl]amino}-N-{4-[1-oxo-6-(propylamino)(2-2-hydroisoquinolyl)]-phenyl}carboxamide. ES-MS (M+H)+=517, 519 (Cl).

Example 1133

{[(5-chloro(2-thienyl))sulfonyl]amino}-N-(4-{6-[(cyclopropylmethyl)amino]-1-oxo(2-2-hydroisoquinolyl)}phenyl) carboxamide. ES-MS (M+H)+=529, 531 (Cl).

Example 1134

{[(5-chloro(2-thienyl))sulfonyl]amino}-N-(4-{6-[(2-fluoroethyl)amino]-1-oxo(2-2-hydroisoquinolyl)}phenyl) carboxamide. ES-MS (M+H)+=521, 523 (Cl).

Example 1135

{[(5-chloro(2-thienyl))sulfonyl]amino}-N-(4-{1-oxo-6-[benzylamino](2-2-hydroisoquinolyl)}-phenyl)carboxamide. ES-MS (M+H)+=565, 567 (Cl).

Example 1136

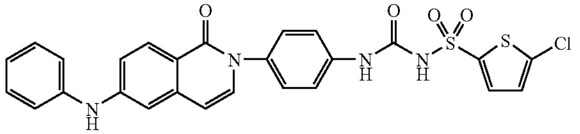

Preparation of {[(5-chloro(2-thienyl))sulfonyl] amino}-N-{4-[1-oxo-6-(phenylamino)(2-2-hydroisoquinolyl)]phenyl}carboxamide A. 2-(4-nitrophenyl)-6-(phenylamino)-2-hydroisoquinolin-1-one To a dry RBF under argon was added 6-bromo-2-(4-nitrophenyl)-2-hydroisoquinolin-1-one (66 mg, 0.191 mmol) (prepared as outlined in Example 1125), cesium carbonate (106 mg, 0.325 mmol), tris(dibenzylideneacetone) dipalladium(0) (3.5 mg, 0.076 mmol), 9,9-dimethyl-4,5-bis(diphenylphosphino) xanthene (12 mg, 0.0207 mmol) and neat aniline (0.026 mL, 0.285 mmol). To this flask was added dry dioxane (0.5 mL) and dry toluene (0.5 mL). The reaction was stirred at 80° C. for 5 hr, concentrated and chromatographed on silica gel to give pure 2-(4-nitrophenyl)-6-(phenylamino)-2-hydroisoquinolin-1-one (55 mg, 81%). ES-MS (M+H)+=358.

B. {[(5-chloro(2-thienyl))sulfonyl]amino}-N-{4-[1-oxo-6-(phenylamino)(2-2-hydroisoquinolyl)]phenyl}carboxamide Preparation of the final target was accomplished using the general procedure outlined in Scheme 6, steps D-E, to give the above named sulfonyl urea. ES-MS (M+H)+=551, 553 (Cl).

Example 1137

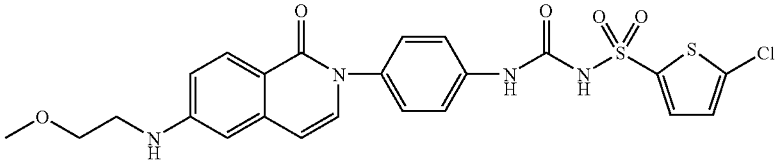

Preparation of {[(5-chloro(2-thienyl))sulfonyl]amino}-N-(4-{6-[(2-methoxyethyl)amino]-1-oxo(2-2-hydroisoquinolyl)}phenyl)carboxamide was accomplished using a similar Buchwald procedure as shown in Example 1136. ES-MS (M+H)+=533.0 (Cl).

Example 1138

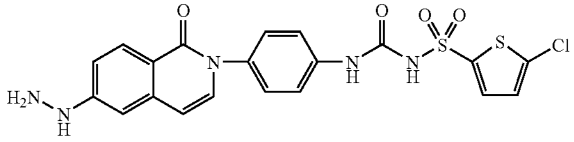

Preparation of {[(5-chloro(2-thienyl))sulfonyl] amino}-N-[4-(6-hydrazino-1-oxo(2-2-hydroisoquinolyl))phenyl]carboxamide A 5 mg (0.011 mmol) sample of {[(5-chloro(2-thienyl)) sulfonyl]amino}-N-[4-(6-fluoro-1-oxo(2-2-hydroisoquinolyl))-phenyl]carboxamide was dissolved in 50 μL of neat anhydrous hydrazine and stirred for 18 h. The solution was diluted with 250 uL of water and lyophilized to give 3.8 mg (74%) of the desired material. ES-MS (M+H)+=490.0 (Cl).

Example 1139

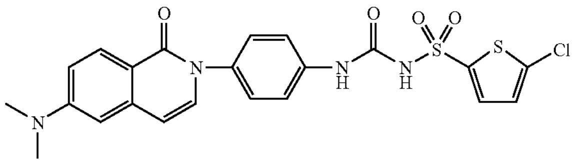

Preparation of N-{4-[6-(dimethylamino)-1-oxo(2-2-hydroisoquinolyl)]phenyl}{[(5-chloro(2-thienyl))sulfonyl] amino}carboxamide: To a suspension of {[(5-chloro(2-thienyl))sulfonyl]amino}-N-{4-[6-(methylamino)-1-oxo(2-2-hydroisoquinolyl)]phenyl}carboxamide (17 mg, 0.035 mmol) (prepared in Example 373) in glacial acetic acid (0.7 mL) was added formaldehyde (12 μL, 0.15 mmol) followed by sodium triacetoxyborohydride (14 mg, 0.067 mmol). The reaction mixture was stirred at 45° C. for 2 hr. HPLC purification yielded the final product (7 mg, 40%). ES-MS (M+H)+= 503, 505 (Cl).

Example 1140

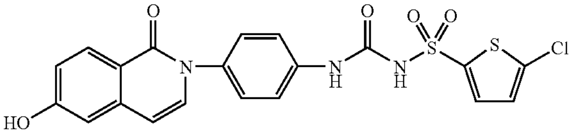

Preparation of {[(5-chloro(2-thienyl))sulfonyl] amino}-N-[4-(6-hydroxy-1-oxo(2-2-hydroisoquinolyl))phenyl]carboxamide A. Synthesis of 6-hydroxy-2-(4-nitrophenyl)-2-hydroisoquinolin-1-one To a solution of 6-methoxy-2-(4-nitrophenyl)-2-hydroisoquinolin-1-one (100 mg, 0.338 mmol) (prepared by the general procedure outline in Scheme 6) in $CH_2Cl_2$ (3 mL) was added a 1M $BBr_3$ solution in $CH_2Cl_2$ (1.35 mL, 1.35 mmol). The solution was refluxed for 18 h, the solvent was removed in vacuo, the residue was triturated with water, and the resulting greenish solid was collected and dried to give 6-hydroxy-2-(4-nitrophenyl)-2-hydroisoquinolin-1-one (89 mg, 93%).

B. Synthesis of 2-(4-aminophenyl)-6-hydroxy-2-hydroisoquinolin-1-one 6-hydroxy-2-(4-nitrophenyl)-2-hydroisoquinolin-1-one was reduced according to the general procedure in Scheme 6 to give the corresponding aniline in 27% yield. ES-MS (M+H)+=252.9.

C. Synthesis of {[(5-chloro(2-thienyl))sulfonyl] amino}-N-[4-(6-hydroxy-1-oxo(2-2-hydroisoquinolyl))phenyl]carboxamide 2-(4-aminophenyl)-6-hydroxy-2-hydroisoquinolin-1-one was coupled according to the general procedure outlined in Scheme 6 to give the above named sulfonyl urea. ES-MS (M+H)+=476 (Cl).

Example 1141

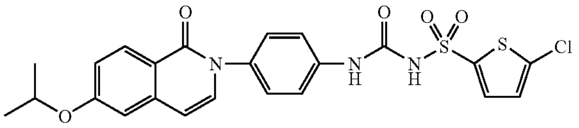

Preparation of {[(5-chloro(2-thienyl))sulfonyl]amino}-N-{4-[6-(methylethoxy)-1-oxo(2-2-hydroisoquinolyl)]phenyl}carboxamide A. Synthesis of 6-(methylethoxy)-2-(4-nitrophenyl)-2-hydroisoquinolin-1-one To a solution of 6-hydroxy-2-(4-nitrophenyl)-2-hydroisoquinolin-1-one (50 mg, 0.177 mmol) in DMF (0.38 mL) was added 2-bromopropane (0.03 mL) and cesium carbonate (86 mg, 0.267 mmol). After heating at 60° C. for 18 h, water was added and the solution stirred and cooled to 0° C. The precipitate was collected and dried to give 6-(methylethoxy)-2-(4-nitrophenyl)-2-hydroisoquinolin-1-one (34 mg, 59%).

B. Synthesis of 2-(4-aminophenyl)-6-(methylethoxy)-2-hydroisoquinolin-1-one

This material was reduced according to the general procedure in Scheme 6 to give the corresponding aniline in 91% yield. ES-MS (M+H)+=295.

C. Synthesis of {[(5-chloro(2-thienyl))sulfonyl]amino}-N-{4-[6-(methylethoxy)-1-oxo(2-2-hydroisoquinolyl)]phenyl}carboxamide 2-(4-aminophenyl)-6-(methylethoxy)-2-hydroisoquinolin-1-one was coupled according to the general procedure outlined in Scheme 6 to give the above named sulfonyl urea. ES-MS (M+H)+=518 (Cl); ES-MS (M−H)+=516.

Example 1142

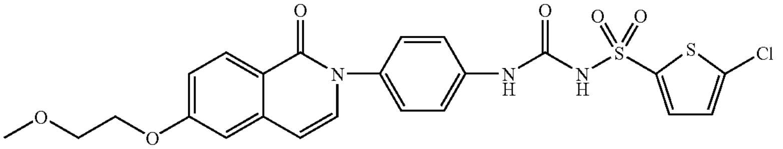

Preparation of {[(5-chloro(2-thienyl))sulfonyl]amino}-N-{4-[6-(2-methoxyethoxy)-1-oxo(2-2-hydroisoquinolyl)]phenyl}carboxamide was accomplished according to the procedure of Example 1141 to give the desired sulfonyl urea. ES-MS (M+H)+=534.1 (Cl).

Example 1143

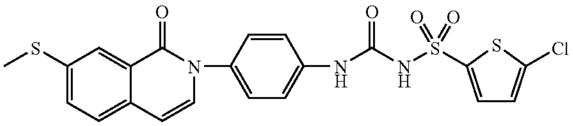

Preparation of {[(5-chloro(2-thienyl))sulfonyl]amino}-N-[4-(7-methylthio-1-oxo(2-2-hydroisoquinolyl))phenyl]carboxamide was accomplished according to the procedure of Example 1145, using {[(5-chloro(2-thienyl))sulfonyl]amino}-N-[4-(7-fluoro-1-oxo(2-2-hydroisoquinolyl))phenyl]-carboxamide as starting material, to give the desire sulfonyl urea. ES-MS (M+H)+=506 (Cl).

Scheme 7:
General Synthetic Scheme for the Preparation of Quinazolinones:

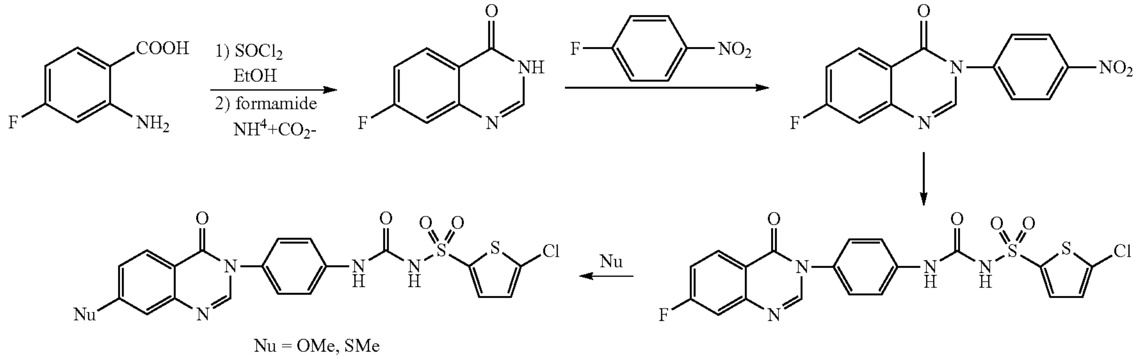

Example 1144

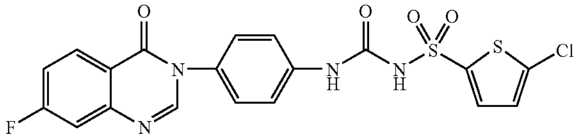

Preparation of {[(5-chloro(2-thienyl))sulfonyl]amino}-N-[4-(7-fluoro-4-oxo(3-hydroquinazolin-3-yl))phenyl]carboxamide A. Synthesis of ethyl 2-amino-4-fluorobenzoate To a chilled solution of 2-amino-4-fluorobenzoic acid (1.57 g, 10.1 mmol) in absolute ethanol (20 mL) was added neat thionyl chloride (4.4 mL, 60 mmol). The reaction mixture was refluxed for 4 days total, with addition of more $SOCl_2$ (8 mL, 110 mmol), then concentrated, diluted with EtOAc, washed with 2N NaOH, dried and concentrated in vacuo to give ethyl 2-amino-4-fluorobenzoate (1.73 g, 94%).

B. Synthesis of 7-fluoro-3-hydroquinazolin-4-one

To a suspension of ethyl 2-amino-4-fluorobenzoate (1.73 g, 9.45 mmol) in formamide (8 mL) was added ammonium formate (0.9 g, 14 mmol). The reaction mixture was stirred at 140° C. for 24 hr, with additional ammonium formate (0.92 g, 15 mmol) at 6 hr. The reaction was dilute with EtOAc, washed with water, back-extracted with EtOAc, dried and concentrated in vacuo to give 7-fluoro-3-hydroquinazolin-4-one (2.82 g) which contains some formamide. ES-MS (M+H)+=165.

C. Synthesis of {[(5-chloro(2-thienyl))sulfonyl]amino}-N-[4-(7-fluoro-4-oxo(3-hydroquinazolin-3-yl))phenyl]carboxamide {[(5-chloro(2-thienyl))sulfonyl]amino}-N-[4-(7-fluoro-4-oxo(3-hydroquinazolin-3-yl))phenyl]carboxamide was synthesized from the quinazolinone using the procedures for alkylation, reduction and coupling outlined in Scheme 6, steps C, D and E. The alkylation product was chromatographed on silica gel to remove formamide carried over from the previous step to give pure intermediate in 42% yield. The reduction step was performed in EtOAc instead of EtOH. The coupling proceeded in 50% yield. ES-MS (M+H)+=479, 481 (Cl).

Example 507

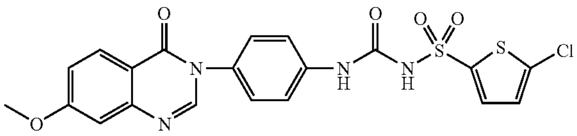

Preparation of {[(5-chloro(2-thienyl))sulfonyl]amino}-N-[4-(7-methoxy-4-oxo(3-hydroquinazolin-3-yl))phenyl]carboxamide: To a solution of {[(5-chloro(2-thienyl))sulfonyl]amino}-N-[4-(7-fluoro-4-oxo(3-hydro-quinazolin-3-yl))phenyl]carboxamide (20 mg, 0.042 mmol) in methanol (0.75 mL) and DMF (0.3 mL) was added 0.5 M NaOMe in MeOH (0.42 mL, 0.21 mmol). The reaction mixture was stirred at 70° C. for 24 hr, acidified and HPLC purified to give pure {[(5-chloro(2-thienyl))sulfonyl]amino}-N-[4-(7-methoxy-4-oxo(3-hydroquinazolin-3-yl))phenyl]carboxamide (7 mg, 33%). ES-MS (M+H)+=491, 493 (Cl).

Example 1145

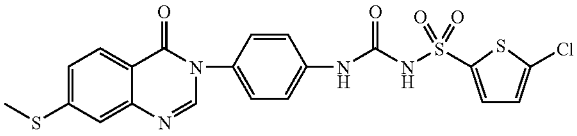

Preparation of {[(5-chloro(2-thienyl))sulfonyl]amino}-N-[4-(7-methylthio-4-oxo(3-hydroquinazolin-3-yl))phenyl]carboxamide: To a solution of {[(5-chloro(2-thienyl))sulfonyl]amino}-N-[4-(7-fluoro-4-oxo(3-hydro-quinazolin-3-yl))phenyl]carboxamide (20 mg, 0.042 mmol) in DMF (0.21 mL) was added NaSMe (7 mg, 0.1 mmol). The reaction mixture was stirred at room temp for 3 hr, acidified and HPLC purified to give pure {[(5-chloro(2-thienyl))sulfonyl]amino}-N-[4-(7-methylthio-4-oxo(3-hydroquinazolin-3-yl))phenyl]carboxamide (17 mg, 80%). ES-MS (M+H)+=507, 509 (Cl).

Scheme 8:
General synthetic system for preparing quinazolinedione-containing sulfonyl ureas

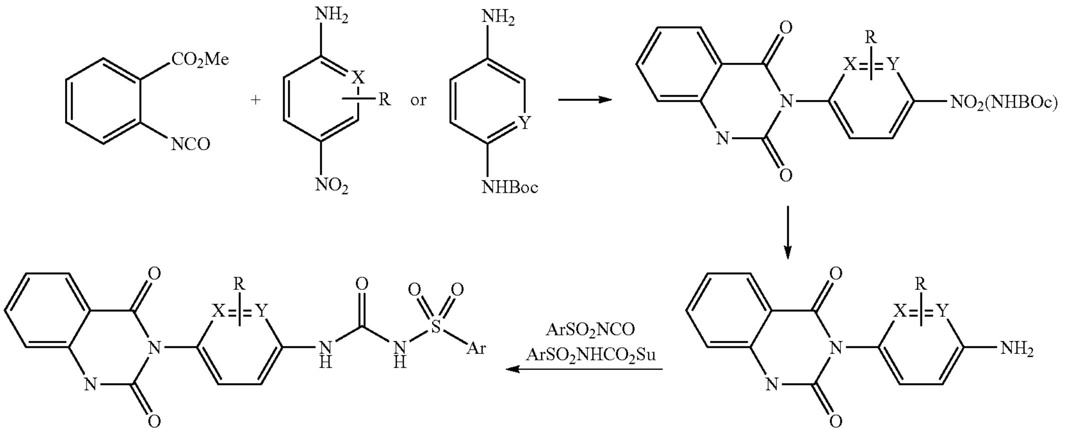

R = Br: Ar = 5-Cl thiophene (1)
X = N: Ar = 5-Cl thiophene (1)
Y = N: Ar = 5-Cl thiophene, Ph (2)
R = H: Ar = Ph, subsituted Ph, substituted thiophenes, etc. (30)

Example 1146

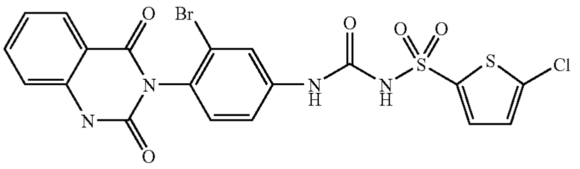

Preparation of N-[4-(2,4-dioxo(1,3-dihydroquinazolin-3-yl))-3-bromophenyl]{[(5-chloro(2-thienyl))sulfonyl]amino}carboxamide A. Synthesis of 3-(2-bromo-4-nitrophenyl)-1,3-dihydroquinazoline-2,4-dione To a solution of methyl 2-isocyanatobenzoate (0.266 g, 1.5 mmol) and 2-bromo-4-nitroaniline (0.325 g, 1.5 mmol) in DMF (2 mL) was added DIEA (0.79 mL). The reaction mixture was stirred at room temp for 24 hr, with addition of DBU (0.22 mL) at 17 hr. The reaction mixture was extracted with EtOAc, washed with 1 N HCl and brine, dried and concentrated to give crude product, which was chromatographed on silica gel with 10% $EtOAc/CH_2Cl_2$ to give 3-(2-bromo-4-nitrophenyl)-1,3-dihydroquinazoline-2,4-dione (0.24 g, 44%). ES-MS (M+H)+=362, 364 (Br).

B. Synthesis of 3-(4-amino-2-bromophenyl)-1,3-dihydroquinazoline-2,4-dione

A suspension of 3-(2-bromo-4-nitrophenyl)-1,3-dihydroquinazoline-2,4-dione (0.18 g, 0.5 mmol) and tin(II) chloride dihydrate (0.45 g, 2.0 mmol) in ethyl acetate (5 mL) was heated at 70° C. for 4 hr. The reaction mixture was then cooled, mixed with Celite, made basic with 4N NaOH (3 mL), filtered through Celite, and concentrated in vacuo to give the desired compound (0.155 g, 94%). ES-MS (M+H)+=332, 334 (Br).

C. General Procedure for Coupling Anilines with Aryl Sulfonamides to Form Sulfonyl Ureas A solution of the aryl sulfonamide (0.15 mmol) and DSC (0.18 mmol) in $CH_2Cl_2$ (1 mL) and DBU (45 μL, 0.3 mmol) was stirred at room temp for 16 hr. To this mixture was added the aniline intermediate (0.15 mmol) and $CH_3CN$ (1 mL) and DBU (23 μL, 0.15 mmol) (if aniline is TFA salt). The reaction was heated at 60° C. for 17 hr, acidified and HPLC purified to give sulfonyl urea product in typical yields between 25-70%.

Preparation of N-[4-(2,4-dioxo(1,3-dihydroquinazolin-3-yl))-3-bromophenyl]{[(5-chloro(2-thienyl))sulfonyl]amino}carboxamide was achieved in 25% yield. ES-MS (M+H)+=556.9. 558.9 (Br, Cl).

Example 302

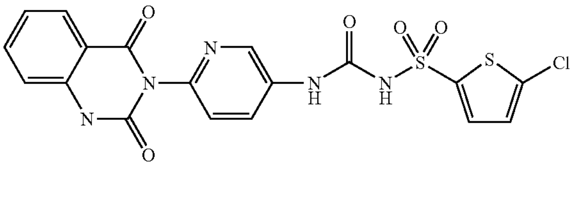

Preparation of N-[6-(2,4-dioxo(1,3-dihydroquinazolin-3-yl))(3-pyridyl)]{[(5-chloro(2-thienyl))sulfonyl]amino}carboxamide This compound was prepared by first following step A in Example 1146, reacting 2-amino-5-nitropyridine with methyl 2-isocyanatobenzoate. The nitro group was reduced under 1 atm $H_2$, 10% Pd/C, 1 eq. HCl, MeOH conditions for 6 hr. After filtration and concentration, the aniline was coupled with 5-chlorothiophene-2-sulfonamide using the conditions outlined in step C in Example 1146 to give N-[6-(2,4-dioxo(1,3-dihydroquinazolin-3-yl))(3-pyridyl)]{[(5-chloro(2-thienyl))sulfonyl]amino}carboxamide (47 mg, 33%). ES-MS (M+H)+=478, 480 (Cl).

Example 1147

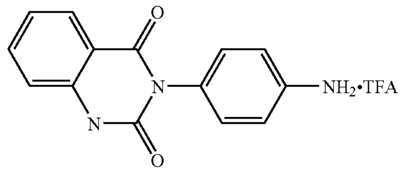

Preparation of 3-(4-aminophenyl)-1,3-dihydroquinazoline-2,4-dione trifluoroacetate salt A. Synthesis of (tert-butoxy)-N-[4-(2,4-dioxo(1,3-dihydroquinazolin-3-yl))phenyl]carboxamide To a solution of methyl 2-isocyanatobenzoate (0.97 g, 5.5 mmol) and Boc 1,4-phenylenediamine (1.04 g, 5 mmol) in THF (15 mL) was added DIEA (0.87 mL, 5 mmol) and DBU (0.75 mL, 5 mmol). The reaction mixture stirred at room temp for 5 hr, the off-white solid filtered and washed with ethyl ether to give desired compound (1.49 g, 85%). ES-MS (M+Na)+=376.1, (M−tBu+H)+=298.0.

B. Synthesis of 3-(4-aminophenyl)-1,3-dihydroquinazoline-2,4-dione trifluoroacetate salt To a chilled suspension of (tert-butoxy)-N-[4-(2,4-dioxo(1,3-dihydroquinazolin-3-yl))phenyl]carboxamide (0.35 g, 1 mmol) in $CH_2Cl_2$ (2 mL) was added neat TFA (2 mL). The resulting solution was stirred cold for 1 hr, concentrated in vacuo, azeotroped with heptane and dried to give desired compound (0.376 g, 99%) as the mono TFA salt. ES-MS (M+H)+=254.

Synthesis of Various Aryl Sulfonylurea Analogs

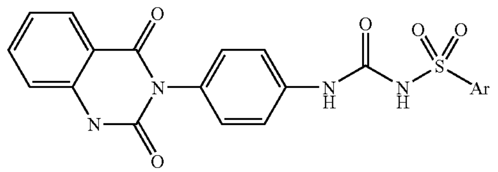

The sulfonyl urea targets above were prepared using the procedure outlined in Example 1146 Step C, reacting the aniline from Example 1146 with the following 13 commercially available sulfonamides: 5-nitrothiophene-2-sulfonamide; thiophene-2-sulfonamide; 5-chloro-3-methylbenzothiophene-2-sulfonamide; 3,5-dimethylisoxazole-4-sulfonamide; N-(3-methyl-5-sulfamoyl)-3H(1,3,4)thiadiazol-2-ylidene)acetamide; 2,4-dimethyl-1,3-thiazole-5-sulfonamide; 3-bromo-5-chlorothiophene-2-sulfonamide; azetazolamide; 5-isoxazol-3-ylthiophene-2-sulfonamide; 2-chlorobenzenesulfonamide; 3-chlorobenzenesulfonamide; 4-methoxybenzenesulfonamide; 4-(trifluoromethyl)benzene-sulfonamide.

Example 1148

N-[4-(2,4-dioxo(1,3-dihydroquinazolin-3-yl))phenyl]{[(5-nitro(2-thienyl))sulfonyl]amino}carboxamide. ES-MS (M+H)+=488.

Example 1149

N-[4-(2,4-dioxo(1,3-dihydroquinazolin-3-yl))phenyl][(2-thienylsulfonyl)amino]carboxamide. ES-MS (M+H)+=443.0.

Example 1150

N-[4-(2,4-dioxo(1,3-dihydroquinazolin-3-yl))phenyl]{[(5-chloro-3-methyl-benzo[b]thiophen-2-yl)sulfonyl]amino}carboxamide. ES-MS (M+H)+=541, 543 (Cl).

Example 1151

{[(3,5-dimethylisoxazol-4-yl)sulfonyl]amino}-N-[4-(2,4-dioxo(1,3-dihydroquinazolin-3-yl))phenyl]carboxamide. ES-MS (M+H)+=456.

Example 1152

({[2-(1-aza-2-oxopropylidene)-3-methyl(1,3,4-thiadiazolin-5-yl)]sulfonyl}amino)-N-[4-(2,4-dioxo(1,3-dihydroquinazolin-3-yl))phenyl]carboxamide. ES-MS (M+H)+=516.

Example 1153

{[(2,4-dimethyl(1,3-thiazol-5-yl))sulfonyl]amino}-N-[4-(2,4-dioxo(1,3-dihydroquinazolin-3-yl))phenyl]carboxamide. ES-MS (M+H)+=472.

Example 1154

N-[4-(2,4-dioxo(1,3-dihydroquinazolin-3-yl))phenyl]{[(3-bromo-5-chloro(2-thienyl))-sulfonyl]amino}carboxamide. ES-MS (M+H)+=554.8, 556.9, 558.8 (BrCl).

Example 1155

N-{5-[({N-[4-(2,4-dioxo-1,3-dihydroquinazolin-3-yl)phenyl]carbamoyl}amino)sulfonyl]-1,3,4-thiadiazol-2-yl}acetamide. ES-MS (M+H)+=502.

Example 1156

N-[4-(2,4-dioxo(1,3-dihydroquinazolin-3-yl))phenyl]{[(5-isoxazol-3-yl(2-thienyl))-sulfonyl]amino}carboxamide. ES-MS (M+H)+=510.

Example 1157

N-[4-(2,4-dioxo(1,3-dihydroquinazolin-3-yl))phenyl]{[(2-chlorophenyl)sulfonyl]amino}-carboxamide. ES-MS (M+H)+=471, 473 (Cl).

Example 1158

N-[4-(2,4-dioxo(1,3-dihydroquinazolin-3-yl))phenyl]{[(3-chlorophenyl)sulfonyl]-amino}carboxamide. ES-MS (M+H)+=471, 473 (Cl).

Example 1159

N-[4-(2,4-dioxo(1,3-dihydroquinazolin-3-yl))phenyl]{[(4-methoxyphenyl)sulfonyl]amino}-carboxamide. ES-MS (M+H)+=467.

Example 1160

N-[4-(2,4-dioxo(1,3-dihydroquinazolin-3-yl))phenyl]({[4-(trifluoromethyl)phenyl]-sulfonyl}amino)carboxamide. ES-MS (M+H)+=505.

An additional 6 sulfonamides were prepared from the following commercially available sulfonyl chlorides, and were subsequently coupled with the aniline using the procedure in Example 1146 step C: 2-acetamido-4-methyl-5-thiazole-sulfonyl chloride; 4-fluorobenzenesulfonyl chloride; 5-(pyrid-2-yl)thiophene-2-sulfonyl chloride; 3,4-dichlorobenzenesulfonyl chloride; 2-(trifluoromethyl)benzenesulfonyl chloride; 3-(trifluoromethyl)benzenesulfonyl chloride.

Example 1161

N-{5-[({N-[4-(2,4-dioxo(1,3-dihydroquinazolin-3-yl))phenyl]carbamoyl}amino)sulfonyl]-4-methyl-1,3-thiazol-2-yl}acetamide. ES-MS (M+H)+=515.

Example 1162

N-[4-(2,4-dioxo(1,3-dihydroquinazolin-3-yl))phenyl]{[(4-fluorophenyl)sulfonyl]amino}-carboxamide. ES-MS (M+H)+=455.1.

Example 1163

N-[4-(2,4-dioxo(1,3-dihydroquinazolin-3-yl))phenyl]{[(5-(2-pyridyl)(2-thienyl))sulfonyl]-amino}carboxamide. ES-MS (M+H)+=520.

Example 1164

{[(3,4-dichlorophenyl)sulfonyl]amino}-N-[4-(2,4-dioxo(1,3-dihydroquinazolin-3-yl))phenyl]carboxamide. ES-MS (M+H)+=505, 507 (2Cl).

Example 1165

N-[4-(2,4-dioxo(1,3-dihydroquinazolin-3-yl))phenyl]({[2-(trifluoromethyl)phenyl]sulfonyl}-amino)carboxamide. ES-MS (M+H)+=505.

Example 1166

N-[4-(2,4-dioxo(1,3-dihydroquinazolin-3-yl))phenyl]({[3-(trifluoromethyl)phenyl]-sulfonyl}amino)carboxamide. ES-MS (M+H)+=505.

Example 1167

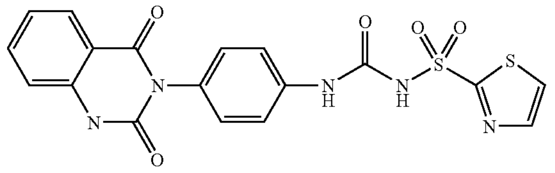

Preparation of N-[4-(2,4-dioxo(1,3-dihydroquinazolin-3-yl))phenyl][(1,3-thiazol-2-ylsulfonyl)amino]carboxamide A. Synthesis of (tert-butyl)(1,3-thiazol-2-ylsulfonyl)amine To a suspension of 2-mercaptothiazole (0.16 g, 1.37 mmol) in $CH_2Cl_2$ (14 mL) was added water (7 mL) followed by N-chlorosuccinimide (0.75 g, 5.6 mmol). The reaction mixture was stirred vigorously for 1.5 hr, diluted with $CH_2Cl_2$, washed with sat. $NaHCO_3$, water and brine, dried and concentrated in vacuo to give the crude sulfonyl chloride (0.25 g). A solution of the sulfonyl chloride and t-butylamine (0.75 mL, 7.1 mmol) in THF (2.5 mL) was stirred at room temp for 3 hr. The reaction was diluted with EtOAc, washed with 1N HCl, water and brine, dried and concentrated in vacuo to give desired compound (0.16 g, 53%).

B. Synthesis of 1,3-thiazole-2-sulfonamide

To a solution of (tert-butyl)(1,3-thiazol-2-ylsulfonyl)amine (0.22 g, 1.0 mmol) in 1,2-dichloroethane (10 mL) was added methanesulfonic acid (0.26 mL, 4 mmol). The reaction mixture was heated at 80° C. for 9 hr, concentrated in vacuo and chromatographed to give pure sulfonamide (0.14 g, 88%). ES-MS (M+H)+=164.9.

C. Synthesis of N-[4-(2,4-dioxo(1,3-dihydroquinazolin-3-yl))phenyl][(1,3-thiazol-2-ylsulfonyl)amino]carboxamide The sulfonyl urea was prepared by coupling the aniline from Example 1147 with 1,3-thiazole-2-sulfonamide using the procedure outlined in Example 1146 step C. ES-MS (M+H)+=444.0.

Example 1168

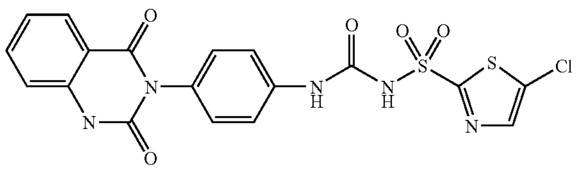

Preparation of N-[4-(2,4-dioxo(1,3-dihydroquinazolin-3-yl))phenyl][(5-chloro-1,3-thiazol-2-ylsulfonyl)amino]carboxamide A. Synthesis of (tert-butyl)[(5-chloro(1,3-thiazol-2-yl))sulfonyl]amine To a solution of (tert-butyl)(1,3-thiazol-2-ylsulfonyl)amine (0.15 g, 0.7 mmol) in ethyl ether (3 mL) at −78° C. was added a 1.6M solution of n-butyllithium (0.875 mL, 1.4 mmol) in hexanes via syringe under argon. The reaction mixture was stirred at −78° C. for 1 hr, then neat benzenesulfonyl chloride (90 μL, 0.7 mmol) was added. The resulting suspension was stirred at room temp for 2 hr. The reaction was diluted with EtOAc, washed with water and brine, dried, concentrated in vacuo and chromatographed (15% EtOAc/hexane) to give pure desired compound (58 mg, 33%). ES-MS (M+Na)+=277, 279 (Cl), (M−tBu+H)+=199, 201 (Cl).

B. Synthesis of 5-chloro-1,3-thiazole-2-sulfonamide

To a solution of (tert-butyl)[(5-chloro(1,3-thiazol-2-yl))sulfonyl]amine (56 mg, 0.22 mmol) in 1,2-dichloroethane (2 mL) was added methanesulfonic acid (50 μL, 0.77 mol). The reaction mixture was heated at 80° C. for 3 hr, concentrated in vacuo and chromatographed (30% EtOAc/hexane) to give pure sulfonamide (42 mg, 96%). ES-MS (M+H)+=199 (Cl).

C. Synthesis of N-[4-(2,4-dioxo(1,3-dihydroquinazolin-3-yl))phenyl][(5-chloro-1,3-thiazol-2-ylsulfonyl)amino]carboxamide The sulfonyl urea was prepared by coupling the aniline from Example 1147 with 5-chloro-1,3-thiazole-2-sulfonamide using the procedure outlined in Example 1146 step C. ES-MS (M+H)+=478, 480 (Cl).

Example 1169

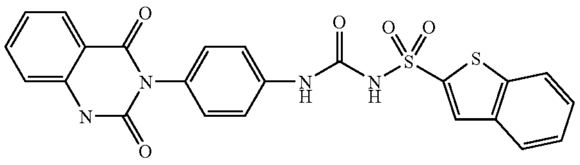

Preparation of [(benzo[b]thiophen-2-ylsulfonyl)amino]-N-[4-(2,4-dioxo(1,3-dihydroquinazolin-3-yl))phenyl]carboxamide A. Synthesis of benzo[b]thiophene-2-sulfonamide To a solution of benzothiophene (1.63 g, 12.1 mmol) in THF (8 mL) at 0° C. was added a 1.6M solution of n-butyllithium (8.5 mL, 13.6 mmol) in hexanes slowly over 10 min via syringe. The reaction was stirred cold for 10 min. THF (8 mL) was added and the entire reaction was transferred via cannula to a vessel containing sulfuryl chloride (2 mL, 25 mmol) in hexane (8 mL) at 0° C. The resulting yellow suspension was stirred at 0° C. for 1 hr and eventually became a clear yellow solution. This solution was concentrated to about 10 mL volume, diluted with acetone (12 mL) and added to a solution of ammonium hydroxide (8 mL) in acetone (25 mL). The reaction mixture was stirred at room temp for 2 hr, added to 200 mL of water on ice bath, acidified with conc. HCl (6 mL). A precipitate was filtered to obtain light yellow solid (1.78 g). This crude product was dissolved in 0.5 N KOH (100 mL) and washed with ethyl ether (50 mL). Upon acidification with conc. HCl (6 mL), the product was extracted into EtOAc (2×60 mL), washed with water and brine, dried and concentrated in vacuo to give pure sulfonamide (0.99 g, 39%).

B. Synthesis of [(benzo[b]thiophen-2-ylsulfonyl)amino]-N-[4-(2,4-dioxo(1,3-dihydroquinazolin-3-yl))phenyl]carboxamide The sulfonyl urea was prepared by coupling the aniline from Example 1147 with benzo[b]thiophene-2-sulfonamide using the procedure outlined in Example 1146 step C. ES-MS (M+H)+=493.

Example 1170

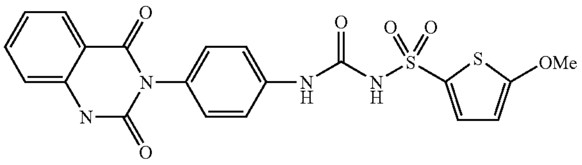

Preparation of N-[4-(2,4-dioxo(1,3-dihydroquinazolin-3-yl))phenyl]{[(5-methoxy(2-thienyl))sulfonyl]amino}carboxamide A. Synthesis of 5-methoxythiophene-2-sulfonamide To a solution of 2-methoxythiophene (1 mL, 10 mmol) in dry THF (36 mL) at −78° C. was added a 1.6 M solution of n-butyllithium (8 mL, 12.8 mmol) in hexanes over 10 min via syringe. The reaction was stirred at −78° C. for 2 hr. $SO_2$ (gas) was bubbled into the reaction mixture for about 10 min, then the reaction was allowed to come to room temp and stirred for 1 hr. A solution of sodium acetate (6.56 g, 80 mmol) and hydroxylamine-O-sulfonic acid (3.14 g, 27.8 mmol) in water (40 mL) was then added, and the reaction was stirred vigorously for 2 hr. The reaction was basified with 4N NaOH (15 mL), washed with ethyl ether, acidified with 6N HCl (15 ml), extracted with $CH_2Cl_2$, washed with water and brine, dried and concentrated in vacuo to give pure sulfonamide (1.01 g, 53%). ES-MS (M+H)+=194.

B. Synthesis of N-[4-(2,4-dioxo(1,3-dihydroquinazolin-3-yl))phenyl]{[(5-methoxy(2-thienyl))sulfonyl]amino}carboxamide.

The sulfonyl urea was prepared by coupling the aniline from Example 1147 with 5-methoxythiophene-2-sulfonamide using the procedure outlined in Example 1146 step C. ES-MS (M+H)+=473.

Example 1171

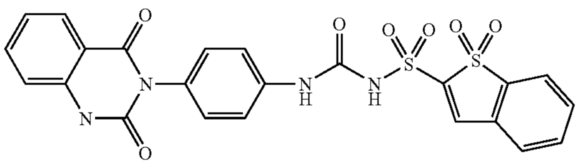

Preparation of N-[4-(2,4-dioxo(1,3-dihydroquinazolin-3-yl))phenyl]{[(1,1-dioxobenzo[d]thiol-2-yl)sulfonyl]amino}carboxamide A. Synthesis of N-[4-(1,3-dioxobenzo[c]azolidin-2-yl)naphthyl]{[(5-chloro(2-thienyl))sulfonyl]amino}carboxamide To a solution of the sulfonamide from Example 7 (0.213 g, 1 mmol) in $CH_2Cl_2$ (4 mL) was added m-chloroperbenzoic acid (0.49 g, 2.2 mmol). The reaction mixture was refluxed for 20 hr, diluted with EtOAc, washed with 5% $NaHCO_3$, 1N HCl and brine, dried and concentrated in vacuo to give sulfonamide (0.17 g, 71%). ES-MS (M+H)+=246.

B. Synthesis of N-[4-(2,4-dioxo(1,3-dihydroquinazolin-3-yl)phenyl]{[(1,1-dioxobenzo[d]thiol-2-yl)sulfonyl]amino}carboxamide The sulfonyl urea was prepared by coupling the aniline from Example 1147 with N-[4-(1,3-dioxobenzo[c]azolidin-2-yl)naphthyl]{[(5-chloro(2-thienyl))sulfonyl]amino}carboxamide using the procedure outlined in Example 1146 step C. ES-MS (M+H)+=525.

Example 1172

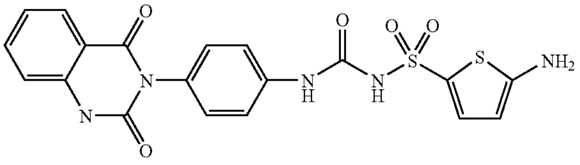

Preparation of {[(5-amino(2-thienyl))sulfonyl]amino}-N-[4-(2,4-dioxo(1,3-dihydroquinazolin-3-yl))phenyl]carboxamide To a solution of N-[4-(2,4-dioxo(1,3-dihydroquinazolin-3-yl))phenyl]{[(5-nitro(2-thienyl))sulfonyl]amino}carboxamide (from Example 1148) (20 mg, 0.041 mmol) in methanol (1.5 mL) and triethylamine (11 μL, 0.08 mmol) was added 10% Pd/C (5 mg, 0.005 mmol) under argon. The reaction mixture was hydrogenated under 1 atm $H_2$ for 3 hr, filtered, concentrated and HPLC purified to give the aniline (6 mg, 33%). ES-MS (M+H)+=458.

Example 1173

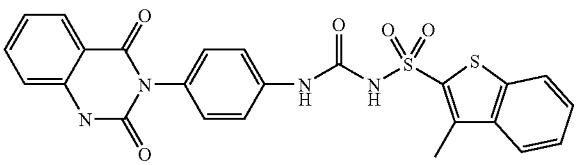

Preparation of N-[4-(2,4-dioxo(1,3-dihydroquinazolin-3-yl))phenyl]{[(3-methylbenzo[b]thiophen-2-yl)sulfonyl]amino}carboxamide To a solution of the sulfonylurea from Example 1150 (52 mg, 0.046 mmol) in methanol (1.5 mL) and triethylamine (12 μL) was added 10% Pd/C (50 mg) and $PtO_2$ (7 mg). The reaction mixture was hydrogenated under 250 psi $H_2$ for 4 days, filtered, concentrated and HPLC purified to give the dehalogenated product (2 mg, 10%). ES-MS (M+H)+=507.

Examples 1174-1176

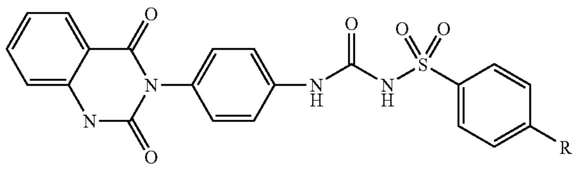

The sulfonyl urea targets above were prepared by reaction of the aniline 3-(4-aminophenyl)-1,3-dihydroquinazoline-2,4-dione trifluoroacetate salt (Example 1147) with 3 commercially available substituted phenylsulfonylisocyanates (1.5 eq.) (R=H, Cl, $CH_3$) in DMF. Products were typically isolated by precipitation from DMF reaction mixture with water and filtration.

Example 1174

N-[4-(2,4-dioxo(1,3-dihydroquinazolin-3-yl))phenyl][(phenylsulfonyl)amino]carboxamide. ES-MS (M+H)+=437.0.

Example 1175

N-[4-(2,4-dioxo(1,3-dihydroquinazolin-3-yl))phenyl]{[(4-chlorophenyl)sulfonyl]amino}carboxamide. ES-MS (M+H)+=471, 473 (Cl).

Example 1176

N-[4-(2,4-dioxo(1,3-dihydroquinazolin-3-yl))phenyl]{[(4-methylphenyl)sulfonyl]amino}carboxamide. ES-MS (M+H)+=451.

Example 1177

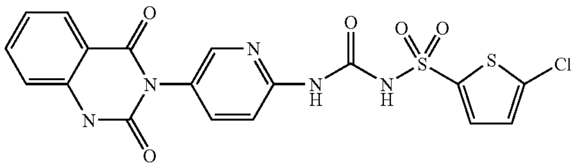

Preparation of N-[5-(2,4-dioxo(1,3-dihydroquinazolin-3-yl))(2-pyridyl)]{[(5-chloro(2-thienyl))sulfonyl]amino}carboxamide A. Synthesis of (tert-butoxy)-N-(5-nitro(2-pyridyl))carboxamide To a solution of 2-amino-5-nitropyridine (0.555 g, 4 mmol) in THF (10 mL) was added 1M NaHMDS in THF (8 mL, 8 mmol). The resulting dark red suspension was stirred for 15 min, followed by addition of a solution of Boc anhydride (0.87 mL, 3.8 mmol) in THF (5 mL). The reaction mixture was stirred at room temp for 21 hr, dilute with EtOAc, washed with 1N HCl and brine, dried and concentrated in vacuo to give desired compound (0.63 g, 70%). ES-MS (M+H)+=240, (M−tBu+H)+=184.

B. Synthesis of N-(5-amino(2-pyridyl))(tert-butoxy)carboxamide

To a suspension of (tert-butoxy)-N-(5-nitro(2-pyridyl))carboxamide (0.27 g, 1.13 mmol) in methanol (2 mL), ethyl acetate (4 mL) and TEA (0.16 mL) was added 10% Pd/C (60 mg, 0.056 mmol) under argon. The reaction mixture was hydrogenated under 1 atm $H_2$ for 20 hr, filtered through Celite and concentrated in vacuo to give desired compound (0.226 g, 97%).

C. Synthesis of [(tert-butyl)amino]-N-[5-(2,4-dioxo(1,3-dihydroquinazolin-3-yl))(2-pyridyl)]carboxamide The above named compound was prepared using the procedure outlined in Example 1146 step A by reaction of N-(5-amino(2-pyridyl))(tert-butoxy)carboxamide with methyl 2-isocyanatobenzoate. ES-MS (M+H)+=355.

D. Synthesis of N-[5-(2,4-dioxo(1,3-dihydroquinazolin-3-yl))(2-pyridyl)]{[(5-chloro(2-thienyl)sulfonyl]amino}carboxamide To a solution of 5-chlorothiophene-2-sulfonamide (20 mg, 0.1 mmol) and [(tert-butyl)amino]-N-[5-(2,4-dioxo(1,3-dihydroquinazolin-3-yl))(2-pyridyl)]carboxamide (35 mg, 0.1 mmol) in DMF (1 mL) was added DBU (30 μL). The reaction mixture was heated at 90° C. for 3 days, acidified and HPLC purified to give the sulfonyl urea (7 mg, 16%). ES-MS (M+H)+=478, 480 (Cl).

Example 1178

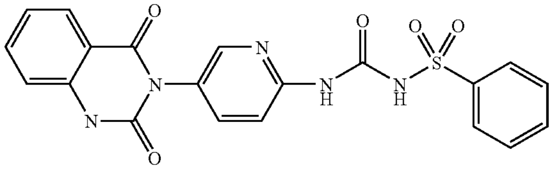

Preparation of N-[5-(2,4-dioxo(1,3-dihydroquinazolin-3-yl))(2-pyridyl)][(phenylsulfonyl)amino]carboxamide This compound was prepared by TFA deprotection of [(tert-butyl)amino]-N-[5-(2,4-dioxo(1,3-dihydroquinazolin-3-yl))(2-pyridyl)]carboxamide from Example 1177, step C, followed by reaction of the aminopyridine with phenylsulfonylisocyanate (1.5 eq) in DMF, precipitation from 0.1% TFA and filtration of product to give the sulfonyl urea desired compound (40% yield). ES-MS (M+H)+=438.

Example 1179

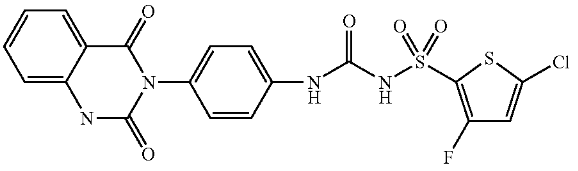

N-[4-(2,4-dioxo(1,3-dihydroquinazolin-3-yl))phenyl]{[(5-chloro-3-fluoro(2-thienyl))sulfonyl]amino}carboxamide A. Synthesis of (tert-butyl)[(5-chloro(2-thienyl))sulfonyl]amine A solution of 5.5 g (27.5 mmol) of 5-chlorothiophenesulfonyl chloride in dry THF at 0° C. was treated with a solution of 5.7 mL (75.5 mmol) of t-butylamine. After warming to 23° C., the reaction mixture was diluted with 125 mL of diethyl ether, filtered, and washed with 1 N HCl, brine, and dried ($MgSO_4$). Concentration in vacuo affords 6.4 g (98%) of the named compound as an oil.

B. Synthesis of (tert-butyl)[(5-chloro-3-fluoro(2-thienyl))sulfonyl]amine

A THF solution (1.5 mL) of 128 mg (0.50 mmol) of (tert-butyl)[(5-chloro(2-thienyl))sulfonyl]amine was cooled to −78° C. and treated with 954 μL (1.5 mmol) of a 1.6 M solution of butyl lithium in hexane. After 1 h, 159 mg (0.5 mmol) of bis(phenylsulfonyl)fluoroamine was added and the solution was allowed to warm to 23° C. The reaction was quenched with 1 mL of sat. $NH_4Cl$, extracted 3 times with diethyl ether, dried ($MgSO_4$), concentrated in vacuo to afford a quantitative yield (147 mg) of the desire product. $^{19}F$-NMR ($CDCl_3$) δ (ppm): −113.4.

C. Synthesis of N-[4-(2,4-dioxo(1,3-dihydroquinazolin-3-yl))phenyl]{[(5-chloro-3-fluoro(2-thienyl))sulfonyl]amino}carboxamide A 19 mg-sample (0.07 mmol) of (tert-butyl)[(5-chloro-3-fluoro(2-thienyl))sulfonyl]amine was dissolved in neat TFA and stirred for 1 h, concentrated in vacuo and used directly in the next transformation. This sample was dissolved in 150 μL of DCM and 21 mg (0.084 mmol) of DSC was added followed by 21 μL (0.14 mmol) of DBU. This solution was stirred for 18 h, 26 mg (0.07) of 3-(4-aminophenyl)-1,3-dihydroquinazoline-2,4-dione trifluoroacetate salt was added plus 150 μL of dry acetonitrile and refluxed for 2 h. This material was then purified on RP-HPLC to afford 11 mg (34%) of the desired product. ES-MS: M+H+=495 (Cl).

Pharmaceutical Compositions and Methods of Treatment

A compound of formulae (I)-(VIII) according to the invention may be formulated into pharmaceutical compositions. Accordingly, the invention also relates to a pharmaceutical composition for preventing or treating thrombosis in a mammal, particularly those pathological conditions involving platelet aggregation, containing a therapeutically effective amount of a compound of formulae (I)-(VIII) or a pharmaceutically acceptable salt thereof, each as described above, and a pharmaceutically acceptable carrier or agent. Preferably, a pharmaceutical composition of the invention contains a compound of formulae (I)-(VIII), or a salt thereof, in an amount effective to inhibit platelet aggregation, more preferably, ADP-dependent aggregation, in a mammal, in particular, a human. Pharmaceutically acceptable carriers or agents include those known in the art and are described below.

Pharmaceutical compositions of the invention may be prepared by mixing the compound of formulae (I)-(VIII) with a physiologically acceptable carrier or agent. Pharmaceutical compositions of the invention may further include excipients, stabilizers, diluents and the like and may be provided in sustained release or timed release formulations. Acceptable carriers, agents, excipients, stablilizers, diluents and the like for therapeutic use are well known in the pharmaceutical field, and are described, for example, in *Remington's Pharmaceutical Sciences*, Mack Publishing Co., ed. A. R. Gennaro (1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN, or polyethyleneglycol.

Methods for preventing or treating thrombosis in a mammal embraced by the invention administer a therapeutically effective amount of a compound of formulae (I)-(VIII) alone or as part of a pharmaceutical composition of the invention as described above to a mammal, in particular, a human. Compounds of formulae (I)-(VIII) and pharmaceutical compositions of the invention containing a compound of formulae (I)-(VIII) of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses.

Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. Coadministration may also allow for application of reduced doses of the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Compounds and pharmaceutical compositions of the invention may be in the form of solutions or suspensions. In the management of thrombotic disorders the compounds or pharmaceutical compositions of the invention may also be in such forms as, for example, tablets, capsules or elixirs for oral administration, suppositories, sterile solutions or suspensions or injectable administration, and the like, or incorporated into shaped articles. Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of formulae (I)-(VIII) employed, the specific use for which the compound or pharmaceutical composition is employed, and other factors which those skilled in the medical arts will recognize.

Dosage formulations of compounds of formulae (I)-(VIII), or pharmaceutical compositions contain a compound of the invention, to be used for therapeutic administration must be sterile. Sterility is readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of formulae (I)-(VIII) or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of formulae (I)-(VIII) and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of formulae (I)-(VIII) is compounded with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

Typical adjuvants which may be incorporated into tablets, capsules and the like include, but are not limited to, binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Pharmacological Assays

The pharmacological activity of each of the compounds according to the invention is determined by the following in vitro assays:

I. Inhibition of ADP-Mediated Platelet Aggregation In Vitro

The effect of testing the compound according to the invention on ADP-induced human platelet aggregation is preferably assessed in 96-well microtiter assay (see generally the procedures in Jantzen, H. M. et al. (1999) *Thromb. Hemost.* 81:111-117). Human venous blood is collected from healthy, drug-free volunteers into ACD (85 mM sodium citrate, 111 mM glucose, 71.4 mM citric acid) containing $PGI_2$ (1.25 ml ACD containing 1.6 μM $PGI_2$/10 ml blood; $PGI_2$ was from Sigma, St. Louis, Mo.). Platelet-rich plasma (PRP) is prepared by centrifugation at 160×g for 20 minutes at room temperature. Washed platelets are prepared by centrifuging PRP for 10 minutes at 730 g and resuspending the platelet pellet in CGS (13 mM sodium citrate, 30 mM glucose, 120 mM NaCl; 2 ml CGS/10 ml original blood volume) containing 1 U/ml apyrase (grade V, Sigma, St. Louis, Mo.). After incubation at 37° C. for 15 minutes, the platelets are collected by centrifugation at 730 g for 10 minutes and resuspended at a concentration of $3\times10^8$ platelets/ml in Hepes-Tyrode's buffer (10 mM Hepes, 138 mM NaCl, 5.5 mM glucose, 2.9 mM KCl, 12 mM $NaHCO_3$, pH 7.4) containing 0.1% bovine serum albumin, 1 mM $CaCl_2$ and 1 mM $MgCl_2$. This platelet suspension is kept >45 minutes at 37° C. before use in aggregation assays.

Inhibition of ADP-dependent aggregation is preferably determined in 96-well flat-bottom microtiter plates using a microtiter plate shaker and plate reader similar to the procedure described by Frantantoni et al., *Am. J. Clin. Pathol.* 94, 613 (1990). All steps are performed at room temperature. The total reaction volume of 0.2 ml/well includes in Hepes-Tyrodes buffer/0.1% BSA: $4.5\times10^7$ apyrase-washed platelets, 0.5 mg/ml human fibrinogen (American Diagnostica, Inc., Greenwich, Conn.), serial dilutions of test compounds (buffer for control wells) in 0.6% DMSO. After about 5 minutes preincubation at room temperature, ADP is added to a final concentration of 2:M which induces submaximal aggregation. Buffer is added instead of ADP to one set of control wells ($ADP^-$ control). The OD of the samples is then determined at 490 nm using a microtiter plate reader (Softwax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 490 nm at t=5 minutes compared to t=0 minutes and is expressed as % of the decrease in the ADP control samples after correcting for changes in the unaggregated control samples.

II. Inhibition of [$^3$H]2-MeS-ADP Binding to Platelets

Having first determined that the compounds according to the invention inhibit ADP-dependent platelet aggregation with the above assay, a second assay is used to determine whether such inhibition is mediated by interaction with platelet ADP receptors. Utilizing the second assay the potency of inhibition of such compounds with respect to [$^3$H]2-MeS-ADP binding to whole platelets is determined. [$^3$H]2-MeS-ADP binding experiments are routinely performed with outdated human platelets collected by standard procedures at hospital blood banks. Apyrase-washed outdated platelets are prepared as follows (all steps at room temperature, if not indicated otherwise):

Outdated platelet suspensions are diluted with 1 volume of CGS and platelets pelleted by centrifugation at 1900×g for 45 minutes. Platelet pellets are resuspended at $3\text{-}6\times10^9$ platelets/ ml in CGS containing 1 U/ml apyrase (grade V, Sigma, St. Louis, Mo.) and incubated for 15 minutes at 37° C. After centrifugation at 730×g for 20 minutes, pellets are resuspended in Hepes-Tyrode's buffer containing 0.1% BSA (Sigma, St. Louis, Mo.) at a concentration of $6.66\times10^8$ platelets/ml. Binding experiments are performed after >45 minutes resting of the platelets.

Alternatively, binding experiments are performed with fresh human platelets prepared as described in I (Inhibition of ADP-Mediated Platelet Aggregation in vitro), except that platelets are resuspended in Hepes-Tyrode's buffer containing 0.1% BSA (Sigma, St. Louis, Mo.) at a concentration of $6.66\times10^8$ platelets/ml. Very similar results are obtained with fresh and outdated platelets.

A platelet ADP receptor binding assay using the tritiated potent agonist ligand [$^3$H]2-MeS-ADP (Jantzen, H. M. et al. (1999) Thromb. Hemost. 81:111-117) has been adapted to the 96-well microtiter format. In an assay volume of 0.2 ml Hepes-Tyrode's buffer with 0.1% BSA and 0.6% DMSO, $1\times10^8$ apyrase-washed platelets are preincubated in 96-well flat bottom microtiter plates for 5 minutes with serial dilutions of test compounds before addition of 1 nM [$^3$H]2-MeS-ADP ([$^3$H]2-methylthioadenosine-5'-diphosphate, ammonium salt; specific activity 48-49 Ci/mmole, obtained by custom synthesis from Amersham Life Science, Inc., Arlington Heights, Ill., or NEN Life Science Products, Boston, Mass.). Total binding is determined in the absence of test compounds. Samples for nonspecific binding may contain $10^{-5}$M unlabelled 2-MeS-ADP (RBI, Natick, Mass.). After incubation for 15 minutes at room temperature, unbound radioligand is separated by rapid filtration and two washes with cold (4-8° C.) Binding Wash Buffer (10 mM Hepes pH 7.4, 138 mM NaCl) using a 96-well cell harvester (Minidisc 96, Skatron Instruments, Sterling, Va.) and 8×12 GF/C glass-fiber filtermats (Printed Filtermat A, for 1450 Microbeta, Wallac Inc., Gaithersburg, Md.). The platelet-bound radioactivity on the filtermats is determined in a scintillation counter (Microbeta 1450, Wallac Inc., Gaithersburg, Md.). Specific binding is determined by subtraction of non-specific binding from total binding, and specific binding in the presence of test compounds is expressed as % of specific binding in the absence of test compounds dilutions.

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The claimed invention is:

1. A compound of formula (I):

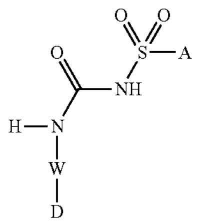

I wherein:

A is thienyl, optionally substituted with lower alkoxy, lower alkylamino or halogen W is heteroaryl, selected from the group consisting of pyridyl, pyrimidinyl, pyrazinyl and pyridazinyl, each of which is optionally substituted with halogen;

D is;

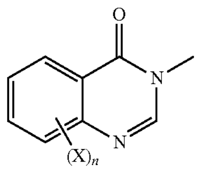

wherein:

n is an integer from 0-4 and each D ring carbon atom is independently substituted by X, wherein X is in each case a member independently selected from the group consisting of:

hydrogen, halogen, polyhaloalkyl, —$OR^3$, —$SR^3$, —CN, —$NO_2$, —$SO_2R^3$, —$C_{1-10}$-alkyl, —$C_{3-8}$-cycloalkyl, aryl, aryl-substituted by 1-4 $R^3$ groups, amino, amino-$C_{1-8}$-alkyl, $C_{1-3}$-acylamino, $C_{1-3}$-acylamino-$C_{1-8}$-alkyl, $C_{1-6}$-alkylamino, $C_{1-6}$alkylamino $C_{1-8}$ alkyl, $C_{1-6}$ dialkylamino, $C_{1-6}$ dialkylamino $C_{1-8}$ alkyl, $C_{1-6}$ alkoxy, $C_{1-6}$ alkoxy-$C_{1-6}$-alkyl, carboxy-$C_{1-6}$-alkyl, $C_{1-3}$-alkoxycarbonyl, $C_{1-3}$-alkoxycarbonyl-$C_{1-6}$-alkyl, carboxy $C_{1-6}$ alkyloxy, hydroxy, hydroxy $C_{1-6}$ alkyl, and a 5 to 10 membered fused or non-fused aromatic or nonaromatic heterocyclic ring system, having 1 to 4 heteroatoms independently selected from N, O, and S, with the proviso that the carbon and nitrogen atoms, when present in the heterocyclic ring system, are unsubstituted, mono- or di-substituted independently with 0-2 $R^4$ groups, wherein $R^3$ and $R^4$ are each independently selected from the group consisting of:

hydrogen, halogen, —CN, —$NO_2$, —$C_{1-10}$ alkyl, $C_{3-8}$-cycloalkyl, aryl, amino, amino-$C_{1-8}$-alkyl, $C_{1-3}$-acylamino, $C_{1-3}$-acylamino-$C_{1-8}$-alkyl, $C_{1-6}$-alkylamino, $C_{1-6}$-alkylamino $C_{1-8}$ alkyl, $C_{1-6}$ dialkylamino, $C_{1-6}$ dialkylamino $C_{1-8}$ alkyl, $C_{1-6}$ alkoxy, $C_{1-6}$ alkoxy-$C_{1-6}$-alkyl, carboxy-$C_{1-6}$-alkyl, $C_{1-3}$-alkoxycarbonyl, $C_{1-3}$-alkoxycarbonyl-$C_{1-6}$-alkyl, carboxy-$C_{1-6}$-alkyloxy, hydroxy, hydroxy-$C_{1-6}$-alkyl, -thio and thio-$C_{1-6}$-alkyl;

or pharmaceutically acceptable salts.

2. A compound according to claim 1, wherein:

A is selected from the group consisting of:

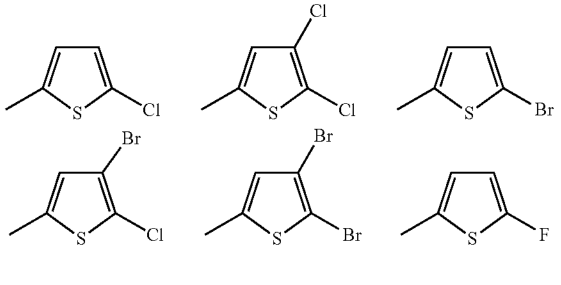

-continued
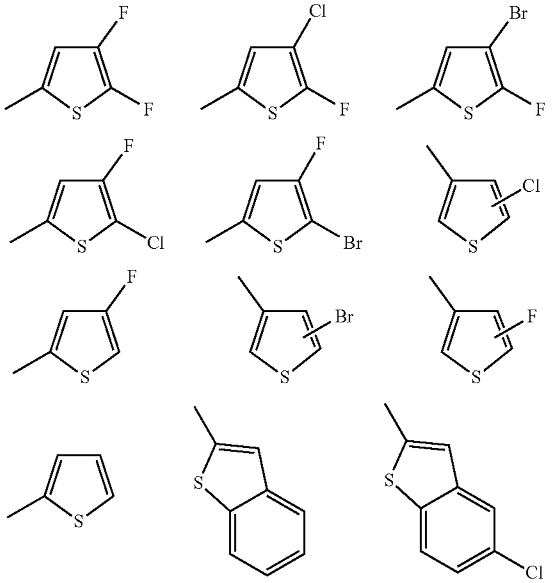
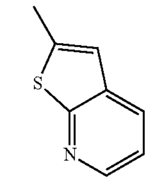
and
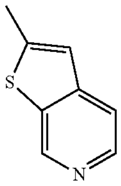
W is selected from the group consisting of:
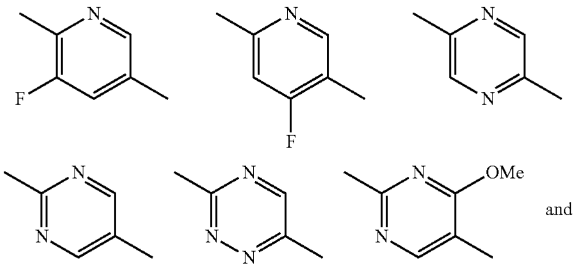
and
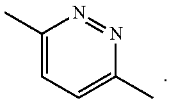
3. A compound of claim 1, selected from the group consisting of:
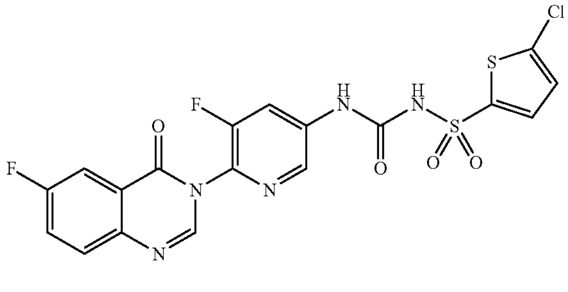
-continued
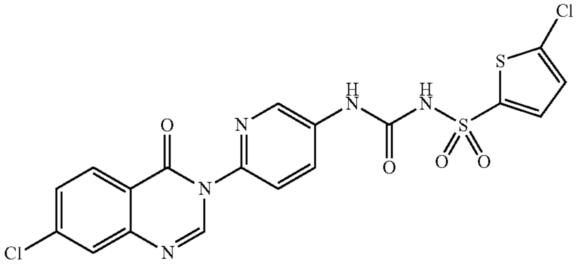
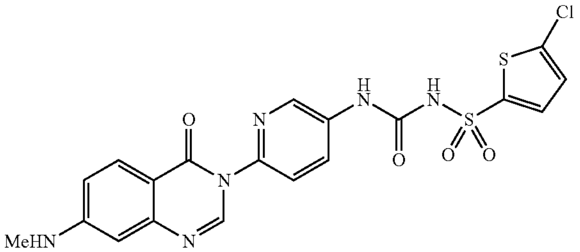
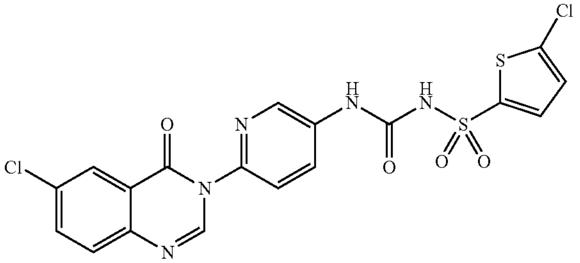
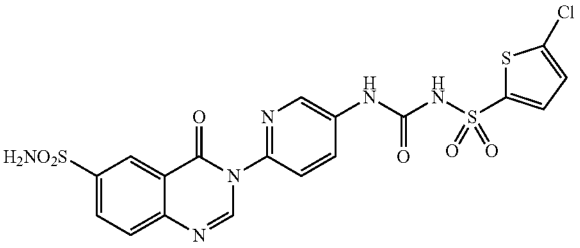
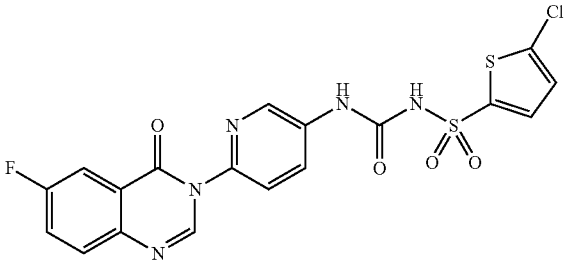
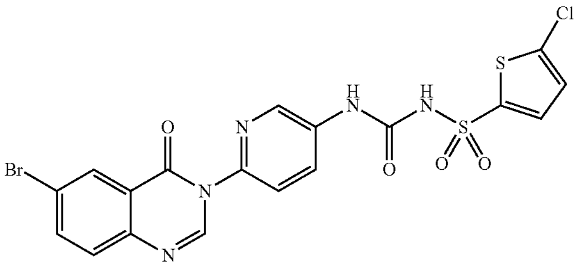

-continued
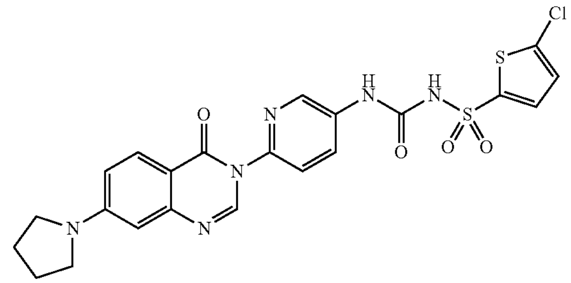
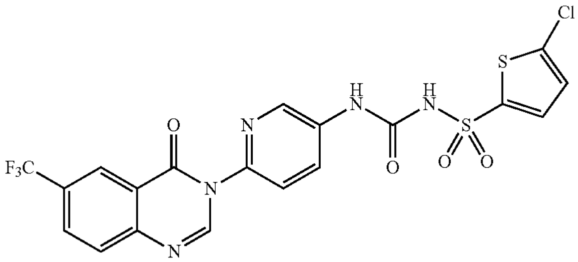
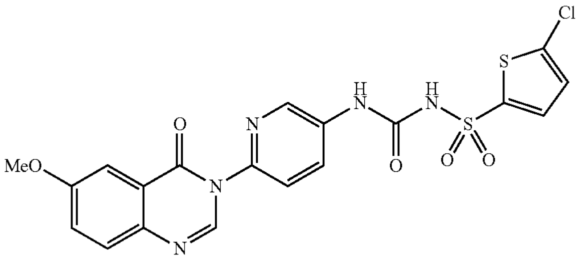
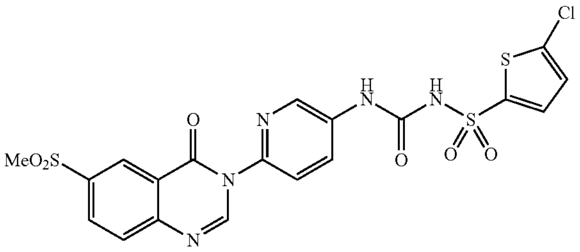
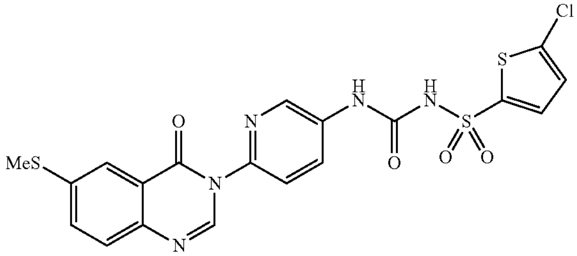
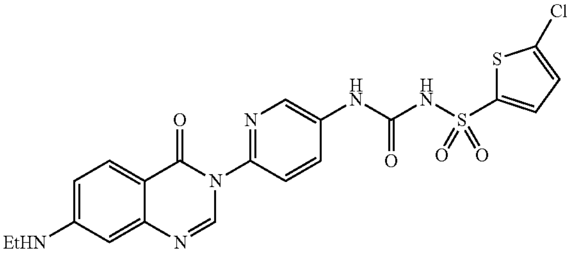
-continued
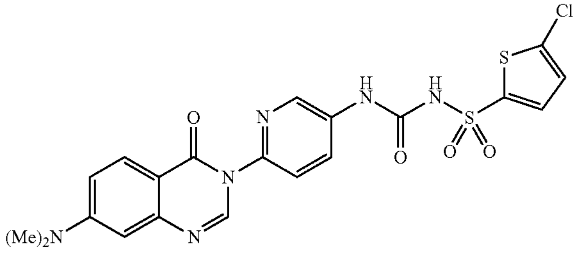
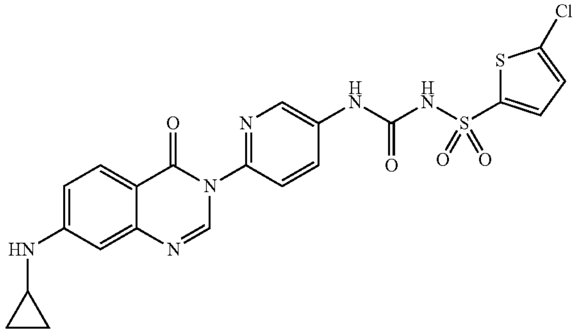
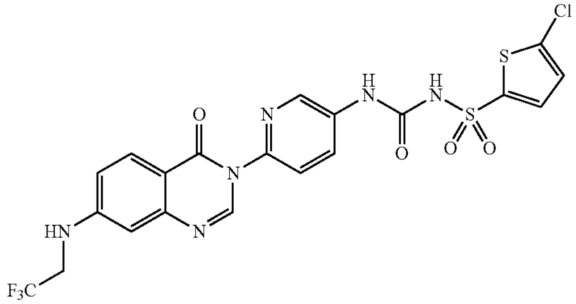
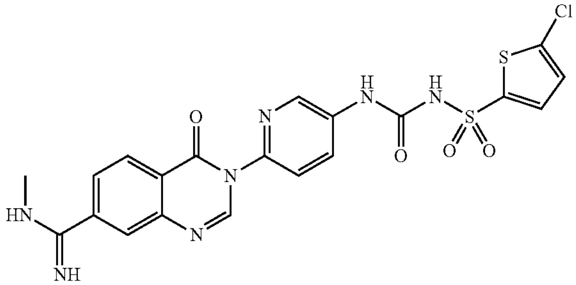
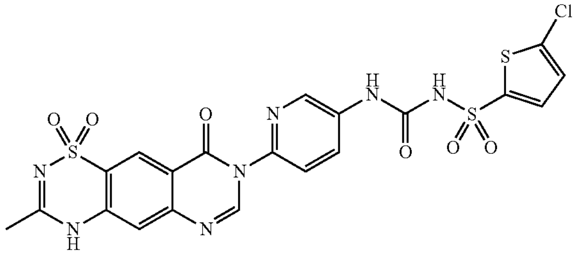
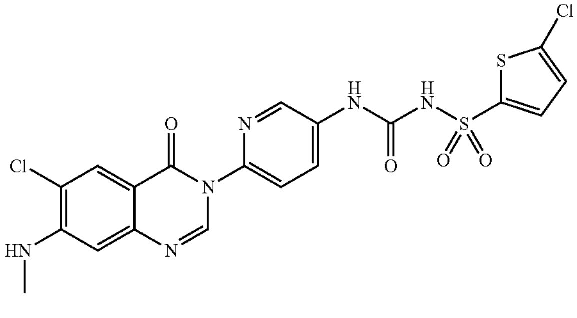

-continued
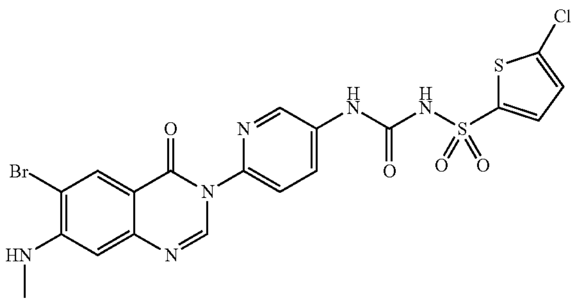
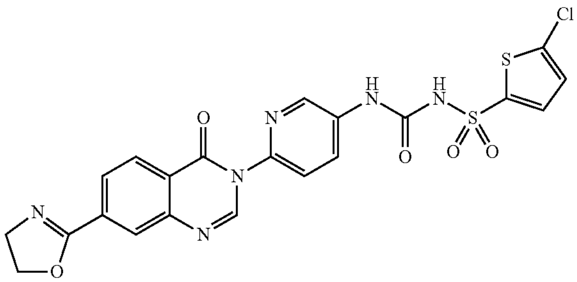
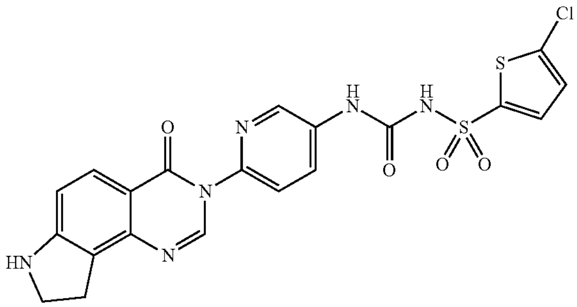
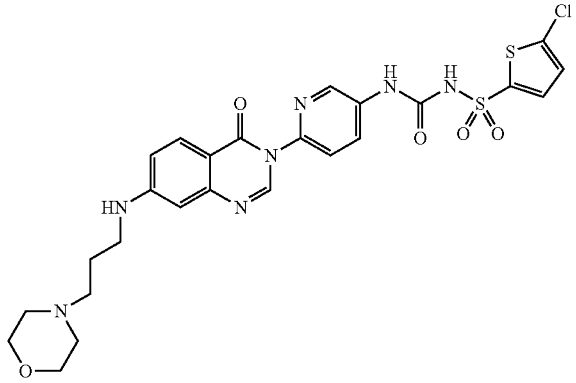
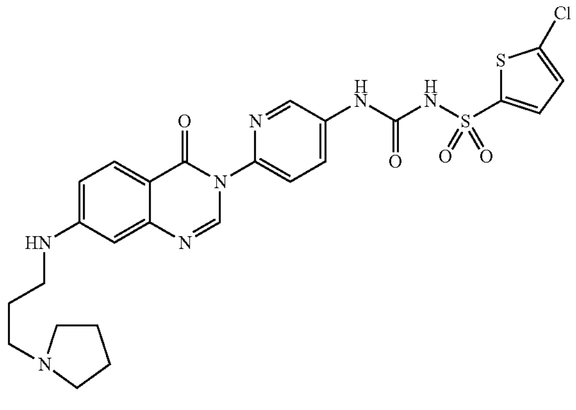
-continued
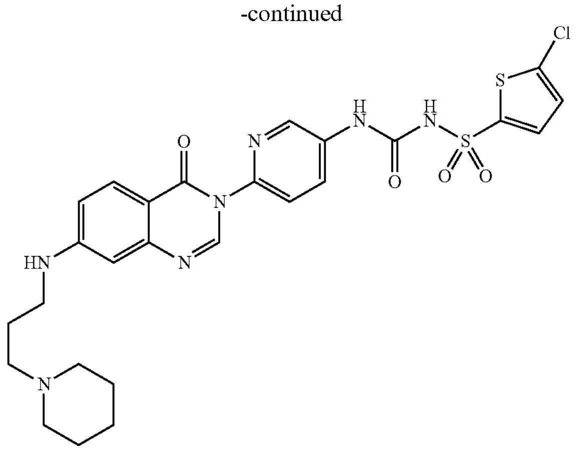
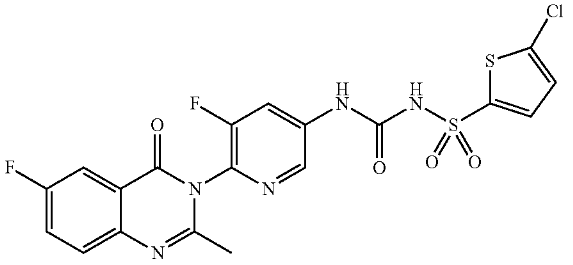
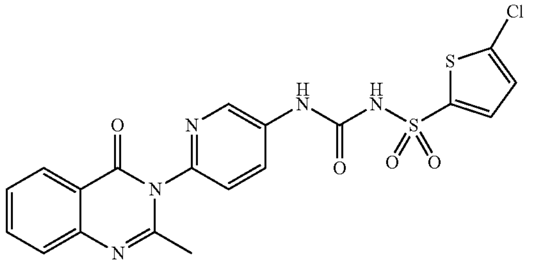
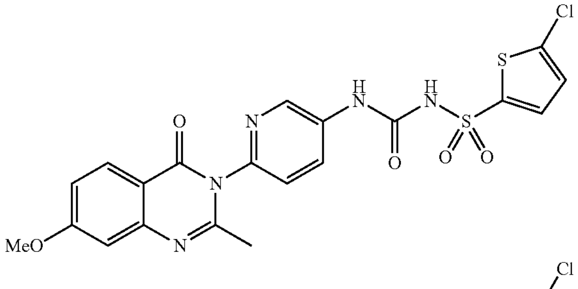
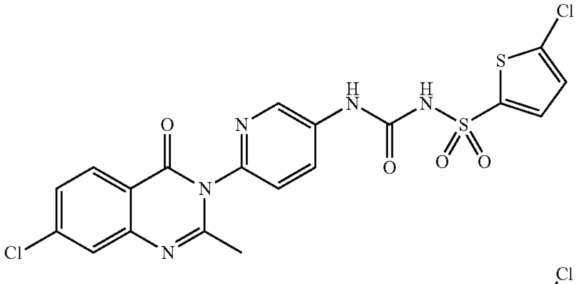
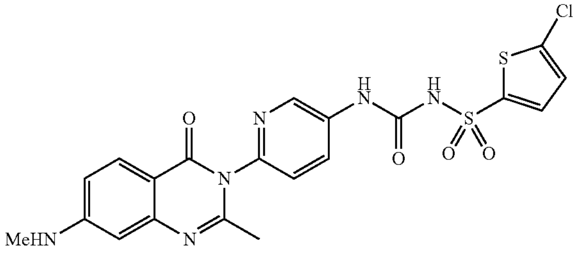

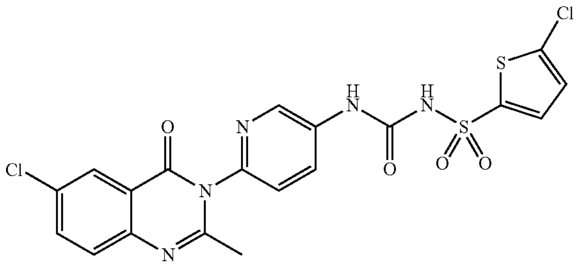
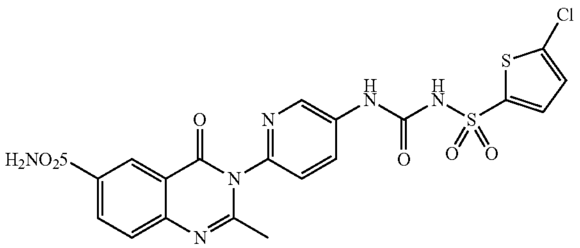
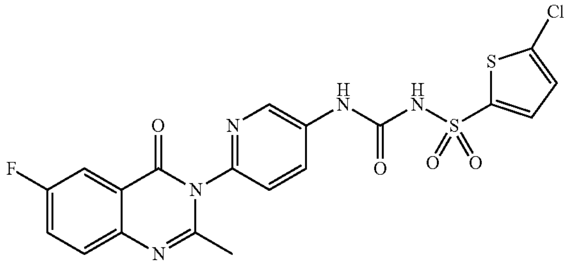
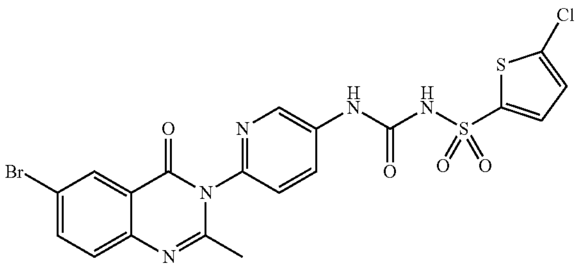
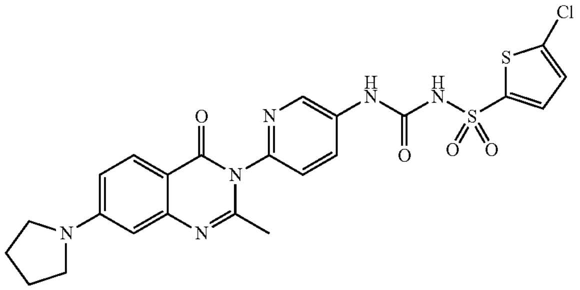
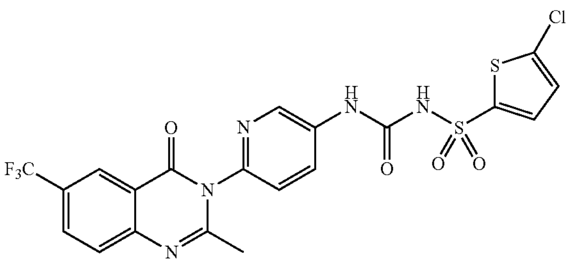
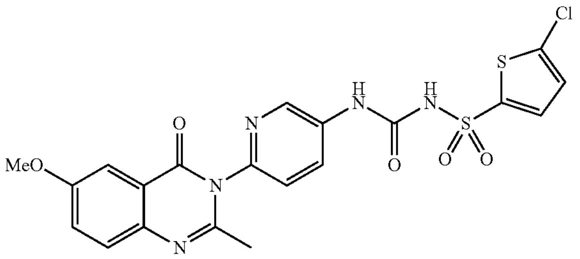
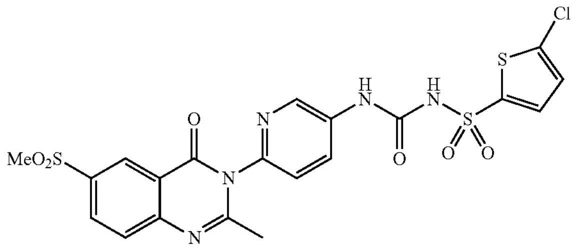
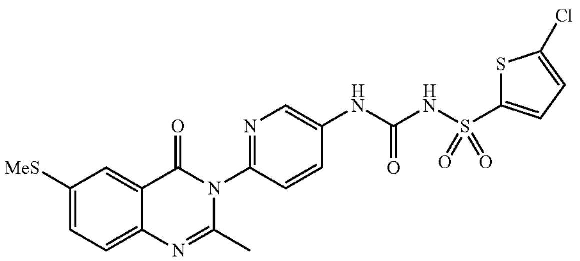
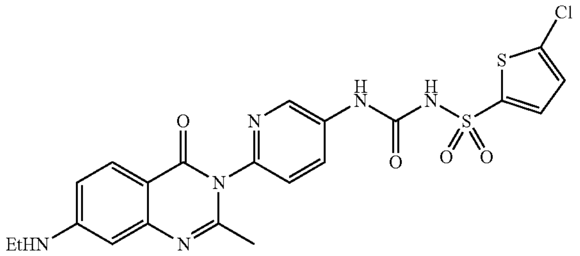
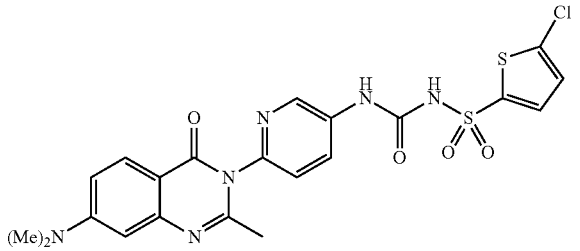
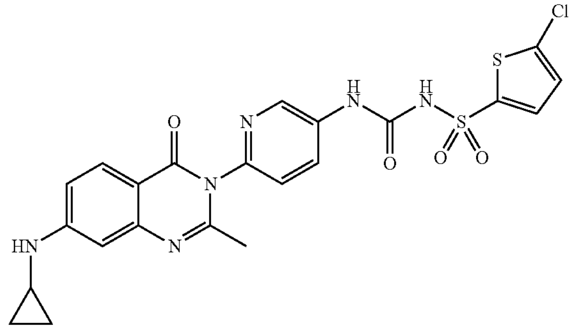

-continued
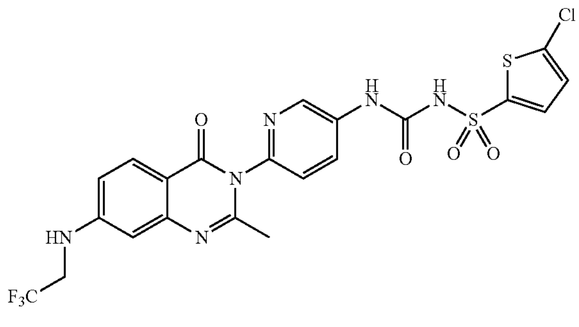
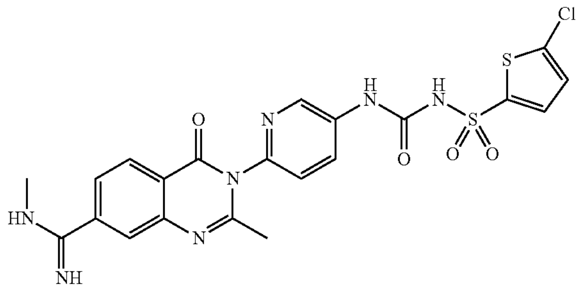
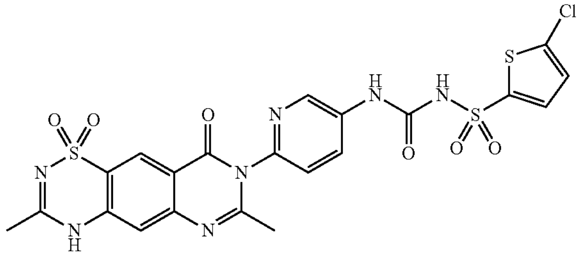
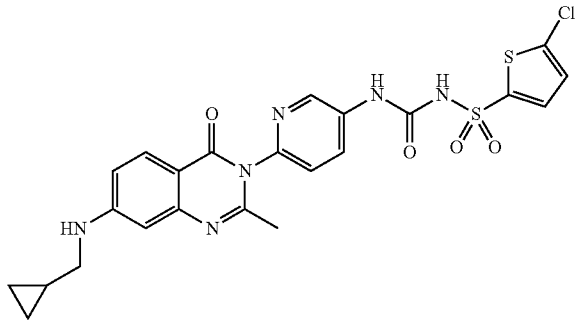
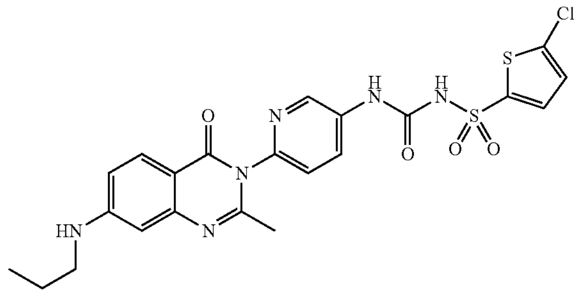
-continued
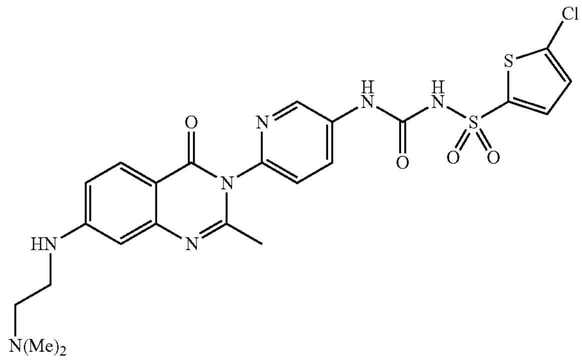
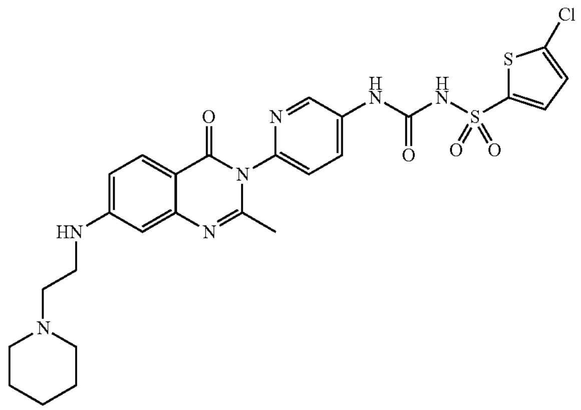
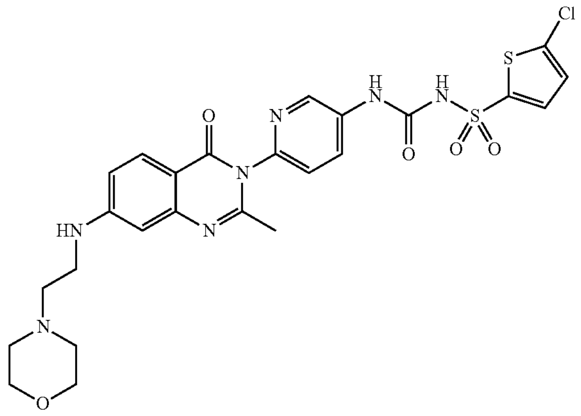
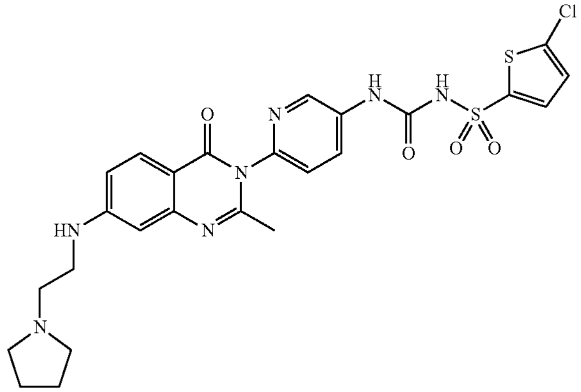

-continued
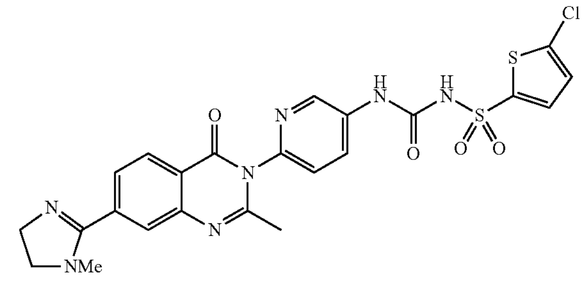
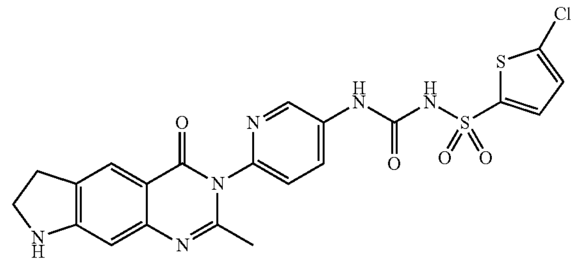
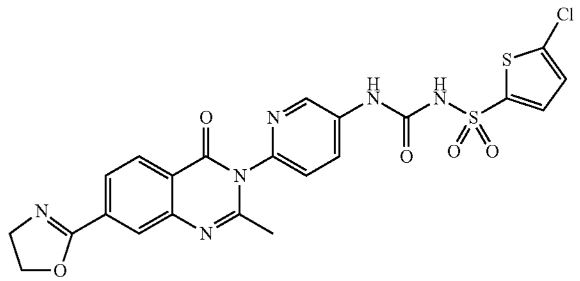
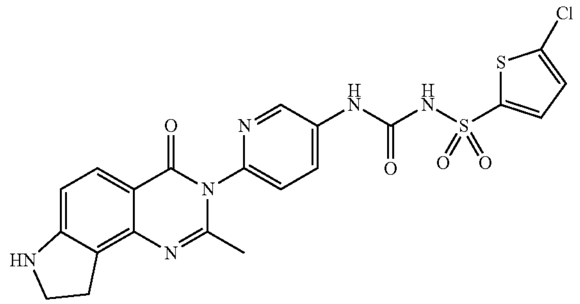
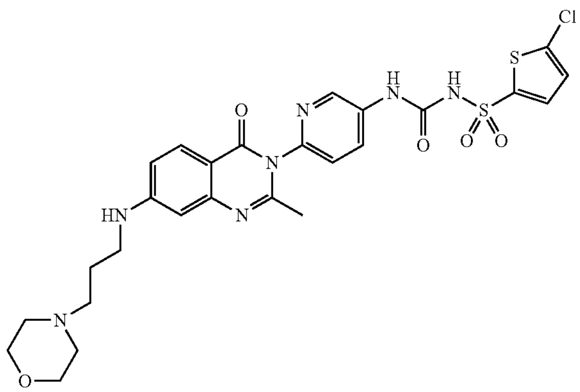
-continued
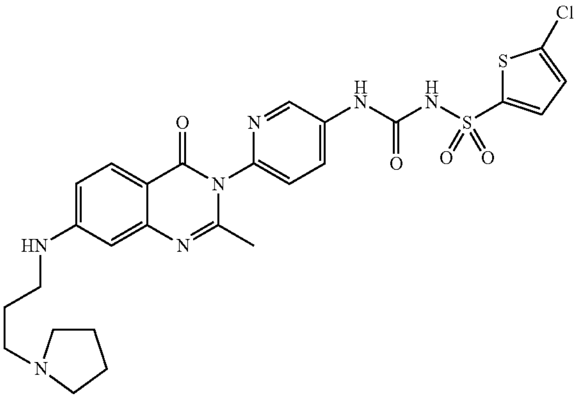
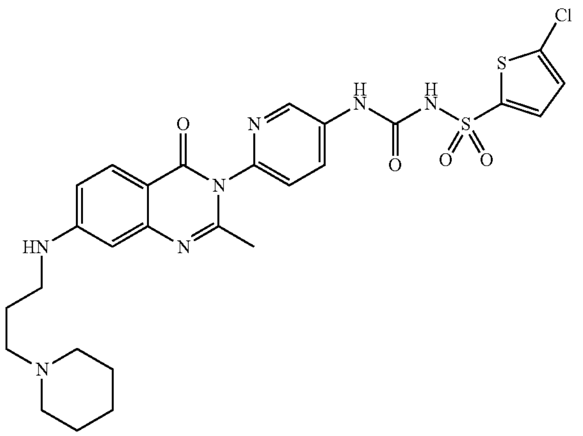
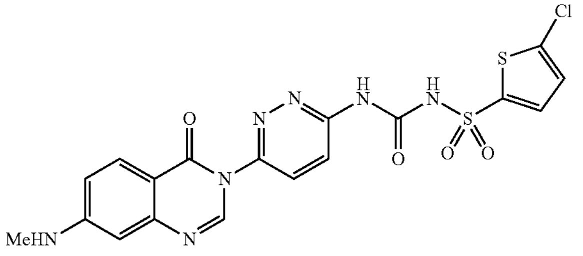
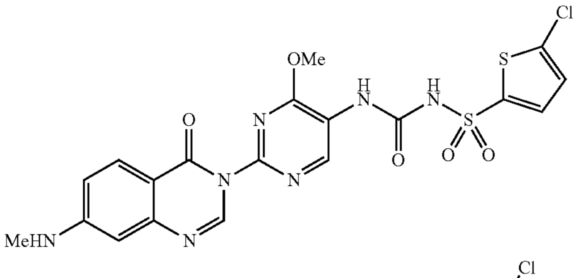
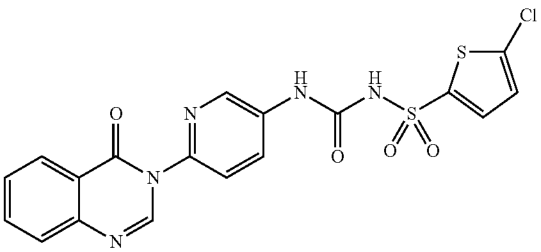
and -continued

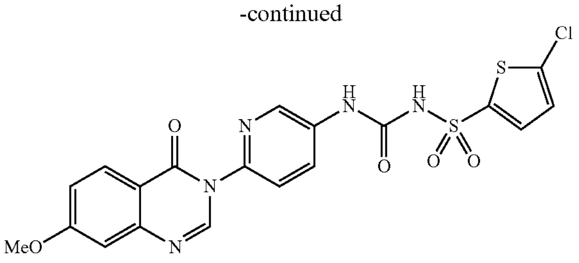

4. A pharmaceutical composition for preventing or treating thrombosis in a mammal comprising a therapeutically effective amount of a compound according to claim 1, or a pharmaceutically acceptable salt thereof, and a pharmaceutically acceptable carrier.

5. A pharmaceutical composition of claim 4, wherein said mammal is a human.

6. A method for preventing or treating thrombosis in a mammal comprising the step of administering to a mammal a therapeutically effective amount of a compound of claim 1 or a pharmaceutically acceptable salt thereof.

7. A method of claim 6, wherein said mammal is a human.

8. A method of claim 6, wherein said mammal is prone to or suffers from a cardiovascular disease selected from the group consisting of acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures resulting from angioplasty, carotid endarterectomy, post CABG (coronary artery bypass graft) surgery, vascular graft surgery, stent placements and insertion of endovascular devices and protheses.

* * * * *